US007807798B2

(12) United States Patent
Jakobovits et al.

(10) Patent No.: US 7,807,798 B2
(45) Date of Patent: *Oct. 5, 2010

(54) HUMAN MONOCLONAL ANTIBODIES TO EPIDERMAL GROWTH FACTOR RECEPTOR

(75) Inventors: Aya Jakobovits, Menlo park, CA (US); Xiao-Dong Yang, Palo Alto, CA (US); Michael Gallo, San Jose, CA (US); Xiao-Chi Jia, San Mateo, CA (US)

(73) Assignee: Amgen Fremont Inc., Fremont, CA (US)

( * ) Notice: Subject to any disclaimer, the term of this patent is extended or adjusted under 35 U.S.C. 154(b) by 1026 days.

This patent is subject to a terminal disclaimer.

(21) Appl. No.: 11/267,860

(22) Filed: Nov. 4, 2005

(65) Prior Publication Data

US 2006/0183887 A1 Aug. 17, 2006

Related U.S. Application Data

(63) Continuation of application No. 11/021,795, filed on Dec. 22, 2004, now abandoned, which is a continuation of application No. 09/187,693, filed on Nov. 5, 1998, now abandoned, which is a continuation-in-part of application No. 09/162,280, filed on Sep. 29, 1998, now abandoned, which is a continuation-in-part of application No. 08/851,362, filed on May 5, 1997, now Pat. No. 6,235,883.

(51) Int. Cl.
*C12P 21/08* (2006.01)
(52) U.S. Cl. .............................. 530/388.15; 530/388.22
(58) Field of Classification Search ............ 530/388.15, 530/388.22
See application file for complete search history.

(56) References Cited

U.S. PATENT DOCUMENTS

| 4,943,533 | A | 7/1990 | Mendelsohn et al. |
| 5,545,806 | A | 8/1996 | Lonberg et al. |
| 5,558,864 | A | 9/1996 | Bendig et al. |
| 6,075,181 | A | 6/2000 | Kucherlapati et al. |
| 6,150,584 | A | 11/2000 | Kucherlapati et al. |
| 6,235,883 | B1 * | 5/2001 | Jakobovits et al. ..... 530/388.22 |
| 6,657,103 | B1 | 12/2003 | Kucherlapati et al. |
| 6,713,610 | B1 * | 3/2004 | Kucherlapati et al. .. 530/388.23 |
| 2003/0070185 | A1 | 4/2003 | Jakobovits et al. |

FOREIGN PATENT DOCUMENTS

| EP | 586 002 A2 | 8/1993 |
| EP | 712 863 A1 | 5/1996 |
| WO | WO 91/00906 | 1/1991 |
| WO | WO 94/02602 | 2/1994 |
| WO | WO 94/25585 A1 | 11/1994 |
| WO | WO 96/33735 | 10/1996 |
| WO | WO 96/34096 A | 10/1996 |
| WO | WO 96/40210 A | 12/1996 |
| WO | WO 98/24893 A | 6/1998 |
| WO | WO 02/076406 | * 10/2002 |

OTHER PUBLICATIONS

Li et al. (1996) J. Mol. Biol., vol. 256, 577-589.*
Defize et al. (1989), J. Cell. Biol. vol. 109, pp. 2495-2507.*
Bruns et al. (2000) Canc. Res., vol. 60, 2926-2935.*
Sunada et al. (1990) J. Cell. Physiol., vol. 142, 284-292.*
Reins et al. (1993) J. Cell. Biochem., vol. 51, 236-248.*
Office Action dated Oct. 21, 2005, for U.S. Appl. No. 10/978,290, filed Oct. 29, 2004.
Office Action dated Oct. 24, 2005, for U.S. Appl. No. 10/978,297, filed Oct. 29, 2004.
Weber et al., "Immunoaffinity purification of the epidermal growth factor receptor. Stoichiometry of binding and kinetics of self-phosphorylation," *JBC*, 259:14631-14636 (1984).
Yarden et al., "Purification of an active EGF receptor kinase with monoclonal antireceptor antibodies," *JBC*, 260:315-319 (1985).
Amendment and Response dated Apr. 19, 2006, for U.S. Appl. No. 10/978,297, filed Oct. 29, 2004.
Office Action mailed Jul. 12, 2006, for U.S. Appl. No. 10/978,297, filed Oct. 29, 2004.
Aboud-Pirak et al., Dec. 21, 1988, "Efficacy of Antibodies to Epidermal Growth Factor Receptor Against KB Carcinoma in Vitro and in Nude Mice." J. Nat'l Cancer Inst. 80: 1605-1611.
Aboud-Pirak et al., 1988, "Monoclonal Anti EGF Receptor Antibodies Inhibit the Growth of Tumor Cells in Nude Mice." J. Cell. Biochem. Supp. 12A: 137.
Baselga et al., 1994, "Receptor Blockade With Monoclonal Antibodies as Anti-Cancer Therapy." Pharmac. Ther. 64: 127-154.
Bruggemann, M. et al., Sep. 1989, "A repertoire of monoclonal antibodies with human heavy chains from transgenic mice." Proceedings of the National Academy of Sciences USA 86: 6709-6713.
Bruggemann, M. et al., 1990, "Construction, Function and Immunogenicity of Recombinant Monoclonal Antibodies." Behring Inst. Mitt. 87: 21-24.

(Continued)

*Primary Examiner*—Anne Marie S Wehbe
(74) *Attorney, Agent, or Firm*—Finnegan, Henderson, Farabow, Garrett & Dunner LLP

(57) ABSTRACT

In accordance with the present invention, there are provided fully human monoclonal antibodies against human epidermal growth factor receptor (EGF-r). Nucelotide sequences encoding and amino acid sequences comprising heavy and light chain immunoglobulin molecules, particularly sequences corresponding to contiguous heavy and light chain sequences from CDR1 through CDR3, are provided. Hybridomas expressing such immunoglobulin molecules and monoclonal antibodies are also provided. Also provided in accordance with the invention are antibodies that possess one or more of the following functional characteristics: (i) inhibit tyrosine phosphorylation of EGF-r, (ii) do not inhibit EGF-r internalization, (ii) inhibit EGF-r degradation, (iii) inhibition of EGF induced EGF-r degradation, (iv) protect threonine phosphorylation of EGF-r, (v) protect threonine phosphorylation of other molecules, particularly a 62 KD molecule identified by immunoprecipitation, and (vi) inhibit vascular endothelial cell growth factor signal by tumor cells by greater than 50% and endothelial cells by greater than 40% relative to control.

11 Claims, 62 Drawing Sheets

OTHER PUBLICATIONS

Bruggemann, M. et al., 1991, "Human antibody production in transgenic mice: expression from 100 kb of the human IgH locus." Eur. J. Immunol. 21: 1323-1326.

Bruggemann, M. et al., Aug. 1996, "Strategies for expressing human antibody repertoires in transgenic mice." Immunology Today 17: 391-397.

Buttin, G., Aug. 1987, "Exogenous Ig gene rearrangement in transgenic mice: a new strategy for human monoclonal antibody production?" Trends in Genetics 3: 205-206.

Corvalan et al., Jan. 1, 1997, "Generation of fully human high affinity monoclonal antibodies to EGF receptor in mice," The Journal of Allergy and Clinical Immunology, 99(1, part 2, supp.): s15.

Defize et al., Nov. 1989, "Signal transduction by epidermal growth factor occurs through the subclass of high affinity receptors," J. Cell Biology, 109(5): 2495-2507.

Ennis et al., Nov. 1989, "Anti-Epidermal Growth Factor Receptor Antibodies Inhibit the Autocrine-Stimulated Growth of MDA-468 Human Breast Cancer Cells." Molec. Endocrinol. 3: 1830-1838.

Fendly et al., Mar. 1, 1990, "Characterization of Murine Monoclonal Antibodies Reactive to Either the Human Epidermal Growth Factor Receptor or HER2/neu Gene Product." Cancer Res. 50: 1550-1558.

Fishwild, D.M. et al., Jul. 1996, "High-avidity human IgGK monoclonal antibodies from a novel strain of minilocus transgenic mice." Nature Biotechnology 14: 845-851.

Fong et al., Nov. 1, 1992, "Epidermal Growth Factor Receptor Monoclonal Antibody Inhibits Constitutive Receptor Phosphorylation, Reduces Autonomous Growth, and Sensitizes Androgen-independent Prostatic Carcinoma Cells to Tumor Necrosis Factor α." Cancer Res. 52: 5887-5892.

GenBank Accession No. Z70619, *H. sapiens* mRNA for immunoglobulin heavy chain variable regions (6D4-A5, VH4, 4-31/DP-65), accessed Dec. 3, 1998 (1996).

GenBank Accession No. Z70658, *H. sapiens* mRNA for immunoglobulin heavy chain variable regions (83-6H3, VH4, 4-61/DP-66), accessed Dec. 3, 1998 (1996).

Gill et al., Jun. 25, 1984, "Monoclonal Anti-epidermal Growth Factor Receptor Antibodies Which Are Inhibitors of Epidermal Growth Factor Binding and Antagonists of Epidermal Growth Factor-stimulated Tyrosine Protein Kinase Activity." J. Biol. Chem. 259: 7755-7760.

Green, L.L., et al., May 1994, "Antigen-specific human monoclonal antibodies from mice engineered with human Ig heavy and light chain YACs." Nature Genetics 7: 13-21.

Jakobovits, A., 1995, "Production of fully human antibodies by transgenic mice." Curr. Opin. Biotechnol. 6: 561-566.

Jakobovits, A., et al., 1995, "Production of Antigen-Specific Human Antibodies from Mice Engineered with Human Heavy and Light Chain YACs." Annals New York Academy of Sciences 764: 525-535.

Jakobovits, A., et al., 1997, "Humoral immunity in mice engineered with megabase human heavy and kappa light chain YACs." J. Allergy Clin. Immunol. 99: S113.

Jakobovits et al., Jan., 1997, "Humoral immunity in mice engineered with megabase human heavy and kappa light chain YACs," The Journal of Allergy and Clinical Immunology, 99(1, part 2, supp.): s113.

Jakobovits et al., Apr. 6, 1998, "Production and selection of antigen-specific fully human monoclonal antibodies from mice engineered with human Ig loci," Advanced Drug Delivery Reviews, 31(1-2): 33-42.

Jakobovits, Apr. 1998, "The long-awaited magic bullets: therapeutic human monoclonal antibodies from transgenic mice," Expert Opinion on Investigational Drugs, 7(4): 607-614.

Klein, 1982, *Immunology: The Science of Self-Nonself Discrimination*, John Wiley & Sons: New York, NY pp. 176-183.

Lonberg, N. et al., Apr. 28, 1994, "Antigen-specific human antibodies from mice comprising four distinct genetic modifications." Nature 368: 856-859.

Masui et al., Mar. 1984, "Growth Inhibition of Human Tumor Cells in Athymic Mice by Anti-Epidermal Growth Factor Receptor Monoclonal Antibodies." Cancer Res. 44: 1002-1007.

Masui et al., Nov. 1986, "Mechanism of Antitumor Activity in Mice for Anti-Epidermal Growth Factor Receptor Monoclonal Antibodies with Different Isotypes." Cancer Res. 46: 5592-5598.

Matsumoto et al., Mar. 1997, "Chimeric monoclonal antibody (Mab) C225 to the epidermal growth factor receptor (EGF-R) inhibits the growth of human transitional cell carcinoma (TCC) in the bladder of nude mice," Proceedings of the American Association for Cancer Research, 38: 229.

Mendelsohn et al., 1986, "Monoclonal Antibodies to the EGF Receptor Selectively Inhibit the Growth of Human Tumor Cells." J. Cell. Biochem. Supp. 10A: 40.

Mendelsohn et al., 1987, "Anti-Epidermal Growth Factor Receptor Monoclonal Antibodies May Inhibit A431 Tumor Cell Proliferation by Blocking an Autocrine Pathway." Trans. Assoc. Am. Phys. $100^{th}$ session, vol. C, p. 173-178.

Mendelsohn et al., Apr. 1987, "Anti-EGF Receptor Monoclonal Antibodies May Inhibit A431 Tumor Cell Proliferation by Blocking an Autocrine Pathway." Clin. Res. 35: 660A.

Mendelsohn, 1988, "Growth Factor Receptors as Targets for Antitumor Therapy with Monoclonal Antibodies." Monoclonal Antibody Therapy, Progress in Allergy, 45:147-160.

Mendelsohn et al., 1988, "Monoclonal Antibodies Against the Receptor for Epidermal Growth Factor as Potential Anticancer Agents." Cell. Molec. Biol. of Tumors and Pot. Clin. Appl. 307-312.

Mendelsohn, 1989, "Anti-EGF Receptor Monoclonal Antibodies: Biological Studies and Potential Clinical Applications." Trans. Am. Clin. Climatological Assoc. vol. C, p. 31-38.

Mendelsohn, Dec. 20, 1990, "Anti-Epidermal Growth Factor Receptor Monoclonal Antibodies as Potential Anti-Cancer Agents." J. Steroid Biochem. Molec. Biol. 37: 889-892.

Mendez et al., Feb. 1997, "Functional transplant of megabase human immunoglobulin loci recapitulates human antibody response in mice," Nature Genetics, 15: 146-156.

Modjtahedi et al., 1994, "The receptor for EGF and its ligands: expression, prognostic value and target for therapy in cancer (Review)," International Journal of Oncology 4:277-296.

Morrison, S.L., Apr. 28, 1994, "Success in specification." Nature 368: 812-813.

Petit et al., Dec. 1997, "Neutralizing antibodies against epidermal growth factor and ErbB-2/neu receptor tyrosine kinases down-regulate vascular endothelial growth factor production by tumor cells in vitro and in vivo: angiogenic implications for signal transduction therapy of solid tumors," Am J Pathol 151(6): 1523-1530.

Reins et al., 1993, "Anti-epidermal growth factor receptor monoclonal antibodies affecting signal transduction," J. Cellular Biochemistry, 51(2): 236-248.

Rodeck et al., Jul. 15, 1987, "Tumor Growth Modulation by a Monoclonal Antibody to the Epidermal Growth Factor Receptor: Immunologically Mediated and Effector Cell-independent Effects." Cancer Res. 47: 3692-3696.

Sato et al., Dec. 1983, "Biological Effects in Vitro of Monoclonal Antibodies to Human Epidermal Growth Factor Receptors." Mol. Biol. Med. 1: 511-529.

Sato et al., 1987, "Derivation and Assay of Biological Effects of Monoclonal Antibodies to Epidermal Growth Factor Receptors." Meth. Enzymol. 146: 63-81.

Schulz et al., 1979, *Principles of Protein Structure*, Springer-Verlag: New York, NY, pp. 14-16.

Sunada et al., Jun. 1986, "Monoclonal antibody against epidermal growth factor receptor is internalized without stimulating receptor phosphorylation." Proc. Natl. Acad. Sci. USA 83: 3825-3829.

Udayachander et al., 1997, "Anti-tumor activity of monoclonal antibody CIBCNSH3 generated to the human EGF receptor." Human Antibodies 8: 60-64.

Wagner, S.D., et al., 1994, "The diversity of antigen-specific monoclonal antibodies from transgenic mice bearing human immunoglobulin gene miniloci." Eur. J. Immunol. 24: 2672-2681.

Werner et al., Mar. 1988, "The Effect of Epidermal Growth Factor (EGF) and a Monoclonal Antibody (528) Against the EGF Receptor (EGFR) on the Growth of Four Human Malignant Glioma (HMG)-Derived HMG Cell Lines (HMGCL)." Neurology 38 (Suppl. 1): 103.

Yang, X.-D. et al., 1997, "Human monoclonal antibodies to human TNF-α generated from mice carrying human Ig loci." J. Allergy Clin. Immunol. 99: S15.

International Search Report for PCT Application No. PCT/US98/09160.

Restriction Requirement dated Jun. 24, 1996, for U.S. Appl. No. 08/430,938, filed Apr. 27, 1995.

Response to Office Action Under 37 C.F.R. § 1.115 dated Jul. 24, 1996, for U.S. Appl. No. 08/430,938, filed Apr. 27, 1995.

Office Action dated Mar. 4, 1997, for U.S. Appl. No. 08/430,938, filed Apr. 27, 1995.

Office Action dated Oct. 1, 1997, including Cox Declaration, for U.S. Appl. No. 08/486,857, filed Jun. 7, 1995.

Amendment and Response dated Apr. 1, 1998, for U.S. Appl. No. 08/486,857, filed Jun. 7, 1995.

Office Action dated Jul. 7, 1998, for U.S. Appl. No. 08/486,857, filed Jun. 7, 1995.

Amendment and Response dated Jan. 7, 1999, for U.S. Appl. No. 08/486,857, filed Jun. 7, 1995.

Office Action dated Apr. 9, 1999, for U.S. Appl. No. 08/486,857, filed Jun. 7, 1995.

Amendment and Response dated Oct. 12, 1999, for U.S. Appl. No. 08/486,857, filed Jun. 7, 1995.

Preliminary Amendment and Request for Interference Under 37 C.F.R. § 1.607, dated Jan. 17, 1997, for U.S. Appl. No. 08/724,752, filed Oct. 2, 1996.

Office Action dated Aug. 5, 1997, for U.S. Appl. No. 08/724,752, filed Oct. 2, 1996.

Amendment and Response dated Feb. 5, 1999, for U.S. Appl. No. 08/724,752, filed Oct. 2, 1996.

Interview Summary of Interview conducted on Dec. 14, 1999, for U.S. Appl. No. 08/724,752, filed Oct. 2, 1996.

Office Action dated Dec. 23, 1999, for U.S. Appl. No. 08/724,752, filed Oct. 2, 1996.

Amendment and Reply to Office Action dated Feb. 23, 2000, for U.S. Appl. No. 08/724,752, filed Oct. 2, 1996.

Office Action dated Feb. 3, 1999, for U.S. Appl. No. 08/759,620, filed Dec. 3, 1996.

Amendment and Response dated Aug. 3, 1999, for U.S. Appl. No. 08/759,620, filed Dec. 3, 1996.

Office Action dated Oct. 26, 1999, for U.S. Appl. No. 08/759,620, filed Dec. 3, 1996.

Preliminary Amendment dated Nov. 27, 2000, for U.S. Appl. No. 08/759,620, filed Dec. 3, 1996.

Office Action dated Jan. 17, 2001, for U.S. Appl. No. 08/759,620, filed Dec. 3, 1996.

Response to Final Official Action dated Jul. 17, 2001, for U.S. Appl. No. 08/759,620, filed Dec. 3, 1996.

Advisory Action dated Sep. 13, 2001, for U.S. Appl. No. 08/759,620, filed Dec. 3, 1996.

Office Action dated May 14, 1999, for U.S. Appl. No. 08/923,138, filed Sep. 4, 1997.

Office Action dated Dec. 20, 2000, for U.S. Appl. No. 08/923,138, filed Sep. 4, 1997.

Declaration of Jane T. Gunnison dated Jun. 20, 2001, for U.S. Appl. No. 08/923,138, filed Sep. 4, 1997.

Amendment and Response dated Jun. 20, 2001, for U.S. Appl. No. 08/923,138, filed Sep. 4, 1997.

Office Action dated Oct. 2, 2001, for U.S. Appl. No. 08/923,138, filed Sep. 4, 1997.

Amendment and Response dated Apr. 2, 2002, for U.S. Appl. No. 08/923,138, filed Sep. 4, 1997.

Office Action dated Jun. 18, 2002, for U.S. Appl. No. 08/923,138, filed Sep. 4, 1997.

Declaration of R. Minako Pazdera dated Jul. 18, 2002, for U.S. Appl. No. 08/923,138, filed Sep. 4, 1997.

Amendment and Response dated Jul. 18, 2002, for U.S. Appl. No. 08/923,138, filed Sep. 4, 1997.

Office Action dated Oct. 22, 2002, for U.S. Appl. No. 08/923,138, filed Sep. 4, 1997.

Amendment and Response dated Jan. 22, 2003, for U.S. Appl. No. 08/923,138, filed Sep. 4, 1997.

Office Action dated Mar. 19, 2003, for U.S. Appl. No. 08/923,138, filed Sep. 4, 1997.

Amendment and Response dated May 19, 2003, for U.S. Appl. No. 08/923,138, filed Sep. 4, 1997.

Restriction Requirement dated Jun. 20, 2001, for U.S. Appl. No. 09/614,092, filed Jul. 11, 2000.

Response to Restriction Requirement dated Jul. 18, 2001, for U.S. Appl. No. 09/614,092, filed Jul. 11, 2000.

Preliminary Amendment dated Feb. 23, 2001, for U.S. Appl. No. 09/614,092, filed Jul. 11, 2000.

Office Action dated Jul. 5, 2002, for U.S. Appl. No. 09/614,092, filed Jul. 11, 2000.

Amendment and Response dated Oct. 7, 2002, for U.S. Appl. No. 09/614,092, filed Jul. 11, 2000.

Office Action dated Dec. 12, 2002, for U.S. Appl. No. 09/614,092, filed Jul. 11, 2000.

Amendment and Response dated Apr. 14, 2003, for U.S. Appl. No. 09/614,092, filed Jul. 11, 2000.

Interview Summary of interview conducted on Jun. 27, 2003, for U.S. Appl. No. 09/614,092, filed Jul. 11, 2000.

Preliminary Amendment dated Feb. 19, 2002, for U.S. Appl. No. 10/078,958, filed Feb. 19, 2002.

Preliminary Amendment dated Jul. 16, 2002, for U.S. Appl. No. 10/078,958, filed Feb. 19, 2002.

Office Action dated Dec. 3, 2003, for U.S. Appl. No. 10/078,958, filed Feb. 19, 2002.

Amendment and Response dated Jun. 3, 2004, for U.S. Appl. No. 10/078,958, filed Feb. 19, 2002.

Office Action dated Sep. 9, 2004, for U.S. Appl. No. 10/078,958, filed Feb. 19, 2002.

Taylor et al. "A transgenic mouse that expresses a diversity of human sequence heavy and light chain immunoglobulins," Nucl. Acids Res., 20: 6287-6295 (1992).

European Search Report dated Aug. 13, 2008, in European Patent Application No. 08003509.0-2405.

Office Action dated Sep. 25, 2008, in Korean Patent Application No. 10-2008-7012502.

Korean counsel's translation of Office Action dated Sep. 25, 2008, in Korean Patent Application No. 10-2008-7012502.

* cited by examiner

VSGGGSIN SG DYYWSWIRQHPGKGL DC IGYIYYSGSTYYNPSLKSRVTISVDTSKNQF LKL T SVTAADTAVYYCARSTVNPGWFDPWGQGTLVTVSS (SEQ ID NO: 39)
       CDR1                        CDR2                                CDR3

FIG. 1

GTCTCTGGTG GCTCCATCAA CAGTGGTGAT TACTACTGGA GCTGGATCCG CCAGCACCCA GGGAAGGGCC TGGACTGCAT TGGGTACATC TATTACAGTG GGAGCACCTA CTACAACCCG
TCCCTCAAGA GTCGAGTCAC CATATCAGTA GACACGTCTA AGAATCAGTT CTTCCTGAAG CTGACCTCTG TGACTGCCGC GGACACGGCC GTGTATTACT GTGCGAGATC TACGGTGGTA
AATCCGGGGT GGTTCGACCC CTGGGGCCAR GGAACCCTGG TCACCGTCTC CTCA (SEQ ID NO: 3)

FIG. 2

TITCQRASQDDI NNYLNW F QQKPGKAPK VLIH DASNLETG GPSRFSGSGSGTDFTFTIS GLQPEDIATYYCQQY E SLPLTFGGGTKVEIKRTVAAPSVFIFPPSDEQ (SEQ ID NO: 40)
   CDR1                    CDR2                                     CDR3

FIG. 3

ACCATACACTT GCCAGGGCGAG TCAGGACATT AACAACTATT TAAATTGGTT TCAGCAGAAA CCAGGGAAAG CCCCT AAGGTCCTGA TCCACGATGC TCCACGATGC TCCAATTTG GAAACAGGGG
GCCCATCAAG GTTCAGTGGA AGTGGATCTG GGACA GATTTTACTT TCACCATCAG CGGCCTGCAG CCTGAAGACA TTGCAACATA TTATTGTCAA CAGTATGAAA GTCTC CCACTCACTT
TCGGCGGAGG GACCAAGGTG GAGATCAAA (SEQ ID NO: 4)

FIG. 4

VSGGSI NSG DYYWSVIRQHPGKGLEWIG STYYSGNT FYNPSLKSRVTISL DTSKNQFSLKLSSVTAADTAV CYCARNIVTTGAFDIWGQGTMVTVSS (SEQ ID NO: 41)
      CDR1                  CDR2                                            CDR3

FIG. 5

GTCTCTGGTG GCTCCATCAA CAGTGGTGAT TACTACTGGA GCTGGATCCG CCAGCACCCA GGGAAGGGCC TGGAGTGGAT TGGTTCCATC TATTACAGTG GGAACACCTT CTACAACCCG
TCCCTCAAGA GTCGAGTTAC CATATCACTA GACACGTCTA AGAACCAGTT CTCCCTGAAG CTGAGTCTG TGACTGCCGC GGACACGGCC GTGTATTACT GTGCGAGAAA TATAGTGACT
ACGGGTGCTT TTGATATCTG GGGCCAAGGG ACAATGGTCA CCGTCTCTTC A (SEQ ID NO: 5)

FIG. 6

TITCQASQDIT IYLNWYQQKPGKAPKLLIN DASS LETGVPL RFSGSGSGTDFTFTISSLQPEDIATYYCQQYD HLPLTFGGGTKVAIKRTVAAPSVFIFPPSDEQ (SEQ ID NO: 42)
   CDR1             CDR2                                                   CDR3

FIG. 7

ACCATCACTT GTCAGGGCAG TCAGGACATT ACCATTTATT TAAATTGGTA TCAACAGAAA CCAGGGAAAG CCCCT AAGCTCCTGA TCAACGACGC ATCCAGTTTG GAAACAGGGG
TCCCATCAAG GTTCAGTGGA AGTGGATCTG GGACA GATTTACTT TCACCATCAG CAGCCTGCAG CCTGAAGATA TTGCAACATA TTACTGTCAA CAGTATGAT ATCTC CCGCTCACTT
TCGGCGGCGG GACCAAGGTG GCGATCAAA (SEQ ID NO: 6)

FIG. 8

VSGGSISSGDYYWTWIRQHPGKGLEWIGYIYYSGNTYYNPSLKSRVSMSIDTSENQFSLKLSSVTAADTAVYYCARKPVTGGEDYWGQGTLVTVSS (SEQ ID NO: 43)
　　　CDR1　　　　　　　　　　　　　　CDR2　　　　　　　　　　　　　　　　　　　　　　　　CDR3

FIG. 9

GTCTCTGGTG GTCCATCAG CAGTGGTGAT TACTACTGGA CCTGGATCCG CCAGCACCCA GGGAAGGGCC TGGAGTGGAT TGGGTACATC TATTACAGTG GGAACACCTA CTACAACCCG
TCCCTCAAGA GTCGAGTTTC CATGTCAGAT ACGTCCGAGA ATCAGTTCTC CCTGAAGCTG AGCTCTGTGA CTGCCGCGGA CACGGCCGTG TATTACTGTG CGAGAAAA ACCAGTGACT
GGGGGGAGG ACTACTGGGG CCAGGGAACC CTGGTCACCG TCTCCTCA (SEQ ID NO: 7)

FIG. 10

TITCCAASQDISNYLNWYQQKPGKAPKLLIYDASNLETGVPSRFSGSGSGTDFTFTISSLQPEDIVGYYVQQYESLPCGFGQGTKLEIKRTVAAPSVFIFPPSDEQ (SEQ ID NO: 44)
　　　CDR1　　　　　　　　　　　　　CDR2　　　　　　　　　　　　　　　　　　　　CDR3

FIG. 11

ACCATCACTT GCCAGGCGAG TCAGGACATT AGTAACTATT TAAATTGGTA TCAGCAGAAA CCAGGGAAAG CCCT AAGCTCCTGA TCTACGATGC TTCCAATTTG GAAACAGGGG TCCCATCAAG
GTTCAGTGGA GTGGATCTGG GACA GATTTTACT TCACCATCAG CAGCCTGCAG CCTGAAGATA TTGGAACATA TGTCTGTCAA CAGTATGAGA GTCTC CCGTGCGGTT TTGGCCAGGG
GACCAAACTG GAGATCAAA (SEQ ID NO: 8)

FIG. 12

/SGGSI N SG DF YWS WIRQHPGKGLEWIGYIYYSGSTYYNPSLKS RVTMS ID P SKNQFSLKL I SVTAADTAVYYCA T SLYYGGGMDVWGQGTTVTVSS (SEQ ID NO: 45)
   CDR1                           CDR2                                  CDR3

FIG. 13

GTCTCTGGTG GCTCCATCAA CAGTGGTGAT TTCTACTGGA GCTGGATCCG CCAACACCCA GGGAAGGGCC TGGAGTGGAT TGGGTACATC TATTACAGTG GGAGCACCTA CTACAACCCG
TCCCTCAAGA GTCGAGTTAC CATGTCAATA GACCCGTCTA AGAACCAGTT CTCCCTGAAA CTGATCTCTG TGACTGCCGC GGACACGGCC GTTATTACT GTGCGACNTC CCTTTACTAT
GGCGGGGGTA TGGACGTCTG GGGCCAAGGG ACCACGGTCA CCGTCTCCTC A (SEQ ID NO: 9)

FIG. 14

TITCQASQDISN N LNWYQQK R G N APKLLI YDASNLETGVPSRFSGSGSGTDFTFTIS N LQPEDIATYYCQ HYD H LPWTFGQGTKVEXKRTVAAPSVFIFPPSDEQ (SEQ ID NO: 46)
         CDR1                    CDR2                                                CDR3

FIG. 15

ACCATCACTT GCCAGGCGAG TCAGGACATT AACAACTATT TGAATTGGTA TCAGCAGAGG CCCCT AAACTCCTGA TCTACGATGC ATCCAATTTG GAAACAGGGG
TCCCATCAAG GTTCAGTGGA AGTGGATCTG GGACA GATTTACT TCACCATCAA CAGCCTGCAG CCTGAAGATA TTGGCACATA TTATTGTCAA CACTATGATC ATCTC CCGTGGACGT
TCGGCCAAGG GACCAAGGTG GAANTCAAA (SEQ ID NO: 10)

FIG. 16

VSGGSINNGDYYWSIRQHPGKGLEWIGHIYYSGSTYYJPSLKSRTTISVDTSKNQFSLKLNSVTAADIAVYYCARGTVTTYYFDYWGQGTTVTVSS (SEQ ID NO: 47)

CDR1 — CDR2 — CDR3

FIG. 17

GTCTCTGGTG GCTCCATCAA CAATGGTGAT TACTACTGGA GCTGGATCCG CCAGCACCCA GGGAAGGGCC TGGAGTGGAT TGGGCACATC TATTACAGTG GGAGCACCTA CTACATCCCG
TCCCTCAAGA GTCGAACTAC CATATCAGTA GACACGTCTA AGAACCAGTT CTCCCTGAAG CTGAACTCTG TGACTGCCGC GGACACGGCC GTGTATTACT GTGCGAGAGG GACAGTAACT
ACGTACTACT TTGACTACTG GGGCCAGGGA ACCCTGGTCA CCGTCTCCTC A (SEQ ID NO: 11)

FIG. 18

TITCRASQSISSYLNWYQQKPGKAPKLLIYAASSLQSGVPSRFSGSGSGTDFTLTISSLQPEDFATYYCQQGYRTPPECSFGQGTKLEIKRTVAAPSVFIFPPSDEQ (SEQ ID NO: 48)

CDR1 — CDR2 — CDR3

FIG. 19

ACCATCACTT GCCGGGCAAG TCAGAGCATT AGCAGCTATT TAAATTGGTA TCAGCAGAAA CCAGGGAAAG CCCCT AAGCTCCTGA TCTATGCTGC ATCCAGTTTG CAAAGTGGGG
TCCCATCAAG GTTCAGTGGC AGTGGATCTG GGACA GATTTCACTC TCACCATCAG CAGTCTGCAA CCTGAAGATT TTGCAACTTA CTACTGTCAA CAGGGTTACA GAACC CCTCCGGAGT
GCAGTTTTGG CCAGGGGACC AAGCTGGAGA TCAAA (SEQ ID NO: 12)

FIG. 20

VSGGSVSSG DYYWSWIRQPPGKGLEWIGHL YYSGNTNYNPSLKSRVTISL DTSKNQFSLKLSSVTAADTAVYYCARDFLIGSFFDYWGQGTLVTVSS (SEQ ID NO: 49)
    CDR1                        CDR2                                              CDR3

FIG. 21

GTCTCTGGTG GCTCCGTCAG CAGTGGTGAT TACTACTGGA GCTGGATCCG GCAGCCCCCA GGGAAGGGAC TGGAGTGGAT TGGACATCTC TATTACAGTG GAACACCAA CTACAACCCC
TCCCTCAAGA GTCAGAGTCA CATATCATTA GACACGTCCA AGAACCAGTT CTCCCTGAAG CTGAGCTCTG TGACCGCTGC GGACACGGCC GTGTATTACT GTGCGAGAGA TTTTTTGACT
GGTTCCTTCT TTGACTACTG GGGCCAGGGA ACCCTGGTCA CCGTCTCCTC A (SEQ ID NO: 13)

FIG. 22

TITCQASQDISNYLNWYQQKPGKAPKLLIN DASDLETGVPSR ISGSGSGTDFTFTISNLQPEDIATYYCQQYD SLPLTFGGGTKVEIRRTVAAPSVFIFPPSDEQ (SEQ ID NO: 50)
    CDR1                         CDR2                                              CDR3

FIG. 23

ACCATCACTT GCCAGGCGAG TCAGGACATA AGCAACTATT TAAATTGGTA TCAGCAGAAA CCAGGGAAAG CCCCT AAGCTCCTGA TCAACGATGC ATCCGATTTG GAAACAGGGG
TCCCATCAAG GATCAGTGGA AGTGGATCTG GGACA GATTTTACTT TCACCATCAG CAACCTGGAG CCTGAAGATA TTGCAACATA TTACTGTCAA CAATATGATA GTCTC CCGCTCACTT
TCGGCGGAGG GACCAAGGTG GAGATCAGA (SEQ ID NO: 14)

FIG. 24

VSGGSVYSGDYYWSWIRQPPGKGLEWIGYIYYSGSTNYNPSLKSRVTISVDTSKNQFSLKLSSVTAADTAVYYCARDSILGATNYWGQGTLVTVSS (SEQ ID NO: 51)
                CDR1          CDR2                                              CDR3

FIG. 25

GTCTCTGGTG GCTCCGGTCTA CAGTGGTGAT TACTACTGGA GCTGGATCCG GCAGCCCCC GGGAAGGGAC TGGAGTGGAT TGGGTATATC TATTACAGTG GGAGCACCAA TTACAATCCC
TCCCTCAAGA GTCGAGTCAC CATATCAGTA GACACGTCCA AGAACCAGTT CTCCCTGAAG CTGAGCTCTG TGACCGCTGC TGACACGGCC GTGTATTACT GTGCGAGAGA CTCCATACTG
GGAGCTACCA ACTACTGGGG CCAGGGAACC CTGGTCACCG TCTCCTCA (SEQ ID NO: 15)

FIG. 26

TITCQASQXISNYLXWYQQKPGKAPKXLISDASNLETGVPSRFSGSGSGTXXIFTISSLQPEDIATYHCXQYXSLPLTFGGGTKVEIKRTVAAPSVFIFPPSDEQ (SEQ ID NO: 52)
       CDR1           CDR2                                                      CDR3

FIG. 27

ACCATCACTT GCCAGGCGAG TCNGGACATT AATAACTATT TANATTGGTN TCAGCAGAAA CCAGGGAAAG CCCCT AAASTCCTGA TCTCCGATGC ATCAATTTA GAAACAGGGG
TCCCATCGAG GTTCAGTGGA AGTGGATCTG GGACA GANTNTACTT TCACCATCAG CAGCCTGCAG CCTGAAGATA TTGCNACATA TCACTGTCNA CAGTATNATA GTCTC CCGCTGACTT
TCGGCGGAGG GACCAAGGTA GAGATCAAA (SEQ ID NO: 16)

FIG. 28

VSGGSVSSGDYYWTWIRQSPGKGLEWIGHIYYSGNTNYNPSLKSRLTISIDTSKTQFSLKLSSVTAADTAIYCVRDRVTGAFDIWGQGTMVTSS (SEQ ID NO: 53)
        CDR1                    CDR2                                CDR3

FIG. 29

GTCTCTGGTG GCTCCGTCAG CAGTGGTGAT TACTACTGGA CCTGGATCCG GCAGTCCCCA GGGAAGGGAC TGGAGTGGAT TGGACACATC TATTACAGTG GGAACACCAA TTATAACCCC
TCCCTCAAGA GTCGACTCAC CATATCAATT GACACGTCCA AGACTCAGTT CTCCCTGAAG CTGAGTCTG TGACCGCTGC GGACACGGCC ATTTATTACT GTGTGCGAGA TCGAGTGACT
GGTGCTTTTG ATATCTGGGG CCAAGGGACA ATGGTCACCG TCTCTTCA (SEQ ID NO: 17)

FIG. 30

TITCQASQDISNYLNWYQQKPGKAPKLLIYDASNLETGVPSRFSGSGSGTDFTFTISSLQPEDIATYFCQHFDHLPLAFGGGTKVEIKRTVAAPSVFIFPPSDEQ (SEQ ID NO: 54)
        CDR1                    CDR2                                      CDR3

FIG. 31

ACCATCACTT GCCAGGCGAG TCAGGACATC AGCAACTATT TAAATTGGTA TCAGCAGAAA CCAGGGAAAG CCCCT AAACTCCTGA TCTACGATGC ATCCAATTTG GAAACAGGGG
TCCCATCAAG GTTCAGTGGA AGTGGATCTG GGACA GATTTACTT TCACCATCAG CAGCCTGCAG CCTGAAGATA TTGCAACATA TTTCTGTCAA CACTTTGATC ATCTC CCGCTCGCTT
TCGGGCGGAGG GACCAAGGTG GAGATCAAA (SEQ ID NO: 18)

FIG. 32

Amino Acid Sequences and Structure of Human Heavy Chain Derived from EGFR-Specific Hybridomas

```
            CDR1                              CDR2                                              CDR3
Human γ2
4-31   VSGGSISSGGYYWSWIRQHPGKGLEWIGYIYYSGSTYYNPSLKSRVTISVDTSKNQFSLKLSSVTAADTAVYYCAR                                    ASTKGPSVFPPLAPCSRSTST    SEQ ID NO: 73
E1.1   ---------N--D-------------DC-----------------F---T------------------------                  STVVNPG WFDP VGQGYLVTVSS                   SEQ ID NO: 35
E2.4   ---------N--D--------------------N-F----------L-----------------C---------                  NIVTTG  AFDI VGQGTMVTVSS                   SEQ ID NO: 39
E2.5   ---------N--D--T-----------------N-------SM-I-E---------------------------                  KPVTGG  EDY  VGQGTLVTVSS                   SEQ ID NO: 41
E6.2   ---------N--DF-------------------N-------------M-I-P--------I-------------                  TSLYYGG GMDV VGQGTTVTVSS                   SEQ ID NO: 43
E6.4   ---------NN-D--------------------I---------T---------N--------------------                  GTVTTYY YFDY VGQGTTVTVSS                   SEQ ID NO: 45
                                                                                                                                               SEQ ID NO: 47

CDR1                              CDR2                                              CDR3
4-61   VSGGSVSSGSYYWSWIRQPPGKGLEWIGYIYYSGSTNYNPSLKSRVTISVDTSKNQFSLKLSSVTAADTAVYYCAR                                                               SEQ ID NO: 38
E2.11  ---------D--------------HL--N------------L--------------------------------                  DFLTGSF FDY  VGQGTMVTVSS                   SEQ ID NO: 49
E6.3   ---------Y--D--------------------I---------I------------------------------                  DSILGA  TNY  VGQGLVTVSS                    SEQ ID NO: 51
E7.6.3 ---------D--T-------S------------N---------I-----------L-------I-V-------                  DRVTGA  FDI  VGQGTMVTVSS                    SEQ ID NO: 76
```

FIG. 33

Inhibition of Human Epidermoid Carcinoma
Formation in Nude Mice by ABX-EGF

| Treatment | Dose (mg) | Tumor Formation[b] (incidence) | Tumor size[c] (cm³) |
|---|---|---|---|
| PBS | 1 | 6/6 | 1.376 |
| Human IgG2[a] | 1 | 6/6 | 1.727 |
| E7.6.3 | 0.2 | 0/5 | 0 |
| | 1 | 0/4 | 0 |
| E2.5 | 0.2 | 0/3 | 0 |
| | 1 | 0/3 | 0 |
| E1.1 | 1 | 0/3 | 0 |

[a] control human myeloma IgG2
[b] incidence determined 19 days post tumor inoculation
[c] tumor size measured 19 days post tumor inoculation

FIG. 41

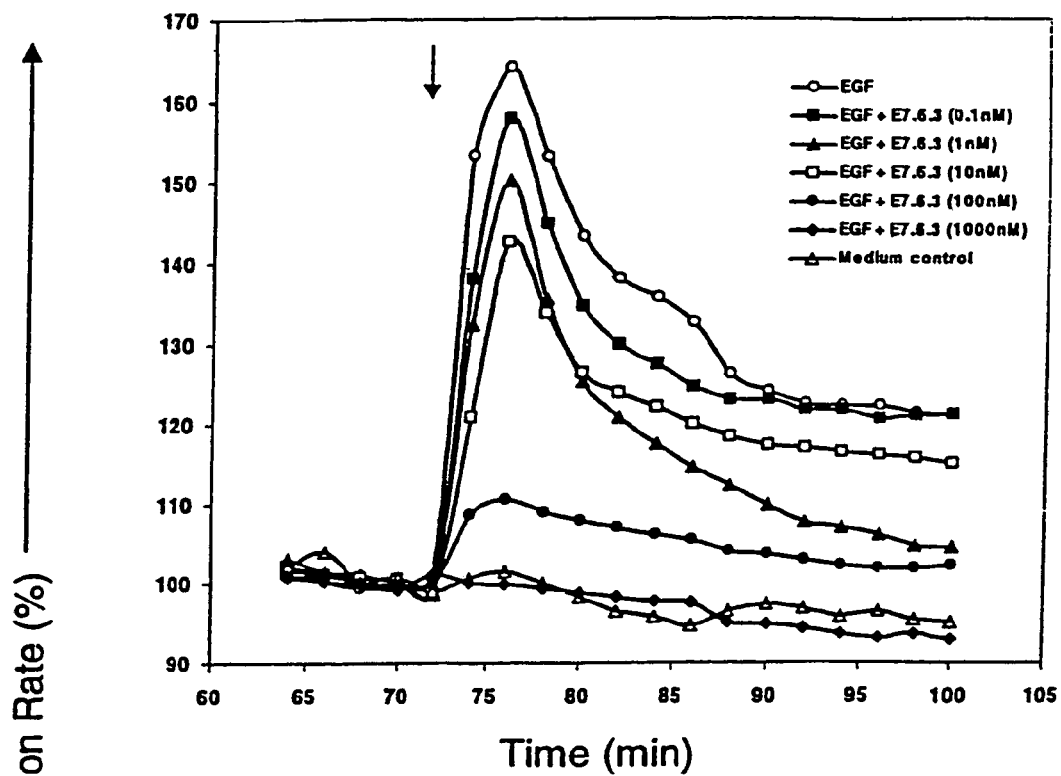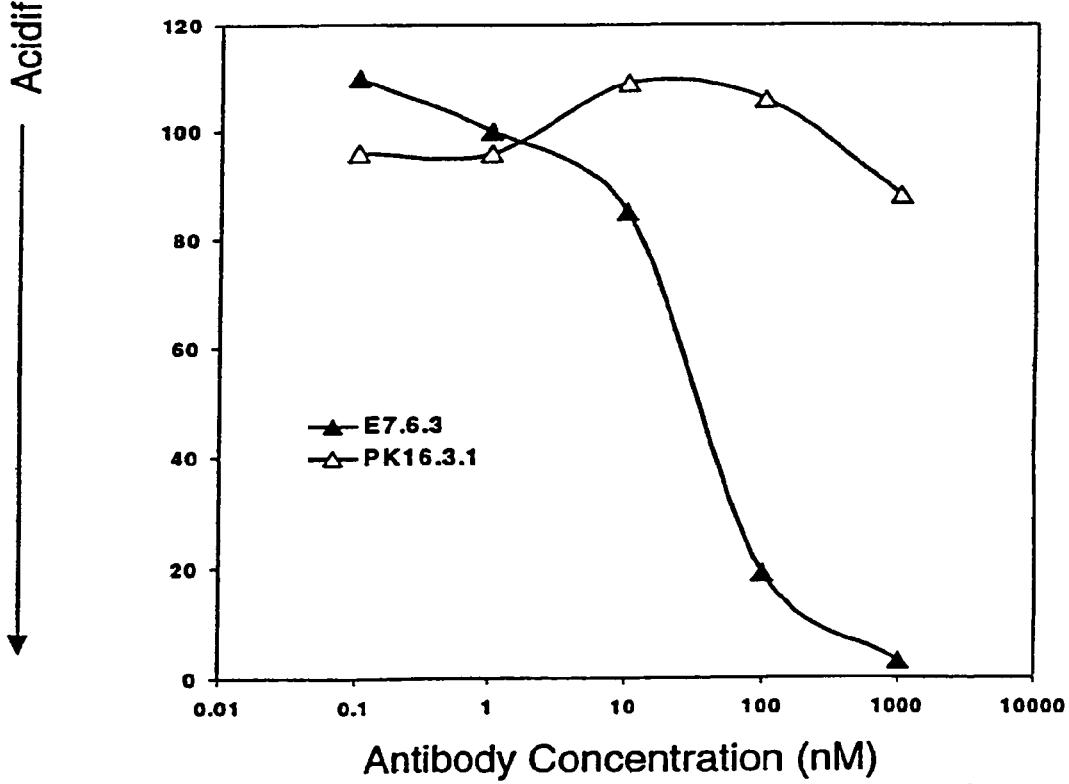
FIG. 47

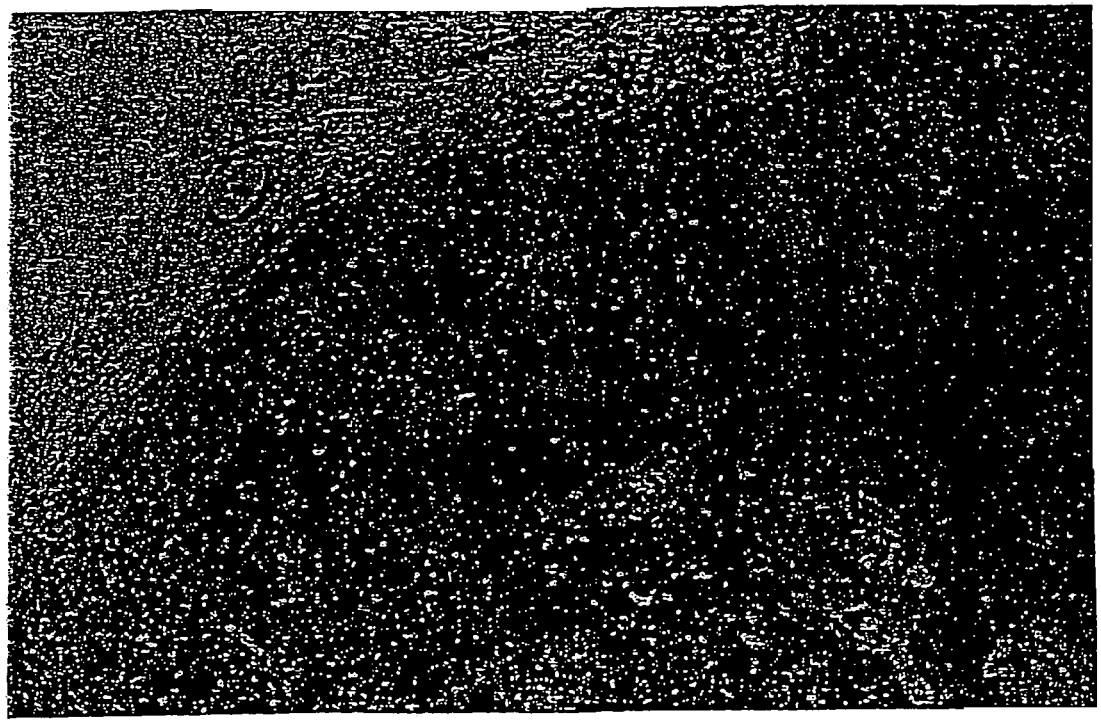
FIG. 51

| Time (day) | Incidence of Tumor Formation | | | |
|---|---|---|---|---|
| | PBS | PK16.3.1 (1 mg) | E7.6.3 (0.2 mg) | E7.6.3 (1 mg) |
| 0 | 0/5 | 0/5 | 0/10 | 0/10 |
| 3 | 4/5 | 0/5 | 0/10 | 0/10 |
| 8 | 4/5 | 3/5 | 0/10 | 0/10 |
| 10 | 5/5 | 5/5 | 0/10 | 0/10 |
| 25 | 5/5 | 5/5 | 0/10 | 0/10 |
| 100 | ND | ND | 0/10 | 0/10 |
| 250 | ND | ND | 0/10 | 0/10 |

FIG. 52

| Treatment (dose/injection) | Total Dose | Total No. of Mice | Tumor-free Mice on Day 60 | |
|---|---|---|---|---|
| | | | No. | % |
| None | | 71 | 0 | 0 |
| Control IgG$_2$κ (1 mg) | 6 mg | 16 | 0 | 0 |
| E7.6.3 (1 mg) | 6 mg | 50 | 50 | 100 |
| E7.6.3 (0.5 mg) | 3 mg | 20 | 19 | 95 |
| E7.6.3 (0.25 mg) | 1.5 mg | 5 | 3 | 60 |
| E7.6.3 (0.2 mg) | 1.2 mg | 19 | 5 | 26 |
| E7.6.3 (0.1 mg) | 0.6 mg | 20 | 13 | 65 |
| E7.6.3 (0.05 mg) | 0.3 mg | 15 | 1 | 7 |

FIG. 53

E20.1MG30.Seq Sequence

|  | 10 | 20 | 30 | 40 | 50 |  |
|--|--|--|--|--|--|--|
|  | 1234567890 | 1234567890 | 1234567890 | 1234567890 | 1234567890 |  |
|  | GCGATCCAGC | CTTTTAGGTC | CATGCCNTTC | TCCTGTGNAG | CGTCTGGATT | 50 |
|  | A I Q P | F R S | M P F | S C X A | S G F |  |
|  | CCCCTTCAGT | AGNTNTGGCA | TGCACTGGGT | CGGCCAGGCT | CCAGGCAAGG | 100 |
|  | P F S | X X G | M H W V | R Q A | P G K G |  |
|  | GGCTGGAGTG | GGTGGCAGTT | ATATGGTATG | ATGGAAGTAA | TAAATACTAT | 150 |
|  | L E W | V A V | I W Y D | G S N | K Y Y |  |
|  | GCAGACTCCG | TGAAGGGCCG | ATTCACCATC | TCCAGAGACA | ATTCCAAGAA | 200 |
|  | A D S V | K G R | F T I | S R D N | S K N |  |
|  | CACGCTGTAT | CTGCAAATGA | ACAGACTGAG | AGCCGAGGAC | ACGGCTGTGT | 250 |
|  | T L Y | L Q M N | R L R | A E D | T A V Y |  |
|  | ATTACTGTGC | GAGATTTTTG | GAGTGGCTCCCCTTTTGACTAC | | | 300 |
|  | Y C A R F L | E W L | P F D Y | W G Q |  |  |
|  | GGCCAGGGAACCCTGGTCACCGTC | | CTCC | ACCAAGGGCC | CATCGGTCTT | 350 |
|  | G T L V | T V X | S D S | T K G P | S V F |  |
|  | CNCCCTGGCG | CCCTGCTTCC | AGGAGCACCC | TCNGANAGCA | CANANGGCCC | 400 |
|  | X L A | P C F Q | E H P | X X A | X X A P |  |
|  | CTGGGACTGN | CTGNTACAAG | GACNCTTTC | CCTCNAACCN | GGTGACCNTN | 450 |
|  | G T X | X Y K | D X F P | S N X | V T X |  |
|  | TCNTGGGAAA | CTCAGNGCNC | NTCTNNATNA | C | (SEQ ID NO: 19) | 481 |
|  | S W E T | Q X X | S X X |  | (SEQ ID NO: 55) |  |

FIG. 57

E20.1VK.Seq Sequence

```
          10          20          30          40          50
  1234567890  1234567890  1234567890  1234567890  1234567890
  GGAACCTTTN  GGTTCGCNCC  TTTTGGAGNC  AGACCCANCA  TCACTTGTCG     50
   G  T  F  X   F  A  P    F  G  X    R  P  X  I   T  C  R

GGCGAGTCAG  GGCATTAGCA  ATTTTTTAGC  CTGGTTTCAG  CAGAAACCAG    100
   A  S  Q    G  I  S  N   F  L  A    W  F  Q    Q  K  P  G

GGATAGCCCC  TAAGTCCCTG  ATCTATGCTG  CATCCACTTT  GCAAAGTGGG    150
    I  A  P    K  S  L    I  Y  A  A   S  T  L    Q  S  G

GTCCCATCAA  AGTTCACCGG  CAGTGGATAT  GGGACAGATT  TCACTCTCAC    200
    V  P  S  K   F  T  G    S  G  Y    G  T  D  F   T  L  T

CATCAGCAGC  CTGCAGCCTG  AAGACTTTGC  AACTTATTAT  TGTCAACAAT    250
   I  S  S    L  Q  P  E   D  F  A    T  Y  Y    C  Q  Q  Y

ATAATGTTTA  CCCATTCACT  TTCGGCCCTG  GGACCAAAGT  GGATATCAAA    300
    N  V  Y    P  F  T    F  G  P  G   T  K  V    D  I  K

CGAACTGTGG  CTGCACCATC  TGTCTTCATC  TTCCCGCCAT  CTGATGAGCC    350
    R  T  V  A   P  S  V  I   F  P  P  S   D  E  P

AGTTGAAATC  TGGAACTGCC  TCTGTTGTGT  GCCTGCTGAA  TAACTTCTAT    400
   V  E  I    W  N  C    L  C  V    P  A  E        L  L  S

CCCAGAGAGG  CCAAAGTACA  GTGGAAGGTG  GATAACGCCN  CNNTTGGCGG    450
    Q  R  G    Q  S  T    V  E  G    G     R  X    X  W  R

NNTCCTTTCN  CTCNCCCNTC  CTCNNCCCNC  CTCTCNCNA   (SEQ ID NO: 20)  489
   X  P  F  X   X  P  S    S  X  X    L  S  X   (SEQ ID NO: 56)
```

FIG. 58

E20.3MG30.Seq Sequence

```
         10         20         30         40         50
1234567890 1234567890 1234567890 1234567890 1234567890
AAGCCTGTTG CCTCAGTGCA GGTCTCCTGC AAGGCTTCTG GATACACCTT     50
 K  P  V  A  S  V  Q  V  S  C  K  A  S  G  Y  T  F

CACCAGTTAT GATATCAACT GGGTGCGACA GGCCACTGGA CAAGGGCTTG    100
 T  S  Y  D  I  N  W  V  R  Q  A  T  G  Q  G  L  E

AGTGGATGGG ATGGATGAAC CCTAACAGTG GTAACACAGG CTATGCACAG    150
 W  M  G  W  M  N  P  N  S  G  N  T  G  Y  A  Q

AAGTTCCAGG GCAGAGTCAC CATGACCAGG AACACCTCCA TAAGCACAGC    200
 K  F  Q  G  R  V  T  M  T  R  N  T  S  I  S  T  A

CTACATGGAG CTGAGCAGCC TGAGATCTGA GGACACGGCC GTGTATTACT    250
 Y  M  E  L  S  S  L  R  S  E  D  T  A  V  Y  Y  C
                                      DNI
GTGCGAGAGG AGGCCCCTAT AGCAGTGGCT GGACCTTCTT TGACTACTGG    300
 A  R  G  G  P  Y  S  S  G  W  T  F  F  D  Y  W

GGCCAGGGAA CCCTGGTCAC CGTCTCCTCA GCCCTCCACC AAGGGCCCAT    350
 G  Q  G  T  L  V  T  V  S  S  A  L  H  Q  G  P  I

CGGTCTTCCC CCTGGCGCCC TGCTCCAGGA GCACCTCCGA GAGCACANTC    400
 G  L  P  P  G  A  L  Q  E  H  L  P  E  H  X  X

NNCCCTTGGG CTGCCTGGNN CAAGGACTCT TTCCCCNAAC CCCGGNTGA     (SEQ ID NO: 21) 449
 P  L  G  C  L  X  Q  G  L  F  P  X  T  P  X          (SEQ ID NO: 57)
```

FIG. 59

E20.3VK.Seq Sequence

```
         10         20         30         40         50
1234567890 1234567890 1234567890 1234567890 1234567890
TTTGAACCCT TCNTGGCCGT GTCTCTNGGC GCGAGGGCCA CCATCAACTG    50
 F  E  P  F  X  A  V  S  L  G  A  R  A  T  I  N  C

CAAGTCCAGC CAGCGTGTTT TATACANCTC CAACAATAAG AACTGCTTAG   100
 K  S  S  Q  R  V  L  Y  X  S  N  N  K  N  C  L  A

CTTGGTACCA GCAGAAACCA GGACAGCCTC CTAAGCTGCT CATTTACTGG   150
 W  Y  Q  Q  K  P  G  Q  P  P  K  L  L  I  Y  W

ACATCTACCC GGGAATCCGG GGTCCCTGCC CGATTCAGTG GCAGCGGGTC   200
 T  S  T  R  E  S  G  V  P  A  R  F  S  G  S  G  S

TGGGACAGAT TTCACTCTCA CCATCAGCAG CCTGCAGGCT GAAGATGTGG   250
 G  T  D  F  T  L  T  I  S  S  L  Q  A  E  D  V  A

CAGTTTATTA CTGTCAGCAA TATTATAGTA CTCCACTCAC TTTCGGCGGA   300
 V  Y  Y  C  Q  Q  Y  Y  S  T  P  L  T  F  G  G

GGGACCATGG TGGAGATCAA GCGAACTGTG GCTGCACCAT CTGTCTTCAT   350
 G  T  M  V  E  I  K  R  T  V  A  A  P  S  V  F  I

CTTCCCGCCA TCTGATGAGC CNGTNTGAAA TCTGGAACTG CCTCTGTTTG   400
 F  P  P  S  D  E  P  V  N  L  E  L  P  L  F  V

TGTGCCCTGC TGAATAACTT CTATCCCAGA GAGGCCAAAG TACCAGTGGA   450
 C  P  A  E  L  L  S  Q  R  G  Q  S  T  G

AGGTGGATAA    (SEQ ID NO: 22)                            460
 R  W  I      (SEQ ID NO: 58)
```

FIG. 60

E20.8.1MG30.Seq Sequence

```
          10          20          30          40          50
  1234567890  1234567890  1234567890  1234567890  1234567890
  CNGCCTGTTA  GGTCCNTGCG  ACTCTCCTGT  GCAGCGTCTG  GATTCATCTT        50
   X  P  V    R  S  X    R  L  S     C  A  A     S  G  F  I  F

CAGTAGNTAT  GGCATGCACT  GGGTCCGCCA  GGCTCCAGGC  AAGGGGCTGG       100
   S  X  Y    G  M  H  W    V  R  Q    A  P  G    K  G  L  E

AGTGGGTGGC  AATTATATGG  TATGATGGAA  GTAATAAATA  CTATGCAGAC       150
   W  V  A    I  I  W     Y  D  G  S    N  K  Y    Y  A  D

TCCGTGAAGG  GCCGATTCAC  CATCTCCAGA  GACAATTCCA  AGAACACGCT       200
   S  V  K  G    R  F  T    I  S  R    D  N  S     K  N  T  L

GTATCTGCAA  ATGAACAGCC  TGAGAGCCGA  GGACACGGCT  GTGTATTACT       250
   Y  L  Q    M  N  S  L    R  A  E    D  T  A    V  Y  Y  C

GTGCGAGAGA  CGGGGGGCCA  CGGTGGTTTC  TGCTTCTGA   CTACTGGGGC       300
   A  R  D    G  G  P     R  W  F    L  A  S  D    Y  W  G

CAGGGAACCC  TGGTCACCGT  CTCCTCAGCC  TCCACCAAGG  GCCCATCGGT       350
   Q  G  T  L    V  T  V    S  S  A    S  T  K     G  P  S  V

CTTCCCCCTG  GCGCCCTGCT  CCAGGAGCAC  CCTTCGAGAG  CACAGCGGCC       400
   F  P  L     A  P  C  S    R  S  T    L  R  E    H  S  G  P

CTGGGCTGCC  TGGTCAAGG   ACTACTTTCC  CCGAACCGGT  GACGGTGTNC       450
   G  L  P     G  S  R     T  T  F  P    E  P  V    T  V  X

GTTGGAACTC  ATGAC         (SEQ ID NO: 23)                        465
   V  G  T  H    D           (SEQ ID NO: 59)
```

FIG. 61

E20.8.1MG18.Seq Sequence

```
         10         20         30         40         50
1234567890 1234567890 1234567890 1234567890 1234567890
AGTCTCCAGA CTCCCTGGTT GTGTCTCTGG GCGAGAGGGC CACCATCAAC    50
  S  L  Q   T  P  W  L   C  L  W   A  R  G  P   P  S  T

TGCAAGTCCA GNCAGAGTAT TTTATACAGC TCCAACAATC AAAAACTTCT   100
  A  S  P   X  R  V  F   Y  T  A  P   T  I  K  N  F  L

TAGCTTGGTA CCAGCAGAAA CCAGGACAGC CTCCGAAGTT GCTCATTTAC   150
  A  W  Y   Q  Q  K   P  G  Q  P   P  K  L   L  I  Y

TGGGCATCTA TTGGGAATC CGGGGTCCCT GACCGATTCA GTGGCAGCGG    200
  W  A  S  I   R  E  S   G  V  P   D  R  F  S   G  S  G

GTCTGGGACA GATTTCACTC TCACCATCAG CAGCCTGCAG GCTGAAGATG   250
  S  G  T   D  F  T  L   T  I  S   S  L  Q   A  E  D  V

TGGCAGTTTA TTACTGTCAG CAGTATTATA GTATTCCGTG CACTTTTGGC   300
  A  V  Y   Y  C  Q   Q  Y  Y  S   I  P  C   T  F  G

CAGGGGACCA AGCTGGAGAT CAAACGAACT GTGGCTGCAC CATCTGTCTT   350
  Q  G  T  K   L  E  I   K  R  T   V  A  A   P  S  V  F

CATCTTCCCG CCATCTGATG AGCAGTTGAA ATCTGGAACT GCCTCTGTTG   400
  I  F  P   P  S  D  E   Q  L  K   S  G  T   A  S  V  V

TGTGCCTGCT GAATAACTTC TATCCCAGAA AGGCCAAAGT ACATGAAGGG   450
  C  L  L   N  N  F   Y  P  R  K   A  K  V   H  E  G

TTCAAA  (SEQ ID NO: 24)                                  456
 F  K   (SEQ ID NO: 60)
```

FIG. 62

E20.11.2H Sequence

```
          10         20         30         40         50
 1234567890 1234567890 1234567890 1234567890 1234567890
 GGCGTGGYCC AGCCTGKGAG GTCCCTGAGA CTCTCCTGTG CAGCGTCTGG      50
   G  V  X   Q   P  X   R   S  L   R  L  S   C  A  A  S  G

ATTCAYCTTC AGTARCTATG GCATGCACTG GGTCCGCCAG GCTCCAGGCA     100
   F  X  F   S  X  Y   G  M  H  W   V  R  Q   A  P  G  K

AGGGGCTGGA GTGGGTGGCA ATTATATGGT ATGATGGAAG TAGCAAATAC     150
  G  L  E   W  V  A   I  I  W  Y   D  G  S   S  K  Y

TATGCAGACT CCGTGAAGGG CCGATTCACC ATCTCCAGAG ACAATTCCAA     200
   Y  A  D   S  V  K   G  R  F  T   I  S  R   D  N  S  K

GAACACGCTG TATCTGCAAA TGAACAGCCT GAGAGCCGAG GACACGGCTG     250
   N  T  L   Y  L  Q   M  N  S  L   R  A  E   D  T  A  V

TGTATTACTG TGCGAGAGAC GGGGGCCAC GGTGGTTTCT CGCTTCTGAC      300
   Y  Y  C   A  R  D   G  G  P   R  W  L   A  S  D

TACTGGGGCC AGGGAACCCT GGTCACCGTC TCCTCAGCCT CCACCAAGGG     350
   Y  W  G   Q  G  T   L  V  T  V   S  S  A   S  T  K  G

CCCATCGGTC TTCCCCCTGG CGCCCTGCTC CAGGAGCACC TCCGAGAGC      400
   P  S  V   F  P  L   A  P  C  S   R  S  T   F  R  E  H

ACAGCGGCCC TGGGCTGCCT GGTCAAGGAC TACTTCCCCG AAMCGGTGAC     450
   S  G  P   G  L  P   G  Q  G  L   L  P  R   X  G  D

GGTGTCGTGG AACTCAGGCG CTCTGACCAG NGGCGTGCAC AATTCCCAGC     500
   G  V  V   E  L  R   R  S  D  Q   X  R  A   Q  F  P  A

NGTCCTNAAG GTTGAAATCG TAANGGTTCA AA (SEQ ID NO: 25)        532
   V  L  K   V  E  I   V  X  V   Q    (SEQ ID NO: 61)
```

FIG. 63

E20.11.2MG18.Seq Sequence

```
         10         20         30         40         50
1234567890 1234567890 1234567890 1234567890 1234567890
ACTCAGTCTC CAGACTCCCT GGCTGTGTCT CTGGGCGAGA GGGCCACCAT      50
 T  Q  S  P  D  S  L  A  V  S  L  G  E  R  A  T  I

CAACTGCAAG TCCAGCCAGA GTGTTTTATA CGGCTCCAAG AATCAGAACT     100
 N  C  K  S  S  Q  S  V  L  Y  G  S  K  N  Q  N  Y

ACTTAGCTTG GTACCAGCAG AAACCAGGAC AGCCTCCTAA GCTGCTCATT     150
 L  A  W  Y  Q  Q  K  P  G  Q  P  P  K  L  L  I

TACTGGGCAT CTACCCGGGA ATCCGGGGTC CCTGACCGAT TCAGGGGCAG     200
 Y  W  A  S  T  R  E  S  G  V  P  D  R  F  R  G  S

CGGGTCTAGG ACAGATTTCA CTCTCACCAT CAGCAGCCTG CAGGCTGAAG     250
 G  S  R  T  D  F  T  L  T  I  S  S  L  Q  A  E  D

ATGTGGCAGT TTACTTCTGT CACCAATATT ATAGTACTCC GTGGACGTTC     300
 V  A  V  Y  F  C  H  Q  Y  Y  S  T  P  W  T  F

GGCCAAGGGA CCAAGGTGGA AATCAAACGA ACTGTGGCTG CACCATCTGT     350
 G  Q  G  T  K  V  E  I  K  R  T  V  A  A  P  S  V

CTTCATCTTC CCGCCATCTG ATGAGCAGTT GAAATCTGGA ACTGCCTCTG     400
 F  I  F  P  P  S  D  E  Q  L  K  S  G  T  A  S  V

TTGTGTGCCT GCTGAATAAC TTGTATCCCA GAAAGCCAAG GACACGAAAG     450
 V  C  L  N  N  L  Y  P  R  K  P  R  T  R  K

GTCANACCNA CCC   (SEQ ID NO: 26)                           463
 V  X  P  T    (SEQ ID NO: 62)
```

FIG. 64

E20.18MG30.Seq Sequence

```
              10         20         30         40         50
         1234567890 1234567890 1234567890 1234567890 1234567890
         CGTGATCCNC CTGGNTGGTC CCTGAGACTC TCCTGTGCAG CGTCTGGATT    50
          R  D  P    P  G  W    S  L  R    L  S  C    A  A  S  G  F

CATCTTCANT AACTATTNCA TGCACTGGGT CCGCCAGGCT CCAGGCAAGG   100
          I  F  X    N  Y  X    M  H  W    V  R  Q    A  P  G  K  G

GGCTGGAGTG GGTGGCAATT ATATGGTATG ATGGAAGTAG CAAATACTAT   150
          L  E  W    V  A  I    I  W  Y    D  G  S    S  K  Y  Y

GCAGACTCCG NGAAGGGCCG ATTCACCATC TCCAGAGACA ATTCCAAGAA   200
          A  D  S    X  K  G  R  F  T  I    S  R  D    N  S  K  N

CACGCTGTAT CTGCAAATGA ACAGCCTGAG AGCCGAGGAC ACGGCTGATG   250
          T  L  Y    L  Q  M  N  S  L  R    A  E  D    T  A  D  V

TATTACTGTG CGAGAGACGG TTGGGCCACG GTGGCTTCTC GCTTCTGACT   300
          L  L  C    E  R  R    L  G  H  G  G  F  S    L  L  T

ACTGGNGCNC AGGGCAACNC TGNCTNACCG TNTTCCTCAN CCCTNTACNC   350
          T  G  A  Q  G  N  X    X  X  P    X  S  S  X  L  Y  X

AAGGGCCNCC ATTNGGTCTT TCCCCCCTGG NNNNCCTGCT CNATGNNNCA   400
          R  A  X    I  X  S  F  P  P  G    X  P  A    X  X  X  T

CCCTNCGACA NCNACAN                          (SEQ ID NO: 27)   417
          L  R  X    X  X                             (SEQ ID NO: 63)
```

FIG. 65

E20.18VK.Seq Sequence

```
          10         20         30         40         50
 1234567890 1234567890 1234567890 1234567890 1234567890
 TTCGTGGCTG TGTCTCTTGG CGAGAGGNCC ACCATCAACT GCAAGTCCAG     50
  F  V  A  V  S  L  G  E  R  X  T  I  N  C  K  S  S

CCAGAGTATT TTATACAGCT CCAACAATCA AAACTTCTTA GCTTGGTACC    100
  Q  S  I  L  Y  S  S  N  N  Q  N  F  L  A  W  Y  Q

AGCAGAAACC AGGACAGCCT CCGAAGTTGC TCATTTACTG GGCATCTATT    150
  Q  K  P  G  Q  P  P  K  L  L  I  Y  W  A  S  I

CGGGAATCCG GGGTCCCTGA CCGATTCAGT GGCAGCGGGT CTGGGACAGA    200
  R  E  S  G  V  P  D  R  F  S  G  S  G  T  D

TTTCACTCTC ACCATCAGCA GCCTGCAGGC TGAAGATGTG GCAGTTTATT    250
  F  T  L  T  I  S  S  L  Q  A  E  D  V  A  V  Y  Y

ACTGTCAGCA GTATTATAGT ATTCCGTGCA CTTTTGGCCA GGGGACCAAG    300
  C  Q  Q  Y  Y  S  I  P  C  T  F  G  Q  G  T  K

CTGGAGATCA AACGAACTGT GGCTGCACCA TCTGTCTTCA TCTTCCCGCC    350
  L  E  I  K  R  T  V  A  A  P  S  V  F  I  F  P  P

ATCTGATGAG CCAAGNTTGA AAATCTGGAA CTGCCTCTGT TGTGTGCCCT    400
  S  D  E  P  X  L  K  I  W  N  C  L  C  C  V  P  C

GCTTGAATAA CTTCTATCCC AGAGANGGCC AAAGTCCNGT GGAAGGTGGA    450
  L  N  N  F  Y  P  R  X  G  Q  S  P  V  E  G  G

TAC   (SEQ ID NO: 28)                                     453
  Y   (SEQ ID NO: 64)
```

E20.19.2MG30.Seq Sequence

```
          10         20         30         40         50
          1234567890 1234567890 1234567890 1234567890 1234567890
CTCACTTGCA CTGTCTCTGG TGCTCCATC AGTAGTTACT NTTGGAGNTG                50
 L  T  C   T  V  S  G  G  S  I   S  S  Y  X  W  X  W

GATCGGGCAG CCCGAGGA AGGACTGGA GTGGATTGG TGTTCTATT                    100
 I  R  Q   P  X  G  K  G  L  E   W  I  G  C  F  Y  Y

ACAGNGGGAG CACCAACTAC AACCCCTCC TNAAGCTCA TGTCCACCATA                150
 X  G  S   T  N  Y  N  P  S  L   K  S  H  V  T  I

TCAGTAGACA CGTCCAAGAA CCAGTTCTAC NTGAAGCTGA GCTNTGTGAC               200
 S  V  D   T  S  K  N  Q  F  Y   X  K  L  S  X  V  T

CGNTGCGGAC AGGGAGNGA ATAACTGNGC NAGAGATAGG GGAGAGAGN                 250
 X  A  D   T  X  X  N  N  X  A   R  D  R  G  X  V  X

NNTGGCNTNC TACTNTGACT ACTGAGGCCA GNGAACCNTG GNTCCAGTA                300
 W  X  X   T  X  T  T  E  A  X   E  P  W  X  T  V

ATCCNTAAGN CTNNCAANCA AANGNGNCCC AANGNGANAC NNNCTNCNC                350 (SEQ ID NO: 29)
 I  X  X   X  X  X  Q  X  X  P   X  X  X  X  X  X  X     (SEQ ID NO: 65)
```

E20.19.2VK.Seq Sequence

```
          10         20         30         40         50
  1234567890 1234567890 1234567890 1234567890 1234567890
  TCTTTGGTAG CNGTCTTGG CGAGAGGCCC ACCATCAACT GCAAGTCCAG         50
   S  L  V   A  X  L  G   E  R  P   T  I  N   C  K  S  S

CCAGAGTGTT TTATACNGCT CCAAGAATCA GAACTACTTA GCTTGGTACC       100
   Q  S  V    L  Y  X  S   K  N  Q   N  Y  L    A  W  Y  Q

AGCAGAAACC AGGACAGCCT CCTAAGCTGC TCATTTACTG GGCATCTACC       150
   Q  K  P    G  Q  P    P  K  L  L   I  Y  W    A  S  T

CGGGAATCCG GGGTCCCTGA CCGATTCAGG GGCAGCGGGT CTAGGACAGA       200
   R  E  S  G   V  P  D    R  F  R    G  S  G    R  T  D

TTTCACTCTC ACCATCAGCA GCCTGCAGGC TGAAGATGTG GCAGTTTACT       250
   F  T  L    T  I  S  S   L  Q  A    E  D  V    A  V  Y  F

TCTGTCACCA ATATTATAGT ACTCCGTGGA CGTTCGGCCA AGGGACCAAG       300
   C  H  Q    Y  Y  S    T  P  W    T  F  G  Q    G  T  K

GTGGAAATCA AACGAACTGT GGCTGCACCA TCTGTCTTCA TCTTCCCGCC       350
   V  E  I  K   R  T  V    A  A  P    S  V  F  I    F  P  P

ATCTGATGAG CAGCTTGAAA TCTGGAACT GCCTCTGNTG NGTGCCTGCT        400
   S  D  E    H  L  E  I   L  E  L    P  L  X   X  A  C

GAACNAACTC TATCCCAGA GANGGCCCAA AAGTNTCAAG NNGGNNAGGC        450
   T  N  S    I  P  R   X  G  P    K  V  S  X    X  X  G

NNGATAACGC CTNTTCNCCN NCNTNC       (SEQ ID NO: 30)          476
   X  I  T  P   X  X  X    X          (SEQ ID NO: 66)
```

FIG. 68

20.20.21MG30.Seq Sequenc

```
              10         20         30         40         50
         1234567890 1234567890 1234567890 1234567890 1234567890
         AAGCCTTTTC AGACCNTGCC CTTCACCTGC ACTGTCTCTG GTGGCTCCAT    50
          K  P  F  Q  T  X  P  F  T  C  T  V  S  G  G  S  I

CAGCAGTGGT GGTTACTACT GGAGCTGGAT CCGCCAGCAC CCAGGGAAGG   100
          S  S  G  G  Y  Y  W  S  W  I  R  Q  H  P  G  K  G

GCCTGGAGTG GATTGGGTAC ATCTATAACA GTGGGAGCAC CTACTACAAC   150
          L  E  W  I  G  Y  I  Y  N  S  G  S  T  Y  Y  N

CCGTCCCTCC AGAGTCGAGT TACCATATCA GTAGACACGT CTAAGAACCA   200
          P  S  L  Q  S  R  V  T  I  S  V  D  T  S  K  N  Q

GTTCTCCCTG AAGCTGAGCT CTGTGACTGC CGCGGACACG GCCGTGTATT   250
          F  S  L  K  L  S  S  V  T  A  A  D  T  A  V  Y  Y

ACTGTGCGGG TCAGAAATGG TCCTACTACT ACTACTACGG TATGGACGTC   300
          C  A  G  Q  K  W  S  Y  Y  Y  Y  G  M  D  V

TGGGGCCAAG GGACCACGGT CACCGTCTCC TNAGCCTCCA CCAANGGCCC   350
          W  G  Q  G  T  T  V  T  V  S  X  A  S  T  X  G  P

ATCGGTCTTC CCCCTGGCGC CCTGNTCTAG GAGCACCTCC CANAGCACAG   400
          S  V  F  P  L  A  P  X  S  R  S  T  S  X  S  T  D

ACGGATNCTG GGCCTGCCTG NATCAATGGA CTACTTTCCC CGAACCGGTT   450
          G  X  W  A  C  L  X  Q  W  T  T  F  P  E  P  V

GNNTGTGNNN CCTGGNAACT N  (SEQ ID NO: 31)                 471
          X  C  X  X  W  X  L     (SEQ ID NO: 67)
```

FIG. 69

E20-22MG30.Seq Sequence

```
          10         20         30         40         50
1234567890 1234567890 1234567890 1234567890 1234567890
AAGCCTTTNG AGACCNTGCC CCTCACCTGC ACTGTCTCTG GTGGCTCCAT       50
 K  P  X   E  T  X  P  L  T  C   T  V  S   G  S  I

CAGTAATTAC TACTGGAGCT GGATCCGGCA GCCCCCAGGG AAGGGACTGG      100
 S  N  Y   Y  W  S   W  I  R  Q   P  P  G   K  G  L  E

AGTGGATTGG GTATATCTAT TACAGTGGGA GCACCAACTA CAACCCCTCC      150
 W  I  G   Y  I  Y   Y  S  G   S  T  N  Y   N  P  S

CTCAAGAGTC GAGTCACCAT ATCAGTAGAC ACGTCCAAGA ACCAGTTCTC      200
 L  K  S   R  V  T  I   S  V  D   T  S  K  N   Q  F  S

CCTGAAGCTG AGCTCTGTGA CCGCTGCGGA CACGGCCGTG TATTACTGTG      250
 L  K  L   S  S  V  T   A  A  D   T  A  V   Y  Y  C  A

CGAGAGGGCC CGGGGGGAGC TACTACTACT ACGGTATGGA CGTCTGGGGC      300
 R  G  P   G  G  S   Y  Y  Y   Y  G  M  D   V  W  G

CAAGGGACCA CGGTCACCGT CTCCTCAGCC TCCACCAAGG GCCCATCGGT      350
 Q  G  T   T  V  T  V   S  S  A   S  T  K  G   P  S  V

CTTCCCCCTG GCGCCCTGCT CCAGGAGCAC CTCCGAGAGC ACAGCGGCCC      400
 F  P  L   A  P  C  S   R  S  T   S  E  S   T  A  A  L

TGGGCTGCCT GGTCAAGGA CTACTTCCCC GAACCGGTGA CGGTGTTCGN       450
 G  C  L   G  Q  G   L  L  P   R  T  G  D   G  V  R

NGGAAC    (SEQ ID NO: 32)                                   456
 X  N     (SEQ ID NO: 68)
```

FIG. 70

Amino Acid Sequences and Structure of Human Heavy Chain Derived from EGFR-Specific Hybridomas

E7.5.2.K.aa Sequence

```
          10         20         30         40         50
 1234567890 1234567890 1234567890 1234567890 1234567890
CTGTCTGCAT CTGTAGGAGA CAGAGTCATA ATCACTTGCC GGGCAAGTCA    50
 L  S  A  S  V  G  D  R  V  I  I  T  C  R  A  S  Q

AAACATCACC GACCATTTAA ATTGGTATCA GCAGATAGCA GGAAAAGCCC   100
 N  I  T  D  H  L  N  W  Y  Q  Q  I  A  G  K  A  P

CTAGGCCCCT GATATACACT GCATCCAGTT TGCAAGGTGG GGTCCCATCA   150
 R  P  L  I  Y  T  A  S  S  L  Q  G  G  V  P  S

AGGTTCAGTG GCAGTGGATC TGGGACAGAT TTCACTCTCA CCATCAGCAG   200
 R  F  S  G  S  G  S  G  T  D  F  T  L  T  I  S  S

TCTGCAACCT GAAGATTTTT CAACTTACTA CTGTCAACAG AGTTACAGTA   250
 L  Q  P  E  D  F  S  T  Y  Y  C  Q  Q  S  Y  S  T

CCCCGTGGCA TTTTGGCCAG GGGACCAAGC TGGAGATCAA ACGAACTGTG   300
 P  C  S  F  G  Q  G  T  K  L  E  I  K  R  T  V

GCTGCACCAT CTGTCTTCAT CTTCCCGCCA TCTGATGAGC AGTTGAAATC   350
 A  A  P  S  V  F  I  F  P  P  S  D  E  Q  L  K  S

TGGAACTGCC TCTGTTGTGT GCCTGCTGAA TAACTTCTAT CCCA         394   (SEQ ID NO: 33)
 G  T  A  S  V  V  C  L  L  N  N  F  Y  P                      (SEQ ID NO: 69)
```

E7.5.2.v.aa Sequence

|  | 10 | 20 | 30 | 40 | 50 |  |
|---|---|---|---|---|---|---|
|  | 1234567890 | 1234567890 | 1234567890 | 1234567890 | 1234567890 |  |
|  | GTGAAGGTCT | CCTGCAAGGC | TTCTGGATAC | ACCTTCAGCG | GCTACTATAT | 50 |
|  | V K V S | C K A | S G Y | T F S G | Y Y M |  |
|  | GCACTGGGTG | CGACAGGCCC | CTGGACAAGG | GCTTGAGTGG | ATGGGATCGA | 100 |
|  | H W V | R Q A P | G Q G | L E W | M G S I |  |
|  | TCCACCCTAA | CAGTGGTGGC | ANAAACTTTG | CACAGAAGTT | TCAGGGCAGG | 150 |
|  | H P N | S G G | X N F A | Q K F | Q G R |  |
|  | GTCACCATGA | CCAGGGACAC | GTCCATCAAC | ACAGCCTACT | TGGAGCTGAG | 200 |
|  | V T M T | R D T | S I N | T A Y L | E L S |  |
|  | CAGGCTGAGA | TCTGACGACA | CGGCCGTGTA | TTACTGTGCG | AGAGATAAAA | 250 |
|  | R L R | S D D T | A V Y | Y C A | R D K N |  |
|  | ACTACGGTGA | CTACGTCTTT | GACTATTGGG | GCCAGGGAAC | CCTGGTCACC | 300 |
|  | Y G D | Y V F | D Y W G | Q G T | L V T |  |
|  | GTCTCCTCAG | (SEQ ID NO: 34) |  |  |  | 310 |
|  | V S S | (SEQ ID NO: 70) |  |  |  |  |

FIG. 73

| 125I-EGF | Time (min | Surface | Internalize | Total | % internalized |
|---|---|---|---|---|---|
| | 0 | 67.153 | 1.515 | 68.668 | 2.2 |
| | 5 | 68.997 | 7.649 | 76.646 | 10 |
| | 20 | 39.986 | 37.406 | 77.392 | 48 |

| 125I-E763 | Time (min | Surface | Internalize | Total | % internalized |
|---|---|---|---|---|---|
| | 0 | 41.051 | 1.684 | 42.735 | 3.9 |
| | 5 | 44.567 | 9.876 | 54.443 | 18 |
| | 20 | 27.969 | 26.998 | 54.967 | 49 |

Degradation of $^{125}$I-EGF or $^{125}$I-E76. ¬ A431 c w/ or w/o chloroquine (100μM)

| | | w/chloroq | w/o chloroquine | % degradation | % competition |
|---|---|---|---|---|---|
| cpmx10⁴ | Buffer | 36.0898 | 21.8277 | 40 | 0 |
| | EGF | 0.3684 | 0.3776 | | 98 |
| | E763 | 0.481 | 0.2132 | | 99 |
| | m225 | 1.5468 | 0.4882 | | 98 |
| | m29.1 | 23.9704 | 14.459 | | 34 |
| | K221 | 35.5084 | 23.2694 | 34 | 1.6 | w/ or w/o chloroquine (100μM)

| | | w/chloroq | w/o chloroquine | % degradation | % competition |
|---|---|---|---|---|---|
| cpmx10⁴ | Buffer | 54.608 | 57.824 | 0 | 0 |
| | E763 | 0.536 | 0.441 | | 99 |
| | K221 | 58.956 | 54.83 | 7 | 5 |

Effects of E763 and m225 on EGFr degradation

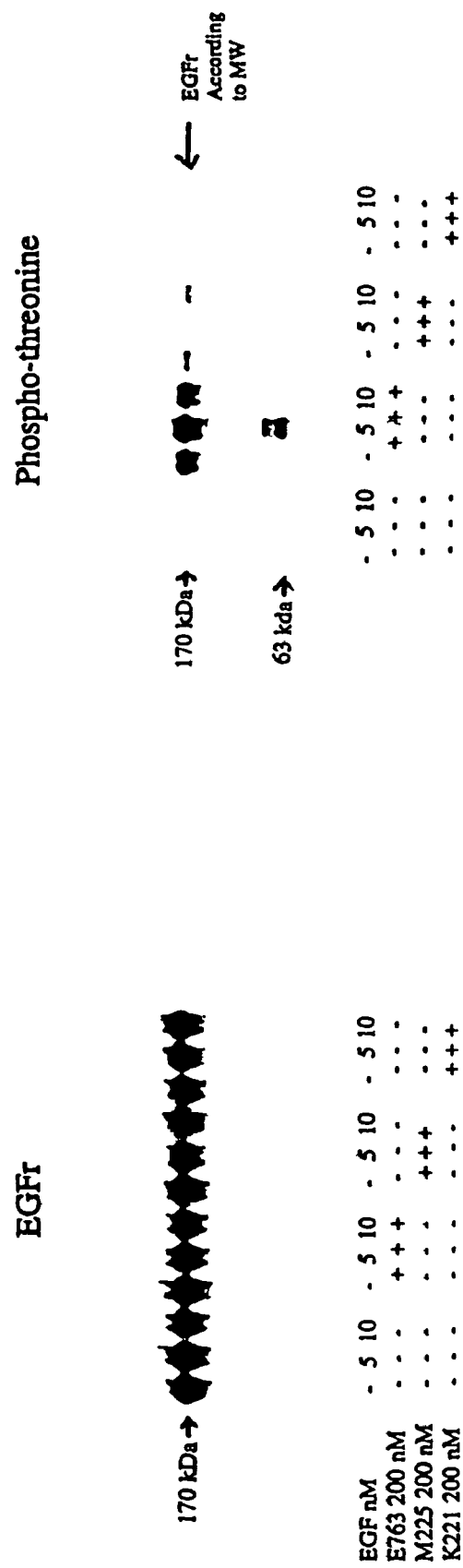

E763 on VEGF secretion

Effects of E763 and m225 on
VEGF secretion
in cultured A431 cells

Effects of E763 and E752 on
VEGF secretion
in cultured A431 cells

Effects of E763 and E752 on
VEGF secretion
in cultured A431 cells (24 hr)

Effect of E763 on VEGF secretion in
cultured A431 cells

Effects of E763 and m225 on VEGF secretion in cultured endothelial cells

11/5/98 VEGF in endothelial cells (ECV304)(ATTCC, CRL-1998)

| | VEGF ng/ml | no serum | |
|---|---|---|---|
| | 0 | 30 | 60 |
| EGF only | 0.4 | 0.49 | 0.68 |
| w/ E763 | 0.29 | 0.28 | 0.38 |
| w/ m225 | 0.37 | 0.39 | 0.54 |
| w/ K221 | 0.4 | 0.57 | 0.72 |

SEQUENCE LISTING

```
<160> NUMBER OF SEQ ID NOS: 76

<210> SEQ ID NO 1
<211> LENGTH: 23
<212> TYPE: DNA
<213> ORGANISM: Homo sapiens
<220> FEATURE:
<221> NAME/KEY: modified_base
<222> LOCATION: (21)
<223> OTHER INFORMATION: inosine

<400> SEQUENCE: 1
caggtgcagc tggagcagtc ngg                                              23

<210> SEQ ID NO 2
<211> LENGTH: 24
<212> TYPE: DNA
<213> ORGANISM: Homo sapiens

<400> SEQUENCE: 2
gctgagggag tagagtcctg agga                                             24

<210> SEQ ID NO 3
<211> LENGTH: 294
<212> TYPE: DNA
<213> ORGANISM: Homo sapiens

<400> SEQUENCE: 3
gtctctggtg gctccatcaa cagtggtgat tactactgga gctggatccg ccagcaccca      60
gggaagggcc tggactgcat tgggtacatc tattacagtg ggagcaccta ctacaacccg     120
tccctcaaga gtcgagttac catatcagta gacacgtcta agaatcagtt cttcctgaag     180
ctgacctctg tgactgccgc ggacacggcc gtgtattact gtgcgagatc tacggtggta     240
```

```
aatccggggt ggttcgaccc ctggggccar ggaaccctgg tcaccgtctc ctca         294
```

<210> SEQ ID NO 4
<211> LENGTH: 264
<212> TYPE: DNA
<213> ORGANISM: Homo sapiens

<400> SEQUENCE: 4

```
accatcactt gccaggcgag tcaggacatt aacaactatt taaattggtt tcagcagaaa    60
ccagggaaag cccctaaggt cctgatccac gatgcatcca atttggaaac aggggggccca   120
tcaaggttca gtggaagtgg atctgggaca gattttactt tcaccatcag cggcctgcag   180
cctgaagaca ttgcaacata ttattgtcaa cagtatgaaa gtctcccact cactttcggc   240
ggagggacca aggtggagat caaa                                          264
```

<210> SEQ ID NO 5
<211> LENGTH: 291
<212> TYPE: DNA
<213> ORGANISM: Homo sapiens

<400> SEQUENCE: 5

```
gtctctggtg gctccatcaa cagtggtgat tactactgga gctggatccg ccagcaccca    60
gggaagggcc tggagtggat tgggtccatc tattacagtg gaacaccttc tacaacccg    120
tccctcaaga gtcgagttac catatcacta gacacgtcta agaaccagtt ctccctgaag   180
ctgagttctg tgactgccgc ggacacggcc gtgtgttact gtgcgagaaa tatagtgact   240
acgggtgctt tgatatctg gggccaaggg acaatggtca ccgtctcttc a             291
```

<210> SEQ ID NO 6
<211> LENGTH: 264
<212> TYPE: DNA
<213> ORGANISM: Homo sapiens

<400> SEQUENCE: 6

```
accatcactt gtcaggcgag tcaggacatt accatttatt taaattggta tcaacagaaa    60
ccagggaaag cccctaagct cctgatcaac gacgcatcca gtttggaaac aggggtccca   120
ttaaggttca gtggaagtgg atctgggaca gattttactt tcaccatcag cagcctgcag   180
cctgaagata ttgcaacata ttactgtcaa cagtatgatc atctcccgct cactttcggc   240
ggcgggacca aggtggcgat caaa                                          264
```

<210> SEQ ID NO 7
<211> LENGTH: 288
<212> TYPE: DNA
<213> ORGANISM: Homo sapiens

<400> SEQUENCE: 7

```
gtctctggtg gctccatcag cagtggtgat tactactgga cctggatccg ccagcaccca    60
gggaagggcc tggagtggat tgggtacatc tattacagtg gaacaccta ctacaacccg    120
tccctcaaga gtcgagtttc catgtcaata gacacgtctg agaaccagtt ctccctgaag   180
ctgagctctg tgactgccgc ggacacggcc gtgtattact gtgcgagaaa accagtgact   240
gggggggagg actactgggg ccagggaacc ctggtcaccg tctcctca                288
```

<210> SEQ ID NO 8
<211> LENGTH: 262
<212> TYPE: DNA

<213> ORGANISM: Homo sapiens

<400> SEQUENCE: 8

| | | | | |
|---|---|---|---|---|
| accatcactt | gccaggcgag | tcaggacatt | agtaactatt | taaattggta tcagcagaaa | 60 |
| ccagggaaag | ccctaagctc | ctgatctacg | atgcttccaa | tttggaaaca ggggtcccat | 120 |
| caaggttcag | tggagtggat | ctgggacaga | ttttactttc | accatcagca gcctgcagcc | 180 |
| tgaagatgtt | ggaacatatg | tctgtcaaca | gtatgagagt | ctcccgtgcg gttttggcca | 240 |
| ggggaccaaa | ctggagatca | aa | | | 262 |

<210> SEQ ID NO 9
<211> LENGTH: 291
<212> TYPE: DNA
<213> ORGANISM: Homo sapiens
<220> FEATURE:
<221> NAME/KEY: modified_base
<222> LOCATION: (228)
<223> OTHER INFORMATION: a, c, g, t, unknown or other

<400> SEQUENCE: 9

| | | | | |
|---|---|---|---|---|
| gtctctggtg | gctccatcaa | cagtggtgat | ttctactgga | gctggatccg ccaacaccca | 60 |
| gggaagggcc | tggagtggat | tgggtacatc | tattacagtg | ggagcaccta ctacaacccg | 120 |
| tccctcaaga | gtcgagttac | catgtcaata | gacccgtcta | agaaccagtt ctccctgaaa | 180 |
| ctgatctctg | tgactgccgc | ggacacggcc | gtttattact | gtgcgacntc cctttactat | 240 |
| ggcgggggta | tggacgtctg | gggccaaggg | accacggtca | ccgtctcctc a | 291 |

<210> SEQ ID NO 10
<211> LENGTH: 264
<212> TYPE: DNA
<213> ORGANISM: Homo sapiens
<220> FEATURE:
<221> NAME/KEY: modified_base
<222> LOCATION: (63)
<223> OTHER INFORMATION: a, c, g, t, unknown or other
<220> FEATURE:
<221> NAME/KEY: modified_base
<222> LOCATION: (259)
<223> OTHER INFORMATION: a, c, g, t, unknown or other

<400> SEQUENCE: 10

| | | | | |
|---|---|---|---|---|
| accatcactt | gccaggcgag | tcaggacatt | aacaactatt | tgaattggta tcagcagagg | 60 |
| ccngggaacg | ccctaaaact | cctgatctac | gatgcatcca | atttggaaac aggggtccca | 120 |
| tcaaggttca | gtggaagtgg | atctgggaca | gattttactt | tcaccatcaa cagcctgcag | 180 |
| cctgaagata | ttgcgacata | ttattgtcaa | cactatgatc | atctcccgtg gacgttcggc | 240 |
| caagggacca | aggtggaant | caaa | | | 264 |

<210> SEQ ID NO 11
<211> LENGTH: 291
<212> TYPE: DNA
<213> ORGANISM: Homo sapiens

<400> SEQUENCE: 11

| | | | | |
|---|---|---|---|---|
| gtctctggtg | gctccatcaa | caatggtgat | tactactgga | gctggatccg ccagcaccca | 60 |
| gggaagggcc | tggagtggat | tgggcacatc | tattacagtg | ggagcaccta ctacatcccg | 120 |
| tccctcaaga | gtcgaactac | catatcagta | gacacgtcta | agaaccagtt ctccctgaag | 180 |
| ctgaactctg | tgactgccgc | ggacacggcc | gtgtattact | gtgcgagagg gacagtaact | 240 |
| acgtactact | ttgactactg | gggccaggga | accctggtca | ccgtctcctc a | 291 |

<210> SEQ ID NO 12
<211> LENGTH: 270
<212> TYPE: DNA
<213> ORGANISM: Homo sapiens

<400> SEQUENCE: 12

```
accatcactt gccgggcaag tcagagcatt agcagctatt taaattggta tcagcagaaa    60
ccagggaaag cccctaagct cctgatctat gctgcatcca gtttgcaaag tggggtccca   120
tcaaggttca gtggcagtgg atctgggaca gatttcactc tcaccatcag cagtctgcaa   180
cctgaagatt ttgcaactta ctactgtcaa cagggttaca gaacccctcc ggagtgcagt   240
tttggccagg ggaccaagct ggagatcaaa                                    270
```

<210> SEQ ID NO 13
<211> LENGTH: 291
<212> TYPE: DNA
<213> ORGANISM: Homo sapiens

<400> SEQUENCE: 13

```
gtctctggtg gctccgtcag cagtggtgat tactactgga gctggatccg gcagccccca    60
gggaagggac tggagtggat tggacatctc tattacagtg gaacaccaa ctacaacccc    120
tccctcaaga gtcgagtcac catatcatta gacacgtcca agaaccagtt ctccctgaag   180
ctgagctctg tgaccgctgc ggacacggcc gtgtattact gtgcgagaga tttttttgact   240
ggttccttct tgactactg gggccaggga accctggtca ccgtctcctc a             291
```

<210> SEQ ID NO 14
<211> LENGTH: 264
<212> TYPE: DNA
<213> ORGANISM: Homo sapiens

<400> SEQUENCE: 14

```
accatcactt gccaggcgag tcaggacata agcaactatt taaattggta tcagcagaaa    60
ccagggaaag cccctaagct cctgatcaac gatgcatccg atttggaaac aggggtccca   120
tcaaggatca gtggaagtgg atctgggaca gattttactt tcaccatcag caacctgcag   180
cctgaagata ttgcaacata ttactgtcaa caatatgata gtctcccgct cactttcggc   240
ggagggacca aggtggagat caga                                          264
```

<210> SEQ ID NO 15
<211> LENGTH: 288
<212> TYPE: DNA
<213> ORGANISM: Homo sapiens

<400> SEQUENCE: 15

```
gtctctggtg gctccgtcta cagtggtgat tactactgga gctggatccg gcagccccc     60
gggaagggac tggagtggat tgggtatatc tattacagtg ggagcaccaa ttacaatccc   120
tccctcaaga gtcgagtcac catatcagta gacacgtcca agaaccagtt ctccctgaag   180
ctgagctctg tgaccgctgc ggacacggcc gtgtattact gtgcgagaga ctccatactg   240
ggagctacca actactgggg ccagggaacc ctggtcaccg tctcctca                288
```

<210> SEQ ID NO 16
<211> LENGTH: 264
<212> TYPE: DNA
<213> ORGANISM: Homo sapiens
<220> FEATURE:

```
<221> NAME/KEY: modified_base
<222> LOCATION: (23)
<223> OTHER INFORMATION: a, c, g, t, unknown or other
<220> FEATURE:
<221> NAME/KEY: modified_base
<222> LOCATION: (43)
<223> OTHER INFORMATION: a, c, g, t, unknown or other
<220> FEATURE:
<221> NAME/KEY: modified_base
<222> LOCATION: (50)
<223> OTHER INFORMATION: a, c, g, t, unknown or other
<220> FEATURE:
<221> NAME/KEY: modified_base
<222> LOCATION: (153)
<223> OTHER INFORMATION: a, c, g, t, unknown or other
<220> FEATURE:
<221> NAME/KEY: modified_base
<222> LOCATION: (155)
<223> OTHER INFORMATION: a, c, g, t, unknown or other
<220> FEATURE:
<221> NAME/KEY: modified_base
<222> LOCATION: (195)
<223> OTHER INFORMATION: a, c, g, t, unknown or other
<220> FEATURE:
<221> NAME/KEY: modified_base
<222> LOCATION: (209)
<223> OTHER INFORMATION: a, c, g, t, unknown or other
<220> FEATURE:
<221> NAME/KEY: modified_base
<222> LOCATION: (217)
<223> OTHER INFORMATION: a, c, g, t, unknown or other

<400> SEQUENCE: 16
accatcactt gccaggcgag tcnggacatt aataactatt tanattggtn tcagcagaaa      60
ccagggaaag cccctaaast cctgatctcc gatgcatcca atttagaaac aggggtccca     120
tcgaggttca gtggaagtgg atctgggaca gantntactt tcaccatcag cagcctgcag     180
cctgaagata ttgcnacata tcactgtcna cagtatnata gtctcccgct cactttcggc     240
ggagggacca aggtagagat caaa                                             264

<210> SEQ ID NO 17
<211> LENGTH: 288
<212> TYPE: DNA
<213> ORGANISM: Homo sapiens

<400> SEQUENCE: 17
gtctctggtg gctccgtcag cagtggtgat tactactgga cctggatccg gcagtcccca      60
gggaagggac tggagtggat tggacacatc tattacagtg ggaacaccaa ttataacccc     120
tccctcaaga gtcgactcac catatcaatt gacacgtcca agactcagtt ctcccctgaag    180 ctgagttctg tgaccgctgc ggacacggcc atttattact gtgtgcgaga tcgagtgact     240
ggtgcttttg atatctgggg ccaagggaca atggtcaccg tctcttca                  288

<210> SEQ ID NO 18
<211> LENGTH: 264
<212> TYPE: DNA
<213> ORGANISM: Homo sapiens

<400> SEQUENCE: 18
accatcactt gccaggcgag tcaggacatc agcaactatt taaattggta tcagcagaaa      60
ccagggaaag cccctaaact cctgatctac gatgcatcca atttggaaac aggggtccca     120
tcaaggttca gtggaagtgg atctgggaca gatttacttt tcaccatcag cagcctgcag     180
cctgaagata ttgcaacata tttctgtcaa cactttgatc atctcccgct cgctttcggc     240
ggagggacca aggtggagat caaa                                             264
```

```
<210> SEQ ID NO 19
<211> LENGTH: 481
<212> TYPE: DNA
<213> ORGANISM: Homo sapiens
<220> FEATURE:
<221> NAME/KEY: CDS
<222> LOCATION: (1)..(480)
<220> FEATURE:
<221> NAME/KEY: modified_base
<222> LOCATION: (27)..(27)
<223> OTHER INFORMATION: a, c, g, t, unknown or other
<220> FEATURE:
<221> NAME/KEY: modified_base
<222> LOCATION: (38)..(38)
<223> OTHER INFORMATION: a, c, g, t, unknown or other
<220> FEATURE:
<221> NAME/KEY: modified_base
<222> LOCATION: (63)..(63)
<223> OTHER INFORMATION: a, c, g, t, unknown or other
<220> FEATURE:
<221> NAME/KEY: modified_base
<222> LOCATION: (65)..(65)
<223> OTHER INFORMATION: a, c, g, t, unknown or other
<220> FEATURE:
<221> NAME/KEY: modified_base
<222> LOCATION: (320)..(320)
<223> OTHER INFORMATION: a, c, g, t, unknown or other
<220> FEATURE:
<221> NAME/KEY: modified_base
<222> LOCATION: (352)..(352)
<223> OTHER INFORMATION: a, c, g, t, unknown or other
<220> FEATURE:
<221> NAME/KEY: modified_base
<222> LOCATION: (383)..(383)
<223> OTHER INFORMATION: a, c, g, t, unknown or other
<220> FEATURE:
<221> NAME/KEY: modified_base
<222> LOCATION: (386)..(386)
<223> OTHER INFORMATION: a, c, g, t, unknown or other
<220> FEATURE:
<221> NAME/KEY: modified_base
<222> LOCATION: (393)..(393)
<223> OTHER INFORMATION: a, c, g, t, unknown or other
<220> FEATURE:
<221> NAME/KEY: modified_base
<222> LOCATION: (395)..(395)
<223> OTHER INFORMATION: a, c, g, t, unknown or other
<220> FEATURE:
<221> NAME/KEY: modified_base
<222> LOCATION: (410)..(410)
<223> OTHER INFORMATION: a, c, g, t, unknown or other
<220> FEATURE:
<221> NAME/KEY: modified_base
<222> LOCATION: (414)..(414)
<223> OTHER INFORMATION: a, c, g, t, unknown or other
<220> FEATURE:
<221> NAME/KEY: modified_base
<222> LOCATION: (425)..(425)
<223> OTHER INFORMATION: a, c, g, t, unknown or other
<220> FEATURE:
<221> NAME/KEY: modified_base
<222> LOCATION: (435)..(435)
<223> OTHER INFORMATION: a, c, g, t, unknown or other
<220> FEATURE:
<221> NAME/KEY: modified_base
<222> LOCATION: (440)..(440)
<223> OTHER INFORMATION: a, c, g, t, unknown or other
<220> FEATURE:
<221> NAME/KEY: modified_base
<222> LOCATION: (448)..(448)
<223> OTHER INFORMATION: a, c, g, t, unknown or other
<220> FEATURE:
<221> NAME/KEY: modified_base
<222> LOCATION: (450)..(450)
<223> OTHER INFORMATION: a, c, g, t, unknown or other
<220> FEATURE:
<221> NAME/KEY: modified_base
```

```
<222> LOCATION: (453)..(453)
<223> OTHER INFORMATION: a, c, g, t, unknown or other
<220> FEATURE:
<221> NAME/KEY: modified_base
<222> LOCATION: (466)..(466)
<223> OTHER INFORMATION: a, c, g, t, unknown or other
<220> FEATURE:
<221> NAME/KEY: modified_base
<222> LOCATION: (469)..(469)
<223> OTHER INFORMATION: a, c, g, t, unknown or other
<220> FEATURE:
<221> NAME/KEY: modified_base
<222> LOCATION: (471)..(471)
<223> OTHER INFORMATION: a, c, g, t, unknown or other
<220> FEATURE:
<221> NAME/KEY: modified_base
<222> LOCATION: (475)..(476)
<223> OTHER INFORMATION: a, c, g, t, unknown or other
<220> FEATURE:
<221> NAME/KEY: modified_base
<222> LOCATION: (479)..(479)
<223> OTHER INFORMATION: a, c, g, t, unknown or other

<400> SEQUENCE: 19
```

| | | | | | | | | | | | | | | | | |
|---|---|---|---|---|---|---|---|---|---|---|---|---|---|---|---|---|
| gcg | atc | cag | cct | ttt | agg | tcc | atg | ccn | ttc | tcc | tgt | gna | gcg | tct | gga | 48 |
| Ala | Ile | Gln | Pro | Phe | Arg | Ser | Met | Pro | Phe | Ser | Cys | Xaa | Ala | Ser | Gly | |
| 1 | | | | 5 | | | | | 10 | | | | | 15 | | |
| ttc | ccc | ttc | agt | agn | tnt | ggc | atg | cac | tgg | gtc | cgc | cag | gct | cca | ggc | 96 |
| Phe | Pro | Phe | Ser | Xaa | Xaa | Gly | Met | His | Trp | Val | Arg | Gln | Ala | Pro | Gly | |
| | | | 20 | | | | | 25 | | | | | 30 | | | |
| aag | ggg | ctg | gag | tgg | gtg | gca | gtt | ata | tgg | tat | gat | gga | agt | aat | aaa | 144 |
| Lys | Gly | Leu | Glu | Trp | Val | Ala | Val | Ile | Trp | Tyr | Asp | Gly | Ser | Asn | Lys | |
| | | 35 | | | | | 40 | | | | | 45 | | | | |
| tac | tat | gca | gac | tcc | gtg | aag | ggc | cga | ttc | acc | atc | tcc | aga | gac | aat | 192 |
| Tyr | Tyr | Ala | Asp | Ser | Val | Lys | Gly | Arg | Phe | Thr | Ile | Ser | Arg | Asp | Asn | |
| 50 | | | | | 55 | | | | | 60 | | | | | | |
| tcc | aag | aac | acg | ctg | tat | ctg | caa | atg | aac | aga | ctg | aga | gcc | gag | gac | 240 |
| Ser | Lys | Asn | Thr | Leu | Tyr | Leu | Gln | Met | Asn | Arg | Leu | Arg | Ala | Glu | Asp | |
| 65 | | | | 70 | | | | | 75 | | | | | 80 | | |
| acg | gct | gtg | tat | tac | tgt | gcg | aga | ttt | ttg | gag | tgg | tta | ccc | ttt | gac | 288 |
| Thr | Ala | Val | Tyr | Tyr | Cys | Ala | Arg | Phe | Leu | Glu | Trp | Leu | Pro | Phe | Asp | |
| | | | 85 | | | | | 90 | | | | | 95 | | | |
| tac | tgg | ggc | cag | gga | acc | ctg | gtc | acc | gtc | tnc | tca | gac | tcc | acc | aag | 336 |
| Tyr | Trp | Gly | Gln | Gly | Thr | Leu | Val | Thr | Val | Xaa | Ser | Asp | Ser | Thr | Lys | |
| | | 100 | | | | | 105 | | | | | 110 | | | | |
| ggc | cca | tcg | gtc | ttc | ncc | ctg | gcg | ccc | tgc | ttc | cag | gag | cac | cct | cng | 384 |
| Gly | Pro | Ser | Val | Phe | Xaa | Leu | Ala | Pro | Cys | Phe | Gln | Glu | His | Pro | Xaa | |
| | | 115 | | | | | 120 | | | | | 125 | | | | |
| ana | gca | can | ang | gcc | cct | ggg | act | gnc | tgn | tac | aag | gac | tnc | ttt | ccc | 432 |
| Xaa | Ala | Xaa | Xaa | Ala | Pro | Gly | Thr | Xaa | Xaa | Tyr | Lys | Asp | Xaa | Phe | Pro | |
| | 130 | | | | | 135 | | | | | 140 | | | | | |
| tcn | aac | cng | gtg | acc | ntn | tcn | tgg | gaa | act | cag | ngc | ncn | tct | nna | tna c | 481 |
| Xaa | Asn | Xaa | Val | Thr | Xaa | Xaa | Trp | Glu | Thr | Gln | Xaa | Xaa | Ser | Xaa | Xaa | |
| 145 | | | | 150 | | | | | 155 | | | | | 160 | | |

```
<210> SEQ ID NO 20
<211> LENGTH: 489
<212> TYPE: DNA
<213> ORGANISM: Homo sapiens
<220> FEATURE:
<221> NAME/KEY: CDS
<222> LOCATION: (1)..(390)
<220> FEATURE:
<221> NAME/KEY: modified_base
<222> LOCATION: (10)..(10)
<223> OTHER INFORMATION: a, c, g, t, unknown or other
<220> FEATURE:
<221> NAME/KEY: modified_base
```

```
<222> LOCATION: (18)..(18)
<223> OTHER INFORMATION: a, c, g, t, unknown or other
<220> FEATURE:
<221> NAME/KEY: modified_base
<222> LOCATION: (29)..(29)
<223> OTHER INFORMATION: a, c, g, t, unknown or other
<220> FEATURE:
<221> NAME/KEY: modified_base
<222> LOCATION: (38)..(38)
<223> OTHER INFORMATION: a, c, g, t, unknown or other
<220> FEATURE:
<221> NAME/KEY: CDS
<222> LOCATION: (394)..(432)
<220> FEATURE:
<221> NAME/KEY: CDS
<222> LOCATION: (436)..(489)
<220> FEATURE:
<221> NAME/KEY: modified_base
<222> LOCATION: (440)..(440)
<223> OTHER INFORMATION: a, c, g, t, unknown or other
<220> FEATURE:
<221> NAME/KEY: modified_base
<222> LOCATION: (442)..(443)
<223> OTHER INFORMATION: a, c, g, t, unknown or other
<220> FEATURE:
<221> NAME/KEY: modified_base
<222> LOCATION: (451)..(452)
<223> OTHER INFORMATION: a, c, g, t, unknown or other
<220> FEATURE:
<221> NAME/KEY: modified_base
<222> LOCATION: (460)..(460)
<223> OTHER INFORMATION: a, c, g, t, unknown or other
<220> FEATURE:
<221> NAME/KEY: modified_base
<222> LOCATION: (464)..(464)
<223> OTHER INFORMATION: a, c, g, t, unknown or other
<220> FEATURE:
<221> NAME/KEY: modified_base
<222> LOCATION: (468)..(468)
<223> OTHER INFORMATION: a, c, g, t, unknown or other
<220> FEATURE:
<221> NAME/KEY: modified_base
<222> LOCATION: (474)..(475)
<223> OTHER INFORMATION: a, c, g, t, unknown or other
<220> FEATURE:
<221> NAME/KEY: modified_base
<222> LOCATION: (479)..(479)
<223> OTHER INFORMATION: a, c, g, t, unknown or other
<220> FEATURE:
<221> NAME/KEY: modified_base
<222> LOCATION: (486)..(486)
<223> OTHER INFORMATION: a, c, g, t, unknown or other
<220> FEATURE:
<221> NAME/KEY: modified_base
<222> LOCATION: (488)..(488)
<223> OTHER INFORMATION: a, c, g, t, unknown or other

<400> SEQUENCE: 20 gga acc ttt ngg ttc gcn cct ttt gga gnc aga ccc anc atc act tgt      48
Gly Thr Phe Xaa Phe Ala Pro Phe Gly Xaa Arg Pro Xaa Ile Thr Cys
1               5                   10                  15 cgg gcg agt cag ggc att agc aat ttt tta gcc tgg ttt cag cag aaa      96
Arg Ala Ser Gln Gly Ile Ser Asn Phe Leu Ala Trp Phe Gln Gln Lys
            20                  25                  30 cca ggg ata gcc cct aag tcc ctg atc tat gct gca tcc act ttg caa     144
Pro Gly Ile Ala Pro Lys Ser Leu Ile Tyr Ala Ala Ser Thr Leu Gln
        35                  40                  45 agt ggg gtc cca tca aag ttc acc ggc agt gga tat ggg aca gat ttc     192
Ser Gly Val Pro Ser Lys Phe Thr Gly Ser Gly Tyr Gly Thr Asp Phe
    50                  55                  60 act ctc acc atc agc agc ctg cag cct gaa gac ttt gca act tat tat     240
Thr Leu Thr Ile Ser Ser Leu Gln Pro Glu Asp Phe Ala Thr Tyr Tyr
65                  70                  75                  80
```

| | | | | | | | | | | | | | | | | |
|---|---|---|---|---|---|---|---|---|---|---|---|---|---|---|---|---|
| tgt | caa | caa | tat | aat | gtt | tac | cca | ttc | act | ttc | ggc | cct | ggg | acc | aaa | 288 |
| Cys | Gln | Gln | Tyr | Asn | Val | Tyr | Pro | Phe | Thr | Phe | Gly | Pro | Gly | Thr | Lys | |
| | | | 85 | | | | 90 | | | | 95 | | | | | |

| | | | | | | | | | | | | | | | | |
|---|---|---|---|---|---|---|---|---|---|---|---|---|---|---|---|---|
| gtg | gat | atc | aaa | cga | act | gtg | gct | gca | cca | tct | gtc | ttc | atc | ttc | ccg | 336 |
| Val | Asp | Ile | Lys | Arg | Thr | Val | Ala | Ala | Pro | Ser | Val | Phe | Ile | Phe | Pro | |
| | | | 100 | | | | 105 | | | | 110 | | | | | |

| | | | | | | | | | | | | | | | | |
|---|---|---|---|---|---|---|---|---|---|---|---|---|---|---|---|---|
| cca | tct | gat | gag | caa | gtt | gaa | atc | tgg | aac | tgc | ctc | tgt | tgt | gtg | cct | 384 |
| Pro | Ser | Asp | Glu | Gln | Val | Glu | Ile | Trp | Asn | Cys | Leu | Cys | Cys | Val | Pro | |
| | | | 115 | | | | 120 | | | | 125 | | | | | |

| | | | | | | | | | | | | | | | | |
|---|---|---|---|---|---|---|---|---|---|---|---|---|---|---|---|---|
| gct | gaa | taa | ctt | cta | tcc | cag | aga | ggc | caa | agt | aca | gtg | gaa | ggt | gga | 432 |
| Ala | Glu | | Leu | Leu | Ser | Gln | Arg | Gly | Gln | Ser | Thr | Val | Glu | Gly | Gly | |
| | 130 | | | | | 135 | | | | | 140 | | | | | |

| | | | | | | | | | | | | | | | | |
|---|---|---|---|---|---|---|---|---|---|---|---|---|---|---|---|---|
| taa | cgc | cnc | nnt | tgg | cgg | nnt | cct | ttc | nct | cnc | ccn | tcc | tcn | ncc | cnc | 480 |
| | Arg | Xaa | Xaa | Trp | Arg | Xaa | Pro | Phe | Xaa | Xaa | Pro | Ser | Xaa | Xaa | Xaa | |
| | | 145 | | | | 150 | | | | | 155 | | | | | |

| | | | |
|---|---|---|---|
| ctc | tcn | cna | 489 |
| Leu | Xaa | Xaa | |
| | 160 | | |

<210> SEQ ID NO 21
<211> LENGTH: 449
<212> TYPE: DNA
<213> ORGANISM: Homo sapiens
<220> FEATURE:
<221> NAME/KEY: CDS
<222> LOCATION: (1)..(447)
<220> FEATURE:
<221> NAME/KEY: modified_base
<222> LOCATION: (336)..(336)
<223> OTHER INFORMATION: a, c, g, t, unknown or other
<220> FEATURE:
<221> NAME/KEY: modified_base
<222> LOCATION: (401)..(402)
<223> OTHER INFORMATION: a, c, g, t, unknown or other
<220> FEATURE:
<221> NAME/KEY: modified_base
<222> LOCATION: (419)..(420)
<223> OTHER INFORMATION: a, c, g, t, unknown or other
<220> FEATURE:
<221> NAME/KEY: modified_base
<222> LOCATION: (437)..(437)
<223> OTHER INFORMATION: a, c, g, t, unknown or other
<220> FEATURE:
<221> NAME/KEY: modified_base
<222> LOCATION: (446)..(446)
<223> OTHER INFORMATION: a, c, g, t, unknown or other

<400> SEQUENCE: 21

| | | | | | | | | | | | | | | | | |
|---|---|---|---|---|---|---|---|---|---|---|---|---|---|---|---|---|
| aag | cct | gtt | gcc | tca | gtg | cag | gtc | tcc | tgc | aag | gct | tct | gga | tac | acc | 48 |
| Lys | Pro | Val | Ala | Ser | Val | Gln | Val | Ser | Cys | Lys | Ala | Ser | Gly | Tyr | Thr | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ttc | acc | agt | tat | gat | atc | aac | tgg | gtg | cga | cag | gcc | act | gga | caa | ggg | 96 |
| Phe | Thr | Ser | Tyr | Asp | Ile | Asn | Trp | Val | Arg | Gln | Ala | Thr | Gly | Gln | Gly | |
| | | | 20 | | | | 25 | | | | 30 | | | | | |

| | | | | | | | | | | | | | | | | |
|---|---|---|---|---|---|---|---|---|---|---|---|---|---|---|---|---|
| ctt | gag | tgg | atg | gga | tgg | atg | aac | cct | aac | agt | ggt | aac | aca | ggc | tat | 144 |
| Leu | Glu | Trp | Met | Gly | Trp | Met | Asn | Pro | Asn | Ser | Gly | Asn | Thr | Gly | Tyr | |
| | | 35 | | | | 40 | | | | | 45 | | | | | |

| | | | | | | | | | | | | | | | | |
|---|---|---|---|---|---|---|---|---|---|---|---|---|---|---|---|---|
| gca | cag | aag | ttc | cag | ggc | aga | gtc | acc | atg | acc | agg | aac | acc | tcc | ata | 192 |
| Ala | Gln | Lys | Phe | Gln | Gly | Arg | Val | Thr | Met | Thr | Arg | Asn | Thr | Ser | Ile | |
| | 50 | | | | | 55 | | | | | 60 | | | | | |

| | | | | | | | | | | | | | | | | |
|---|---|---|---|---|---|---|---|---|---|---|---|---|---|---|---|---|
| agc | aca | gcc | tac | atg | gag | ctg | agc | agc | ctg | aga | tct | gag | gac | acg | gcc | 240 |
| Ser | Thr | Ala | Tyr | Met | Glu | Leu | Ser | Ser | Leu | Arg | Ser | Glu | Asp | Thr | Ala | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| gtg | tat | tac | tgt | gcg | aga | gga | ggc | ccc | tat | agc | agt | ggc | tgg | acc | ttc | 288 |
| Val | Tyr | Tyr | Cys | Ala | Arg | Gly | Gly | Pro | Tyr | Ser | Ser | Gly | Trp | Thr | Phe | |
| | | | 85 | | | | 90 | | | | 95 | | | | | |

```
ttt gac tac tgg ggc cag gga acc ctg gtc acc gtc tcc tca gcc ctn      336
Phe Asp Tyr Trp Gly Gln Gly Thr Leu Val Thr Val Ser Ser Ala Xaa
            100                 105                 110 cac caa ggg ccc atc ggt ctt ccc cct ggc gcc ctg ctc cag gag cac      384
His Gln Gly Pro Ile Gly Leu Pro Pro Gly Ala Leu Leu Gln Glu His
        115                 120                 125 ctc cga gag cac agc gnn ccc ttg ggc tgc ctg gnn caa gga ctc ttt      432
Leu Arg Glu His Ser Xaa Pro Leu Gly Cys Leu Xaa Gln Gly Leu Phe
130                 135                 140 ccc cna acc ccg gnt ga                                               449
Pro Xaa Thr Pro Xaa
145

<210> SEQ ID NO 22
<211> LENGTH: 460
<212> TYPE: DNA
<213> ORGANISM: Homo sapiens
<220> FEATURE:
<221> NAME/KEY: CDS
<222> LOCATION: (1)..(375)
<220> FEATURE:
<221> NAME/KEY: modified_base
<222> LOCATION: (13)..(13)
<223> OTHER INFORMATION: a, c, g, t, unknown or other
<220> FEATURE:
<221> NAME/KEY: modified_base
<222> LOCATION: (27)..(27)
<223> OTHER INFORMATION: a, c, g, t, unknown or other
<220> FEATURE:
<221> NAME/KEY: modified_base
<222> LOCATION: (77)..(77)
<223> OTHER INFORMATION: a, c, g, t, unknown or other
<220> FEATURE:
<221> NAME/KEY: modified_base
<222> LOCATION: (372)..(372)
<223> OTHER INFORMATION: a, c, g, t, unknown or other
<220> FEATURE:
<221> NAME/KEY: modified_base
<222> LOCATION: (375)..(375)
<223> OTHER INFORMATION: a, c, g, t, unknown or other
<220> FEATURE:
<221> NAME/KEY: CDS
<222> LOCATION: (379)..(414)
<220> FEATURE:
<221> NAME/KEY: CDS
<222> LOCATION: (418)..(459)

<400> SEQUENCE: 22 ttt gaa ccc ttc ntg gcc gtg tct ctn ggc gcg agg gcc acc atc aac      48
Phe Glu Pro Phe Xaa Ala Val Ser Xaa Gly Ala Arg Ala Thr Ile Asn
1               5                   10                  15 tgc aag tcc agc cag cgt gtt tta tac anc tcc aac aat aag aac tgc     96
Cys Lys Ser Ser Gln Arg Val Leu Tyr Xaa Ser Asn Asn Lys Asn Cys
            20                  25                  30 tta gct tgg tac cag cag aaa cca gga cag cct cct aag ctg ctc att     144
Leu Ala Trp Tyr Gln Gln Lys Pro Gly Gln Pro Pro Lys Leu Leu Ile
        35                  40                  45 tac tgg aca tct acc cgg gaa tcc ggg gtc cct gcc cga ttc agt ggc     192
Tyr Trp Thr Ser Thr Arg Glu Ser Gly Val Pro Ala Arg Phe Ser Gly
    50                  55                  60 agc ggg tct ggg aca gat ttc act ctc acc atc agc agc ctg cag gct     240
Ser Gly Ser Gly Thr Asp Phe Thr Leu Thr Ile Ser Ser Leu Gln Ala
65                  70                  75                  80 gaa gat gtg gca gtt tat tac tgt cag caa tat tat agt act cca ctc     288
Glu Asp Val Ala Val Tyr Tyr Cys Gln Gln Tyr Tyr Ser Thr Pro Leu
                85                  90                  95 act ttc ggc gga ggg acc atg gtg gag atc aag cga act gtg gct gca     336
Thr Phe Gly Gly Gly Thr Met Val Glu Ile Lys Arg Thr Val Ala Ala
```

```
cca tct gtc ttc atc ttc ccg cca tct gat gag ccn gtn tga aat ctg      384
Pro Ser Val Phe Ile Phe Pro Pro Ser Asp Glu Pro Val     Asn Leu
            115                 120                 125 gaa ctg cct ctg ttt gtg tgc cct gct gaa taa ctt cta tcc cag aga      432
Glu Leu Pro Leu Phe Val Cys Pro Ala Glu     Leu Leu Ser Gln Arg
        130                 135                     140 ggc caa agt acc agt gga agg tgg ata a                                460
Gly Gln Ser Thr Ser Gly Arg Trp Ile
            145                 150

<210> SEQ ID NO 23
<211> LENGTH: 465
<212> TYPE: DNA
<213> ORGANISM: Homo sapiens
<220> FEATURE:
<221> NAME/KEY: CDS
<222> LOCATION: (1)..(465)
<220> FEATURE:
<221> NAME/KEY: modified_base
<222> LOCATION: (2)..(2)
<223> OTHER INFORMATION: a, c, g, t, unknown or other
<220> FEATURE:
<221> NAME/KEY: modified_base
<222> LOCATION: (16)..(16)
<223> OTHER INFORMATION: a, c, g, t, unknown or other
<220> FEATURE:
<221> NAME/KEY: modified_base
<222> LOCATION: (449)..(449)
<223> OTHER INFORMATION: a, c, g, t, unknown or other

<400> SEQUENCE: 23 cng cct gtt agg tcc ntg cga ctc tcc tgt gca gcg tct gga ttc atc      48
Xaa Pro Val Arg Ser Xaa Arg Leu Ser Cys Ala Ala Ser Gly Phe Ile
1               5                   10                  15 ttc agt agc tat ggc atg cac tgg gtc cgc cag gct cca ggc aag ggg      96
Phe Ser Ser Tyr Gly Met His Trp Val Arg Gln Ala Pro Gly Lys Gly
            20                  25                  30 ctg gag tgg gtg gca att ata tgg tat gat gga agt aat aaa tac tat      144
Leu Glu Trp Val Ala Ile Ile Trp Tyr Asp Gly Ser Asn Lys Tyr Tyr
        35                  40                  45 gca gac tcc gtg aag ggc cga ttc acc atc tcc aga gac aat tcc aag      192
Ala Asp Ser Val Lys Gly Arg Phe Thr Ile Ser Arg Asp Asn Ser Lys
    50                  55                  60 aac acg ctg tat ctg caa atg aac agc ctg aga gcc gag gac acg gct      240
Asn Thr Leu Tyr Leu Gln Met Asn Ser Leu Arg Ala Glu Asp Thr Ala
65                  70                  75                  80 gtg tat tac tgt gcg aga gac ggg ggg cca cgg tgg ttt ctc gct tct      288
Val Tyr Tyr Cys Ala Arg Asp Gly Gly Pro Arg Trp Phe Leu Ala Ser
                85                  90                  95 gac tac tgg ggc cag gga acc ctg gtc acc gtc tcc tca gcc tcc acc      336
Asp Tyr Trp Gly Gln Gly Thr Leu Val Thr Val Ser Ser Ala Ser Thr
            100                 105                 110 aag ggc cca tcg gtc ttc ccc ctg gcg ccc tgc tcc agg agc acc ctt      384
Lys Gly Pro Ser Val Phe Pro Leu Ala Pro Cys Ser Arg Ser Thr Leu
        115                 120                 125 cga gag cac agc ggc cct ggg ctg cct ggt tca agg act act ttc ccc      432
Arg Glu His Ser Gly Pro Gly Leu Pro Gly Ser Arg Thr Thr Phe Pro
    130                 135                 140 gaa ccg gtg acg gtg tnc gtt gga act cat gac                          465
Glu Pro Val Thr Val Xaa Val Gly Thr His Asp
145                 150                 155

<210> SEQ ID NO 24
```

```
<211> LENGTH: 456
<212> TYPE: DNA
<213> ORGANISM: Homo sapiens
<220> FEATURE:
<221> NAME/KEY: CDS
<222> LOCATION: (1)..(456)
<220> FEATURE:
<221> NAME/KEY: modified_base
<222> LOCATION: (62)..(62)
<223> OTHER INFORMATION: a, c, g, t, unknown or other

<400> SEQUENCE: 24 agt ctc cag act ccc tgg ttg tgt ctc tgg gcg aga ggg cca cca tca      48
Ser Leu Gln Thr Pro Trp Leu Cys Leu Trp Ala Arg Gly Pro Pro Ser
1               5                   10                  15 act gca agt cca gnc aga gta ttt tat aca gct cca aca atc aaa aac      96
Thr Ala Ser Pro Xaa Arg Val Phe Tyr Thr Ala Pro Thr Ile Lys Asn
            20                  25                  30 ttc tta gct tgg tac cag cag aaa cca gga cag cct ccg aag ttg ctc     144
Phe Leu Ala Trp Tyr Gln Gln Lys Pro Gly Gln Pro Pro Lys Leu Leu
        35                  40                  45 att tac tgg gca tct att cgg gaa tcc ggg gtc cct gac cga ttc agt     192
Ile Tyr Trp Ala Ser Ile Arg Glu Ser Gly Val Pro Asp Arg Phe Ser
50                  55                  60 ggc agc ggg tct ggg aca gat ttc act ctc acc atc agc agc ctg cag     240
Gly Ser Gly Ser Gly Thr Asp Phe Thr Leu Thr Ile Ser Ser Leu Gln
65                  70                  75                  80 gct gaa gat gtg gca gtt tat tac tgt cag cag tat tat agt att ccg     288
Ala Glu Asp Val Ala Val Tyr Tyr Cys Gln Gln Tyr Tyr Ser Ile Pro
                85                  90                  95 tgc act ttt ggc cag ggg acc aag ctg gag atc aaa cga act gtg gct     336
Cys Thr Phe Gly Gln Gly Thr Lys Leu Glu Ile Lys Arg Thr Val Ala
            100                 105                 110 gca cca tct gtc ttc atc ttc ccg cca tct gat gag cag ttg aaa tct     384
Ala Pro Ser Val Phe Ile Phe Pro Pro Ser Asp Glu Gln Leu Lys Ser
        115                 120                 125 gga act gcc tct gtt gtg tgc ctg ctg aat aac ttc tat ccc aga aag     432
Gly Thr Ala Ser Val Val Cys Leu Leu Asn Asn Phe Tyr Pro Arg Lys
130                 135                 140 gcc aaa gta cat gaa ggg ttc aaa                                     456
Ala Lys Val His Glu Gly Phe Lys
145                 150

<210> SEQ ID NO 25
<211> LENGTH: 532
<212> TYPE: DNA
<213> ORGANISM: Homo sapiens
<220> FEATURE:
<221> NAME/KEY: CDS
<222> LOCATION: (1)..(531)
<220> FEATURE:
<221> NAME/KEY: modified_base
<222> LOCATION: (481)..(481)
<223> OTHER INFORMATION: a, c, g, t, unknown or other
<220> FEATURE:
<221> NAME/KEY: modified_base
<222> LOCATION: (501)..(501)
<223> OTHER INFORMATION: a, c, g, t, unknown or other
<220> FEATURE:
<221> NAME/KEY: modified_base
<222> LOCATION: (507)..(507)
<223> OTHER INFORMATION: a, c, g, t, unknown or other
<220> FEATURE:
<221> NAME/KEY: modified_base
<222> LOCATION: (524)..(524)
<223> OTHER INFORMATION: a, c, g, t, unknown or other

<400> SEQUENCE: 25
```

```
ggc gtg gyc cag cct gkg agg tcc ctg aga ctc tcc tgt gca gcg tct      48
Gly Val Xaa Gln Pro Xaa Arg Ser Leu Arg Leu Ser Cys Ala Ala Ser
 1               5                  10                  15 gga ttc ayc ttc agt arc tat ggc atg cac tgg gtc cgc cag gct cca      96
Gly Phe Xaa Phe Ser Xaa Tyr Gly Met His Trp Val Arg Gln Ala Pro
             20                  25                  30 ggc aag ggg ctg gag tgg gtg gca att ata tgg tat gat gga agt agc     144
Gly Lys Gly Leu Glu Trp Val Ala Ile Ile Trp Tyr Asp Gly Ser Ser
         35                  40                  45 aaa tac tat gca gac tcc gtg aag ggc cga ttc acc atc tcc aga gac     192
Lys Tyr Tyr Ala Asp Ser Val Lys Gly Arg Phe Thr Ile Ser Arg Asp
     50                  55                  60 aat tcc aag aac acg ctg tat ctg caa atg aac agc ctg aga gcc gag     240
Asn Ser Lys Asn Thr Leu Tyr Leu Gln Met Asn Ser Leu Arg Ala Glu
 65                  70                  75                  80 gac acg gct gtg tat tac tgt gcg aga gac ggg ggg cca cgg tgg ttt     288
Asp Thr Ala Val Tyr Tyr Cys Ala Arg Asp Gly Gly Pro Arg Trp Phe
                 85                  90                  95 ctc gct tct gac tac tgg ggc cag gga acc ctg gtc acc gtc tcc tca     336
Leu Ala Ser Asp Tyr Trp Gly Gln Gly Thr Leu Val Thr Val Ser Ser
            100                 105                 110 gcc tcc acc aag ggc cca tcg gtc ttc ccc ctg gcg ccc tgc tcc agg     384
Ala Ser Thr Lys Gly Pro Ser Val Phe Pro Leu Ala Pro Cys Ser Arg
        115                 120                 125 agc acc ttc cga gag cac agc ggc cct ggg ctg cct ggt caa gga cta     432
Ser Thr Phe Arg Glu His Ser Gly Pro Gly Leu Pro Gly Gln Gly Leu
    130                 135                 140 ctt ccc cga amc ggt gac ggt gtc gtg gaa ctc agg cgc tct gac cag     480
Leu Pro Arg Xaa Gly Asp Gly Val Val Glu Leu Arg Arg Ser Asp Gln
145                 150                 155                 160 ngg cgt gca caa ttc cca gcn gtc ctn aag gtt gaa atc gta ang gtt     528
Xaa Arg Ala Gln Phe Pro Ala Val Xaa Lys Val Glu Ile Val Xaa Val
                165                 170                 175 caa a                                                                532
Gln

<210> SEQ ID NO 26
<211> LENGTH: 463
<212> TYPE: DNA
<213> ORGANISM: Homo sapiens
<220> FEATURE:
<221> NAME/KEY: CDS
<222> LOCATION: (1)..(462)
<220> FEATURE:
<221> NAME/KEY: modified_base
<222> LOCATION: (455)..(455)
<223> OTHER INFORMATION: a, c, g, t, unknown or other
<220> FEATURE:
<221> NAME/KEY: modified_base
<222> LOCATION: (459)..(459)
<223> OTHER INFORMATION: a, c, g, t, unknown or other

<400> SEQUENCE: 26 act cag tct cca gac tcc ctg gct gtg tct ctg ggc gag agg gcc acc      48
Thr Gln Ser Pro Asp Ser Leu Ala Val Ser Leu Gly Glu Arg Ala Thr
 1               5                  10                  15 atc aac tgc aag tcc agc cag agt gtt tta tac ggc tcc aag aat cag      96
Ile Asn Cys Lys Ser Ser Gln Ser Val Leu Tyr Gly Ser Lys Asn Gln
             20                  25                  30 aac tac tta gct tgg tac cag cag aaa cca gga cag cct cct aag ctg     144
Asn Tyr Leu Ala Trp Tyr Gln Gln Lys Pro Gly Gln Pro Pro Lys Leu
         35                  40                  45
```

```
ctc att tac tgg gca tct acc cgg gaa tcc ggg gtc cct gac cga ttc      192
Leu Ile Tyr Trp Ala Ser Thr Arg Glu Ser Gly Val Pro Asp Arg Phe
 50              55                  60 agg ggc agc ggg tct agg aca gat ttc act ctc acc atc agc agc ctg      240
Arg Gly Ser Gly Ser Arg Thr Asp Phe Thr Leu Thr Ile Ser Ser Leu
 65              70                  75                  80 cag gct gaa gat gtg gca gtt tac ttc tgt cac caa tat tat agt act      288
Gln Ala Glu Asp Val Ala Val Tyr Phe Cys His Gln Tyr Tyr Ser Thr
                 85                  90                  95 ccg tgg acg ttc ggc caa ggg acc aag gtg gaa atc aaa cga act gtg      336
Pro Trp Thr Phe Gly Gln Gly Thr Lys Val Glu Ile Lys Arg Thr Val
            100                 105                 110 gct gca cca tct gtc ttc atc ttc ccg cca tct gat gag cag ttg aaa      384
Ala Ala Pro Ser Val Phe Ile Phe Pro Pro Ser Asp Glu Gln Leu Lys
            115                 120                 125 tct gga act gcc tct gtt gtg tgc ctg ctg aat aac ttg tat ccc aga      432
Ser Gly Thr Ala Ser Val Val Cys Leu Leu Asn Asn Leu Tyr Pro Arg
130             135                 140 aag cca agg aca cga aag gtc ana ccn acc c                            463
Lys Pro Arg Thr Arg Lys Val Xaa Pro Thr
145             150
```

<210> SEQ ID NO 27
<211> LENGTH: 417
<212> TYPE: DNA
<213> ORGANISM: Homo sapiens
<220> FEATURE:
<221> NAME/KEY: CDS
<222> LOCATION: (1)..(417)
<220> FEATURE:
<221> NAME/KEY: modified_base
<222> LOCATION: (9)..(9)
<223> OTHER INFORMATION: a, c, g, t, unknown or other
<220> FEATURE:
<221> NAME/KEY: modified_base
<222> LOCATION: (15)..(15)
<223> OTHER INFORMATION: a, c, g, t, unknown or other
<220> FEATURE:
<221> NAME/KEY: modified_base
<222> LOCATION: (59)..(59)
<223> OTHER INFORMATION: a, c, g, t, unknown or other
<220> FEATURE:
<221> NAME/KEY: modified_base
<222> LOCATION: (68)..(68)
<223> OTHER INFORMATION: a, c, g, t, unknown or other
<220> FEATURE:
<221> NAME/KEY: modified_base
<222> LOCATION: (161)..(161)
<223> OTHER INFORMATION: a, c, g, t, unknown or other
<220> FEATURE:
<221> NAME/KEY: modified_base
<222> LOCATION: (306)..(306)
<223> OTHER INFORMATION: a, c, g, t, unknown or other
<220> FEATURE:
<221> NAME/KEY: modified_base
<222> LOCATION: (309)..(309)
<223> OTHER INFORMATION: a, c, g, t, unknown or other
<220> FEATURE:
<221> NAME/KEY: modified_base
<222> LOCATION: (319)..(319)
<223> OTHER INFORMATION: a, c, g, t, unknown or other
<220> FEATURE:
<221> NAME/KEY: modified_base
<222> LOCATION: (323)..(323)
<223> OTHER INFORMATION: a, c, g, t, unknown or other
<220> FEATURE:
<221> NAME/KEY: modified_base
<222> LOCATION: (326)..(326)
<223> OTHER INFORMATION: a, c, g, t, unknown or other
<220> FEATURE:
<221> NAME/KEY: modified_base
<222> LOCATION: (332)..(332)

```
<223> OTHER INFORMATION: a, c, g, t, unknown or other
<220> FEATURE:
<221> NAME/KEY: modified_base
<222> LOCATION: (340)..(340)
<223> OTHER INFORMATION: a, c, g, t, unknown or other
<220> FEATURE:
<221> NAME/KEY: modified_base
<222> LOCATION: (345)..(345)
<223> OTHER INFORMATION: a, c, g, t, unknown or other
<220> FEATURE:
<221> NAME/KEY: modified_base
<222> LOCATION: (349)..(349)
<223> OTHER INFORMATION: a, c, g, t, unknown or other
<220> FEATURE:
<221> NAME/KEY: modified_base
<222> LOCATION: (358)..(358)
<223> OTHER INFORMATION: a, c, g, t, unknown or other
<220> FEATURE:
<221> NAME/KEY: modified_base
<222> LOCATION: (364)..(364)
<223> OTHER INFORMATION: a, c, g, t, unknown or other
<220> FEATURE:
<221> NAME/KEY: modified_base
<222> LOCATION: (381)..(384)
<223> OTHER INFORMATION: a, c, g, t, unknown or other
<220> FEATURE:
<221> NAME/KEY: modified_base
<222> LOCATION: (392)..(392)
<223> OTHER INFORMATION: a, c, g, t, unknown or other
<220> FEATURE:
<221> NAME/KEY: modified_base
<222> LOCATION: (396)..(398)
<223> OTHER INFORMATION: a, c, g, t, unknown or other
<220> FEATURE:
<221> NAME/KEY: modified_base
<222> LOCATION: (405)..(405)
<223> OTHER INFORMATION: a, c, g, t, unknown or other
<220> FEATURE:
<221> NAME/KEY: modified_base
<222> LOCATION: (411)..(411)
<223> OTHER INFORMATION: a, c, g, t, unknown or other
<220> FEATURE:
<221> NAME/KEY: modified_base
<222> LOCATION: (413)..(413)
<223> OTHER INFORMATION: a, c, g, t, unknown or other
<220> FEATURE:
<221> NAME/KEY: modified_base
<222> LOCATION: (417)..(417)
<223> OTHER INFORMATION: a, c, g, t, unknown or other

<400> SEQUENCE: 27 cgt gat ccn cct ggn tgg tcc ctg aga ctc tcc tgt gca gcg tct gga      48
Arg Asp Pro Pro Gly Trp Ser Leu Arg Leu Ser Cys Ala Ala Ser Gly
 1               5                  10                  15 ttc atc ttc ant aac tat tnc atg cac tgg gtc cgc cag gct cca ggc      96
Phe Ile Phe Xaa Asn Tyr Xaa Met His Trp Val Arg Gln Ala Pro Gly
            20                  25                  30 aag ggg ctg gag tgg gtg gca att ata tgg tat gat gga agt agc aaa     144
Lys Gly Leu Glu Trp Val Ala Ile Ile Trp Tyr Asp Gly Ser Ser Lys
        35                  40                  45 tac tat gca gac tcc gng aag ggc cga ttc acc atc tcc aga gac aat     192
Tyr Tyr Ala Asp Ser Xaa Lys Gly Arg Phe Thr Ile Ser Arg Asp Asn
    50                  55                  60 tcc aag aac acg ctg tat ctg caa atg aac agc ctg aga gcc gag gac     240
Ser Lys Asn Thr Leu Tyr Leu Gln Met Asn Ser Leu Arg Ala Glu Asp
65                  70                  75                  80 acg gct gat gta tta ctg tgc gag aga cgg ttg ggc cac ggt ggc ttc     288
Thr Ala Asp Val Leu Leu Cys Glu Arg Arg Leu Gly His Gly Gly Phe
                85                  90                  95 tcg ctt ctg act act ggn gcn cag ggc aac nct gnc tna ccg tnt tcc     336
Ser Leu Leu Thr Thr Gly Ala Gln Gly Asn Xaa Xaa Xaa Pro Xaa Ser
            100                 105                 110
```

| | | | | | | | | | | | | |
|---|---|---|---|---|---|---|---|---|---|---|---|---|
| tca | ncc | ctn | tac | nca | agg | gcc | ncc | att | ngg | tct | ttc | ccc | cct | ggn | nnn | 384 |
| Ser | Xaa | Xaa | Tyr | Xaa | Arg | Ala | Xaa | Ile | Xaa | Ser | Phe | Pro | Pro | Gly | Xaa | |
| | | 115 | | | | 120 | | | | | 125 | | | | | |

| | | | | | | | | | |
|---|---|---|---|---|---|---|---|---|---|
| cct | gct | cna | tgn | nnc | acc | ctn | cga | can | cna | can | 417 |
| Pro | Ala | Xaa | Xaa | Xaa | Thr | Xaa | Arg | Xaa | Xaa | Xaa | |
| | 130 | | | | | 135 | | | | | |

<210> SEQ ID NO 28
<211> LENGTH: 453
<212> TYPE: DNA
<213> ORGANISM: Homo sapiens
<220> FEATURE:
<221> NAME/KEY: CDS
<222> LOCATION: (1)..(453)
<220> FEATURE:
<221> NAME/KEY: modified_base
<222> LOCATION: (28)..(28)
<223> OTHER INFORMATION: a, c, g, t, unknown or other
<220> FEATURE:
<221> NAME/KEY: modified_base
<222> LOCATION: (366)..(366)
<223> OTHER INFORMATION: a, c, g, t, unknown or other
<220> FEATURE:
<221> NAME/KEY: modified_base
<222> LOCATION: (426)..(426)
<223> OTHER INFORMATION: a, c, g, t, unknown or other
<220> FEATURE:
<221> NAME/KEY: modified_base
<222> LOCATION: (438)..(438)
<223> OTHER INFORMATION: a, c, g, t, unknown or other

<400> SEQUENCE: 28 ttc gtg gct gtg tct ctt ggc gag agg ncc acc atc aac tgc aag tcc    48
Phe Val Ala Val Ser Leu Gly Glu Arg Xaa Thr Ile Asn Cys Lys Ser
1               5                   10                  15 agc cag agt att tta tac agc tcc aac aat caa aac ttc tta gct tgg    96
Ser Gln Ser Ile Leu Tyr Ser Ser Asn Asn Gln Asn Phe Leu Ala Trp
            20                  25                  30 tac cag cag aaa cca gga cag cct ccg aag ttg ctc att tac tgg gca   144
Tyr Gln Gln Lys Pro Gly Gln Pro Pro Lys Leu Leu Ile Tyr Trp Ala
        35                  40                  45 tct att cgg gaa tcc ggg gtc cct gac cga ttc agt ggc agc ggg tct   192
Ser Ile Arg Glu Ser Gly Val Pro Asp Arg Phe Ser Gly Ser Gly Ser
    50                  55                  60 ggg aca gat ttc act ctc acc atc agc agc ctg cag gct gaa gat gtg   240
Gly Thr Asp Phe Thr Leu Thr Ile Ser Ser Leu Gln Ala Glu Asp Val
65                  70                  75                  80 gca gtt tat tac tgt cag cag tat tat agt att ccg tgc act ttt ggc   288
Ala Val Tyr Tyr Cys Gln Gln Tyr Tyr Ser Ile Pro Cys Thr Phe Gly
                85                  90                  95 cag ggg acc aag ctg gag atc aaa cga act gtg gct gca cca tct gtc   336
Gln Gly Thr Lys Leu Glu Ile Lys Arg Thr Val Ala Ala Pro Ser Val
            100                 105                 110 ttc atc ttc ccg cca tct gat gag cca agn tg aaa atc tgg aac tgc    384
Phe Ile Phe Pro Pro Ser Asp Glu Pro Xaa Leu Lys Ile Trp Asn Cys
        115                 120                 125 ctc tgt tgt gtg ccc tgc ttg aat aac ttc tat ccc aga gan ggc caa   432
Leu Cys Cys Val Pro Cys Leu Asn Asn Phe Tyr Pro Arg Xaa Gly Gln
    130                 135                 140 agt ccn gtg gaa ggt gga tac                                       453
Ser Pro Val Glu Gly Gly Tyr
145                 150

<210> SEQ ID NO 29
<211> LENGTH: 350

```
<212> TYPE: DNA
<213> ORGANISM: Homo sapiens
<220> FEATURE:
<221> NAME/KEY: CDS
<222> LOCATION: (1)..(348)
<220> FEATURE:
<221> NAME/KEY: modified_base
<222> LOCATION: (41)..(41)
<223> OTHER INFORMATION: a, c, g, t, unknown or other
<220> FEATURE:
<221> NAME/KEY: modified_base
<222> LOCATION: (48)..(48)
<223> OTHER INFORMATION: a, c, g, t, unknown or other
<220> FEATURE:
<221> NAME/KEY: modified_base
<222> LOCATION: (65)..(65)
<223> OTHER INFORMATION: a, c, g, t, unknown or other
<220> FEATURE:
<221> NAME/KEY: modified_base
<222> LOCATION: (105)..(105)
<223> OTHER INFORMATION: a, c, g, t, unknown or other
<220> FEATURE:
<221> NAME/KEY: modified_base
<222> LOCATION: (132)..(132)
<223> OTHER INFORMATION: a, c, g, t, unknown or other
<220> FEATURE:
<221> NAME/KEY: modified_base
<222> LOCATION: (181)..(181)
<223> OTHER INFORMATION: a, c, g, t, unknown or other
<220> FEATURE:
<221> NAME/KEY: modified_base
<222> LOCATION: (194)..(194)
<223> OTHER INFORMATION: a, c, g, t, unknown or other
<220> FEATURE:
<221> NAME/KEY: modified_base
<222> LOCATION: (203)..(203)
<223> OTHER INFORMATION: a, c, g, t, unknown or other
<220> FEATURE:
<221> NAME/KEY: modified_base
<222> LOCATION: (215)..(215)
<223> OTHER INFORMATION: a, c, g, t, unknown or other
<220> FEATURE:
<221> NAME/KEY: modified_base
<222> LOCATION: (218)..(218)
<223> OTHER INFORMATION: a, c, g, t, unknown or other
<220> FEATURE:
<221> NAME/KEY: modified_base
<222> LOCATION: (228)..(228)
<223> OTHER INFORMATION: a, c, g, t, unknown or other
<220> FEATURE:
<221> NAME/KEY: modified_base
<222> LOCATION: (231)..(231)
<223> OTHER INFORMATION: a, c, g, t, unknown or other
<220> FEATURE:
<221> NAME/KEY: modified_base
<222> LOCATION: (245)..(245)
<223> OTHER INFORMATION: a, c, g, t, unknown or other
<220> FEATURE:
<221> NAME/KEY: modified_base
<222> LOCATION: (250)..(252)
<223> OTHER INFORMATION: a, c, g, t, unknown or other
<220> FEATURE:
<221> NAME/KEY: modified_base
<222> LOCATION: (257)..(257)
<223> OTHER INFORMATION: a, c, g, t, unknown or other
<220> FEATURE:
<221> NAME/KEY: modified_base
<222> LOCATION: (259)..(259)
<223> OTHER INFORMATION: a, c, g, t, unknown or other
<220> FEATURE:
<221> NAME/KEY: modified_base
<222> LOCATION: (265)..(265)
<223> OTHER INFORMATION: a, c, g, t, unknown or other
<220> FEATURE:
<221> NAME/KEY: modified_base
<222> LOCATION: (282)..(282)
<223> OTHER INFORMATION: a, c, g, t, unknown or other
<220> FEATURE:
<221> NAME/KEY: modified_base
```

```
<222> LOCATION: (288)..(288)
<223> OTHER INFORMATION: a, c, g, t, unknown or other
<220> FEATURE:
<221> NAME/KEY: modified_base
<222> LOCATION: (292)..(292)
<223> OTHER INFORMATION: a, c, g, t, unknown or other
<220> FEATURE:
<221> NAME/KEY: modified_base
<222> LOCATION: (305)..(305)
<223> OTHER INFORMATION: a, c, g, t, unknown or other
<220> FEATURE:
<221> NAME/KEY: modified_base
<222> LOCATION: (310)..(310)
<223> OTHER INFORMATION: a, c, g, t, unknown or other
<220> FEATURE:
<221> NAME/KEY: modified_base
<222> LOCATION: (313)..(314)
<223> OTHER INFORMATION: a, c, g, t, unknown or other
<220> FEATURE:
<221> NAME/KEY: modified_base
<222> LOCATION: (318)..(318)
<223> OTHER INFORMATION: a, c, g, t, unknown or other
<220> FEATURE:
<221> NAME/KEY: modified_base
<222> LOCATION: (323)..(323)
<223> OTHER INFORMATION: a, c, g, t, unknown or other
<220> FEATURE:
<221> NAME/KEY: modified_base
<222> LOCATION: (325)..(325)
<223> OTHER INFORMATION: a, c, g, t, unknown or other
<220> FEATURE:
<221> NAME/KEY: modified_base
<222> LOCATION: (327)..(327)
<223> OTHER INFORMATION: a, c, g, t, unknown or other
<220> FEATURE:
<221> NAME/KEY: modified_base
<222> LOCATION: (333)..(333)
<223> OTHER INFORMATION: a, c, g, t, unknown or other
<220> FEATURE:
<221> NAME/KEY: modified_base
<222> LOCATION: (335)..(335)
<223> OTHER INFORMATION: a, c, g, t, unknown or other
<220> FEATURE:
<221> NAME/KEY: modified_base
<222> LOCATION: (338)..(338)
<223> OTHER INFORMATION: a, c, g, t, unknown or other
<220> FEATURE:
<221> NAME/KEY: modified_base
<222> LOCATION: (341)..(341)
<223> OTHER INFORMATION: a, c, g, t, unknown or other
<220> FEATURE:
<221> NAME/KEY: modified_base
<222> LOCATION: (343)..(344)
<223> OTHER INFORMATION: a, c, g, t, unknown or other
<220> FEATURE:
<221> NAME/KEY: modified_base
<222> LOCATION: (347)..(347)
<223> OTHER INFORMATION: a, c, g, t, unknown or other
<220> FEATURE:
<221> NAME/KEY: modified_base
<222> LOCATION: (349)..(349)
<223> OTHER INFORMATION: a, c, g, t, unknown or other

<400> SEQUENCE: 29 ctc acc tgc act gtc tct ggt ggc tcc atc agt agt tac tnt tgg agn      48
Leu Thr Cys Thr Val Ser Gly Gly Ser Ile Ser Ser Tyr Xaa Trp Xaa
1               5                   10                  15 tgg atc cgg cag ccc gna ggg aag gga ctg gag tgg att ggg tgt ttc      96
Trp Ile Arg Gln Pro Xaa Gly Lys Gly Leu Glu Trp Ile Gly Cys Phe
            20                  25                  30 tat tac agn ggg agc acc aac tac aac ccc tcc ctn aag agt cat gtc     144
Tyr Tyr Xaa Gly Ser Thr Asn Tyr Asn Pro Ser Xaa Lys Ser His Val
        35                  40                  45 acc ata tca gta gac acg tcc aag aac cag ttc tac ntg aag ctg agc     192
Thr Ile Ser Val Asp Thr Ser Lys Asn Gln Phe Tyr Xaa Lys Leu Ser
```

```
                50                  55                  60
tnt gtg acc gnt gcg gac acg gnc gng aat aac tgn gcn aga gat agg        240
Xaa Val Thr Xaa Ala Asp Thr Xaa Xaa Asn Asn Xaa Ala Arg Asp Arg
 65                  70                  75                  80 gga gna gtg nnn tgg cnt nct act ntg act act gag gcc agn gaa ccn        288
Gly Xaa Val Xaa Trp Xaa Xaa Thr Xaa Thr Thr Glu Ala Xaa Glu Pro
                 85                  90                  95 tgg ntc aca gta atc cnt aag nct nnc aan caa ang ngn ccc aan gng        336
Trp Xaa Thr Val Ile Xaa Lys Xaa Xaa Xaa Gln Xaa Xaa Pro Xaa Xaa
            100                 105                 110 ana cnt nnc tnc nc                                                     350
Xaa Xaa Xaa Xaa
        115

<210> SEQ ID NO 30
<211> LENGTH: 476
<212> TYPE: DNA
<213> ORGANISM: Homo sapiens
<220> FEATURE:
<221> NAME/KEY: CDS
<222> LOCATION: (1)..(399)
<220> FEATURE:
<221> NAME/KEY: modified_base
<222> LOCATION: (13)..(13)
<223> OTHER INFORMATION: a, c, g, t, unknown or other
<220> FEATURE:
<221> NAME/KEY: modified_base
<222> LOCATION: (67)..(67)
<223> OTHER INFORMATION: a, c, g, t, unknown or other
<220> FEATURE:
<221> NAME/KEY: modified_base
<222> LOCATION: (388)..(388)
<223> OTHER INFORMATION: a, c, g, t, unknown or other
<220> FEATURE:
<221> NAME/KEY: modified_base
<222> LOCATION: (391)..(391)
<223> OTHER INFORMATION: a, c, g, t, unknown or other
<220> FEATURE:
<221> NAME/KEY: CDS
<222> LOCATION: (403)..(474)
<220> FEATURE:
<221> NAME/KEY: modified_base
<222> LOCATION: (405)..(405)
<223> OTHER INFORMATION: a, c, g, t, unknown or other
<220> FEATURE:
<221> NAME/KEY: modified_base
<222> LOCATION: (423)..(423)
<223> OTHER INFORMATION: a, c, g, t, unknown or other
<220> FEATURE:
<221> NAME/KEY: modified_base
<222> LOCATION: (435)..(435)
<223> OTHER INFORMATION: a, c, g, t, unknown or other
<220> FEATURE:
<221> NAME/KEY: modified_base
<222> LOCATION: (441)..(442)
<223> OTHER INFORMATION: a, c, g, t, unknown or other
<220> FEATURE:
<221> NAME/KEY: modified_base
<222> LOCATION: (445)..(446)
<223> OTHER INFORMATION: a, c, g, t, unknown or other
<220> FEATURE:
<221> NAME/KEY: modified_base
<222> LOCATION: (451)..(452)
<223> OTHER INFORMATION: a, c, g, t, unknown or other
<220> FEATURE:
<221> NAME/KEY: modified_base
<222> LOCATION: (463)..(463)
<223> OTHER INFORMATION: a, c, g, t, unknown or other
<220> FEATURE:
<221> NAME/KEY: modified_base
<222> LOCATION: (467)..(467)
<223> OTHER INFORMATION: a, c, g, t, unknown or other
<220> FEATURE:
<221> NAME/KEY: modified_base
```

-continued

```
<222> LOCATION: (470)..(471)
<223> OTHER INFORMATION: a, c, g, t, unknown or other
<220> FEATURE:
<221> NAME/KEY: modified_base
<222> LOCATION: (473)..(473)
<223> OTHER INFORMATION: a, c, g, t, unknown or other
<220> FEATURE:
<221> NAME/KEY: modified_base
<222> LOCATION: (475)..(475)
<223> OTHER INFORMATION: a, c, g, t, unknown or other

<400> SEQUENCE: 30 tct ttg gta gcg ngt ctt ggc gag agg ccc acc atc aac tgc aag tcc    48
Ser Leu Val Ala Xaa Leu Gly Glu Arg Pro Thr Ile Asn Cys Lys Ser
1               5                  10                  15 agc cag agt gtt tta tac ngc tcc aag aat cag aac tac tta gct tgg    96
Ser Gln Ser Val Leu Tyr Xaa Ser Lys Asn Gln Asn Tyr Leu Ala Trp
            20                  25                  30 tac cag cag aaa cca gga cag cct cct aag ctg ctc att tac tgg gca   144
Tyr Gln Gln Lys Pro Gly Gln Pro Pro Lys Leu Leu Ile Tyr Trp Ala
        35                  40                  45 tct acc cgg gaa tcc ggg gtc cct gac cga ttc agg ggc agc ggg tct   192
Ser Thr Arg Glu Ser Gly Val Pro Asp Arg Phe Arg Gly Ser Gly Ser
    50                  55                  60 agg aca gat ttc act ctc acc atc agc agc ctg cag gct gaa gat gtg   240
Arg Thr Asp Phe Thr Leu Thr Ile Ser Ser Leu Gln Ala Glu Asp Val
65                  70                  75                  80 gca gtt tac ttc tgt cac caa tat tat agt act ccg tgg acg ttc ggc   288
Ala Val Tyr Phe Cys His Gln Tyr Tyr Ser Thr Pro Trp Thr Phe Gly
                85                  90                  95 caa ggg acc aag gtg gaa atc aaa cga act gtg gct gca cca tct gtc   336
Gln Gly Thr Lys Val Glu Ile Lys Arg Thr Val Ala Ala Pro Ser Val
            100                 105                 110 ttc atc ttc ccg cca tct gat gag cac ctt gaa att ctg gaa ctg cct   384
Phe Ile Phe Pro Pro Ser Asp Glu His Leu Glu Ile Leu Glu Leu Pro
        115                 120                 125 ctg ntg ngt gcc tgc tga acn aac tct atc ccc aga gan ggc cca aaa   432
Leu Xaa Xaa Ala Cys     Thr Asn Ser Ile Pro Arg Xaa Gly Pro Lys
    130                 135                 140 gtn tca agn ngg nna ggc nng ata acg cct ntt cnc cnn cnt nc        476
Val Ser Xaa Xaa Xaa Gly Xaa Ile Thr Pro Xaa Xaa Xaa Xaa
145                 150                 155

<210> SEQ ID NO 31
<211> LENGTH: 471
<212> TYPE: DNA
<213> ORGANISM: Homo sapiens
<220> FEATURE:
<221> NAME/KEY: CDS
<222> LOCATION: (1)..(471)
<220> FEATURE:
<221> NAME/KEY: modified_base
<222> LOCATION: (16)..(16)
<223> OTHER INFORMATION: a, c, g, t, unknown or other
<220> FEATURE:
<221> NAME/KEY: modified_base
<222> LOCATION: (59)..(59)
<223> OTHER INFORMATION: a, c, g, t, unknown or other
<220> FEATURE:
<221> NAME/KEY: modified_base
<222> LOCATION: (332)..(332)
<223> OTHER INFORMATION: a, c, g, t, unknown or other
<220> FEATURE:
<221> NAME/KEY: modified_base
<222> LOCATION: (345)..(345)
<223> OTHER INFORMATION: a, c, g, t, unknown or other
<220> FEATURE:
<221> NAME/KEY: modified_base
```

```
<222> LOCATION: (375)..(375)
<223> OTHER INFORMATION: a, c, g, t, unknown or other
<220> FEATURE:
<221> NAME/KEY: modified_base
<222> LOCATION: (393)..(393)
<223> OTHER INFORMATION: a, c, g, t, unknown or other
<220> FEATURE:
<221> NAME/KEY: modified_base
<222> LOCATION: (407)..(407)
<223> OTHER INFORMATION: a, c, g, t, unknown or other
<220> FEATURE:
<221> NAME/KEY: modified_base
<222> LOCATION: (421)..(421)
<223> OTHER INFORMATION: a, c, g, t, unknown or other
<220> FEATURE:
<221> NAME/KEY: modified_base
<222> LOCATION: (452)..(453)
<223> OTHER INFORMATION: a, c, g, t, unknown or other
<220> FEATURE:
<221> NAME/KEY: modified_base
<222> LOCATION: (458)..(460)
<223> OTHER INFORMATION: a, c, g, t, unknown or other
<220> FEATURE:
<221> NAME/KEY: modified_base
<222> LOCATION: (466)..(466)
<223> OTHER INFORMATION: a, c, g, t, unknown or other
<220> FEATURE:
<221> NAME/KEY: modified_base
<222> LOCATION: (471)..(471)
<223> OTHER INFORMATION: a, c, g, t, unknown or other

<400> SEQUENCE: 31 aag cct ttt cag acc ntg ccc ttc acc tgc act gtc tct ggt ggc tcc      48
Lys Pro Phe Gln Thr Xaa Pro Phe Thr Cys Thr Val Ser Gly Gly Ser
1               5                   10                  15 atc agc agt tnt ggt tac tac tgg agc tgg atc cgc cag cac cca ggg      96
Ile Ser Ser Xaa Gly Tyr Tyr Trp Ser Trp Ile Arg Gln His Pro Gly
            20                  25                  30 aag ggc ctg gag tgg att ggg tac atc tat aac agt ggg agc acc tac     144
Lys Gly Leu Glu Trp Ile Gly Tyr Ile Tyr Asn Ser Gly Ser Thr Tyr
        35                  40                  45 tac aac ccg tcc ctc cag agt cga gtt acc ata tca gta gac acg tct     192
Tyr Asn Pro Ser Leu Gln Ser Arg Val Thr Ile Ser Val Asp Thr Ser
50                  55                  60 aag aac cag ttc tcc ctg aag ctg agc tct gtg act gcc gcg gac acg     240
Lys Asn Gln Phe Ser Leu Lys Leu Ser Ser Val Thr Ala Ala Asp Thr
65                  70                  75                  80 gcc gtg tat tac tgt gcg ggt cag aaa tgg tcc tac tac tac tac tac     288
Ala Val Tyr Tyr Cys Ala Gly Gln Lys Trp Ser Tyr Tyr Tyr Tyr Tyr
                85                  90                  95 ggt atg gac gtc tgg ggc caa ggg acc acg gtc acc gtc tcc tna gcc     336
Gly Met Asp Val Trp Gly Gln Gly Thr Thr Val Thr Val Ser Xaa Ala
            100                 105                 110 tcc acc aan ggc cca tcg gtc ttc ccc ctg gcg ccc tgn tct agg agc     384
Ser Thr Xaa Gly Pro Ser Val Phe Pro Leu Ala Pro Xaa Ser Arg Ser
        115                 120                 125 acc tcc can agc aca gac gga tnc tgg gcc tgc ctg nat caa tgg act     432
Thr Ser Xaa Ser Thr Asp Gly Xaa Trp Ala Cys Leu Xaa Gln Trp Thr
130                 135                 140 act ttc ccc gaa ccg gtt gnn tgt gnn ncc tgg naa ctn                 471
Thr Phe Pro Glu Pro Val Xaa Cys Xaa Xaa Trp Xaa Xaa
145                 150                 155

<210> SEQ ID NO 32
<211> LENGTH: 456
<212> TYPE: DNA
<213> ORGANISM: Homo sapiens
<220> FEATURE:
```

-continued

```
<221> NAME/KEY: CDS
<222> LOCATION: (1)..(456)
<220> FEATURE:
<221> NAME/KEY: modified_base
<222> LOCATION: (9)..(9)
<223> OTHER INFORMATION: a, c, g, t, unknown or other
<220> FEATURE:
<221> NAME/KEY: modified_base
<222> LOCATION: (16)..(16)
<223> OTHER INFORMATION: a, c, g, t, unknown or other
<220> FEATURE:
<221> NAME/KEY: modified_base
<222> LOCATION: (450)..(451)
<223> OTHER INFORMATION: a, c, g, t, unknown or other

<400> SEQUENCE: 32 aag cct ttn gag acc ntg ccc ctc acc tgc act gtc tct ggt ggc tcc        48
Lys Pro Xaa Glu Thr Xaa Pro Leu Thr Cys Thr Val Ser Gly Gly Ser
1               5                   10                  15 atc agt aat tac tac tgg agc tgg atc cgg cag ccc cca ggg aag gga        96
Ile Ser Asn Tyr Tyr Trp Ser Trp Ile Arg Gln Pro Pro Gly Lys Gly
            20                  25                  30 ctg gag tgg att ggg tat atc tat tac agt ggg agc acc aac tac aac       144
Leu Glu Trp Ile Gly Tyr Ile Tyr Tyr Ser Gly Ser Thr Asn Tyr Asn
        35                  40                  45 ccc tcc ctc aag agt cga gtc acc ata tca gta gac acg tcc aag aac       192
Pro Ser Leu Lys Ser Arg Val Thr Ile Ser Val Asp Thr Ser Lys Asn
    50                  55                  60 cag ttc tcc ctg aag ctg agc tct gtg acc gct gcg gac acg gcc gtg       240
Gln Phe Ser Leu Lys Leu Ser Ser Val Thr Ala Ala Asp Thr Ala Val
65                  70                  75                  80 tat tac tgt gcg aga ggg ccc ggg ggg agc tac tac tac tac ggt atg       288
Tyr Tyr Cys Ala Arg Gly Pro Gly Gly Ser Tyr Tyr Tyr Tyr Gly Met
                85                  90                  95 gac gtc tgg ggc caa ggg acc acg gtc acc gtc tcc tca gcc tcc acc       336
Asp Val Trp Gly Gln Gly Thr Thr Val Thr Val Ser Ser Ala Ser Thr
            100                 105                 110 aag ggc cca tcg gtc ttc ccc ctg gcg ccc tgc tcc agg agc acc tcc       384
Lys Gly Pro Ser Val Phe Pro Leu Ala Pro Cys Ser Arg Ser Thr Ser
        115                 120                 125 gag agc aca gcg gcc ctg ggc tgc ctg ggt caa gga cta ctt ccc cga       432
Glu Ser Thr Ala Ala Leu Gly Cys Leu Gly Gln Gly Leu Leu Pro Arg
    130                 135                 140 acc ggt gac ggt gtt cgn ngg aac                                       456
Thr Gly Asp Gly Val Arg Xaa Asn
145                 150

<210> SEQ ID NO 33
<211> LENGTH: 394
<212> TYPE: DNA
<213> ORGANISM: Homo sapiens
<220> FEATURE:
<221> NAME/KEY: CDS
<222> LOCATION: (1)..(393)

<400> SEQUENCE: 33 ctg tct gca tct gta gga gac aga gtc ata atc act tgc cgg gca agt        48
Leu Ser Ala Ser Val Gly Asp Arg Val Ile Ile Thr Cys Arg Ala Ser
1               5                   10                  15 caa aac atc acc gac cat tta aat tgg tat cag cag ata gca gga aaa        96
Gln Asn Ile Thr Asp His Leu Asn Trp Tyr Gln Gln Ile Ala Gly Lys
            20                  25                  30 gcc cct agg ccc ctg ata tac act gca tcc agt ttg caa ggt ggg gtc       144
Ala Pro Arg Pro Leu Ile Tyr Thr Ala Ser Ser Leu Gln Gly Gly Val
        35                  40                  45
```

```
cca tca agg ttc agt ggc agt gga tct ggg aca gat ttc act ctc acc      192
Pro Ser Arg Phe Ser Gly Ser Gly Ser Gly Thr Asp Phe Thr Leu Thr
 50                  55                  60 atc agc agt ctg caa cct gaa gat ttt tca act tac tac tgt caa cag      240
Ile Ser Ser Leu Gln Pro Glu Asp Phe Ser Thr Tyr Tyr Cys Gln Gln
 65                  70                  75                  80 agt tac agt acc ccg tgc agt ttt ggc cag ggg acc aag ctg gag atc      288
Ser Tyr Ser Thr Pro Cys Ser Phe Gly Gln Gly Thr Lys Leu Glu Ile
                 85                  90                  95 aaa cga act gtg gct gca cca tct gtc ttc atc ttc ccg cca tct gat      336
Lys Arg Thr Val Ala Ala Pro Ser Val Phe Ile Phe Pro Pro Ser Asp
            100                 105                 110 gag cag ttg aaa tct gga act gcc tct gtt gtg tgc ctg ctg aat aac      384
Glu Gln Leu Lys Ser Gly Thr Ala Ser Val Val Cys Leu Leu Asn Asn
        115                 120                 125 ttc tat ccc a                                                        394
Phe Tyr Pro
        130

<210> SEQ ID NO 34
<211> LENGTH: 310
<212> TYPE: DNA
<213> ORGANISM: Homo sapiens
<220> FEATURE:
<221> NAME/KEY: CDS
<222> LOCATION: (1)..(309)
<220> FEATURE:
<221> NAME/KEY: modified_base
<222> LOCATION: (122)..(122)
<223> OTHER INFORMATION: a, c, g, t, unknown or other

<400> SEQUENCE: 34 gtg aag gtc tcc tgc aag gct tct gga tac acc ttc agc ggc tac tat       48
Val Lys Val Ser Cys Lys Ala Ser Gly Tyr Thr Phe Ser Gly Tyr Tyr
  1               5                  10                  15 atg cac tgg gtg cga cag gcc cct gga caa ggg ctt gag tgg atg gga       96
Met His Trp Val Arg Gln Ala Pro Gly Gln Gly Leu Glu Trp Met Gly
             20                  25                  30 tcg atc cac cct aac agt ggt ggc ana aac ttt gca cag aag ttt cag      144
Ser Ile His Pro Asn Ser Gly Gly Xaa Asn Phe Ala Gln Lys Phe Gln
         35                  40                  45 ggc agg gtc acc atg acc agg gac acg tcc atc aac aca gcc tac ttg      192
Gly Arg Val Thr Met Thr Arg Asp Thr Ser Ile Asn Thr Ala Tyr Leu
 50                  55                  60 gag ctg agc agg ctg aga tct gac gac acg gcc gtg tat tac tgt gcg      240
Glu Leu Ser Arg Leu Arg Ser Asp Asp Thr Ala Val Tyr Tyr Cys Ala
 65                  70                  75                  80 aga gat aaa aac tac ggt gac tac gtc ttt gac tat tgg ggc cag gga      288
Arg Asp Lys Asn Tyr Gly Asp Tyr Val Phe Asp Tyr Trp Gly Gln Gly
                 85                  90                  95 acc ctg gtc acc gtc tcc tca g                                        310
Thr Leu Val Thr Val Ser Ser
            100

<210> SEQ ID NO 35
<211> LENGTH: 76
<212> TYPE: PRT
<213> ORGANISM: Homo sapiens

<400> SEQUENCE: 35

Val Ser Gly Gly Ser Ile Ser Ser Gly Gly Tyr Tyr Trp Ser Trp Ile
  1               5                  10                  15
```

```
Arg Gln His Pro Gly Lys Gly Leu Glu Trp Ile Gly Tyr Ile Tyr Tyr
            20                  25                  30

Ser Gly Ser Thr Tyr Tyr Asn Pro Ser Leu Lys Ser Arg Val Thr Ile
            35                  40                  45

Ser Val Asp Thr Ser Lys Asn Gln Phe Ser Leu Lys Leu Ser Ser Val
        50                  55                  60

Thr Ala Ala Asp Thr Ala Val Tyr Tyr Cys Ala Arg
65                  70                  75

<210> SEQ ID NO 36
<211> LENGTH: 76
<212> TYPE: PRT
<213> ORGANISM: Homo sapiens

<400> SEQUENCE: 36

Thr Ile Thr Cys Gln Ala Ser Gln Asp Ile Ser Asn Tyr Leu Asn Trp
1               5                   10                  15

Tyr Gln Gln Lys Pro Gly Lys Ala Pro Lys Leu Leu Ile Tyr Asp Ala
            20                  25                  30

Ser Asn Leu Glu Thr Gly Val Pro Ser Arg Phe Ser Gly Ser Gly Ser
            35                  40                  45

Gly Thr Asp Phe Thr Phe Thr Ile Ser Ser Leu Gln Pro Glu Asp Ile
        50                  55                  60

Ala Thr Tyr Tyr Cys Gln Gln Tyr Asp Asn Leu Pro
65                  70                  75

<210> SEQ ID NO 37
<211> LENGTH: 76
<212> TYPE: PRT
<213> ORGANISM: Homo sapiens

<400> SEQUENCE: 37

Thr Ile Thr Cys Arg Ala Ser Gln Ser Ile Ser Ser Tyr Leu Asn Trp
1               5                   10                  15

Tyr Gln Gln Lys Pro Gly Lys Ala Pro Lys Leu Leu Ile Tyr Ala Ala
            20                  25                  30

Ser Ser Leu Gln Ser Gly Val Pro Ser Arg Phe Ser Gly Ser Gly Ser
            35                  40                  45

Gly Thr Asp Phe Thr Leu Thr Ile Ser Ser Leu Gln Pro Glu Asp Phe
        50                  55                  60

Ala Thr Tyr Tyr Cys Gln Gln Ser Tyr Ser Thr Pro
65                  70                  75

<210> SEQ ID NO 38
<211> LENGTH: 76
<212> TYPE: PRT
<213> ORGANISM: Homo sapiens

<400> SEQUENCE: 38

Val Ser Gly Gly Ser Val Ser Ser Gly Ser Tyr Tyr Trp Ser Trp Ile
1               5                   10                  15

Arg Gln Pro Pro Gly Lys Gly Leu Glu Trp Ile Gly Tyr Ile Tyr Tyr
            20                  25                  30

Ser Gly Ser Thr Asn Tyr Asn Pro Ser Leu Lys Ser Arg Val Thr Ile
            35                  40                  45

Ser Val Asp Thr Ser Lys Asn Gln Phe Ser Leu Lys Leu Ser Ser Val
        50                  55                  60

Thr Ala Ala Asp Thr Ala Val Tyr Tyr Cys Ala Arg
```

```
                       65                  70                  75

<210> SEQ ID NO 39
<211> LENGTH: 98
<212> TYPE: PRT
<213> ORGANISM: Homo sapiens

<400> SEQUENCE: 39

Val Ser Gly Gly Ser Ile Asn Ser Gly Asp Tyr Tyr Trp Ser Trp Ile
  1               5                  10                  15

Arg Gln His Pro Gly Lys Gly Leu Asp Cys Ile Gly Tyr Ile Tyr Tyr
             20                  25                  30

Ser Gly Ser Thr Tyr Tyr Asn Pro Ser Leu Lys Ser Arg Val Thr Ile
         35                  40                  45

Ser Val Asp Thr Ser Lys Asn Gln Phe Phe Leu Lys Leu Thr Ser Val
     50                  55                  60

Thr Ala Ala Asp Thr Ala Val Tyr Tyr Cys Ala Arg Ser Thr Val Val
 65                  70                  75                  80

Asn Pro Gly Trp Phe Asp Pro Trp Gly Gln Gly Thr Leu Val Thr Val
                 85                  90                  95

Ser Ser

<210> SEQ ID NO 40
<211> LENGTH: 105
<212> TYPE: PRT
<213> ORGANISM: Homo sapiens

<400> SEQUENCE: 40

Thr Ile Thr Cys Gln Ala Ser Gln Asp Ile Asn Asn Tyr Leu Asn Trp
  1               5                  10                  15

Phe Gln Gln Lys Pro Gly Lys Ala Pro Lys Val Leu Ile His Asp Ala
             20                  25                  30

Ser Asn Leu Glu Thr Gly Gly Pro Ser Arg Phe Ser Gly Ser Gly Ser
         35                  40                  45

Gly Thr Asp Phe Thr Phe Thr Ile Ser Gly Leu Gln Pro Glu Asp Ile
     50                  55                  60

Ala Thr Tyr Tyr Cys Gln Gln Tyr Glu Ser Leu Pro Leu Thr Phe Gly
 65                  70                  75                  80

Gly Gly Thr Lys Val Glu Ile Lys Arg Thr Val Ala Ala Pro Ser Val
                 85                  90                  95

Phe Ile Phe Pro Pro Ser Asp Glu Gln
                100                 105

<210> SEQ ID NO 41
<211> LENGTH: 97
<212> TYPE: PRT
<213> ORGANISM: Homo sapiens

<400> SEQUENCE: 41

Val Ser Gly Gly Ser Ile Asn Ser Gly Asp Tyr Tyr Trp Ser Trp Ile
  1               5                  10                  15

Arg Gln His Pro Gly Lys Gly Leu Glu Trp Ile Gly Ser Ile Tyr Tyr
             20                  25                  30

Ser Gly Asn Thr Phe Tyr Asn Pro Ser Leu Lys Ser Arg Val Thr Ile
         35                  40                  45

Ser Leu Asp Thr Ser Lys Asn Gln Phe Ser Leu Lys Leu Ser Ser Val
     50                  55                  60
```

```
Thr Ala Ala Asp Thr Ala Val Cys Tyr Cys Ala Arg Asn Ile Val Thr
 65                  70                  75                  80

Thr Gly Ala Phe Asp Ile Trp Gly Gln Gly Thr Met Val Thr Val Ser
                 85                  90                  95

Ser
```

<210> SEQ ID NO 42
<211> LENGTH: 105
<212> TYPE: PRT
<213> ORGANISM: Homo sapiens

<400> SEQUENCE: 42

```
Thr Ile Thr Cys Gln Ala Ser Gln Asp Ile Thr Ile Tyr Leu Asn Trp
  1               5                  10                  15

Tyr Gln Gln Lys Pro Gly Lys Ala Pro Lys Leu Leu Ile Asn Asp Ala
             20                  25                  30

Ser Ser Leu Glu Thr Gly Val Pro Leu Arg Phe Ser Gly Ser Gly Ser
         35                  40                  45

Gly Thr Asp Phe Thr Phe Thr Ile Ser Ser Leu Gln Pro Glu Asp Ile
 50                  55                  60

Ala Thr Tyr Tyr Cys Gln Gln Tyr Asp His Leu Pro Leu Thr Phe Gly
 65                  70                  75                  80

Gly Gly Thr Lys Val Ala Ile Lys Arg Thr Val Ala Ala Pro Ser Val
                 85                  90                  95

Phe Ile Phe Pro Pro Ser Asp Glu Gln
                100                 105
```

<210> SEQ ID NO 43
<211> LENGTH: 96
<212> TYPE: PRT
<213> ORGANISM: Homo sapiens

<400> SEQUENCE: 43

```
Val Ser Gly Gly Ser Ile Ser Ser Gly Asp Tyr Tyr Trp Thr Trp Ile
  1               5                  10                  15

Arg Gln His Pro Gly Lys Gly Leu Glu Trp Ile Gly Tyr Ile Tyr Tyr
             20                  25                  30

Ser Gly Asn Thr Tyr Tyr Asn Pro Ser Leu Lys Ser Arg Val Ser Met
         35                  40                  45

Ser Ile Asp Thr Ser Glu Asn Gln Phe Ser Leu Lys Leu Ser Ser Val
 50                  55                  60

Thr Ala Ala Asp Thr Ala Val Tyr Tyr Cys Ala Arg Lys Pro Val Thr
 65                  70                  75                  80

Gly Gly Glu Asp Tyr Trp Gly Gln Gly Thr Leu Val Thr Val Ser Ser
                 85                  90                  95
```

<210> SEQ ID NO 44
<211> LENGTH: 105
<212> TYPE: PRT
<213> ORGANISM: Homo sapiens

<400> SEQUENCE: 44

```
Thr Ile Thr Cys Gln Ala Ser Gln Asp Ile Ser Asn Tyr Leu Asn Trp
  1               5                  10                  15

Tyr Gln Gln Lys Pro Gly Lys Ala Pro Lys Leu Leu Ile Tyr Asp Ala
             20                  25                  30

Ser Asn Leu Glu Thr Gly Val Pro Ser Arg Phe Ser Gly Ser Gly Ser
         35                  40                  45
```

-continued

Gly Thr Asp Phe Thr Phe Thr Ile Ser Ser Leu Gln Pro Glu Asp Ile
            50                  55                  60

Val Gly Tyr Tyr Val Gln Gln Tyr Glu Ser Leu Pro Cys Gly Phe Gly
 65                  70                  75                  80

Gln Gly Thr Lys Leu Glu Ile Lys Arg Thr Val Ala Ala Pro Ser Val
                85                  90                  95

Phe Ile Phe Pro Pro Ser Asp Glu Gln
            100                 105

<210> SEQ ID NO 45
<211> LENGTH: 97
<212> TYPE: PRT
<213> ORGANISM: Homo sapiens

<400> SEQUENCE: 45

Val Ser Gly Gly Ser Ile Asn Ser Gly Asp Phe Tyr Trp Ser Trp Ile
 1               5                  10                  15

Arg Gln His Pro Gly Lys Gly Leu Glu Trp Ile Gly Tyr Ile Tyr Tyr
                20                  25                  30

Ser Gly Ser Thr Tyr Tyr Asn Pro Ser Leu Lys Ser Arg Val Thr Met
            35                  40                  45

Ser Ile Asp Pro Ser Lys Asn Gln Phe Ser Leu Lys Leu Ile Ser Val
 50                  55                  60

Thr Ala Ala Asp Thr Ala Val Tyr Tyr Cys Ala Thr Ser Leu Tyr Tyr
 65                  70                  75                  80

Gly Gly Gly Met Asp Val Trp Gly Gln Gly Thr Thr Val Thr Val Ser
                85                  90                  95

Ser

<210> SEQ ID NO 46
<211> LENGTH: 105
<212> TYPE: PRT
<213> ORGANISM: Homo sapiens
<220> FEATURE:
<221> NAME/KEY: MOD_RES
<222> LOCATION: (87)
<223> OTHER INFORMATION: variable amino acid

<400> SEQUENCE: 46

Thr Ile Thr Cys Gln Ala Ser Gln Asp Ile Ser Asn Asn Leu Asn Trp
 1               5                  10                  15

Tyr Gln Gln Lys Arg Gly Asn Ala Pro Lys Leu Leu Ile Tyr Asp Ala
                20                  25                  30

Ser Asn Leu Glu Thr Gly Val Pro Ser Arg Phe Ser Gly Ser Gly Ser
            35                  40                  45

Gly Thr Asp Phe Thr Phe Thr Ile Ser Asn Leu Gln Pro Glu Asp Ile
 50                  55                  60

Ala Thr Tyr Tyr Cys Gln His Tyr Asp His Leu Pro Trp Thr Phe Gly
 65                  70                  75                  80

Gln Gly Thr Lys Val Glu Xaa Lys Arg Thr Val Ala Ala Pro Ser Val
                85                  90                  95

Phe Ile Phe Pro Pro Ser Asp Glu Gln
            100                 105

<210> SEQ ID NO 47
<211> LENGTH: 97
<212> TYPE: PRT
<213> ORGANISM: Homo sapiens

```
<400> SEQUENCE: 47

Val Ser Gly Gly Ser Ile Asn Asn Gly Asp Tyr Tyr Trp Ser Trp Ile
 1               5                  10                  15

Arg Gln His Pro Gly Lys Gly Leu Glu Trp Ile Gly His Ile Tyr Tyr
             20                  25                  30

Ser Gly Ser Thr Tyr Tyr Ile Pro Ser Leu Lys Ser Arg Thr Thr Ile
         35                  40                  45

Ser Val Asp Thr Ser Lys Asn Gln Phe Ser Leu Lys Leu Asn Ser Val
 50                  55                  60

Thr Ala Ala Asp Thr Ala Val Tyr Tyr Cys Ala Arg Gly Thr Val Thr
 65                  70                  75                  80

Thr Tyr Tyr Phe Asp Tyr Trp Gly Gln Gly Thr Thr Val Thr Val Ser
                 85                  90                  95

Ser

<210> SEQ ID NO 48
<211> LENGTH: 107
<212> TYPE: PRT
<213> ORGANISM: Homo sapiens

<400> SEQUENCE: 48

Thr Ile Thr Cys Arg Ala Ser Gln Ser Ile Ser Ser Tyr Leu Asn Trp
 1               5                  10                  15

Tyr Gln Gln Lys Pro Gly Lys Ala Pro Lys Leu Leu Ile Tyr Ala Ala
             20                  25                  30

Ser Ser Leu Gln Ser Gly Val Pro Ser Arg Phe Ser Gly Ser Gly Ser
         35                  40                  45

Gly Thr Asp Phe Thr Leu Thr Ile Ser Ser Leu Gln Pro Glu Asp Phe
 50                  55                  60

Ala Thr Tyr Tyr Cys Gln Gln Gly Tyr Arg Thr Pro Pro Glu Cys Ser
 65                  70                  75                  80

Phe Gly Gln Gly Thr Lys Leu Glu Ile Lys Arg Thr Val Ala Ala Pro
                 85                  90                  95

Ser Val Phe Ile Phe Pro Pro Ser Asp Glu Gln
            100                 105

<210> SEQ ID NO 49
<211> LENGTH: 97
<212> TYPE: PRT
<213> ORGANISM: Homo sapiens

<400> SEQUENCE: 49

Val Ser Gly Gly Ser Val Ser Ser Gly Asp Tyr Tyr Trp Ser Trp Ile
 1               5                  10                  15

Arg Gln Pro Pro Gly Lys Gly Leu Glu Trp Ile Gly His Leu Tyr Tyr
             20                  25                  30

Ser Gly Asn Thr Asn Tyr Asn Pro Ser Leu Lys Ser Arg Val Thr Ile
         35                  40                  45

Ser Leu Asp Thr Ser Lys Asn Gln Phe Ser Leu Lys Leu Ser Ser Val
 50                  55                  60

Thr Ala Ala Asp Thr Ala Val Tyr Tyr Cys Ala Arg Asp Phe Leu Thr
 65                  70                  75                  80

Gly Ser Phe Phe Asp Tyr Trp Gly Gln Gly Thr Leu Val Thr Val Ser
                 85                  90                  95

Ser
```

<210> SEQ ID NO 50
<211> LENGTH: 105
<212> TYPE: PRT
<213> ORGANISM: Homo sapiens

<400> SEQUENCE: 50

Thr Ile Thr Cys Gln Ala Ser Gln Asp Ile Ser Asn Tyr Leu Asn Trp
1               5                   10                  15

Tyr Gln Gln Lys Pro Gly Lys Ala Pro Lys Leu Leu Ile Asn Asp Ala
            20                  25                  30

Ser Asp Leu Glu Thr Gly Val Pro Ser Arg Ile Ser Gly Ser Gly Ser
        35                  40                  45

Gly Thr Asp Phe Thr Phe Thr Ile Ser Asn Leu Gln Pro Glu Asp Ile
    50                  55                  60

Ala Thr Tyr Tyr Cys Gln Gln Tyr Asp Ser Leu Pro Leu Thr Phe Gly
65                  70                  75                  80

Gly Gly Thr Lys Val Glu Ile Arg Arg Thr Val Ala Ala Pro Ser Val
                85                  90                  95

Phe Ile Phe Pro Pro Ser Asp Glu Gln
            100                 105

<210> SEQ ID NO 51
<211> LENGTH: 96
<212> TYPE: PRT
<213> ORGANISM: Homo sapiens

<400> SEQUENCE: 51

Val Ser Gly Gly Ser Val Tyr Ser Gly Asp Tyr Tyr Trp Ser Trp Ile
1               5                   10                  15

Arg Gln Pro Pro Gly Lys Gly Leu Glu Trp Ile Gly Tyr Ile Tyr Tyr
            20                  25                  30

Ser Gly Ser Thr Asn Tyr Asn Pro Ser Leu Lys Ser Arg Val Thr Ile
        35                  40                  45

Ser Val Asp Thr Ser Lys Asn Gln Phe Ser Leu Lys Leu Ser Ser Val
    50                  55                  60

Thr Ala Ala Asp Thr Ala Val Tyr Tyr Cys Ala Arg Asp Ser Ile Leu
65                  70                  75                  80

Gly Ala Thr Asn Tyr Trp Gly Gln Gly Thr Leu Val Thr Val Ser Ser
                85                  90                  95

<210> SEQ ID NO 52
<211> LENGTH: 105
<212> TYPE: PRT
<213> ORGANISM: Homo sapiens
<220> FEATURE:
<221> NAME/KEY: MOD_RES
<222> LOCATION: (9)
<223> OTHER INFORMATION: variable amino acid
<220> FEATURE:
<221> NAME/KEY: MOD_RES
<222> LOCATION: (15)
<223> OTHER INFORMATION: variable amino acid
<220> FEATURE:
<221> NAME/KEY: MOD_RES
<222> LOCATION: (27)
<223> OTHER INFORMATION: variable amino acid
<220> FEATURE:
<221> NAME/KEY: MOD_RES
<222> LOCATION: (51)
<223> OTHER INFORMATION: variable amino acid
<220> FEATURE:
<221> NAME/KEY: MOD_RES

```
<222> LOCATION: (52)
<223> OTHER INFORMATION: variable amino acid
<220> FEATURE:
<221> NAME/KEY: MOD_RES
<222> LOCATION: (70)
<223> OTHER INFORMATION: variable amino acid
<220> FEATURE:
<221> NAME/KEY: MOD_RES
<222> LOCATION: (73)
<223> OTHER INFORMATION: variable amino acid

<400> SEQUENCE: 52

Thr Ile Thr Cys Gln Ala Ser Gln Xaa Ile Ser Asn Tyr Leu Xaa Trp
  1               5                  10                  15

Tyr Gln Gln Lys Pro Gly Lys Ala Pro Lys Xaa Leu Ile Ser Asp Ala
             20                  25                  30

Ser Asn Leu Glu Thr Gly Val Pro Ser Arg Phe Ser Gly Ser Gly Ser
         35                  40                  45

Gly Thr Xaa Xaa Thr Phe Thr Ile Ser Ser Leu Gln Pro Glu Asp Ile
     50                  55                  60

Ala Thr Tyr His Cys Xaa Gln Tyr Xaa Ser Leu Pro Leu Thr Phe Gly
 65                  70                  75                  80

Gly Gly Thr Lys Val Glu Ile Lys Arg Thr Val Ala Ala Pro Ser Val
             85                  90                  95

Phe Ile Phe Pro Pro Ser Asp Glu Gln
            100                 105

<210> SEQ ID NO 53
<211> LENGTH: 95
<212> TYPE: PRT
<213> ORGANISM: Homo sapiens

<400> SEQUENCE: 53

Val Ser Gly Gly Ser Val Ser Ser Gly Asp Tyr Tyr Trp Thr Trp Ile
  1               5                  10                  15

Arg Gln Ser Pro Gly Lys Gly Leu Glu Trp Ile Gly His Ile Tyr Tyr
             20                  25                  30

Ser Gly Asn Thr Asn Tyr Asn Pro Ser Leu Lys Ser Arg Leu Thr Ile
         35                  40                  45

Ser Ile Asp Thr Ser Lys Thr Gln Phe Ser Leu Lys Leu Ser Ser Val
     50                  55                  60

Thr Ala Ala Asp Thr Ala Ile Tyr Tyr Cys Val Arg Asp Arg Val Thr
 65                  70                  75                  80

Gly Ala Phe Asp Ile Trp Gly Gln Gly Thr Met Val Thr Ser Ser
             85                  90                  95

<210> SEQ ID NO 54
<211> LENGTH: 105
<212> TYPE: PRT
<213> ORGANISM: Homo sapiens

<400> SEQUENCE: 54

Thr Ile Thr Cys Gln Ala Ser Gln Asp Ile Ser Asn Tyr Leu Asn Trp
  1               5                  10                  15

Tyr Gln Gln Lys Pro Gly Lys Ala Pro Lys Leu Leu Ile Tyr Asp Ala
             20                  25                  30

Ser Asn Leu Glu Thr Gly Val Pro Ser Arg Phe Ser Gly Ser Gly Ser
         35                  40                  45

Gly Thr Asp Phe Thr Phe Thr Ile Ser Ser Leu Gln Pro Glu Asp Ile
     50                  55                  60
```

```
Ala Thr Tyr Phe Cys Gln His Phe Asp His Leu Pro Leu Ala Phe Gly
 65                  70                  75                  80

Gly Gly Thr Lys Val Glu Ile Lys Arg Thr Val Ala Ala Pro Ser Val
                 85                  90                  95

Phe Ile Phe Pro Pro Ser Asp Glu Gln
                100                 105

<210> SEQ ID NO 55
<211> LENGTH: 160
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: Glu, Gly, Ala, or Val
<220> FEATURE:
<221> NAME/KEY: MOD_RES
<222> LOCATION: (21)..(21)
<223> OTHER INFORMATION: Arg, or Ser
<220> FEATURE:
<221> NAME/KEY: MOD_RES
<222> LOCATION: (22)..(22)
<223> OTHER INFORMATION: Tyr, Cys, Ser, or Phe
<220> FEATURE:
<221> NAME/KEY: MOD_RES
<222> LOCATION: (107)..(107)
<223> OTHER INFORMATION: Tyr, Cys, Ser, or Phe
<220> FEATURE:
<221> NAME/KEY: MOD_RES
<222> LOCATION: (118)..(118)
<223> OTHER INFORMATION: Thr, Ala, Pro, or Ser
<220> FEATURE:
<221> NAME/KEY: MOD_RES
<222> LOCATION: (128)..(128)
<223> OTHER INFORMATION: Gln, Arg, Pro, or Leu
<220> FEATURE:
<221> NAME/KEY: MOD_RES
<222> LOCATION: (129)..(129)
<223> OTHER INFORMATION: Lys, Arg, Thr, or Ile
<220> FEATURE:
<221> NAME/KEY: MOD_RES
<222> LOCATION: (131)..(131)
<223> OTHER INFORMATION: Gln, or His
<220> FEATURE:
<221> NAME/KEY: MOD_RES
<222> LOCATION: (132)..(132)
<223> OTHER INFORMATION: Lys, Arg, Thr, or Met
<220> FEATURE:
<221> NAME/KEY: MOD_RES
<222> LOCATION: (137)..(137)
<223> OTHER INFORMATION: Asp, Gly, Ala, or Val
<220> FEATURE:
<221> NAME/KEY: MOD_RES
<222> LOCATION: (138)..(138)
<223> OTHER INFORMATION: Trp, or Cys
<220> FEATURE:
<221> NAME/KEY: MOD_RES
<222> LOCATION: (142)..(142)
<223> OTHER INFORMATION: Tyr, Cys, Ser, or Phe
<220> FEATURE:
<221> NAME/KEY: MOD_RES
<222> LOCATION: (145)..(145)
<223> OTHER INFORMATION: Ser
<220> FEATURE:
<221> NAME/KEY: MOD_RES
<222> LOCATION: (147)..(147)
<223> OTHER INFORMATION: Gln, Arg, Pro, or Leu
<220> FEATURE:
<221> NAME/KEY: MOD_RES
<222> LOCATION: (150)..(150)
<223> OTHER INFORMATION: Ile, Met, Val, Leu, or Phe
<220> FEATURE:
<221> NAME/KEY: MOD_RES
<222> LOCATION: (151)..(151)
<223> OTHER INFORMATION: Ser
```

```
<220> FEATURE:
<221> NAME/KEY: MOD_RES
<222> LOCATION: (156)..(156)
<223> OTHER INFORMATION: Ser, Gly, Arg, or Cys
<220> FEATURE:
<221> NAME/KEY: MOD_RES
<222> LOCATION: (157)..(157)
<223> OTHER INFORMATION: Thr, Ala, Pro, or Ser
<220> FEATURE:
<221> NAME/KEY: MOD_RES
<222> LOCATION: (159)..(159)
<223> OTHER INFORMATION: Lys, Arg, Thr, Ile, Glu, Gly, Ala, Val, Gln,
      Pro, Leu, or Ser
<220> FEATURE:
<221> NAME/KEY: MOD_RES
<222> LOCATION: (160)..(160)
<223> OTHER INFORMATION: Ser, or Leu

<400> SEQUENCE: 55

Ala Ile Gln Pro Phe Arg Ser Met Pro Phe Ser Cys Xaa Ala Ser Gly
1               5                   10                  15

Phe Pro Phe Ser Xaa Xaa Gly Met His Trp Val Arg Gln Ala Pro Gly
            20                  25                  30

Lys Gly Leu Glu Trp Val Ala Val Ile Trp Tyr Asp Gly Ser Asn Lys
        35                  40                  45

Tyr Tyr Ala Asp Ser Val Lys Gly Arg Phe Thr Ile Ser Arg Asp Asn
    50                  55                  60

Ser Lys Asn Thr Leu Tyr Leu Gln Met Asn Arg Leu Arg Ala Glu Asp
65                  70                  75                  80

Thr Ala Val Tyr Tyr Cys Ala Arg Phe Leu Glu Trp Leu Pro Phe Asp
                85                  90                  95

Tyr Trp Gly Gln Gly Thr Leu Val Thr Val Xaa Ser Asp Ser Thr Lys
            100                 105                 110

Gly Pro Ser Val Phe Xaa Leu Ala Pro Cys Phe Gln Glu His Pro Xaa
        115                 120                 125

Xaa Ala Xaa Xaa Ala Pro Gly Thr Xaa Xaa Tyr Lys Asp Xaa Phe Pro
    130                 135                 140

Xaa Asn Xaa Val Thr Xaa Xaa Trp Glu Thr Gln Xaa Xaa Ser Xaa Xaa
145                 150                 155                 160

<210> SEQ ID NO 56
<211> LENGTH: 161
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Arg, Gly, or Trp
<220> FEATURE:
<221> NAME/KEY: MOD_RES
<222> LOCATION: (10)..(10)
<223> OTHER INFORMATION: Asp, Gly, Ala, or Val
<220> FEATURE:
<221> NAME/KEY: MOD_RES
<222> LOCATION: (13)..(13)
<223> OTHER INFORMATION: Asn, Ser, Thr, or Ile
<220> FEATURE:
<221> NAME/KEY: MOD_RES
<222> LOCATION: (145)..(145)
<223> OTHER INFORMATION: His, Arg, Pro, or Leu
<220> FEATURE:
<221> NAME/KEY: MOD_RES
<222> LOCATION: (146)..(146)
<223> OTHER INFORMATION: Asn, Ser, Thr, Ile, Asp, Gly, Ala, Val, His,
      Arg, Pro, Leu, Tyr, Cys, or Phe
<220> FEATURE:
<221> NAME/KEY: MOD_RES
<222> LOCATION: (149)..(149)
```

-continued

```
<223> OTHER INFORMATION: Asn, Ser, Thr, Ile, Asp, Gly, Ala, Val, His,
      Arg, Pro, Leu, Tyr, Cys, or Phe
<220> FEATURE:
<221> NAME/KEY: MOD_RES
<222> LOCATION: (152)..(152)
<223> OTHER INFORMATION: Thr, Ala, Pro, or Ser
<220> FEATURE:
<221> NAME/KEY: MOD_RES
<222> LOCATION: (153)..(153)
<223> OTHER INFORMATION: His, Arg, Pro, or Leu
<220> FEATURE:
<221> NAME/KEY: MOD_RES
<222> LOCATION: (156)..(156)
<223> OTHER INFORMATION: Ser
<220> FEATURE:
<221> NAME/KEY: MOD_RES
<222> LOCATION: (157)..(157)
<223> OTHER INFORMATION: Thr, Ala, Pro, or Ser
<220> FEATURE:
<221> NAME/KEY: MOD_RES
<222> LOCATION: (158)..(158)
<223> OTHER INFORMATION: His, Arg, Pro, or Leu
<220> FEATURE:
<221> NAME/KEY: MOD_RES
<222> LOCATION: (160)..(160)
<223> OTHER INFORMATION: Ser
<220> FEATURE:
<221> NAME/KEY: MOD_RES
<222> LOCATION: (161)..(161)
<223> OTHER INFORMATION: Gln, Arg, Pro, or Leu

<400> SEQUENCE: 56

Gly Thr Phe Xaa Phe Ala Pro Phe Gly Xaa Arg Pro Xaa Ile Thr Cys
1               5                   10                  15

Arg Ala Ser Gln Gly Ile Ser Asn Phe Leu Ala Trp Phe Gln Gln Lys
            20                  25                  30

Pro Gly Ile Ala Pro Lys Ser Leu Ile Tyr Ala Ala Ser Thr Leu Gln
        35                  40                  45

Ser Gly Val Pro Ser Lys Phe Thr Gly Ser Gly Tyr Gly Thr Asp Phe
    50                  55                  60

Thr Leu Thr Ile Ser Ser Leu Gln Pro Glu Asp Phe Ala Thr Tyr Tyr
65                  70                  75                  80

Cys Gln Gln Tyr Asn Val Tyr Pro Phe Thr Phe Gly Pro Gly Thr Lys
                85                  90                  95

Val Asp Ile Lys Arg Thr Val Ala Ala Pro Ser Val Phe Ile Phe Pro
            100                 105                 110

Pro Ser Asp Glu Gln Val Glu Ile Trp Asn Cys Leu Cys Cys Val Pro
        115                 120                 125

Ala Glu Leu Leu Ser Gln Arg Gly Gln Ser Thr Val Glu Gly Gly Arg
    130                 135                 140

Xaa Xaa Trp Arg Xaa Pro Phe Xaa Xaa Pro Ser Xaa Xaa Xaa Leu Xaa
145                 150                 155                 160

Xaa

<210> SEQ ID NO 57
<211> LENGTH: 149
<212> TYPE: PRT
<213> ORGANISM: Homo sapiens
<220> FEATURE:
<221> NAME/KEY: MOD_RES
<222> LOCATION: (112)..(112)
<223> OTHER INFORMATION: Leu
<220> FEATURE:
<221> NAME/KEY: MOD_RES
<222> LOCATION: (134)..(134)
<223> OTHER INFORMATION: Glu, Asp, Gly, Ala, or Val
<220> FEATURE:
```

```
<221> NAME/KEY: MOD_RES
<222> LOCATION: (140)..(140)
<223> OTHER INFORMATION: Glu, Asp, Gly, Ala, or Val
<220> FEATURE:
<221> NAME/KEY: MOD_RES
<222> LOCATION: (146)..(146)
<223> OTHER INFORMATION: Gln, Arg, Pro, or Leu
<220> FEATURE:
<221> NAME/KEY: MOD_RES
<222> LOCATION: (149)..(149)
<223> OTHER INFORMATION: Asp, Gly, Ala, or Val

<400> SEQUENCE: 57

Lys Pro Val Ala Ser Val Gln Val Ser Cys Lys Ala Ser Gly Tyr Thr
1               5                   10                  15

Phe Thr Ser Tyr Asp Ile Asn Trp Val Arg Gln Ala Thr Gly Gln Gly
            20                  25                  30

Leu Glu Trp Met Gly Trp Met Asn Pro Asn Ser Gly Asn Thr Gly Tyr
        35                  40                  45

Ala Gln Lys Phe Gln Gly Arg Val Thr Met Thr Arg Asn Thr Ser Ile
    50                  55                  60

Ser Thr Ala Tyr Met Glu Leu Ser Ser Leu Arg Ser Glu Asp Thr Ala
65                  70                  75                  80

Val Tyr Tyr Cys Ala Arg Gly Gly Pro Tyr Ser Ser Gly Trp Thr Phe
                85                  90                  95

Phe Asp Tyr Trp Gly Gln Gly Thr Leu Val Thr Val Ser Ser Ala Xaa
            100                 105                 110

His Gln Gly Pro Ile Gly Leu Pro Pro Gly Ala Leu Leu Gln Glu His
        115                 120                 125

Leu Arg Glu His Ser Xaa Pro Leu Gly Cys Leu Xaa Gln Gly Leu Phe
    130                 135                 140

Pro Xaa Thr Pro Xaa
145

<210> SEQ ID NO 58
<211> LENGTH: 151
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Met, Val, or Leu
<220> FEATURE:
<221> NAME/KEY: MOD_RES
<222> LOCATION: (9)..(9)
<223> OTHER INFORMATION: Leu
<220> FEATURE:
<221> NAME/KEY: MOD_RES
<222> LOCATION: (26)..(26)
<223> OTHER INFORMATION: Asn, Ser, Thr, or Ile

<400> SEQUENCE: 58

Phe Glu Pro Phe Xaa Ala Val Ser Xaa Gly Ala Arg Ala Thr Ile Asn
1               5                   10                  15

Cys Lys Ser Ser Gln Arg Val Leu Tyr Xaa Ser Asn Asn Lys Asn Cys
            20                  25                  30

Leu Ala Trp Tyr Gln Gln Lys Pro Gly Gln Pro Pro Lys Leu Leu Ile
        35                  40                  45

Tyr Trp Thr Ser Thr Arg Glu Ser Gly Val Pro Ala Arg Phe Ser Gly
    50                  55                  60

Ser Gly Ser Gly Thr Asp Phe Thr Leu Thr Ile Ser Ser Leu Gln Ala
65                  70                  75                  80
```

-continued

```
Glu Asp Val Ala Val Tyr Tyr Cys Gln Gln Tyr Tyr Ser Thr Pro Leu
                85                  90                  95

Thr Phe Gly Gly Gly Thr Met Val Glu Ile Lys Arg Thr Val Ala Ala
            100                 105                 110

Pro Ser Val Phe Ile Phe Pro Pro Ser Asp Glu Pro Val Asn Leu Glu
        115                 120                 125

Leu Pro Leu Phe Val Cys Pro Ala Glu Leu Leu Ser Gln Arg Gly Gln
    130                 135                 140

Ser Thr Ser Gly Arg Trp Ile
145                 150

<210> SEQ ID NO 59
<211> LENGTH: 155
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Gln, Arg, Pro, or Leu
<220> FEATURE:
<221> NAME/KEY: MOD_RES
<222> LOCATION: (6)..(6)
<223> OTHER INFORMATION: Met, Val, or Leu
<220> FEATURE:
<221> NAME/KEY: MOD_RES
<222> LOCATION: (150)..(150)
<223> OTHER INFORMATION: Tyr, Cys, Ser, or Phe

<400> SEQUENCE: 59

Xaa Pro Val Arg Ser Xaa Arg Leu Ser Cys Ala Ala Ser Gly Phe Ile
1               5                   10                  15

Phe Ser Ser Tyr Gly Met His Trp Val Arg Gln Ala Pro Gly Lys Gly
            20                  25                  30

Leu Glu Trp Val Ala Ile Ile Trp Tyr Asp Gly Ser Asn Lys Tyr Tyr
        35                  40                  45

Ala Asp Ser Val Lys Gly Arg Phe Thr Ile Ser Arg Asp Asn Ser Lys
    50                  55                  60

Asn Thr Leu Tyr Leu Gln Met Asn Ser Leu Arg Ala Glu Asp Thr Ala
65                  70                  75                  80

Val Tyr Tyr Cys Ala Arg Asp Gly Gly Pro Arg Trp Phe Leu Ala Ser
                85                  90                  95

Asp Tyr Trp Gly Gln Gly Thr Leu Val Thr Val Ser Ser Ala Ser Thr
            100                 105                 110

Lys Gly Pro Ser Val Phe Pro Leu Ala Pro Cys Ser Arg Ser Thr Leu
        115                 120                 125

Arg Glu His Ser Gly Pro Gly Leu Pro Gly Ser Arg Thr Thr Phe Pro
    130                 135                 140

Glu Pro Val Thr Val Xaa Val Gly Thr His Asp
145                 150                 155

<210> SEQ ID NO 60
<211> LENGTH: 152
<212> TYPE: PRT
<213> ORGANISM: Homo sapiens
<220> FEATURE:
<221> NAME/KEY: MOD_RES
<222> LOCATION: (21)..(21)
<223> OTHER INFORMATION: Asp, Gly, Ala, or Val

<400> SEQUENCE: 60

Ser Leu Gln Thr Pro Trp Leu Cys Leu Trp Ala Arg Gly Pro Pro Ser
1               5                   10                  15
```

```
Thr Ala Ser Pro Xaa Arg Val Phe Tyr Thr Pro Thr Ile Lys Asn
            20                  25                  30

Phe Leu Ala Trp Tyr Gln Gln Lys Pro Gly Gln Pro Lys Leu Leu
            35                  40                  45

Ile Tyr Trp Ala Ser Ile Arg Glu Ser Gly Val Pro Asp Arg Phe Ser
            50                  55                  60

Gly Ser Gly Ser Gly Thr Asp Phe Thr Leu Thr Ile Ser Ser Leu Gln
65                  70                  75                  80

Ala Glu Asp Val Ala Val Tyr Tyr Cys Gln Gln Tyr Tyr Ser Ile Pro
                85                  90                  95

Cys Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Lys
130                 135                 140

Ala Lys Val His Glu Gly Phe Lys
145                 150

<210> SEQ ID NO 61
<211> LENGTH: 177
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Ala, or Val
<220> FEATURE:
<221> NAME/KEY: MOD_RES
<222> LOCATION: (6)..(6)
<223> OTHER INFORMATION: Gly, or Val
<220> FEATURE:
<221> NAME/KEY: MOD_RES
<222> LOCATION: (19)..(19)
<223> OTHER INFORMATION: Thr, or Ile
<220> FEATURE:
<221> NAME/KEY: MOD_RES
<222> LOCATION: (22)..(22)
<223> OTHER INFORMATION: Ser, or Asn
<220> FEATURE:
<221> NAME/KEY: MOD_RES
<222> LOCATION: (148)..(148)
<223> OTHER INFORMATION: Asn, or Thr
<220> FEATURE:
<221> NAME/KEY: MOD_RES
<222> LOCATION: (161)..(161)
<223> OTHER INFORMATION: Arg, Gly, or Trp
<220> FEATURE:
<221> NAME/KEY: MOD_RES
<222> LOCATION: (169)..(169)
<223> OTHER INFORMATION: Leu
<220> FEATURE:
<221> NAME/KEY: MOD_RES
<222> LOCATION: (175)..(175)
<223> OTHER INFORMATION: Lys, Arg, Thr, or Met

<400> SEQUENCE: 61

Gly Val Xaa Gln Pro Xaa Arg Ser Leu Arg Leu Ser Cys Ala Ala Ser
1               5                   10                  15

Gly Phe Xaa Phe Ser Xaa Tyr Gly Met His Trp Val Arg Gln Ala Pro
            20                  25                  30

Gly Lys Gly Leu Glu Trp Val Ala Ile Ile Trp Tyr Asp Gly Ser Ser
            35                  40                  45

Lys Tyr Tyr Ala Asp Ser Val Lys Gly Arg Phe Thr Ile Ser Arg Asp
            50                  55                  60
```

```
Asn Ser Lys Asn Thr Leu Tyr Leu Gln Met Asn Ser Leu Arg Ala Glu
 65                  70                  75                  80

Asp Thr Ala Val Tyr Tyr Cys Ala Arg Asp Gly Gly Pro Arg Trp Phe
                 85                  90                  95

Leu Ala Ser Asp Tyr Trp Gly Gln Gly Thr Leu Val Thr Val Ser Ser
            100                 105                 110

Ala Ser Thr Lys Gly Pro Ser Val Phe Pro Leu Ala Pro Cys Ser Arg
        115                 120                 125

Ser Thr Phe Arg Glu His Ser Gly Pro Gly Leu Pro Gly Gln Gly Leu
    130                 135                 140

Leu Pro Arg Xaa Gly Asp Gly Val Val Glu Leu Arg Arg Ser Asp Gln
145                 150                 155                 160

Xaa Arg Ala Gln Phe Pro Ala Val Xaa Lys Val Glu Ile Val Xaa Val
                165                 170                 175

Gln

<210> SEQ ID NO 62
<211> LENGTH: 154
<212> TYPE: PRT
<213> ORGANISM: Homo sapiens
<220> FEATURE:
<221> NAME/KEY: MOD_RES
<222> LOCATION: (152)..(152)
<223> OTHER INFORMATION: Lys, Arg, Thr, or Ile

<400> SEQUENCE: 62

Thr Gln Ser Pro Asp Ser Leu Ala Val Ser Leu Gly Glu Arg Ala Thr
  1               5                  10                  15

Ile Asn Cys Lys Ser Ser Gln Ser Val Leu Tyr Gly Ser Lys Asn Gln
                 20                  25                  30

Asn Tyr Leu Ala Trp Tyr Gln Gln Lys Pro Gly Gln Pro Pro Lys Leu
             35                  40                  45

Leu Ile Tyr Trp Ala Ser Thr Arg Glu Ser Gly Val Pro Asp Arg Phe
 50                  55                  60

Arg Gly Ser Gly Ser Arg Thr Asp Phe Thr Leu Thr Ile Ser Ser Leu
 65                  70                  75                  80

Gln Ala Glu Asp Val Ala Val Tyr Phe Cys His Gln Tyr Tyr Ser Thr
                 85                  90                  95

Pro Trp Thr Phe Gly Gln Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Leu Tyr Pro Arg
    130                 135                 140

Lys Pro Arg Thr Arg Lys Val Xaa Pro Thr
145                 150

<210> SEQ ID NO 63
<211> LENGTH: 139
<212> TYPE: PRT
<213> ORGANISM: Homo sapiens
<220> FEATURE:
<221> NAME/KEY: MOD_RES
<222> LOCATION: (20)..(20)
<223> OTHER INFORMATION: Asn, Ser, Thr, or Ile
<220> FEATURE:
<221> NAME/KEY: MOD_RES
<222> LOCATION: (23)..(23)
<223> OTHER INFORMATION: Tyr, Cys, Ser, or Phe
```

```
<220> FEATURE:
<221> NAME/KEY: MOD_RES
<222> LOCATION: (54)..(54)
<223> OTHER INFORMATION: Glu, Gly, Ala, or Val
<220> FEATURE:
<221> NAME/KEY: MOD_RES
<222> LOCATION: (107)..(107)
<223> OTHER INFORMATION: Thr, Ala, Pro, or Ser
<220> FEATURE:
<221> NAME/KEY: MOD_RES
<222> LOCATION: (108)..(108)
<223> OTHER INFORMATION: Asp, Gly, Ala, or Val
<220> FEATURE:
<221> NAME/KEY: MOD_RES
<222> LOCATION: (109)..(109)
<223> OTHER INFORMATION: Ser, or Leu
<220> FEATURE:
<221> NAME/KEY: MOD_RES
<222> LOCATION: (111)..(111)
<223> OTHER INFORMATION: Tyr, Cys, Ser, or Phe
<220> FEATURE:
<221> NAME/KEY: MOD_RES
<222> LOCATION: (114)..(114)
<223> OTHER INFORMATION: Thr, Ala, Pro, or Ser
<220> FEATURE:
<221> NAME/KEY: MOD_RES
<222> LOCATION: (115)..(115)
<223> OTHER INFORMATION: Leu
<220> FEATURE:
<221> NAME/KEY: MOD_RES
<222> LOCATION: (117)..(117)
<223> OTHER INFORMATION: Thr, Ala, Pro, or Ser
<220> FEATURE:
<221> NAME/KEY: MOD_RES
<222> LOCATION: (120)..(120)
<223> OTHER INFORMATION: Thr, Ala, Pro, or Ser
<220> FEATURE:
<221> NAME/KEY: MOD_RES
<222> LOCATION: (122)..(122)
<223> OTHER INFORMATION: Arg, Gly, or Trp
<220> FEATURE:
<221> NAME/KEY: MOD_RES
<222> LOCATION: (128)..(128)
<223> OTHER INFORMATION: Lys, Asn, Arg, Ser, Thr, Ile, Met, Glu, Asp,
      Gly, Ala, Val, Gln, His, Pro, Leu, Tyr, Trp, Cys, or Phe
<220> FEATURE:
<221> NAME/KEY: MOD_RES
<222> LOCATION: (131)..(131)
<223> OTHER INFORMATION: Gln, Arg, Pro, or Leu
<220> FEATURE:
<221> NAME/KEY: MOD_RES
<222> LOCATION: (132)..(132)
<223> OTHER INFORMATION: Trp, or Cys
<220> FEATURE:
<221> NAME/KEY: MOD_RES
<222> LOCATION: (133)..(133)
<223> OTHER INFORMATION: Asn, Ser, Thr, Ile, Asp, Gly, Ala, Val, His,
      Arg, Pro, Leu, Tyr, Cys, or Phe
<220> FEATURE:
<221> NAME/KEY: MOD_RES
<222> LOCATION: (135)..(135)
<223> OTHER INFORMATION: Leu
<220> FEATURE:
<221> NAME/KEY: MOD_RES
<222> LOCATION: (137)..(137)
<223> OTHER INFORMATION: Gln, or His
<220> FEATURE:
<221> NAME/KEY: MOD_RES
<222> LOCATION: (138)..(138)
<223> OTHER INFORMATION: Gln, Arg, Pro, or Leu
<220> FEATURE:
<221> NAME/KEY: MOD_RES
<222> LOCATION: (139)..(139)
<223> OTHER INFORMATION: Gln, or His

<400> SEQUENCE: 63

Arg Asp Pro Pro Gly Trp Ser Leu Arg Leu Ser Cys Ala Ala Ser Gly
1               5                   10                  15
```

```
Phe Ile Phe Xaa Asn Tyr Xaa Met His Trp Val Arg Gln Ala Pro Gly
             20                  25                  30

Lys Gly Leu Glu Trp Val Ala Ile Ile Trp Tyr Asp Gly Ser Ser Lys
         35                  40                  45

Tyr Tyr Ala Asp Ser Xaa Lys Gly Arg Phe Thr Ile Ser Arg Asp Asn
     50                  55                  60

Ser Lys Asn Thr Leu Tyr Leu Gln Met Asn Ser Leu Arg Ala Glu Asp
 65                  70                  75                  80

Thr Ala Asp Val Leu Leu Cys Glu Arg Arg Leu Gly His Gly Gly Phe
                 85                  90                  95

Ser Leu Leu Thr Thr Gly Ala Gln Gly Asn Xaa Xaa Xaa Pro Xaa Ser
            100                 105                 110

Ser Xaa Xaa Tyr Xaa Arg Ala Xaa Ile Xaa Ser Phe Pro Pro Gly Xaa
        115                 120                 125

Pro Ala Xaa Xaa Xaa Thr Xaa Arg Xaa Xaa Xaa
        130                 135
```

<210> SEQ ID NO 64
<211> LENGTH: 151
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Thr, Ala, Pro, or Ser
<220> FEATURE:
<221> NAME/KEY: MOD_RES
<222> LOCATION: (122)..(122)
<223> OTHER INFORMATION: Arg, or Ser
<220> FEATURE:
<221> NAME/KEY: MOD_RES
<222> LOCATION: (142)..(142)
<223> OTHER INFORMATION: Glu, or Asp

<400> SEQUENCE: 64

```
Phe Val Ala Val Ser Leu Gly Glu Arg Xaa Thr Ile Asn Cys Lys Ser
  1               5                  10                  15

Ser Gln Ser Ile Leu Tyr Ser Ser Asn Asn Gln Asn Phe Leu Ala Trp
             20                  25                  30

Tyr Gln Gln Lys Pro Gly Gln Pro Pro Lys Leu Leu Ile Tyr Trp Ala
         35                  40                  45

Ser Ile Arg Glu Ser Gly Val Pro Asp Arg Phe Ser Gly Ser Gly Ser
     50                  55                  60

Gly Thr Asp Phe Thr Leu Thr Ile Ser Ser Leu Gln Ala Glu Asp Val
 65                  70                  75                  80

Ala Val Tyr Tyr Cys Gln Gln Tyr Tyr Ser Ile Pro Cys Thr Phe Gly
                 85                  90                  95

Gln Gly Thr Lys Leu Glu Ile Lys Arg Thr Val Ala Ala Pro Ser Val
            100                 105                 110

Phe Ile Phe Pro Pro Ser Asp Glu Pro Xaa Leu Lys Ile Trp Asn Cys
        115                 120                 125

Leu Cys Cys Val Pro Cys Leu Asn Asn Phe Tyr Pro Arg Xaa Gly Gln
        130                 135                 140

Ser Pro Val Glu Gly Gly Tyr
145                 150
```

<210> SEQ ID NO 65
<211> LENGTH: 116
<212> TYPE: PRT

```
<213> ORGANISM: Homo sapiens
<220> FEATURE:
<221> NAME/KEY: MOD_RES
<222> LOCATION: (14)..(14)
<223> OTHER INFORMATION: Tyr, Cys, Ser, or Phe
<220> FEATURE:
<221> NAME/KEY: MOD_RES
<222> LOCATION: (16)..(16)
<223> OTHER INFORMATION: Arg, or Ser
<220> FEATURE:
<221> NAME/KEY: MOD_RES
<222> LOCATION: (22)..(22)
<223> OTHER INFORMATION: Glu, Gly, Ala, or Val
<220> FEATURE:
<221> NAME/KEY: MOD_RES
<222> LOCATION: (35)..(35)
<223> OTHER INFORMATION: Arg, or Ser
<220> FEATURE:
<221> NAME/KEY: MOD_RES
<222> LOCATION: (44)..(44)
<223> OTHER INFORMATION: Leu
<220> FEATURE:
<221> NAME/KEY: MOD_RES
<222> LOCATION: (61)..(61)
<223> OTHER INFORMATION: Met, Val, or Leu
<220> FEATURE:
<221> NAME/KEY: MOD_RES
<222> LOCATION: (65)..(65)
<223> OTHER INFORMATION: Tyr, Cys, Ser, or Phe
<220> FEATURE:
<221> NAME/KEY: MOD_RES
<222> LOCATION: (68)..(68)
<223> OTHER INFORMATION: Asp, Gly, Ala, or Val
<220> FEATURE:
<221> NAME/KEY: MOD_RES
<222> LOCATION: (72)..(72)
<223> OTHER INFORMATION: Asp, Gly, Ala, or Val
<220> FEATURE:
<221> NAME/KEY: MOD_RES
<222> LOCATION: (73)..(73)
<223> OTHER INFORMATION: Glu, Gly, Ala, or Val
<220> FEATURE:
<221> NAME/KEY: MOD_RES
<222> LOCATION: (76)..(76)
<223> OTHER INFORMATION: Trp, or Cys
<220> FEATURE:
<221> NAME/KEY: MOD_RES
<222> LOCATION: (82)..(82)
<223> OTHER INFORMATION: Glu, Gly, Ala, or Val
<220> FEATURE:
<221> NAME/KEY: MOD_RES
<222> LOCATION: (84)..(84)
<223> OTHER INFORMATION: Lys, Asn, Arg, Ser, Thr, Ile, Met, Glu, Asp,
      Gly, Ala, Val, Gln, His, Pro, Leu, Tyr, Trp, Cys, or Phe
<220> FEATURE:
<221> NAME/KEY: MOD_RES
<222> LOCATION: (86)..(86)
<223> OTHER INFORMATION: His, Arg, Pro, or Leu
<220> FEATURE:
<221> NAME/KEY: MOD_RES
<222> LOCATION: (87)..(87)
<223> OTHER INFORMATION: Thr, Ala, Pro, or Ser
<220> FEATURE:
<221> NAME/KEY: MOD_RES
<222> LOCATION: (89)..(89)
<223> OTHER INFORMATION: Met, Val, or Leu
<220> FEATURE:
<221> NAME/KEY: MOD_RES
<222> LOCATION: (94)..(94)
<223> OTHER INFORMATION: Arg, or Ser
<220> FEATURE:
<221> NAME/KEY: MOD_RES
<222> LOCATION: (98)..(98)
<223> OTHER INFORMATION: Ile, Val, Leu, or Phe
<220> FEATURE:
<221> NAME/KEY: MOD_RES
<222> LOCATION: (102)..(102)
<223> OTHER INFORMATION: His, Arg, Pro, or Leu
<220> FEATURE:
```

```
<221> NAME/KEY: MOD_RES
<222> LOCATION: (104)..(104)
<223> OTHER INFORMATION: Thr, Ala, Pro, or Ser
<220> FEATURE:
<221> NAME/KEY: MOD_RES
<222> LOCATION: (105)..(105)
<223> OTHER INFORMATION: Asn, Ser, Thr, Ile, Asp, Gly, Ala, Val, His,
      Arg, Pro, Leu, Tyr, Cys, or Phe
<220> FEATURE:
<221> NAME/KEY: MOD_RES
<222> LOCATION: (106)..(106)
<223> OTHER INFORMATION: Lys, or Asn
<220> FEATURE:
<221> NAME/KEY: MOD_RES
<222> LOCATION: (108)..(108)
<223> OTHER INFORMATION: Lys, Arg, Thr, or Met
<220> FEATURE:
<221> NAME/KEY: MOD_RES
<222> LOCATION: (109)..(109)
<223> OTHER INFORMATION: Arg, Ser, Gly, Trp, or Cys
<220> FEATURE:
<221> NAME/KEY: MOD_RES
<222> LOCATION: (111)..(111)
<223> OTHER INFORMATION: Lys, or Asn
<220> FEATURE:
<221> NAME/KEY: MOD_RES
<222> LOCATION: (112)..(112)
<223> OTHER INFORMATION: Glu, Gly, Ala, or Val
<220> FEATURE:
<221> NAME/KEY: MOD_RES
<222> LOCATION: (113)..(113)
<223> OTHER INFORMATION: Lys, Arg, Thr, or Ile
<220> FEATURE:
<221> NAME/KEY: MOD_RES
<222> LOCATION: (114)..(114)
<223> OTHER INFORMATION: His, Arg, Pro, or Leu
<220> FEATURE:
<221> NAME/KEY: MOD_RES
<222> LOCATION: (115)..(115)
<223> OTHER INFORMATION: Asn, Ser, Thr, Ile, Asp, Gly, Ala, Val, His,
      Arg, Pro, Leu, Tyr, Cys, or Phe
<220> FEATURE:
<221> NAME/KEY: MOD_RES
<222> LOCATION: (116)..(116)
<223> OTHER INFORMATION: Tyr, Cys, Ser, or Phe

<400> SEQUENCE: 65

Leu Thr Cys Thr Val Ser Gly Gly Ser Ile Ser Ser Tyr Xaa Trp Xaa
1               5                   10                  15

Trp Ile Arg Gln Pro Xaa Gly Lys Gly Leu Glu Trp Ile Gly Cys Phe
            20                  25                  30

Tyr Tyr Xaa Gly Ser Thr Asn Tyr Asn Pro Ser Xaa Lys Ser His Val
        35                  40                  45

Thr Ile Ser Val Asp Thr Ser Lys Asn Gln Phe Tyr Xaa Lys Leu Ser
    50                  55                  60

Xaa Val Thr Xaa Ala Asp Thr Xaa Xaa Asn Asn Xaa Ala Arg Asp Arg
65                  70                  75                  80

Gly Xaa Val Xaa Trp Xaa Xaa Thr Xaa Thr Thr Glu Ala Xaa Glu Pro
                85                  90                  95

Trp Xaa Thr Val Ile Xaa Lys Xaa Xaa Xaa Gln Xaa Xaa Pro Xaa Xaa
            100                 105                 110

Xaa Xaa Xaa Xaa
        115

<210> SEQ ID NO 66
<211> LENGTH: 157
<212> TYPE: PRT
<213> ORGANISM: Homo sapiens
<220> FEATURE:
<221> NAME/KEY: MOD_RES
```

```
<222> LOCATION: (5)..(5)
<223> OTHER INFORMATION: Ser, Gly, Arg, or Cys
<220> FEATURE:
<221> NAME/KEY: MOD_RES
<222> LOCATION: (23)..(23)
<223> OTHER INFORMATION: Ser, Gly, Arg, or Cys
<220> FEATURE:
<221> NAME/KEY: MOD_RES
<222> LOCATION: (130)..(130)
<223> OTHER INFORMATION: Met, Val, or Leu
<220> FEATURE:
<221> NAME/KEY: MOD_RES
<222> LOCATION: (131)..(131)
<223> OTHER INFORMATION: Ser, Gly, Arg, or Cys
<220> FEATURE:
<221> NAME/KEY: MOD_RES
<222> LOCATION: (140)..(140)
<223> OTHER INFORMATION: Glu, or Asp
<220> FEATURE:
<221> NAME/KEY: MOD_RES
<222> LOCATION: (146)..(146)
<223> OTHER INFORMATION: Arg, or Ser
<220> FEATURE:
<221> NAME/KEY: MOD_RES
<222> LOCATION: (147)..(147)
<223> OTHER INFORMATION: Arg, Gly, or Trp
<220> FEATURE:
<221> NAME/KEY: MOD_RES
<222> LOCATION: (148)..(148)
<223> OTHER INFORMATION: Lys, Arg, Thr, Ile, Glu, Gly, Ala, Val, Gln,
      Pro, Leu, or Ser
<220> FEATURE:
<221> NAME/KEY: MOD_RES
<222> LOCATION: (150)..(150)
<223> OTHER INFORMATION: Lys, Arg, Thr, Met, Glu, Gly, Ala, Val, Gln,
      Pro, Leu, Trp, or Ser
<220> FEATURE:
<221> NAME/KEY: MOD_RES
<222> LOCATION: (154)..(154)
<223> OTHER INFORMATION: Ile, Val, Leu, or Phe
<220> FEATURE:
<221> NAME/KEY: MOD_RES
<222> LOCATION: (155)..(155)
<223> OTHER INFORMATION: His, Arg, Pro, or Leu
<220> FEATURE:
<221> NAME/KEY: MOD_RES
<222> LOCATION: (156)..(156)
<223> OTHER INFORMATION: Gln, His, Arg, Pro, or Leu
<220> FEATURE:
<221> NAME/KEY: MOD_RES
<222> LOCATION: (157)..(157)
<223> OTHER INFORMATION: His, Arg, Pro, or Leu

<400> SEQUENCE: 66

Ser Leu Val Ala Xaa Leu Gly Glu Arg Pro Thr Ile Asn Cys Lys Ser
1               5                   10                  15

Ser Gln Ser Val Leu Tyr Xaa Ser Lys Asn Gln Asn Tyr Leu Ala Trp
            20                  25                  30

Tyr Gln Gln Lys Pro Gly Gln Pro Pro Lys Leu Leu Ile Tyr Trp Ala
        35                  40                  45

Ser Thr Arg Glu Ser Gly Val Pro Asp Arg Phe Arg Gly Ser Gly Ser
    50                  55                  60

Arg Thr Asp Phe Thr Leu Thr Ile Ser Ser Leu Gln Ala Glu Asp Val
65                  70                  75                  80

Ala Val Tyr Phe Cys His Gln Tyr Tyr Ser Thr Pro Trp Thr Phe Gly
                85                  90                  95

Gln Gly Thr Lys Val Glu Ile Lys Arg Thr Val Ala Ala Pro Ser Val
            100                 105                 110

Phe Ile Phe Pro Pro Ser Asp Glu His Leu Glu Ile Leu Glu Leu Pro
        115                 120                 125
```

```
Leu Xaa Xaa Ala Cys Thr Asn Ser Ile Pro Arg Xaa Gly Pro Lys Val
    130                 135                 140

Ser Xaa Xaa Xaa Gly Xaa Ile Thr Pro Xaa Xaa Xaa Xaa
145                 150                 155

<210> SEQ ID NO 67
<211> LENGTH: 157
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Met, Val, or Leu
<220> FEATURE:
<221> NAME/KEY: MOD_RES
<222> LOCATION: (20)..(20)
<223> OTHER INFORMATION: Tyr, Cys, Ser, or Phe
<220> FEATURE:
<221> NAME/KEY: MOD_RES
<222> LOCATION: (111)..(111)
<223> OTHER INFORMATION: Ser, or Leu
<220> FEATURE:
<221> NAME/KEY: MOD_RES
<222> LOCATION: (115)..(115)
<223> OTHER INFORMATION: Lys, or Asn
<220> FEATURE:
<221> NAME/KEY: MOD_RES
<222> LOCATION: (125)..(125)
<223> OTHER INFORMATION: Trp, or Cys
<220> FEATURE:
<221> NAME/KEY: MOD_RES
<222> LOCATION: (131)..(131)
<223> OTHER INFORMATION: Gln, or His
<220> FEATURE:
<221> NAME/KEY: MOD_RES
<222> LOCATION: (136)..(136)
<223> OTHER INFORMATION: Tyr, Cys, Ser, or Phe
<220> FEATURE:
<221> NAME/KEY: MOD_RES
<222> LOCATION: (141)..(141)
<223> OTHER INFORMATION: Asn, Asp, His, or Tyr
<220> FEATURE:
<221> NAME/KEY: MOD_RES
<222> LOCATION: (151)..(151)
<223> OTHER INFORMATION: Glu, Asp, Gly, Ala, or Val
<220> FEATURE:
<221> NAME/KEY: MOD_RES
<222> LOCATION: (153)..(153)
<223> OTHER INFORMATION: Glu, Asp, Gly, Ala, or Val
<220> FEATURE:
<221> NAME/KEY: MOD_RES
<222> LOCATION: (154)..(154)
<223> OTHER INFORMATION: Thr, Ala, Pro, or Ser
<220> FEATURE:
<221> NAME/KEY: MOD_RES
<222> LOCATION: (156)..(156)
<223> OTHER INFORMATION: Lys, Glu, or Gln
<220> FEATURE:
<221> NAME/KEY: MOD_RES
<222> LOCATION: (157)..(157)
<223> OTHER INFORMATION: Leu

<400> SEQUENCE: 67

Lys Pro Phe Gln Thr Xaa Pro Phe Thr Cys Thr Val Ser Gly Gly Ser
1               5                   10                  15

Ile Ser Ser Xaa Gly Tyr Tyr Trp Ser Trp Ile Arg Gln His Pro Gly
            20                  25                  30

Lys Gly Leu Glu Trp Ile Gly Tyr Ile Tyr Asn Ser Gly Ser Thr Tyr
        35                  40                  45

Tyr Asn Pro Ser Leu Gln Ser Arg Val Thr Ile Ser Val Asp Thr Ser
    50                  55                  60

Lys Asn Gln Phe Ser Leu Lys Leu Ser Ser Val Thr Ala Ala Asp Thr
```

```
                65                  70                  75                  80
Ala Val Tyr Tyr Cys Ala Gly Gln Lys Trp Ser Tyr Tyr Tyr Tyr
                    85                  90                  95

Gly Met Asp Val Trp Gly Gln Gly Thr Thr Val Thr Val Ser Xaa Ala
                100                 105                 110

Ser Thr Xaa Gly Pro Ser Val Phe Pro Leu Ala Pro Xaa Ser Arg Ser
            115                 120                 125

Thr Ser Xaa Ser Thr Asp Gly Xaa Trp Ala Cys Leu Xaa Gln Trp Thr
    130                 135                 140

Thr Phe Pro Glu Pro Val Xaa Cys Xaa Xaa Trp Xaa Xaa
145                 150                 155

<210> SEQ ID NO 68
<211> LENGTH: 152
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Leu, or Phe
<220> FEATURE:
<221> NAME/KEY: MOD_RES
<222> LOCATION: (6)..(6)
<223> OTHER INFORMATION: Met, Val, or Leu
<220> FEATURE:
<221> NAME/KEY: MOD_RES
<222> LOCATION: (151)..(151)
<223> OTHER INFORMATION: Arg, Gly, or Trp

<400> SEQUENCE: 68

Lys Pro Xaa Glu Thr Xaa Pro Leu Thr Cys Thr Val Ser Gly Gly Ser
1               5                   10                  15

Ile Ser Asn Tyr Tyr Trp Ser Trp Ile Arg Gln Pro Pro Gly Lys Gly
                20                  25                  30

Leu Glu Trp Ile Gly Tyr Ile Tyr Tyr Ser Gly Ser Thr Asn Tyr Asn
            35                  40                  45

Pro Ser Leu Lys Ser Arg Val Thr Ile Ser Val Asp Thr Ser Lys Asn
    50                  55                  60

Gln Phe Ser Leu Lys Leu Ser Ser Val Thr Ala Ala Asp Thr Ala Val
65                  70                  75                  80

Tyr Tyr Cys Ala Arg Gly Pro Gly Gly Ser Tyr Tyr Tyr Tyr Gly Met
                85                  90                  95

Asp Val Trp Gly Gln Gly Thr Thr Val Thr Val Ser Ser Ala Ser Thr
                100                 105                 110

Lys Gly Pro Ser Val Phe Pro Leu Ala Pro Cys Ser Arg Ser Thr Ser
            115                 120                 125

Glu Ser Thr Ala Ala Leu Gly Cys Leu Gly Gln Gly Leu Leu Pro Arg
    130                 135                 140

Thr Gly Asp Gly Val Arg Xaa Asn
145                 150

<210> SEQ ID NO 69
<211> LENGTH: 131
<212> TYPE: PRT
<213> ORGANISM: Homo sapiens

<400> SEQUENCE: 69

Leu Ser Ala Ser Val Gly Asp Arg Val Ile Ile Thr Cys Arg Ala Ser
1               5                   10                  15

Gln Asn Ile Thr Asp His Leu Asn Trp Tyr Gln Gln Ile Ala Gly Lys
```

-continued

```
                20                  25                  30
Ala Pro Arg Pro Leu Ile Tyr Thr Ala Ser Ser Leu Gln Gly Gly Val
        35                  40                  45

Pro Ser Arg Phe Ser Gly Ser Gly Ser Gly Thr Asp Phe Thr Leu Thr
    50                  55                  60

Ile Ser Ser Leu Gln Pro Glu Asp Phe Ser Thr Tyr Tyr Cys Gln Gln
65                  70                  75                  80

Ser Tyr Ser Thr Pro Cys Ser Phe Gly Gln Gly Thr Lys Leu Glu Ile
                85                  90                  95

Lys Arg Thr Val Ala Ala Pro Ser Val Phe Ile Phe Pro Pro Ser Asp
            100                 105                 110

Glu Gln Leu Lys Ser Gly Thr Ala Ser Val Val Cys Leu Leu Asn Asn
        115                 120                 125

Phe Tyr Pro
    130
```

<210> SEQ ID NO 70
<211> LENGTH: 103
<212> TYPE: PRT
<213> ORGANISM: Homo sapiens
<220> FEATURE:
<221> NAME/KEY: MOD_RES
<222> LOCATION: (41)..(41)
<223> OTHER INFORMATION: Lys, Arg, Thr, or Ile.

<400> SEQUENCE: 70

```
Val Lys Val Ser Cys Lys Ala Ser Gly Tyr Thr Phe Ser Gly Tyr Tyr
1               5                   10                  15

Met His Trp Val Arg Gln Ala Pro Gly Gln Gly Leu Glu Trp Met Gly
            20                  25                  30

Ser Ile His Pro Asn Ser Gly Gly Xaa Asn Phe Ala Gln Lys Phe Gln
        35                  40                  45

Gly Arg Val Thr Met Thr Arg Asp Thr Ser Ile Asn Thr Ala Tyr Leu
    50                  55                  60

Glu Leu Ser Arg Leu Arg Ser Asp Asp Thr Ala Val Tyr Tyr Cys Ala
65                  70                  75                  80

Arg Asp Lys Asn Tyr Gly Asp Tyr Val Phe Asp Tyr Trp Gly Gln Gly
                85                  90                  95

Thr Leu Val Thr Val Ser Ser
            100
```

<210> SEQ ID NO 71
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71 tatac                                                               5

<210> SEQ ID NO 72
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72

```
gtata                                                              5
```

<210> SEQ ID NO 73
<211> LENGTH: 21
<212> TYPE: PRT
<213> ORGANISM: Homo sapiens

<400> SEQUENCE: 73

Ala Ser Thr Lys Gly Pro Ser Val Phe Pro Leu Ala Pro Cys Ser
 1               5                  10                  15

Arg Ser Thr Ser Thr
            20

<210> SEQ ID NO 74
<211> LENGTH: 17
<212> TYPE: PRT
<213> ORGANISM: Homo sapiens

<400> SEQUENCE: 74

Arg Thr Val Ala Ala Pro Ser Val Phe Ile Phe Pro Pro Ser Asp Glu
 1               5                  10                  15

Gln

<210> SEQ ID NO 75
<211> LENGTH: 99
<212> TYPE: PRT
<213> ORGANISM: Homo sapiens

<400> SEQUENCE: 75

Val Ser Gly Gly Ser Ile Ser Ser Gly Cys Tyr Tyr Trp Ser Trp Ile
 1               5                  10                  15

Arg Gln His Pro Gly Lys Gly Leu Glu Trp Ile Gly Tyr Ile Tyr Asn
            20                  25                  30

Ser Gly Ser Thr Tyr Tyr Asn Pro Ser Leu Gln Ser Arg Val Thr Ile
        35                  40                  45

Ser Val Asp Thr Ser Lys Asn Gln Phe Ser Leu Lys Leu Ser Ser Val
    50                  55                  60

Thr Ala Ala Asp Thr Ala Val Tyr Tyr Cys Ala Gly Lys Trp Ser Tyr
65                  70                  75                  80

Tyr Tyr Tyr Tyr Gly Met Asp Val Trp Gly Gln Gly Thr Thr Val Thr
                85                  90                  95

Val Ser Ser

<210> SEQ ID NO 76
<211> LENGTH: 96
<212> TYPE: PRT
<213> ORGANISM: Homo sapiens

<400> SEQUENCE: 76

Val Ser Gly Gly Ser Val Ser Ser Gly Asp Tyr Tyr Trp Thr Trp Ile
 1               5                  10                  15

Arg Gln Ser Pro Gly Lys Gly Leu Glu Trp Ile Gly His Ile Tyr Tyr
            20                  25                  30

Ser Gly Asn Thr Asn Tyr Asn Pro Ser Leu Lys Ser Arg Leu Thr Ile
        35                  40                  45

Ser Ile Asp Thr Ser Lys Thr Gln Phe Ser Leu Lys Leu Ser Ser Val
    50                  55                  60

Thr Ala Ala Asp Thr Ala Ile Tyr Tyr Cys Val Arg Asp Arg Val Thr

-continued

```
        65                  70                  75                  80
Gly Ala Phe Asp Ile Trp Gly Gln Gly Thr Met Val Thr Val Ser Ser
                    85                  90                  95
```

HUMAN MONOCLONAL ANTIBODIES TO EPIDERMAL GROWTH FACTOR RECEPTOR

CROSS REFERENCE TO RELATED APPLICATIONS

The present application is a continuation application of U.S. patent application Ser. No. 11/021,795, filed Dec. 22, 2004, abandoned, which is a continuation application of U.S. patent application Ser. No. 09/187,693, filed Nov. 5, 1998, abandoned, which is a continuation-in-part application of U.S. patent application Ser. No. 09/162,280, filed Sep. 29, 1998, abandoned, which is a continuation-in-part application of U.S. patent application Ser. No. 08/851,362, filed May 5, 1997, which issued as U.S. Pat. No. 6,235,883.

BACKGROUND OF THE INVENTION

1. Summary of the Invention

In accordance with the present invention, there are provided fully human contiguous heavy and light chain sequences spanning the complementarity determining regions monoclonal antibodies against human epidermal growth factor receptor (EGF-r). Nucelotide sequences encoding and amino acid sequences comprising heavy and light chain immunoglobulin molecules, particularly sequences corresponding to (CDR's), specifically from CDR1 through CDR3, are provided. Hybridomas expressing such immunoglobulin molecules and monoclonal antibodies are also provided. Also provided in accordance with the invention are antibodies that possess one or more of the following functional characteristics: (i) inhibit tyrosine phosphorylation of EGF-r, (ii) do not inhibit EGF-r internalization, (ii) inhibit EGF-r degradation, (iii) inhibition of EGF induced EGF-r degradation, (iv) protect threonine phosphorylation of EGF-r, (v) protect threonine phosphorylation of other molecules, particularly a 62 KD molecule identified by immunoprecipitation, and (vi) inhibit vascular endothelial cell growth factor signal by tumor cells by greater than 50% and endothelial cells by greater than 40% relative to control.

2. Background of the Technology

Most applications of monoclonal antibodies (MAbs) in cancer therapy rely on the ability of the antibody to specifically deliver to the cancerous tissues cytotoxic effector functions such as immune-enhancing isotypes, toxins or drugs. An alternative approach is to utilize MAbs to directly affect the survival of tumor cells by depriving them of essential extracellular proliferation signals, such as those mediated by growth factors through their cell receptors. One of the attractive targets in this approach is the epidermal growth factor receptor (EGFr), which binds EGF and transforming growth factor α (TGFα) (1-4). Binding of EGF or TGFα to EGFr, a 170 kDa transmembrane ell surface glycoprotein, triggers a cascade of cellular biochemical events, including EGFr autophosphorylation and internalization, which culminates in cell proliferation (1).

Several observations implicate EGFr in supporting development and progression of human solid tumors. Overexpression of EGFr has been shown to induce transformed properties in recipient cells (5). EGFr expression has been found to be up-regulated on many human tumors, including lung, colon, breast, prostate, brain, head and neck, ovarian and renal carcinoma, and the increase in receptor levels has been reported to be associated with a poor clinical prognosis (2, 3, 6-8). In many cases, the increased surface EGFr expression was accompanied by production of TGFα or EGF by the tumor cells, suggesting the involvement of an autocrine growth control in the progression of these tumors (2, 3, 6, 8). These observations suggested that blocking the interaction between the growth factors and EGFr could result in arrest of tumor growth and possibly affect tumor survival (2-4,6).

MAbs specific to the human EGFr, capable of neutralizing EGF and TGFα binding to tumor cells and of inhibiting ligand-mediated cell proliferation in vitro, have been generated from mice and rats (2,3,4,6). Some of these antibodies, such as the mouse 108 (9) 225 and 528 (2,3) or the rat ICR16, ICR62 and ICR64 (6, 10, 11) MAbs, were evaluated extensively for their ability to affect tumor growth in xenograft mouse models. Most of the anti-EGFr MAbs were efficacious in preventing tumor formation in athymic mice when administered together with the human tumor cells (2,11). When injected into mice bearing established human tumor xenografts, the mouse MAbs 225 and 528 caused partial tumor regression and required the co-administration of chemotherapeutic agents, such as doxorubicin or cisplatin, for eradication of the tumors (2, 3, 12, 13). A chimeric version of the 225 MAb (C225), in which the mouse antibody variable regions are linked to human constant regions, exhibited an improved in vivo anti-tumor activity but only at high doses (14, 15). The rat ICR16, ICR62, and ICR64 antibodies caused regression of established tumors but not their complete eradication (11). These results established EGFr as a promising target for antibody therapy against EGFr-expressing solid tumors and led to human clinical trials with the C225 MAb in multiple human solid cancers (2,3,6). However, the limited efficacy of these MAbs as monotherapeutic agents required their assessment in combination with chemotherapy (16, 17). This requirement can limit the utilization of anti-EGFr antibodies in patients for whom chemotherapy is not available. Therefore, the identification of an anti-EGFr antibody capable of eradicating established human tumors by itself can expand the patient populations and cancer indications to which EGFr antibody therapy can be applied successfully. In addition, the MAbs currently pursued in human clinical trials, being murine chimeric antibodies (2,4), are likely to induce immunogenic or allergic responses to the mouse components in immunocompetent patients, leading to reduction in the antibody efficacy and safety. Therefore, anti-EGFr antibody therapy can be fully evaluated with the availability of a fully human anti-EGFr antibody that exhibits therapeutic efficacy on EGFr-expressing tumors and that can be administered repeatedly to all appropriate patient populations.

EGF-r has been demonstrated to be overexpressed on many types of human solid tumors. Mendelsohn *Cancer Cells* 7:359 (1989), Mendelsohn *Cancer Biology* 1:339-344 (1990), Modjtahedi and Dean *Int'l J Oncology* 4:277-296 (1994). For example, EGF-r overexpression has been observed in certain lung, breast, colon, gastric, brain, bladder, head and neck, ovarian, and prostate carcinomas. Modjtahedi and Dean *Int'l J. Oncology* 4:277-296 (1994). Both epidermal growth factor (EGF) and transforming growth factor-alpha (TGF-α) have been demonstrated to bind to EGF-r and to lead to cellular proliferation and tumor growth.

Thus, certain groups have proposed that antibodies against EGF, TGF-α, and EGF-r may be useful in the therapy of tumors expressing or overexpressing EGF-r. Mendelsohn *Cancer Cells* 7:359 (1989), Mendelsohn *Cancer Biology* 1:339-344 (1990), Modjtahedi and Dean *Int'l J. Oncology* 4:277-296 (1994), Tosi et al. *Int'l J. Cancer* 62:643-650 (1995). Indeed, it has been demonstrated that anti-EGF-r antibodies while blocking EGF and TGF-α binding to the receptor appear to inhibit tumor cell proliferation. At the same time, however, anti-EGF-r antibodies have not appeared to inhibit EGF and TGF-α independent cell growth. Modjtahedi and Dean *Int'l J. Oncology* 4:277-296 (1994).

In view of these findings, a number of murine and rat monoclonal antibodies against EGF-r have been developed and tested for their ability inhibit the growth of tumor cells in vitro and in vivo. Modjtahedi and Dean *Int'l J. Oncology* 4:277-296 (1994). The antibody that has apparently advanced the farthest in the clinic is a chimeric antibody, designated C225, which has a murine variable region and a human IgG1 constant region. Modjtahedi and Dean *Int'l J. Oncology* 4:277-296 (1994). The murine antibody, designated 225, upon which the C225 antibody is based, was developed by University of California and Rorer. See U.S. Pat. No. 4,943,533 and European Patent No. 359,282, the disclosures of which are hereby incorporated by reference. The C225 antibody was demonstrated to inhibit EGF-mediated tumor cell growth in vitro and inhibit human tumor formation in vivo in nude mice. The antibody, moreover, appeared to act in synergy with certain chemotherapeutic agents to eradicate human tumors in vivo in xenograft mouse models. Modjtahedi and Dean *Int'l J. Oncology* 4:277-296 (1994).

ImClone has been conducting human clinical trials using the anti-EGF-r antibody designated C225. Phase I and Phase I/II clinical trials in patients with head and neck, prostate, and lung carcinomas apparently have been, or are currently being, conducted with C225. In Phase I clinical trials, no toxicity was detected with multiple injections and with doses of up to perhaps 400 mg/m$^2$, even in cases involving immuno compromised patients. Such studies were conducted as dose escalation studies comprising 5 doses of from about 5 to about 200 mg/m$^2$ and were performed in combination with chemotherapy (i.e., doxorubicin, adriamycin, taxol, and cisplatin). In addition to the apparent safety data that has been generated in these studies, preliminary results from the studies appear to indicate some evidence of tumor shrinkage in 80% of patients having prostate cancer.

Each of these above-mentioned antibodies, however, possess murine or rat variable and/or constant regions. The presence of such murine or rat derived proteins can lead to the rapid clearance of the antibodies or can lead to the generation of an immune response against the antibody by a patient. In order to avoid the utilization of murine or rat derived antibodies, it has been postulated that one could introduce human antibody function into a rodent so that the rodent would produce fully human antibodies.

The ability to clone and reconstruct megabase-sized human loci in YACs and to introduce them into the mouse germline provides a powerful approach to elucidating the functional components of very large or crudely mapped loci as well as generating useful models of human disease. Furthermore, the utilization of such technology for substitution of mouse loci with their human equivalents could provide unique insights into the expression and regulation of human gene products during development, their communication with other systems, and their involvement in disease induction and progression.

An important practical application of such a strategy is the "humanization" of the mouse humoral immune system. Introduction of human immunoglobulin (Ig) loci into mice in which the endogenous Ig genes have been inactivated offers the opportunity to study the mechanisms underlying programmed expression and assembly of antibodies as well as their role in B-cell development. Furthermore, such a strategy could provide an ideal source for production of fully human monoclonal antibodies (Mabs)—an important milestone towards fulfilling the promise of antibody therapy in human disease. Fully human antibodies are expected to minimize the immunogenic and allergic responses intrinsic to mouse or mouse-derivatized Mabs and thus to increase the efficacy and safety of the administered antibodies. The use of fully human antibodies can be expected to provide a substantial advantage in the treatment of chronic and recurring human diseases, such as inflammation, autoimmunity, and cancer, which require repeated antibody administrations.

One approach towards this goal was to engineer mouse strains deficient in mouse antibody production with large fragments of the human Ig loci in anticipation that such mice would produce a large repertoire of human antibodies in the absence of mouse antibodies. Large human Ig fragments would preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains should yield high affinity antibodies against any antigen of interest, including human antigens. Using the hybridoma technology, antigen-specific human Mabs with the desired specificity could be readily produced and selected.

This general strategy was demonstrated in connection with our generation of the first XenoMouse™ strains as published in 1994. See Green et al. *Nature Genetics* 7:13-21 (1994). The XenoMouse™ strains were engineered with yeast artificial chromosomes (YACs) containing 245 kb and 190 kb-sized germline configuration fragments of the human heavy chain locus and kappa light chain locus, respectively, which contained core variable and constant region sequences. Id. The human Ig containing YACs proved to be compatible with the mouse system for both rearrangement and expression of antibodies and were capable of substituting for the inactivated mouse Ig genes. This was demonstrated by their ability to induce B-cell development, to produce an adult-like human repertoire of fully human antibodies, and to generate antigen-specific human Mabs. These results also suggested that introduction of larger portions of the human Ig loci containing greater numbers of V genes, additional regulatory elements, and human Ig constant regions might recapitulate substantially the full repertoire that is characteristic of the human humoral response to infection and immunization. The work of Green et al. was recently extended to the introduction of greater than approximately 80% of the human antibody repertoire through introduction of megabase sized, germline configuration YAC fragments of the human heavy chain loci and kappa light chain loci, respectively. See Mendez et al. *Nature Genetics* 15:146-156 (1997) and U.S. patent application Ser. No. 08/759,620, filed Dec. 3, 1996, the disclosures of which are hereby incorporated by reference.

Such approach is further discussed and delineated in U.S. patent application Ser. No. 07/466,008, filed Jan. 12, 1990, Ser. No. 07/610,515, filed Nov. 8, 1990, Ser. No. 07/919,297, filed Jul. 24, 1992, Ser. No. 07/922,649, filed Jul. 30, 1992, filed Ser. No. 08/031,801, filed Mar. 15, 1993, Ser. No. 08/112,848, filed Aug. 27, 1993, Ser. No. 08/234,145, filed Apr. 28, 1994, Ser. No. 08/376,279, filed Jan. 20, 1995, Ser. No. 08/430,938, Apr. 27, 1995, Ser. No. 08/464,584, filed Jun. 5, 1995, Ser. No. 08/464,582, filed Jun. 5, 1995, Ser. No. 08/463,191, filed Jun. 5, 1995, Ser. No. 08/462,837, filed Jun. 5, 1995, Ser. No. 08/486,853, filed Jun. 5, 1995, Ser. No. 08/486,857, filed Jun. 5, 1995, Ser. No. 08/486,859, filed Jun. 5, 1995, Ser. No. 08/462,513, filed Jun. 5, 1995, Ser. No. 08/724,752, filed Oct. 2, 1996, and Ser. No. 08/759,620, filed Dec. 3, 1996. See also Mendez et al. *Nature Genetics* 15:146-156 (1997). See also European Patent No., EP 0 463 151 B1, grant published Jun. 12, 1996, International Patent Application No., WO 94/02602, published Feb. 3, 1994, International Patent Application No., WO 96/34096, published Oct. 31, 1996, and PCT Application No. PCT/US96/05928, filed Apr. 29, 1996. The disclosures of each of the above-cited patents, applications, and references are hereby incorporated by reference in their entirety.

In an alternative approach, others, including GenPharm International, Inc., have utilized a "minilocus" approach. In the minilocus approach, an exogenous Ig locus is mimicked through the inclusion of pieces (individual genes) from the Ig locus. Thus, one or more $V_H$ genes, one or more $D_H$ genes, one or more $J_H$ genes, a mu constant region, and a second constant region (preferably a gamma constant region) are formed into a construct for insertion into an animal. This approach is described in U.S. Pat. No. 5,545,807 to Surani et al. and U.S. Pat. Nos. 5,545,806 and 5,625,825, both to Lonberg and Kay, and GenPharm International U.S. patent application Ser. No. 07/574,748, filed Aug. 29, 1990, Ser. No. 07/575,962, filed Aug. 31, 1990, Ser. No. 07/810,279, filed Dec. 17, 1991, Ser. No. 07/853,408, filed Mar. 18, 1992, Ser. No. 07/904,068, filed Jun. 23, 1992, Ser. No. 07/990,860, filed Dec. 16, 1992, Ser. No. 08/053,131, filed Apr. 26, 1993, Ser. No. 08/096,762, filed Jul. 22, 1993, Ser. No. 08/155,301, filed Nov. 18, 1993, Ser. No. 08/161,739, filed Dec. 3, 1993, Ser. No. 08/165,699, filed Dec. 10, 1993, Ser. No. 08/209,741, filed Mar. 9, 1994, the disclosures of which are hereby incorporated by reference. See also International Patent Application Nos. WO 94/25585, published Nov. 10, 1994, WO 93/12227, published Jun. 24, 1993, WO 92/22645, published Dec. 23, 1992, WO 92/03918, published Mar. 19, 1992, the disclosures of which are hereby incorporated by reference in their entirety. See further Taylor et al., 1992, Chen et al., 1993, Tuaillon et al., 1993, Choi et al., 1993, Lonberg et al., (1994), Taylor et al., (1994), and Tuaillon et al., (1995), the disclosures of which are hereby incorporated by reference in their entirety.

The inventors of Surani et al., cited above and assigned to the Medical Research Counsel (the "MRC"), produced a transgenic mouse possessing an Ig locus through use of the minilocus approach. The inventors on the GenPharm International work, cited above, Lonberg and Kay, following the lead of the present inventors, proposed inactivation of the endogenous mouse Ig locus coupled with substantial duplication of the Surani et al. work.

An advantage of the minilocus approach is the rapidity with which constructs including portions of the Ig locus can be generated and introduced into animals. Commensurately, however, a significant disadvantage of the minilocus approach is that, in theory, insufficient diversity is introduced through the inclusion of small numbers of V, D, and J genes. Indeed, the published work appears to support this concern. B-cell development and antibody production of animals produced through use of the minilocus approach appear stunted. Therefore, research surrounding the present invention has consistently been directed towards the introduction of large portions of the Ig locus in order to achieve greater diversity and in an effort to reconstitute the immune repertoire of the animals.

Human anti-mouse antibody (HAMA) responses have led the industry to prepare chimeric or otherwise humanized antibodies. While the C225 antibody is a chimeric antibody, having a human constant region and a murine variable region, it is expected that certain human anti-chimeric antibody (HACA) responses will be observed, particularly in chronic or multi-dose utilizations of the antibody.

Thus, it would be desirable to provide fully human antibodies against EGF-r that possess similar or enhanced activities as compared to C225 in order to vitiate concerns and/or effects of HAMA or HACA response.

BRIEF DESCRIPTION OF THE DRAWING FIGURES

FIG. 1 (SEQ ID NO: 39) is an amino acid sequence of a heavy chain immunoglobulin molecule that is secreted by the hybridoma E1.1. Differences between the sequence encoded by heavy chain variable gene 4-31 and the sequence of the E1.1 secreted heavy chain are indicated in bold and enlarged font. The contiguous sequence from CDR1 through CDR3 is indicated by underlining and CDR1, CDR2, and CDR3 sequences are each indicated by double underlining.

FIG. 2 (SEQ ID NO: 3) is a nucleotide sequence of the cDNA encoding the heavy chain immunoglobulin molecule of FIG. 1 that was cloned out of the hybridoma E1.1.

FIG. 3 (SEQ ID NO: 40) is an amino acid sequence of a kappa light chain immunoglobulin molecule that is secreted by the hybridoma E1.1. Differences between the sequence encoded by light chain variable gene 018 and the sequence of the E1.1 secreted light chain are indicated in bold and enlarged font. The contiguous sequence from CDR1 through CDR3 is indicated by underlining and CDR1, CDR2, and CDR3 sequences are each indicated by double underlining.

FIG. 4 (SEQ ID NO: 4) is a nucleotide sequence of the cDNA encoding the kappa light chain immunoglobulin molecule of FIG. 3 that was cloned out of the hybridoma E1.1.

FIG. 5 (SEQ ID NO: 41) is an amino acid sequence of a heavy chain immunoglobulin molecule that is secreted by the hybridoma E2.4. Differences between the sequence encoded by heavy chain variable gene 4-31 and the sequence of the E2.4 secreted heavy chain are indicated in bold and enlarged font. The contiguous sequence from CDR1 through CDR3 is indicated by underlining and CDR1, CDR2, and CDR3 sequences are each indicated by double underlining.

FIG. 6 (SEQ ID NO: 5) is a nucleotide sequence of the cDNA encoding the heavy chain immunoglobulin molecule of FIG. 5 that was cloned out of the hybridoma E2.4.

FIG. 7 (SEQ ID NO: 42) is an amino acid sequence of a kappa light chain immunoglobulin molecule that is secreted by the hybridoma E2.4. Differences between the sequence encoded by light chain variable gene 018 and the sequence of the E2.4 secreted light chain are indicated in bold and enlarged font. The contiguous sequence from CDR1 through CDR3 is indicated by underlining and CDR1, CDR2, and CDR3 sequences are each indicated by double underlining.

FIG. 8 (SEQ ID NO: 6) is a nucleotide sequence of the cDNA encoding the kappa light chain immunoglobulin molecule of FIG. 7 that was cloned out of the hybridoma E2.4.

FIG. 9 (SEQ ID NO: 43) is an amino acid sequence of a heavy chain immunoglobulin molecule that is secreted by the hybridoma E2.5. Differences between the sequence encoded by heavy chain variable gene 4-31 and the sequence of the E2.5 secreted heavy chain are indicated in bold and enlarged font. The contiguous sequence from CDR1 through CDR3 is indicated by underlining and CDR1, CDR2, and CDR3 sequences are each indicated by double underlining.

FIG. 10 (SEQ ID NO: 7) is a nucleotide sequence of the cDNA encoding the heavy chain immunoglobulin molecule of FIG. 9 that was cloned out of the hybridoma E2.5.

FIG. 11 (SEQ ID NO: 44) is an amino acid sequence of a kappa light chain immunoglobulin molecule that is secreted by the hybridoma E2.5. Differences between the sequence encoded by light chain variable gene 018 and the sequence of the E2.5 secreted light chain are indicated in bold and enlarged font. The contiguous sequence from CDR1 through CDR3 is indicated by underlining and CDR1, CDR2, and CDR3 sequences are each indicated by double underlining.

FIG. 12 (SEQ ID NO: 8) is a nucleotide sequence of the cDNA encoding the kappa light chain immunoglobulin molecule of FIG. 11 that was cloned out of the hybridoma E2.5.

FIG. 13 (SEQ ID NO: 45) is an amino acid sequence of a heavy chain immunoglobulin molecule that is secreted by the hybridoma E6.2. Differences between the sequence encoded by heavy chain variable gene 4-31 and the sequence of the E6.2 secreted heavy chain are indicated in bold and enlarged font. The contiguous sequence from CDR1 through CDR3 is indicated by underlining and CDR1, CDR2, and CDR3 sequences are each indicated by double underlining.

FIG. 14 (SEQ ID NO: 9) is a nucleotide sequence of the cDNA encoding the heavy chain immunoglobulin molecule of FIG. 13 that was cloned out of the hybridoma E6.2.

FIG. 15 (SEQ ID NO: 46) is an amino acid sequence of a kappa light chain immunoglobulin molecule that is secreted by the hybridoma E6.2. Differences between the sequence encoded by light chain variable gene 018 and the sequence of the E6.2 secreted light chain are indicated in bold and enlarged font. The contiguous sequence from CDR1 through CDR3 is indicated by underlining and CDR1, CDR2, and CDR3 sequences are each indicated by double underlining.

FIG. 16 (SEQ ID NO: 10) is a nucleotide sequence of the cDNA encoding the kappa light chain immunoglobulin molecule of FIG. 15 that was cloned out of the hybridoma E6.2.

FIG. 17 (SEQ ID NO: 47) is an amino acid sequence of a heavy chain immunoglobulin molecule that is secreted by the hybridoma E6.4. Differences between the sequence encoded by heavy chain variable gene 4-31 and the sequence of the E6.4 secreted heavy chain are indicated in bold and enlarged font. The contiguous sequence from CDR1 through CDR3 is indicated by underlining and CDR1, CDR2, and CDR3 sequences are each indicated by double underlining.

FIG. 18 (SEQ ID NO: 11) is a nucleotide sequence of the cDNA encoding the heavy chain immunoglobulin molecule of FIG. 17 that was cloned out of the hybridoma E6.2.

FIG. 19 (SEQ ID NO: 48) is an amino acid sequence of a kappa light chain immunoglobulin molecule that is secreted by the hybridoma E6.4. Differences between the sequence encoded by light chain variable gene 018 and the sequence of the E6.4 secreted light chain are indicated in bold and enlarged font. The contiguous sequence from CDR1 through CDR3 is indicated by underlining and CDR1, CDR2, and CDR3 sequences are each indicated by double underlining.

FIG. 20 (SEQ ID NO: 12) is a nucleotide sequence of the cDNA encoding the kappa light chain immunoglobulin molecule of FIG. 19 that was cloned out of the hybridoma E6.4.

FIG. 21 (SEQ ID NO: 49) is an amino acid sequence of a heavy chain immunoglobulin molecule that is secreted by the hybridoma E2.11. Differences between the sequence encoded by heavy chain variable gene 4-61 and the sequence of the E2.11 secreted heavy chain are indicated in bold and enlarged font. The contiguous sequence from CDR1 through CDR3 is indicated by underlining and CDR1, CDR2, and CDR3 sequences are each indicated by double underlining.

FIG. 22 (SEQ ID NO: 13) is a nucleotide sequence of the cbNA encoding the heavy chain immunoglobulin molecule of FIG. 21 that was cloned out of the hybridoma E2.11.

FIG. 23 (SEQ ID NO: 50) is an amino acid sequence of a kappa light chain immunoglobulin molecule that is secreted by the hybridoma E2.11. Differences between the sequence encoded by light chain variable gene 018 and the sequence of the E2.11 secreted light chain are indicated in bold and enlarged font. The contiguous sequence from CDR1 through CDR3 is indicated by underlining and CDR1, CDR2, and CDR3 sequences are each indicated by double underlining.

FIG. 24 (SEQ ID NO: 14) is a nucleotide sequence of the cDNA encoding the kappa light chain immunoglobulin molecule of FIG. 23 that was cloned out of the hybridoma E2.11.

FIG. 25 (SEQ ID NO: 51) is an amino acid sequence of a heavy chain immunoglobulin molecule that is secreted by the hybridoma E6.3. Differences between the sequence encoded by heavy chain variable gene 4-61 and the sequence of the E6.3 secreted heavy chain are indicated in bold and enlarged font. The contiguous sequence from CDR1 through CDR3 is indicated by underlining and CDR1, CDR2, and CDR3 sequences are each indicated by double underlining.

FIG. 26 (SEQ, ID NO: 15) is a nucleotide sequence of the cDNA encoding the heavy chain immunoglobulin molecule of FIG. 25 that was cloned out of the hybridoma E6.3.

FIG. 27 (SEQ ID NO: 52) is an amino acid sequence of a kappa light chain immunoglobulin molecule that is secreted by the hybridoma E6.3. Differences between the sequence encoded by light chain variable gene 018 and the sequence of the E6.3 secreted light chain are indicated in bold and enlarged font. The contiguous sequence from CDR1 through CDR3 is indicated by underlining and CDR1, CDR2, and CDR3 sequences are each indicated by double underlining.

FIG. 28 (SEQ ID NO: 16) is a nucleotide sequence of the cDNA encoding the kappa light chain immunoglobulin molecule of FIG. 27 that was cloned out of the hybridoma E6.3.

FIG. 29 (SEQ ID NO: 53) is an amino acid sequence of a heavy chain immunoglobulin molecule that is secreted by the hybridoma E7.6.3. Differences between the sequence encoded by heavy chain variable gene 4-61 and the sequence of the E7.6.3 secreted heavy chain are indicated in bold and enlarged font. The contiguous sequence from CDR1 through CDR3 is indicated by underlining and CDR1, CDR2, and CDR3 sequences are each indicated by double underlining.

FIG. 30 (SEQ ID NO: 17) is a nucleotide sequence of the cDNA encoding the heavy chain immunoglobulin molecule of FIG. 29 that was cloned out of the hybridoma E7.6.3.

FIG. 31 (SEQ ID NO: 54) is an amino acid sequence of a kappa light chain immunoglobulin molecule that is secreted by the hybridoma E7.6.3. Differences between the sequence encoded by light chain variable gene 018 and the sequence of the E7.6.3 secreted light chain are indicated in bold and enlarged font. The contiguous sequence from CDR1 through CDR3 is indicated by underlining and CDR1, CDR2, and CDR3 sequences are each indicated by double underlining.

FIG. 32 (SEQ ID NO: 18) is a nucleotide sequence of the cDNA encoding the kappa light chain immunoglobulin molecule of FIG. 31 that was cloned out of the hybridoma E7.6.3.

FIG. 33 provides a comparison of specific anti-EGF-r antibody heavy chain amino acid sequence comparisons (SEQ ID NOS: 39, 41, 43, 45, 47, 49, 51, and 76) with the amino acid sequence of the particular $V_H$ gene which encodes the heavy chain of the particular antibody (SEQ ID NOS: 35, 38, and 73).

FIG. 34 provides a comparison of specific anti-EGF-r antibody light chain amino acid sequence comparisons (SEQ ID NOS: 40, 42, 44, 50, 46, 52, 48, and 54) with the amino acid sequence of the particular $V_K$ gene which encodes the light chain of the particular antibody (SEQ ID NOS: 36 and 74).

FIG. 35 shows blockage EGF binding to human epidermoid carcinoma A431 cells by human anti-EGF-r antibodies in vitro, where (□) depicts the results achieved by an anti-EGF-r antibody in accordance with the invention, (●) depicts the results achieved by the murine monoclonal antibody 225, and (▲) depicts the results achieved by a control, nonspecific, human IgG2 antibody.

FIG. 36 shows inhibition of EGF binding to human epidermold carcinoma A431 cells by human anti-EGF-r antibodies in vitro, where (□) depicts the results achieved by the murine monoclonal antibody 225, (○) depicts the results achieved by the murine monoclonal antibody 528, (▼) depicts the results achieved using the E1.1 antibody in accordance with the invention, (▲) depicts the results achieved using the E2.4 antibody in accordance with the invention, (▶) depicts the results achieved using the E2.5 antibody in accordance with the invention, (◀) depicts the results achieved using the E2.6 antibody in accordance with the invention, (♦) depicts the results achieved using the E2.11 antibody in accordance with the invention, and (▩) depicts the results achieved using a control, nonspecific human IgG2 antibody.

FIG. 37 shows inhibition of TGF-α binding to human epidermoid carcinoma A431 cells by human anti-EGF-r antibodies in vitro, where (□) depicts the results achieved by the murine monoclonal antibody 225, (♦) depicts the results achieved using the E6.2 antibody in accordance with the invention, (●) depicts the results achieved using the E6.3 antibody in accordance with the invention, (▲) depicts the results achieved using the E7.2 antibody in accordance with the invention, (■) depicts the results achieved using the E7.10 antibody in accordance with the invention, (▼) depicts the results achieved using the E7.6.3, and (⊗) depicts the results achieved using a control, nonspecific human IgG2 antibody.

Figure 40:
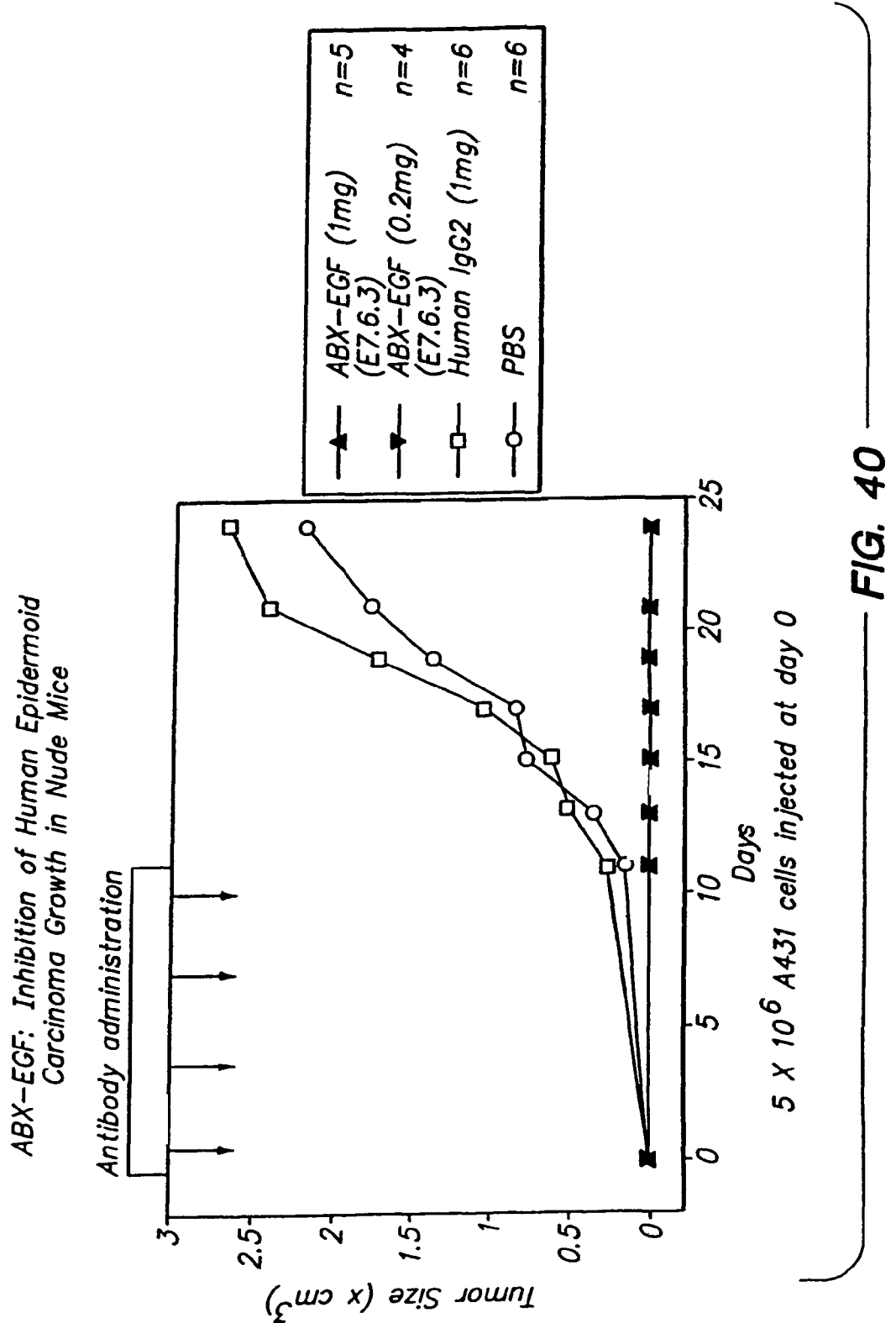

FIG. 40 shows the inhibition of human epidermoid carcinoma A431 cell growth in nude mice through use of human anti-EGF-r antibodies in accordance with the invention in vivo. In the Figure, (▲) depicts the results achieved with a dosage of 1 mg of a human anti-EGF-r antibody in accordance with the present invention, (▼) depicts the results achieved with a dosage of 0.2 mg of a human anti-EGF-r antibody in accordance with the present invention, (□) depicts the results achieved by a control, nonspecific, human IgG2 antibody, and (○) depicts the results achieved utilizing phosphate buffered saline as a control.

FIG. 41 shows data related to the inhibition of epidermoid carcinoma formation in nude mice through use of human anti-EGF-r antibodies in accordance with the invention in vivo showing tumor incidence at day 19.

Figure 42:
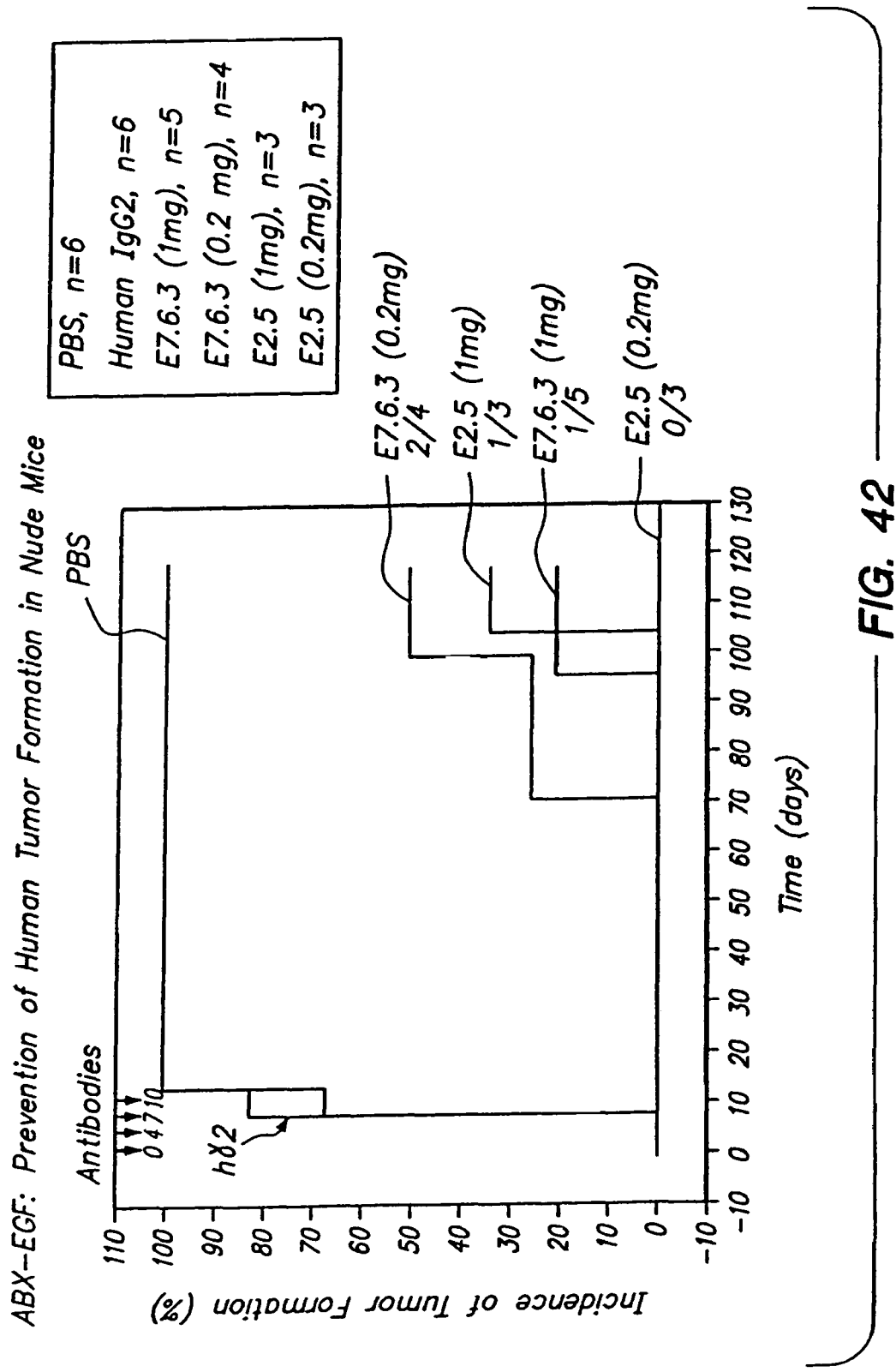

FIG. 42 shows data related to the inhibition of epidermoid carcinoma formation in nude mice through use of human anti-EGF-r antibodies in accordance with the invention in vivo showing tumor incidence at day 120.

Figure 43:
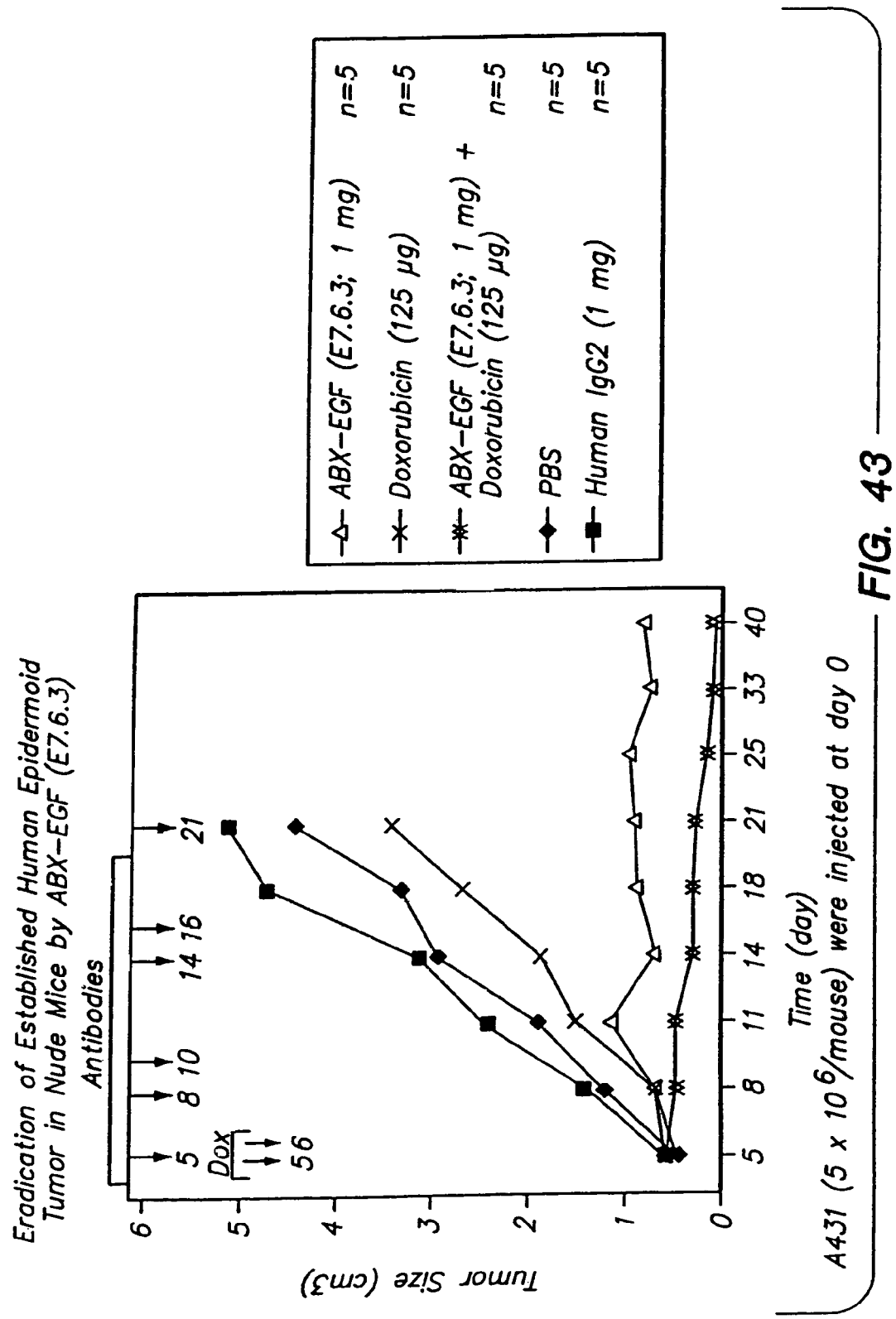

FIG. 43 shows data related to the eradication of an established human epidermoid tumor in nude mice through use of human anti-EGF-r antibodies in accordance with the invention in vivo. In the Figure, (Δ) depicts the results achieved with multiple doses of 1 mg each of a human anti-EGF-r antibody in accordance with the present invention (E7.6.3), (X) depicts the results achieved with two doses of 125 µg each of doxorubicin, (*) depicts the results achieved with a multiple doses of 1 mg each of a human anti-EGF-r antibody in accordance with the present invention (E7.6.3) in combination with two doses of 125 µg each of doxorubicin, (■) depicts the results achieved by a control, nonspecific, human IgG2 antibody, and (♦) depicts the results achieved utilizing phosphate buffered saline as a control.

Figure 44:
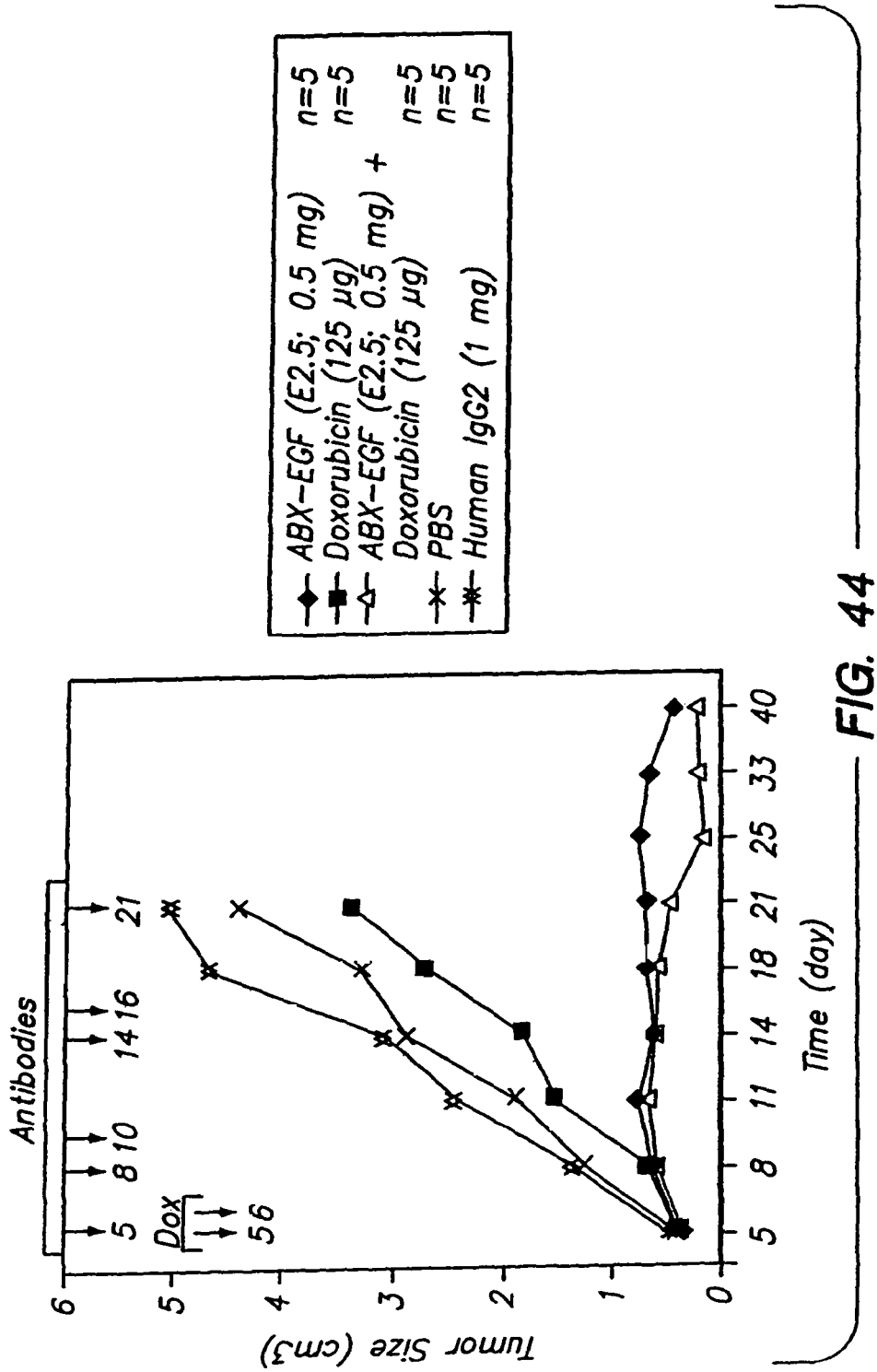

FIG. 44 shows data related to the eradication of an established human epidermoid tumor in nude mice through use of human anti-EGF-r antibodies in accordance with the invention in vivo. In the Figure, (♦) depicts the results achieved with multiple doses of 0.5 mg each of a human anti-EGF-r antibody in accordance with the present invention (E2.5), (■) depicts the results achieved with two doses of 125 µg each of doxorubicin, (Δ) depicts the results achieved with multiple doses of 0.5 mg each of a human anti-EGF-r antibody in accordance with the present invention (E2.5) in combination with two doses of 125 µg each of doxorubicin, (X) depicts the results achieved utilizing phosphate buffered saline as a control, and (*) depicts the results achieved utilizing a control, nonspecific, human IgG2 antibody at a dose of 1 mg.

Figure 45:
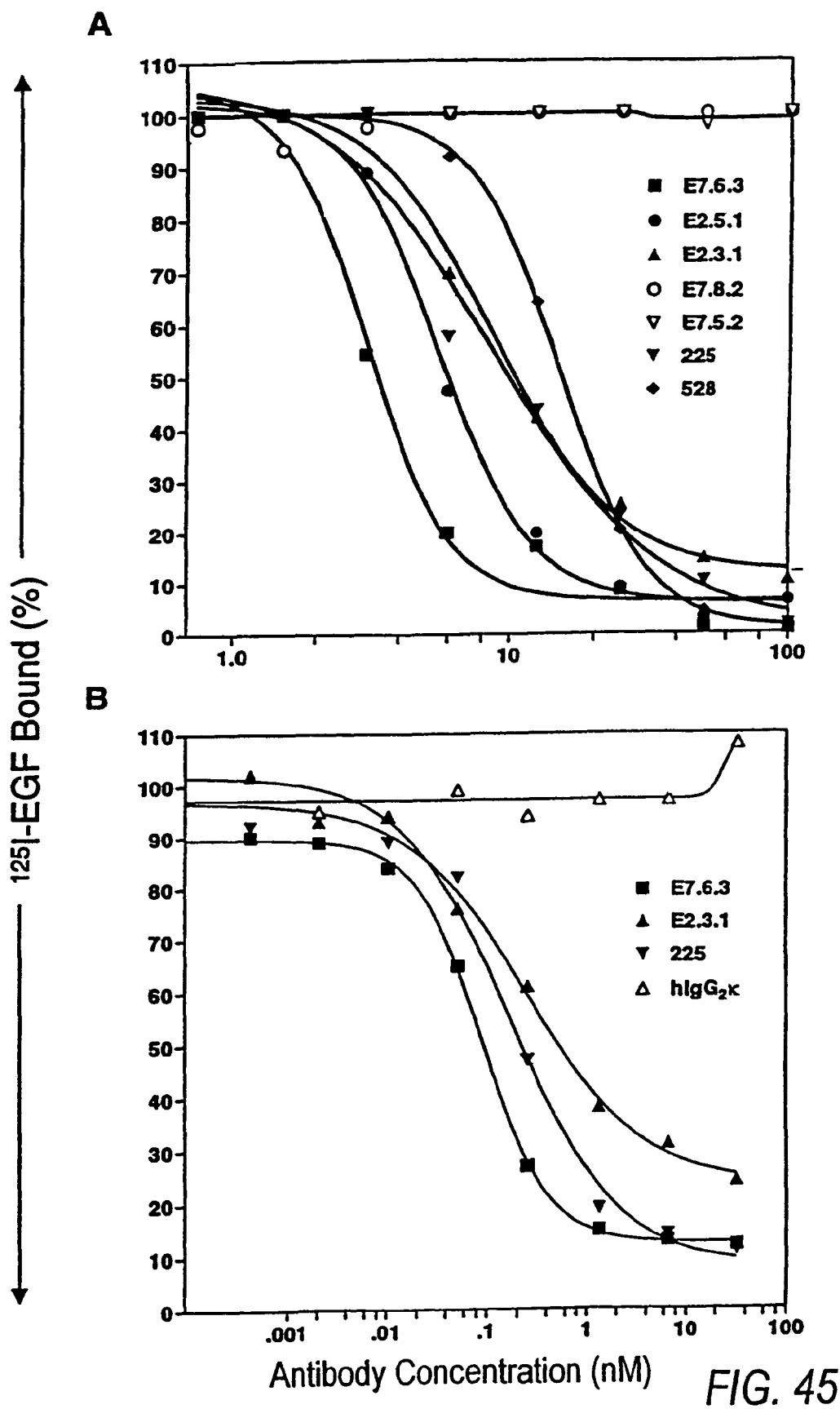

FIG. 45 shows the inhibition of EGF binding to EGFr by anti-EGFr MAbs. The binding of $^{125}$I-EGF (0.1 nM) to (A) A431 or (B) SW948 cells was determined in the presence of XenoMouse-derived human (■ E7.6.3; ● E2.5.1; ▲ E2.3.1; ∇ E7.5.2; ○ E7.8.2) or murine (▼ 225; ♦ 528) anti-EGFr antibodies, or in the presence of the human IgG$_2$κ control antibody (hIgG$_2$κ). The binding of $^{125}$I-EGF to the cells in the absence of antibodies was designated as 100%. The data shown are representative of multiple experiments.

Figure 46:
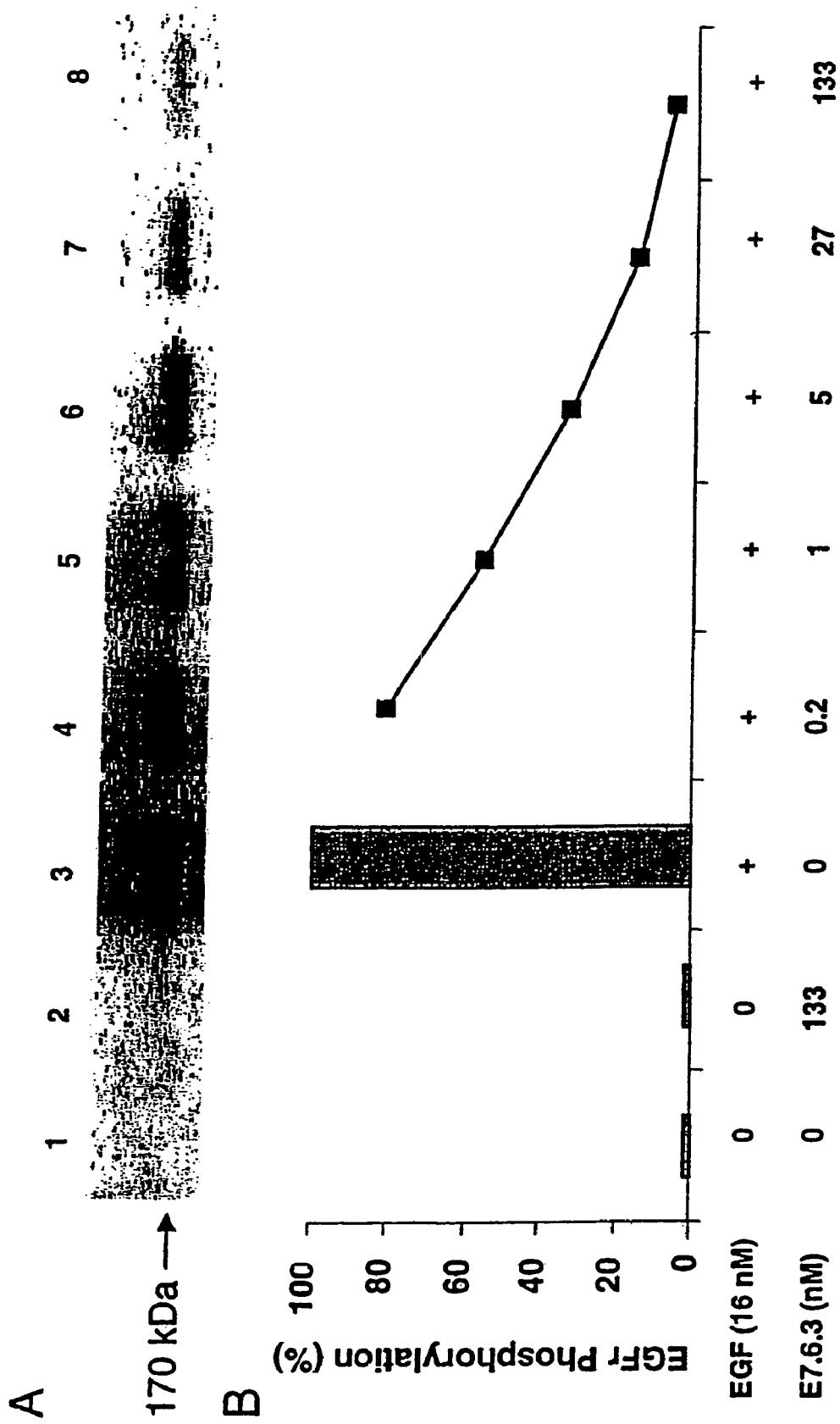

FIG. 46 shows the inhibition of EGF-induced tyrosine phosphorylation of EGFr by E7.6.3 MAb. A431 were incubated with or without EGF (16 nM), in the absence or presence of increasing concentrations of E7.6.3 MAb (0.2~133 nM) as described in "[Materials and Methods]". Total EGFr and EGFr tyrosine phosphorylation in cell lysates was visualized (A) and quantitated (B) using Western blot analysis using an anti-phosphotyrosine antibody as described in "Materials and Methods".

FIG. 47 shows the Inhibition of EGF-mediated cell activation by anti-EGFr antibodies. A. Activation of A431 cells by 1.67 nM EGF, in the absence or presence of different concentrations of E7.6.3, was measured by Cytosensor as changes in extracellular acidification rate. The arrow indicates the times when EGF and/or E7.6.3 were added to the cells. The response is presented as % of baseline acidification rate (designated as 100%). B. Effect of increasing concentrations of E7.6.3 and control PK16.3.1 antibodies on A431 cell activation induced by EGF (1.67 nM), as determined by Cytosensor. The response to EGF was measured at the peak acidification rate shown in A. The response in the absence of antibodies was designated as 100%. The data shown are representative of 2 different experiments.

Figure 48:
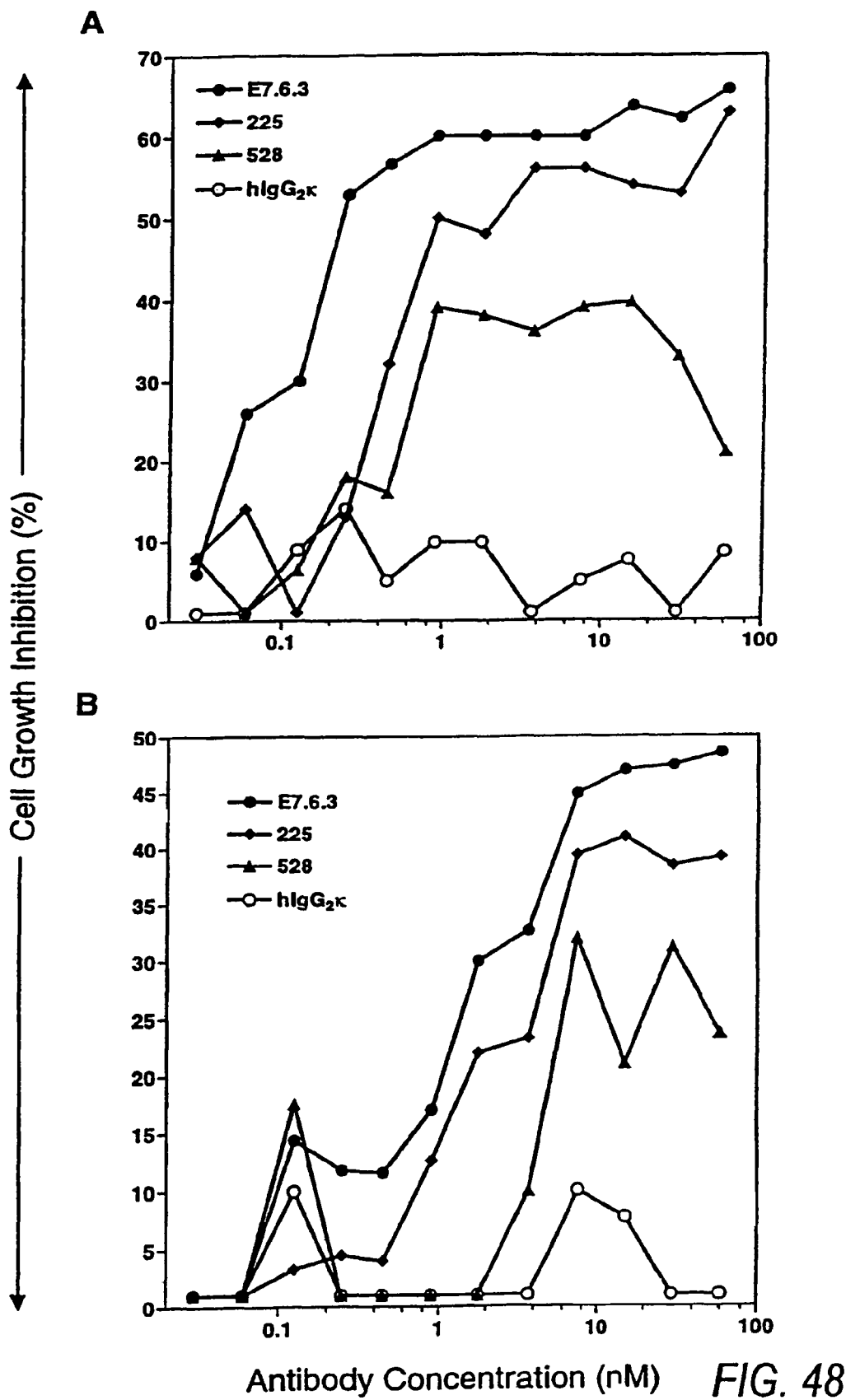

FIG. 48 shows the inhibition of in vitro tumor cell proliferation by anti-EGFr antibodies. A431 (A) or MDA-468 (B) cells were cultured with anti-EGFr MAbs (● E7.6.3; ♦ 225; ▲ 528) or control human myeloma IgG$_2$κ (○), as described in Materials and Methods. Cell viability was assayed by crystal violet staining. Data presented as % of cell growth inhibition.

Figure 49:
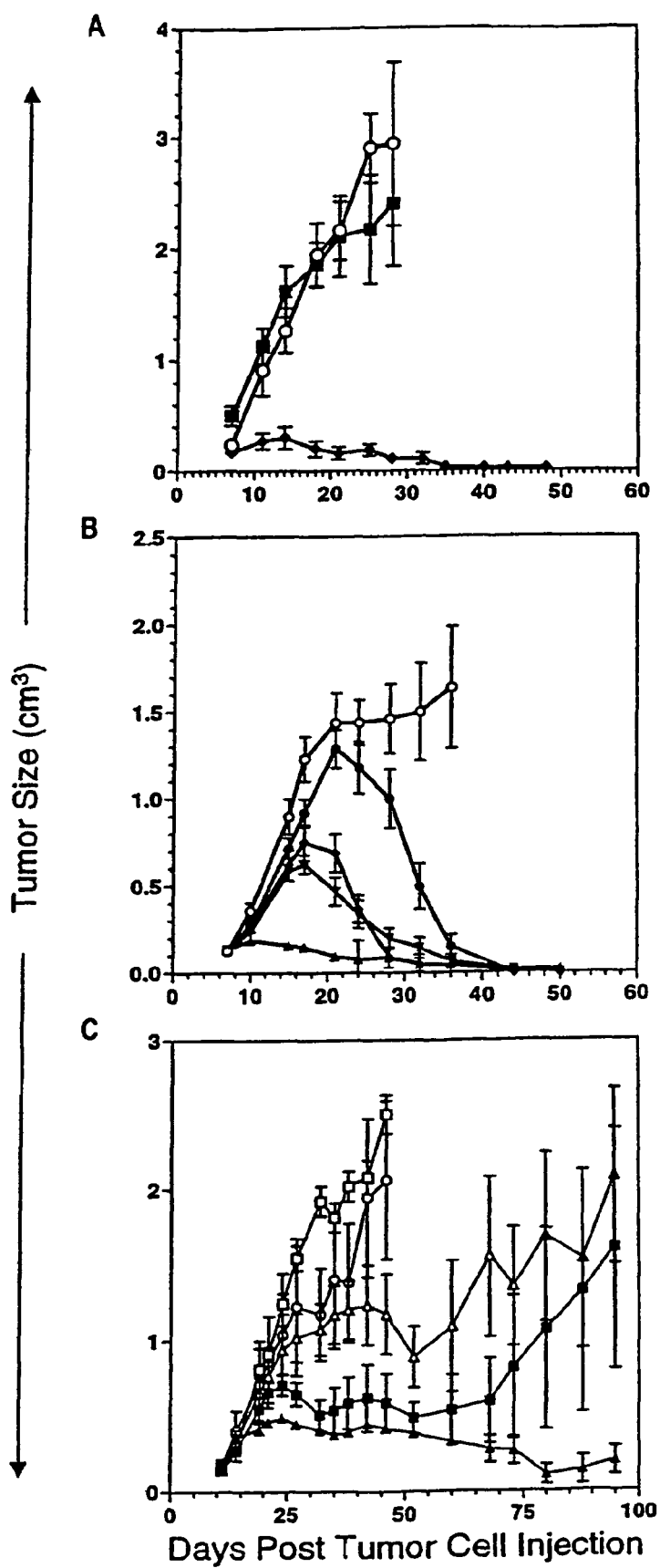

FIG. 49 shows the eradication of established A431 tumor xenografts by E7.6.3 MAb. A431 cells (5×10$^6$) were injected s.c. into the nude mice on day 0. A. At day 7 when tumor size reached an average volume of 0.1~0.25 cm$^2$, mice (n=5) were injected i.p. with PBS (○) or with 1 mg of either E7.6.3 (♦) or the control human myeloma IgG$_2$κ (■) antibodies twice a week for three weeks. B. when the mean tumor sizes reached 0.13 (▲), 0.56 (▼), 0.73 (♦) or 1.2 (●) cm$^3$, mice (n=10)

were treated with 1 mg E7.6.3, twice a week for three weeks. Control mice (O, n=10) received no treatment. C, at day 10 when tumor sizes reached 0.15 cm³, mice (n=8) were injected i.p. with 200 μg (▽) or 50 μg (△) doses of E7.6.3, or 200 μg (▼) or 50 μg (●) doses of 225 MAbs, twice a week for three weeks. Control mice (○) received no treatment. Tumors were measured weekly and their volume was measured as described in "Materials and Methods". The data is presented as the mean tumor size±SEM.

Figure 50:
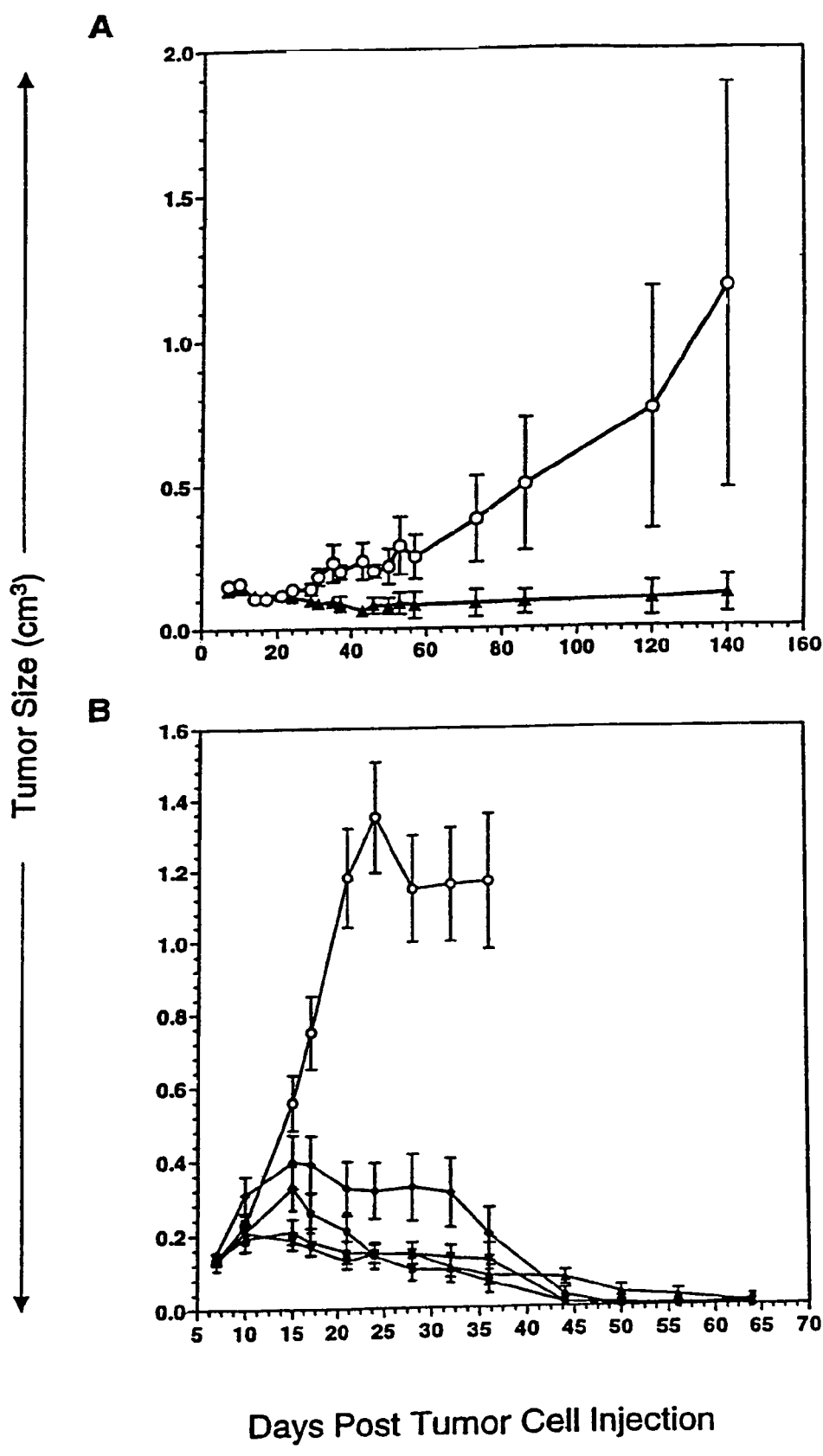

FIG. 50 shows the effect of the E7.6.3 Mab on the growth of established human tumor xenografts. 5×10⁶ MDA468 (A) or A431 (B) cells were injected s.c. into the nude mice on day 0. A. 7 days following injection of MDA468 cells, mice (n=8) were injected i.p. with 2 mg E7.6.3 once a week for two weeks (▲). Control mice (n=8) received no treatment (○). B. Mice (n=10) were given 0.5 mg E7.6.3 via i.p. (■), i.v. (▲), s.c. (▼) or i.m. (♦) injections twice a week for three weeks. Control mice (□) received no treatment. The data represents the mean±SEM.

FIG. 51 shows certain histopathology of E7.6.3-treated A431 xenografts. A. Mice with established A431 xenografts were treated i.p. with 0.5 mg E7.6.3 twice a week for three weeks. On day 76 after tumor cells (5×10⁶) injection, tumor-like nodules were excised and examined histologically as described in Materials and Methods. B. Histological analysis of A431 tumor xenografts excised from an untreated mouse.

FIG. 52 is a table the prevention of tumor formation by the E7.6.3 MAb. On day 0, mice were injected s.c. with 5×10⁶ A431 cells and i.p. with PBS, 1 mg of control antibody PK16.3.1, 0.2 mg or 1 mg of E7.6.3 MAb twice a week, for three weeks. Incidence of tumor formation is expressed as the number of mice with visible tumors/total number of mice within each group. ND: not determined.

FIG. 53 is a table showing the eradication of established A431 xenograft tumors by E7.6.3 MAb. Nude mice with established A431 xenografts (tumor size of 0.13-0.25 cm³ at day 7-10) were treated i.p. with various doses of E7.6.3 MAb or human myeloma IgG$_2$κ control antibody twice a week, for three weeks. The table summarizes the results of 11 experiments. Mice that received no treatment or control IgG$_2$κ antibody were sacrificed between day 35 and 50.

Figure 54:
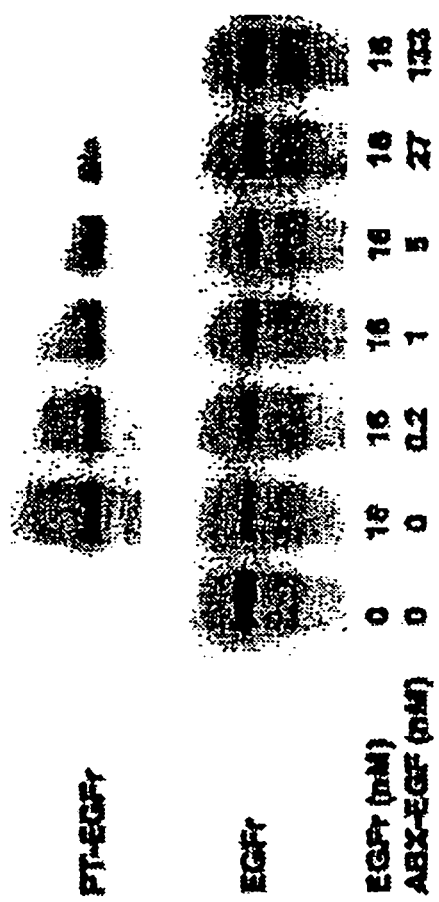

FIG. 54 is a western blot showing the inhibitory effects of the E7.6.3 antibody on EGF-induced tyrosine phosphoylation and degradation of EGFr in cultured A431 cells.

Figure 55:

FIG. 55 is a western blot showing preliminary results obtained comparing the inhibitory effects of the E7.6.3 and 225 antibodies on EGF-induced tyrosine phosphoylation and degradation of EGFr in cultured A431 cells.

Figure 56:

FIG. 56 is a western blot showing preliminary results obtained comparing the inhibitory effects of the E7.6.3 and 225 antibodies on EGF-induced tyrosine phosphoylation and degradation of EGFr in cultured A431 cells.

FIG. 57 (SEQ ID NOs: 19 and 55) provides oligonucleotide and amino acid sequence information on the heavy chain of the antibody produced by the E20.1 hybridoma.

FIG. 58 (SEQ ID NOs: 20 and 56) provides oligonucleotide and amino acid sequence information on the light chain of the antibody produced by the E20.1 hybridoma.

FIG. 59 (SEQ ID NOs: 21 and 57) provides oligonucleotide and amino acid sequence information on the heavy chain of the antibody produced by the E20.3 hybridoma.

FIG. 60 (SEQ ID NOs: 22 and 58) provides oligonucleotide and amino acid sequence information on the light chain of the antibody produced by the E20.3 hybridoma. FIG. 61 (SEQ ID NOs: 23 and 59) provides oligonucleotide and amino acid sequence information on the heavy chain of the antibody produced by the E20.8.1 hybridoma.

FIG. 62 (SEQ ID NOs: 24 and 60) provides oligonucleotide and amino acid sequence information on the light chain of the antibody produced by the E20.8.1 hybridoma.

FIG. 63 (SEQ ID NOs: 25 and 61) provides oligonucleotide and amino acid sequence information on the heavy chain of the antibody produced by the E20.11.2 hybridoma.

FIG. 64 (SEQ ID NOs: 26 and 62) provides oligonucleotide and amino acid sequence information on the light chain of the antibody produced by the E20.11.2 hybridoma.

FIG. 65 (SEQ ID NOs: 27 and 63) provides oligonucleotide and amino acid sequence information on the heavy chain of the antibody produced by the E20.18 hybridoma.

FIG. 66 (SEQ ID NOs: 28 and 64) provides oligonucleotide and amino acid sequence information on the light chain of the antibody produced by the E20.18 hybridoma.

FIG. 67 (SEQ ID NOs: 29 and 65) provides oligonucleotide and amino acid sequence information on the heavy chain of the antibody produced by the E20.19.2 hybridoma.

FIG. 68 (SEQ ID NOs: 30 and 66) provides oligonucleotide and amino acid sequence information on the light chain of the antibody produced by the E20.19.2 hybridoma.

FIG. 69 (SEQ ID NOs: 31 and 67) provides oligonucleotide and amino acid sequence information on the heavy chain of the antibody produced by the E20.21 hybridoma.

FIG. 70 (SEQ ID NOs: 32 and 68) provides oligonucleotide and amino acid sequence information on the heavy chain of the antibody produced by the E20.22 hybridoma.

FIG. 71 provides a mutation analysis of antibodies in accordance with the invention (SEQ ID NOS: 35, 38, 39, 41, 43, 45, 47, 49, 51, 76, 73, and 75). In particular, the sequence of the E20.21 antibody, which comprises a $V_H$ 4-31 heavy chain is shown.

FIG. 72 (SEQ ID NOs: 33 and 69) provides oligonucleotide and amino acid sequence information on the heavy chain of the antibody produced by the E7.5.2 hybridoma.

FIG. 73 (SEQ ID NOs: 34 and 70) provides oligonucleotide and amino acid sequence information on the light chain of the antibody produced by the E7.5.2 hybridoma.

Figure 74:
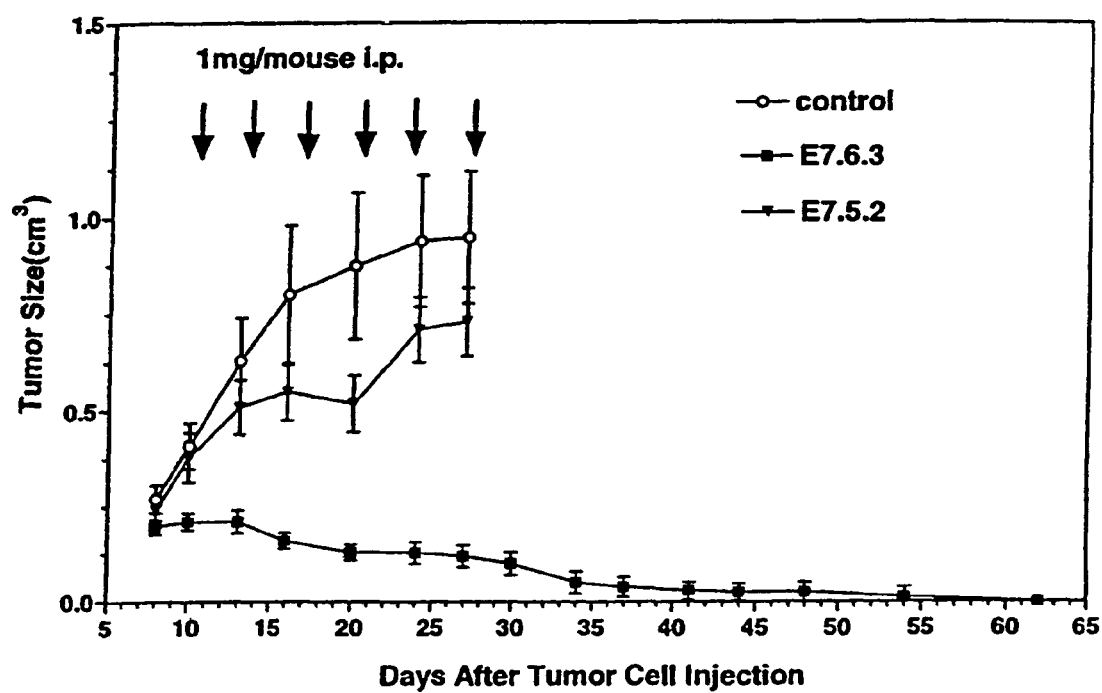

FIG. 74 shows data related to the eradication of an established human epidermoid tumor in nude mice through use of human anti-EGF-r neutralizing antibody E7.6.3 in accordance with the invention in vivo. A431 cells (5×10⁶) were injected s.c. into the nude mice on day 0. At day 8 when tumor become established, mice (n=10) were injected i.p. with 1 mg of either E7.6.3 (filled square) or E7.5.2 (filled triangle), or received no treatment as a control (open circle) twice a week for three weeks. The arrows indicate the timing and number of antibody injections. Tumors were measured twice a week and their volume was measured as described in the "Materials and Methods" section of Example 14. The data is presented as the mean tumor size±SEM.

Figure 75:
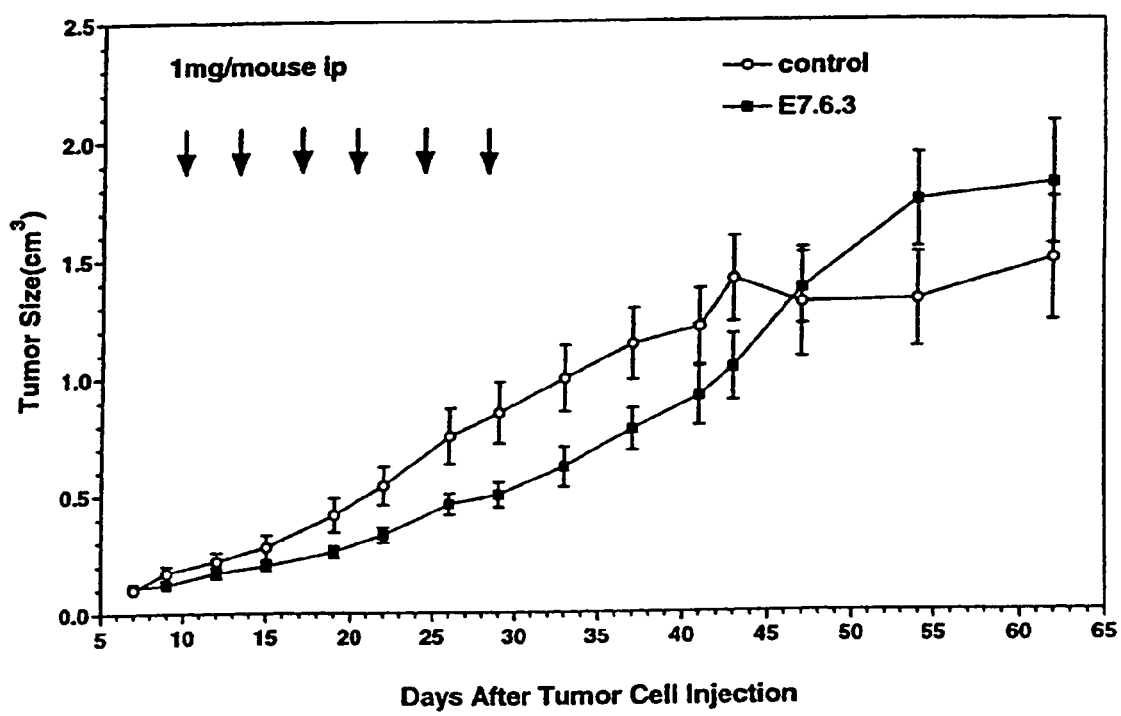

FIG. 75 shows the effect of the E7.6.3 Mab on the growth of established human pancreatic tumor xenografts. HPAC cells (5×10⁶) were injected s.c. into the nude mice on day 0. At day 7 when tumor become established, mice (n=10) were injected i.p. with 1 mg of E7.6.3 (filled square) or received no treatment as a control (open circle) twice a week for three weeks. The arrows indicate the timing and number of antibody injections. Tumors were measured twice a week and their volume was measured as described in the "Materials and Methods" section of Example 14. The data is presented as the mean tumor size±SEM.

Figure 76:
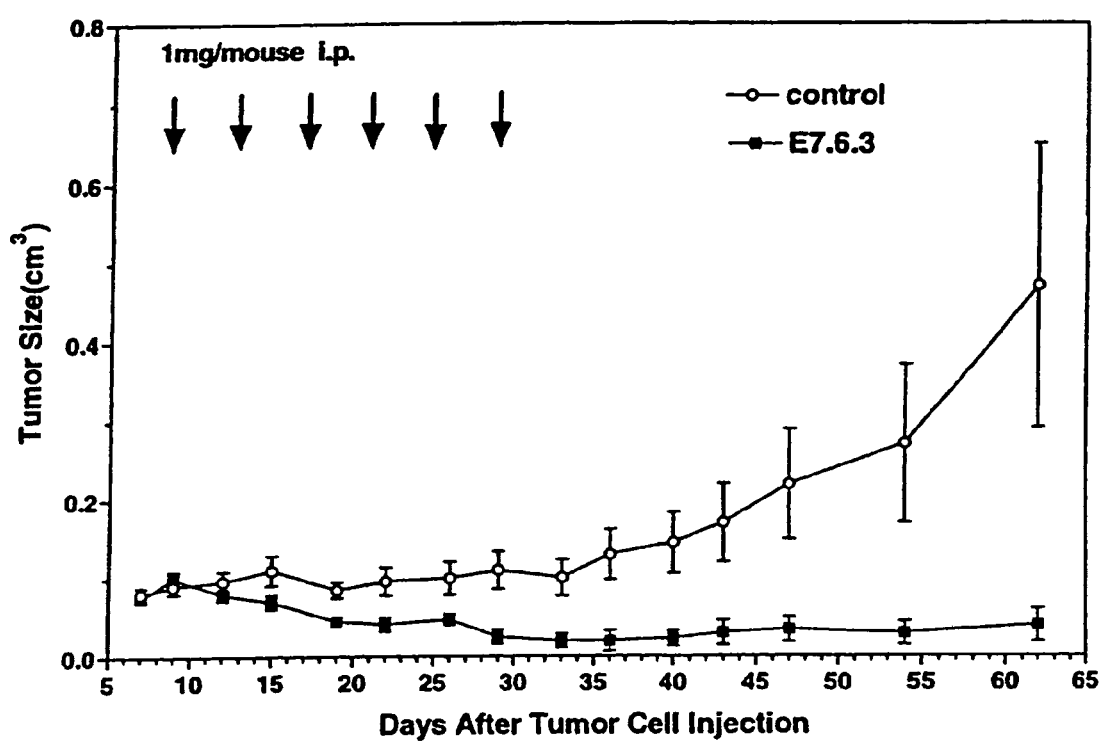

FIG. 76 shows the inhibition of the growth of established human pancreatic tumor xenografts. BxPC3 cells (5×10⁶) were injected s.c. into the nude mice on day 0. At day 7 when tumor become established, mice (n=10) were injected i.p. with 1 mg of E7.6.3 (filled square) or received no treatment as a control (open circle) twice a week for three weeks. The arrows indicate the timing and number of antibody injections. Tumors were measured twice a week and their volume was measured as described in the "Materials and Methods" section of Example 14. The data is presented as the mean tumor size±SEM.

Figure 77:
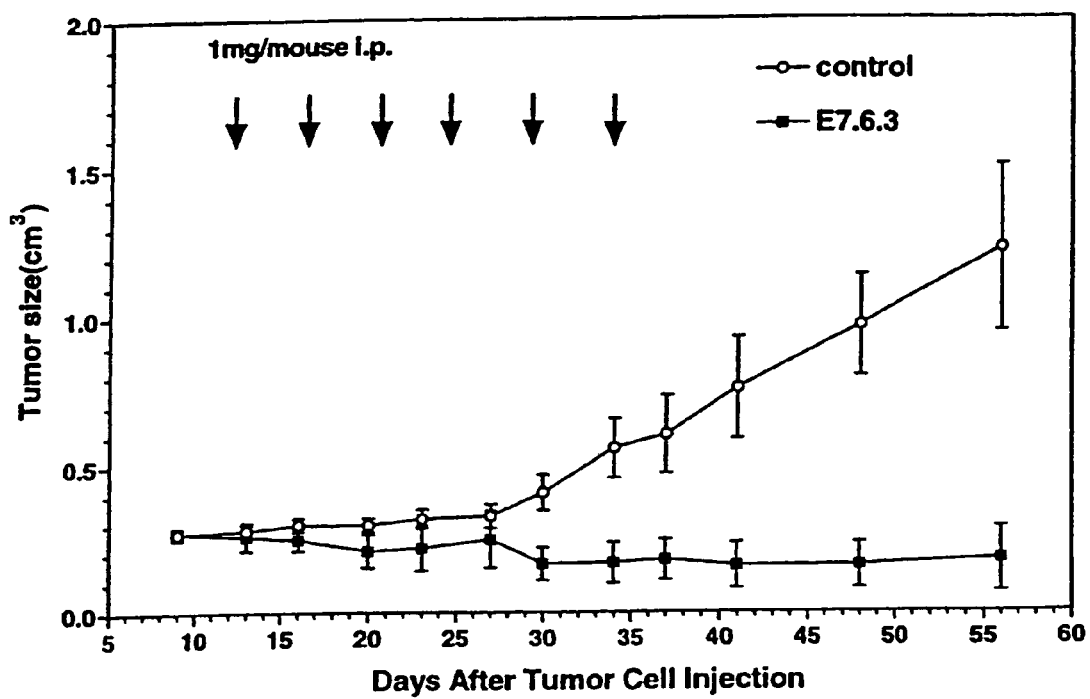

FIG. 77 shows the inhibition of the growth of established human pancreatic tumor xenografts. Hs77T9 cells ($5\times10^6$) were injected s.c. into the nude mice on day 0. At day 7 when tumor become established, mice (n=10) were injected i.p. with 1 mg of E7.6.3 (filled square) or received no treatment as a control (open circle) twice a week, for three weeks. The arrows indicate the timing and number of antibody injections. Tumors were measured twice a week and their volume was measured as described in the "Materials and Methods" section of Example 14. The data is presented as the mean tumor size±SEM.

Figure 78:
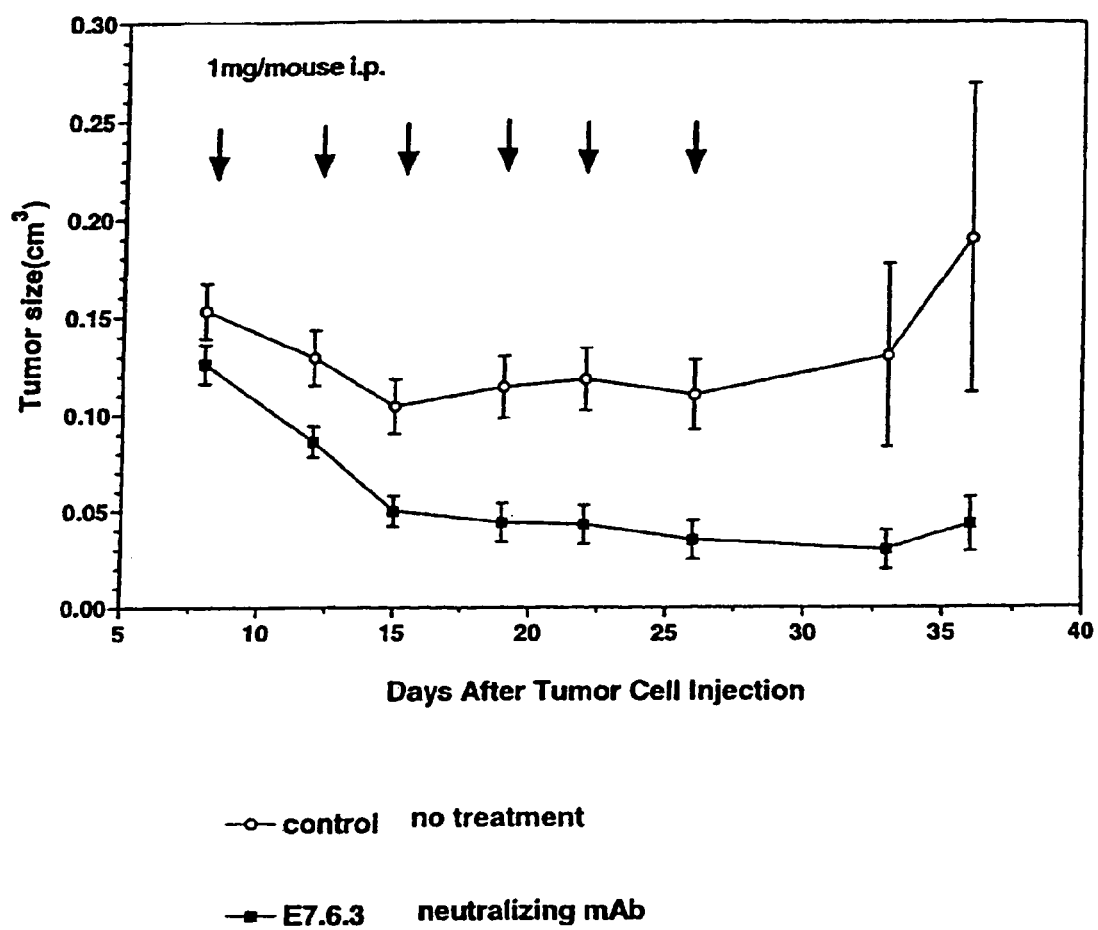

FIG. 78 shows the inhibition of the growth of established human renal tumor xenografts. Sk-RC-29 cells ($5\times10^6$) were injected s.c. into the nude mice on day 0. At day 7 when tumor become established, mice (n=10) were injected i.p. with 1 mg of E7.6.3 (filled square) or received no treatment as a control (open circle) twice a week for three weeks. The arrows indicate the timing and number of antibody injections. Tumors were measured twice a week and their volume was measured as described in the "Materials and Methods" section of Example 14. The data is presented as the mean tumor size±SEM.

Figure 79:
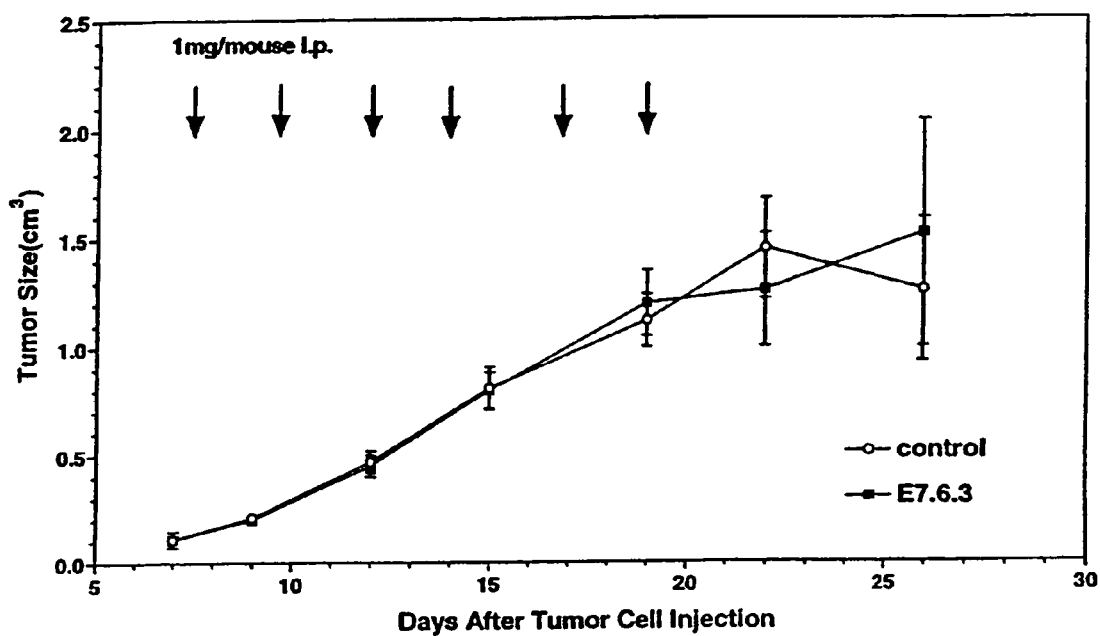

FIG. 79 shows the effect of the E7.6.3 Mab on the growth of established human colon tumor xenografts. SW707 (EGF-r$^-$) cells ($5\times10^6$) were injected s.c. into the nude mice on day 0. At day 7 when tumor become established, mice (n=10) were injected i.p. with 1 mg of E7.6.3 (filled square) or received no treatment as a control (open circle) twice a week for three weeks. The arrows indicate the timing and number of antibody injections. Tumors were measured twice a week and their volume was measured as described in the "Materials and Methods" section of Example 14. The data is presented as the mean tumor size±SEM.

Figure 80A:
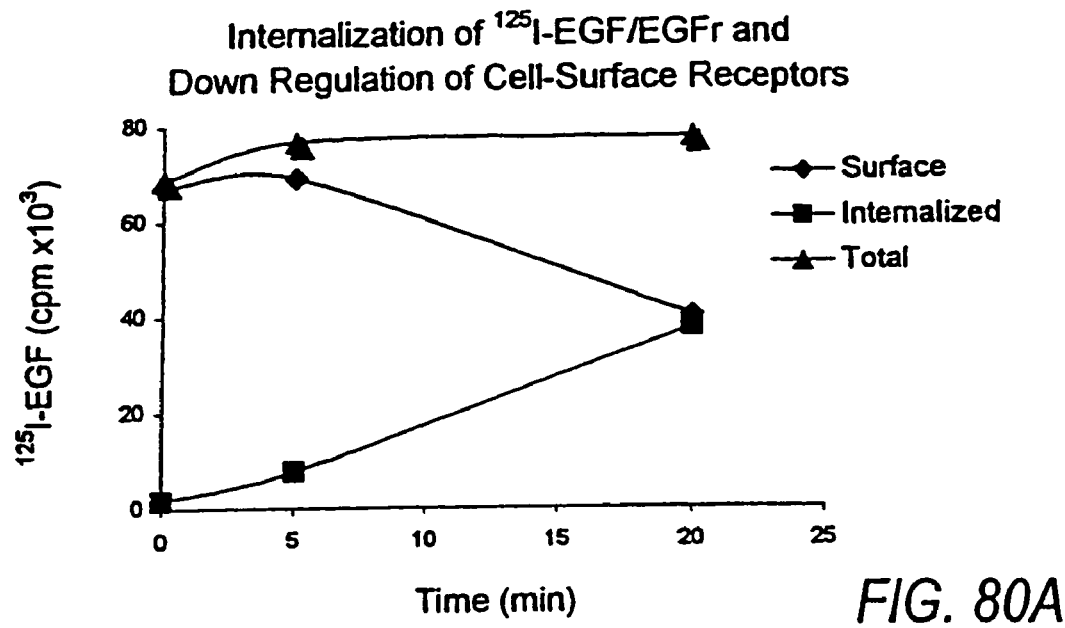
Figure 80B:
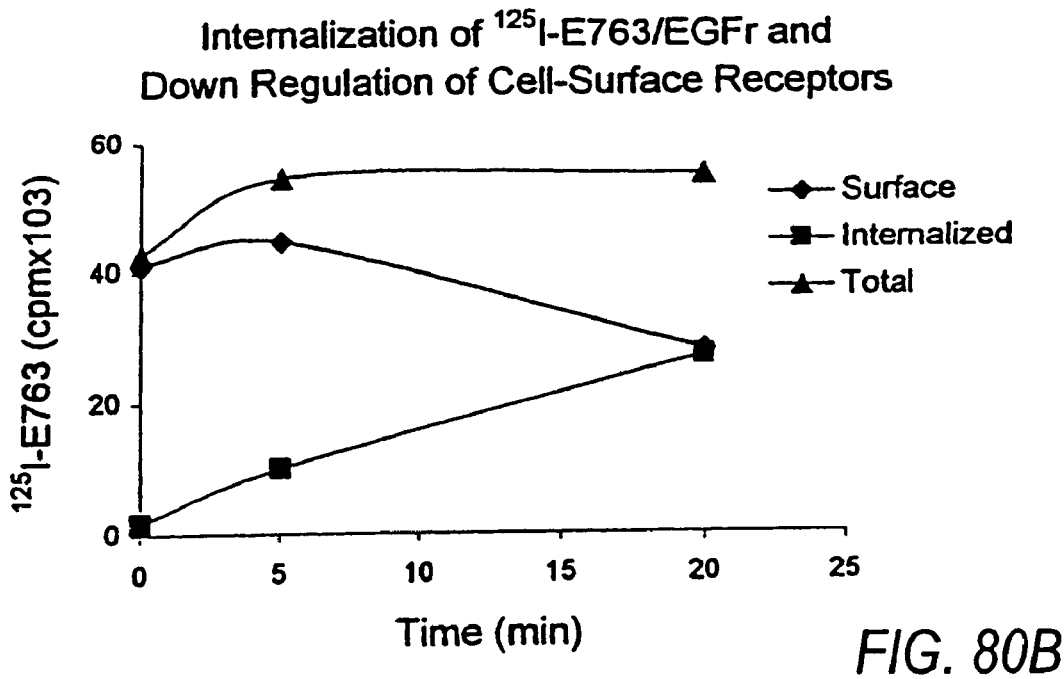

FIG. 80 provides a series of graphs showing the internalization of EGF-r with panel A showing the internalization of EGF-r based on $^{125}$I-EGF and panel B showing the internalization of EGF-r based on $^{125}$I-E7.6.3.

Figure 81A:
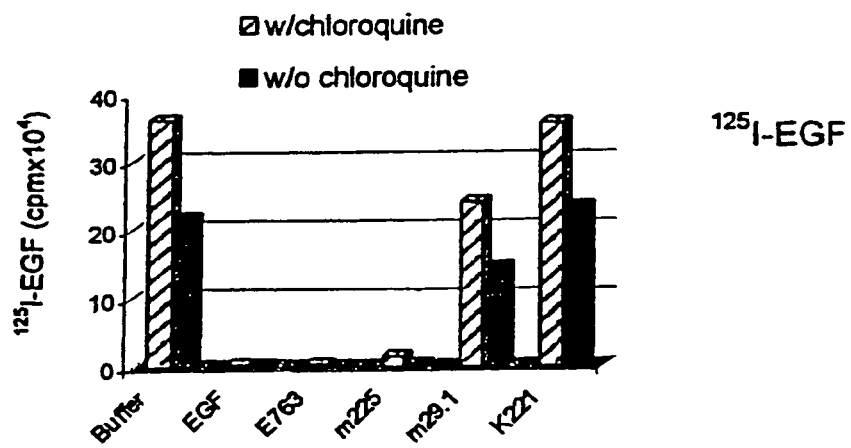
Figure 81B:
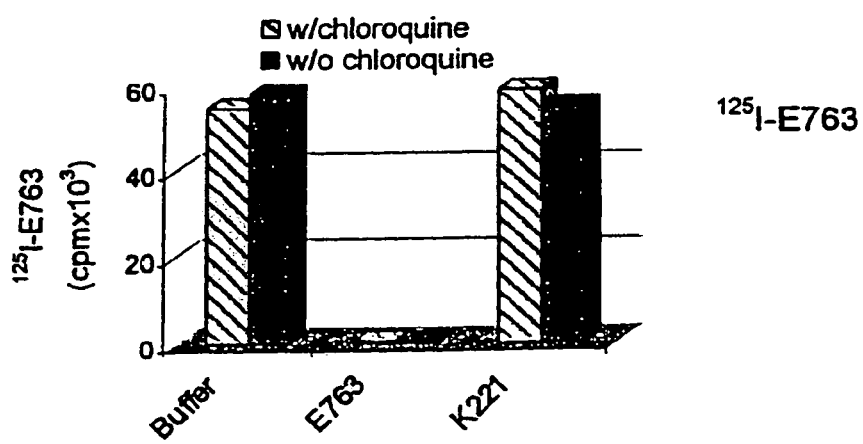

FIG. 81 provides a bar graph that demonstrates the competitive effects of antibodies with EGF as a positive control (panel A) for the bar graph in panel B that demonstrates that E7.6.3 is not degraded.

Figure 82A:
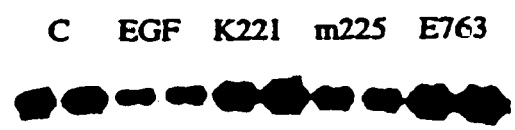
Figure 82B:
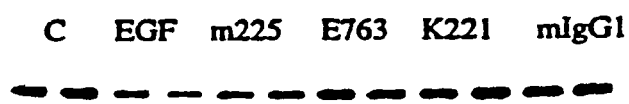
Figure 82C:
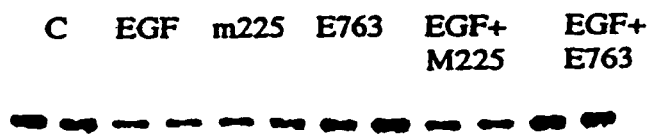

FIGS. 82A-C are a series of immunoprecipitation blots comparing the effects of antibodies on EGF-r degradation.

FIGS. 83A-B are immunoprecipitation blots comparing the effects of antibodies on EGF-r threonine phosphorylation.

Figure 84:
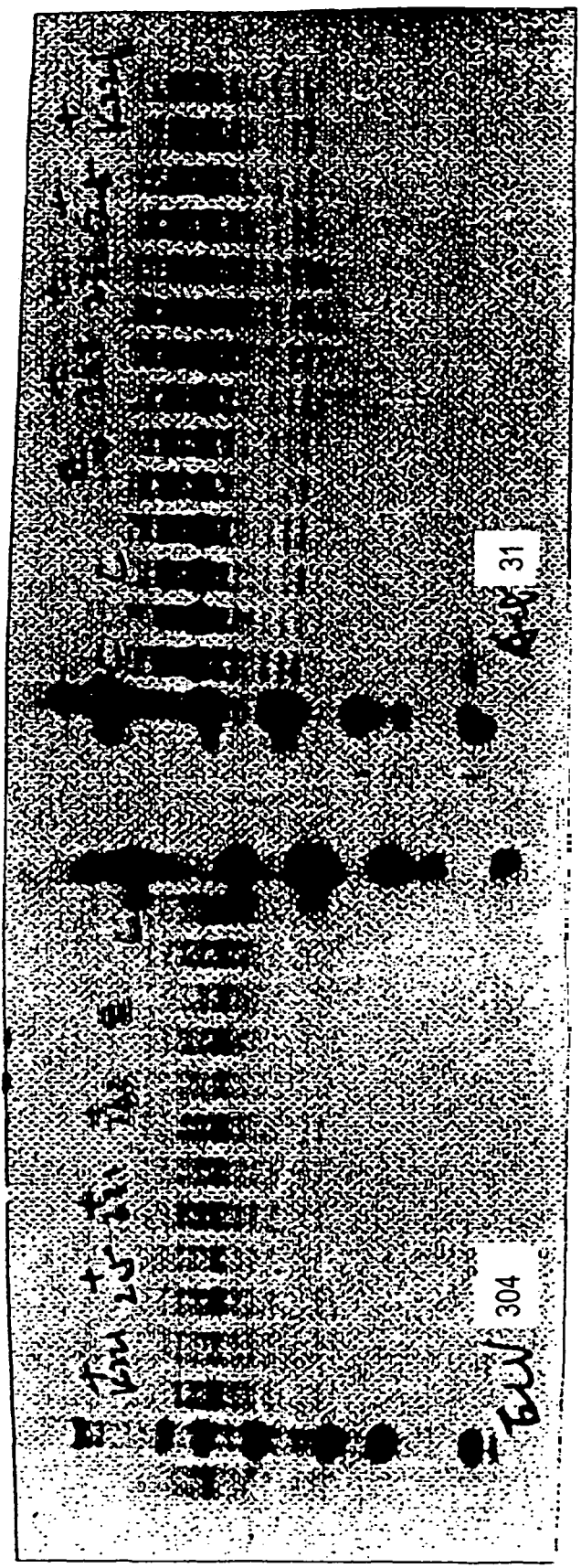
Figure 85A:
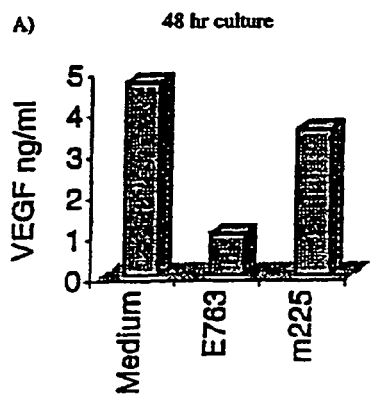
Figure 85B:
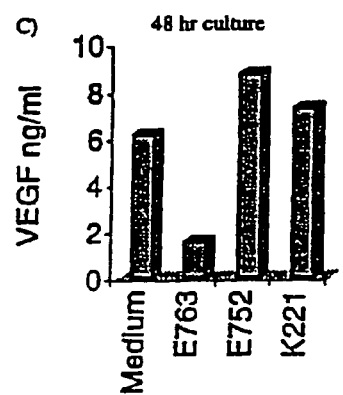
Figure 85C:
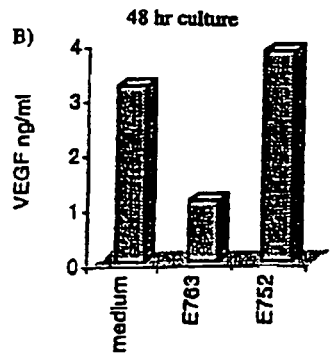
Figure 85D:
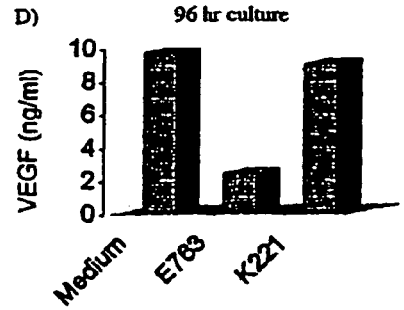

FIG. 84 is a western blot comparing the effects of antibodies on other threonine phosphorylation.

FIGS. 85A-D are a series of bar graphs showing the effects of antibodies on the production of vascular endothelial cell growth factor in tumor (A431) cells.

Figure 86:
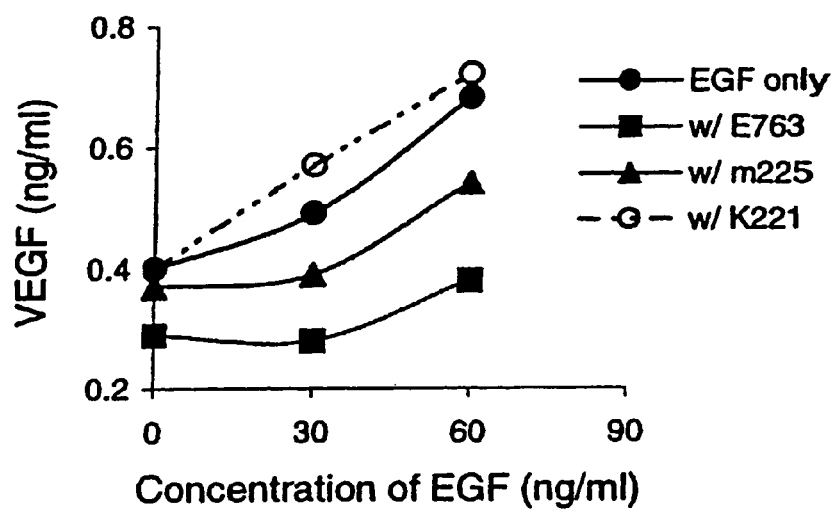

FIG. 86 is a graph showing the effects of antibodies on the production of vascular endothelial cell growth factor in endothelial (ECV304) cells.

SUMMARY OF THE INVENTION

In accordance with the present invention, there is provided an antibody that binds to epidermal growth factor receptor that possesses one or more of the following functional characteristics: (i) inhibit tyrosine phosphorylation of EGF-r, (ii) do not inhibit EGF-r internalization, (ii) inhibit EGF-r degradation, (iii) inhibition of EGF induced EGF-r degradation, (iv) protect threonine phosphorylation of EGF-r, (v) protect threonine phosphorylation of other molecules, particularly a 62 KD molecule identified by immunoprecipitation, and (vi) inhibit vascular endothelial cell growth factor signal by tumor cells by greater than 50% and endothelial cells by greater than 40% relative to control.

DETAILED DESCRIPTION OF THE PREFERRED EMBODIMENTS

In accordance with the present invention, there are provided fully human monoclonal antibodies against human epidermal growth factor receptor (EGF-r). Nucleotide sequences encoding and amino acid sequences comprising heavy and light chain immunoglobulin molecules, particularly sequences corresponding to a contiguous heavy and light chain sequences from CDR1 through CDR3, are provided. Hybridomas expressing such immunoglobulin molecules and monoclonal antibodies are also provided.

To this end we utilized our human antibody-producing XenoMouse strains to generate potent fully human anti-EGFr MAbs. As previously described, these mouse strains were engineered to be deficient in mouse antibody production and to contain integrated megabase-sized fragments from the human heavy and kappa (K) light chain loci with the majority of the human antibody gene repertoire (18). The human Ig loci provided the XenoMouse strains with the ability to produce high affinity human MAbs to a broad spectrum of antigens, including human antigens (18, 19). As presented in this report, using XenoMouse strains we generated a panel of anti-EGFr fully human IgG$_2$κ MAbs from which we selected the E7.6.3 antibody. This antibody exhibits high affinity ($5\times10^{-11}$ M) to the receptor, neutralizes both EGF and TGFα binding to EGFr-expressing human carcinoma cell lines, and inhibits ligand-induced tumor cell proliferation. The antibody not only prevents human tumor formation in athymic mice but, more importantly, effectively eradicates large established human tumor xenografts, independent of chemotherapeutic agents. The potent anti-tumor activity of the E7.6.3 MAb indicates it is a good candidate for use as a monotherapeutic agent for the treatment of EGFr-expressing human solid tumors.

DEFINITIONS

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. *Molecular Cloning: A Laboratory Manual* (2d ed., Cold Spring Harbor Laboratory Press, Cold Spring Harbor, N.Y. (1989)), which is incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, e.g. free of murine proteins, (3) is expressed by a cell from a different species, or (4) does not occur in nature.

The term "polypeptide" is used herein as a generic term to refer to native protein, fragments, or analogs of a polypeptide sequence. Hence, native protein, fragments, and analogs are species of the polypeptide genus. Preferred polypeptides in accordance with the invention comprise the human heavy chain immunoglobulin molecules represented by FIGS. 1, 5, 9, 13, 17, 21, 25, and 29 and the human kappa light chain immunoglobulin molecules represented by FIGS. 3, 7, 11, 15, 19, 23, 27, and 31, as well as antibody molecules formed by combinations comprising the heavy chain immunoglobulin molecules with light chain immunoglobulin molecules, such as the kappa light chain immunoglobulin molecules, and vice versa, as well as fragments and analogs thereof.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences which are necessary to effect the expression and processing of coding sequences to which they are ligated. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

The term "polynucleotide" as referred to herein means a polymeric form of nucleotides of at least 10 bases in length, either ribonucleotides or deoxynucleotides or a modified form of either type of nucleotide. The term includes single and double stranded forms of DNA.

The term "oligonucleotide" referred to herein includes naturally occurring, and modified nucleotides linked together by naturally occurring, and non-naturally occurring oligonucleotide linkages. Oligonucleotides are a polynucleotide subset generally comprising a length of 200 bases or fewer. Preferably oligonucleotides are 10 to 60 bases in length and most preferably 12, 13, 14, 15, 16, 17, 18, 19, or 20 to 40 bases in length. Oligonucleotides are usually single stranded, e.g. for probes; although oligonucleotides may be double stranded, e.g. for use in the construction of a gene mutant. Oligonucleotides of the invention can be either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phoshoraniladate, phosphoroamidate, and the like. See e.g., LaPlanche et al. *Nucl. Acids Res.* 14:9081 (1986); Stec et al. *J. Am. Chem. Soc.* 106:6077 (1984); Stein et al. *Nucl. Acids Res.* 16:3209 (1988); Zon et al. *Anti-Cancer Drug Design* 6:539 (1991); Zon et al. *Oligonucleotides and Analogues: A Practical Approach*, pp. 87-108 (F. Eckstein, Ed., Oxford University Press, Oxford England (1991)); Stec et al. U.S. Pat. No. 5,151,510; Uhlmann and Peyman *Chemical Reviews* 90:543 (1990), the disclosures of which are hereby incorporated by reference. An oligonucleotide can include a label for detection, if desired.

The term "selectively hybridize" referred to herein means to detectably and specifically bind. Polynucleotides, oligonucleotides and fragments thereof in accordance with the invention selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, and fragments of the invention and a nucleic acid sequence of interest will be at least 80%, and more typically with preferably increasing homologies of at least 85%, 90%, 95%, 99%, and 100%. Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of more than 5 (in standard deviation units) using the program ALIGN with the mutation data matrix and a gap penalty of 6 or greater. See Dayhoff, M. O., in *Atlas of Protein Sequence and Structure*, pp. 101-110 (Volume 5, National Biomedical Research Foundation (1972)) and Supplement 2 to this volume, pp. 1-10. The two sequences or parts thereof are more preferably homologous if their amino acids are greater than or equal to 50% identical when optimally aligned using the ALIGN program. The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" (SEQ ID NO:71) corresponds to a reference sequence "TATAC" (SEQ ID NO:71) and is complementary to a reference sequence "GTATA" (SEQ ID NO:72).

The following terms are used to describe the sequence relationships between two or more polynucleotide or amino acid sequences: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing or may comprise a complete cDNA or gene sequence. Generally, a reference sequence is at least 18 nucleotides or 6 amino acids in length, frequently at least 24 nucleotides or 8 amino acids in length, and often at least 48 nucleotides or 16 amino acids in length. Since two polynucleotides or amino acid sequences may each (1) comprise a sequence (i.e., a portion of the complete polynucleotide or amino acid sequence) that is similar between the two molecules, and (2) may further comprise a sequence that is divergent between the two polynucleotides or amino acid sequences, sequence comparisons between two (or more) molecules are typically performed by comparing sequences of the two molecules over a "comparison window" to identify and compare local regions of sequence similarity. A "comparison window", as used herein, refers to a conceptual segment of at least 18 contiguous nucleotide positions or 6 amino acids wherein a polynucleotide sequence or amino acid sequence may be compared to a reference sequence of at least 18 contiguous nucleotides or 6 amino acid sequences and wherein the portion of the polynucleotide sequence in the comparison window may comprise additions, deletions, substitutions, and the like (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman *Adv. Appl. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci.* (U.S.A.) 85:2444 (1988), by computerized implementations of these algorithms (GAP, BESTFIT, FASTA, and TFASTA in the Wisconsin Genetics Software Package Release 7.0, (Genetics Computer Group, 575 Science Dr., Madison, Wis.), Geneworks, or MacVector software packages), or by inspection, and the best alignment (i.e., resulting in the highest percentage of homology over the comparison window) generated by the various methods is selected.

The term "sequence identity", means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U, or I) or residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more usually at least 99 percent sequence identity as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

As used herein, the twenty conventional amino acids and their abbreviations follow conventional usage. *See Immunology—A Synthesis* ($2^{nd}$ Edition, E. S. Golub and D. R. Gren, Eds., Sinauer Associates, Sunderland, Mass. (1991)), which is incorporated herein by reference. Stereoisomers (e.g., D-amino acids) of the twenty conventional amino acids, unnatural amino acids such as $\alpha$-, $\alpha$-disubstituted amino acids, N-alkyl amino acids, lactic acid, and other unconventional amino acids may also be suitable components for polypeptides of the present invention. Examples of unconventional amino acids include: 4-hydroxyproline, $\gamma$-carboxyglutamate, $\epsilon$-N,N,N-trimethyllysine, $\epsilon$-N-acetyllysine, O-phosphoserine, N-acetylserine, N-formylmethionine, 3-methylhistidine, 5-hydroxylysine, $\sigma$-N-methylarginine, and other similar amino acids and imino acids (e.g., 4-hydroxyproline). In the polypeptide notation used herein, the lefthand direction is the amino terminal direction and the righthand direction is the carboxy-terminal direction, in accordance with standard usage and convention.

Similarly, unless specified otherwise, the lefthand end of single-stranded polynucleotide sequences is the 5' end; the lefthand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity. Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, glutamic-aspartic, and asparagine-glutamine.

As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99%. In particular, conservative amino acid replacements are contemplated. Conservative replacements are those that take place within a family of amino acids that are related in their side chains. Genetically encoded amino acids are generally divided into families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. *Science* 253:164 (1991). Thus, the foregoing examples demonstrate that those of skill in the art can recognize sequence motifs and structural conformations that may be used to define structural and functional domains in accordance with the invention.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in *Proteins, Structures and Molecular Principles* (Creighton, Ed., W. H. Freeman and Company, New York (1984)); *Introduction to Protein Structure* (C. Branden and J. Tooze, eds., Garland Publishing, New York, N.Y. (1991)); and Thornton et at. *Nature* 354:105 (1991), which are each incorporated herein by reference.

The term "polypeptide fragment" as used herein refers to a polypeptide that has an amino-terminal and/or carboxy-terminal deletion, but where the remaining amino acid sequence is identical to the corresponding positions in the naturally-occurring sequence deduced, for example, from a full-length cDNA sequence. Fragments typically are at least 5, 6, 8 or 10 amino acids long, preferably at least 14 amino acids long, more preferably at least 20 amino acids long, usually at least 50 amino acids long, and even more preferably at least 70 amino acids long. The term "analog" as used herein refers to polypeptides which are comprised of a segment of at least 25 amino acids that has substantial identity to a portion of a deduced amino acid sequence and which has at least one of the following properties: (1) specific binding to a EGF-r, under suitable binding conditions, (2) ability to EGF binding to its receptor, or (3) ability to inhibit EGF-r expressing cell growth in vitro or in vivo. Typically, polypeptide analogs comprise a conservative amino acid substitution (or addition or deletion) with respect to the naturally-occurring sequence. Analogs typically are at least 20 amino acids long, preferably at least 50 amino acids long or longer, and can often be as long as a full-length naturally-occurring polypeptide.

Peptide analogs are commonly used in the pharmaceutical industry as non-peptide drugs with properties analogous to those of the template peptide. These types of non-peptide compound are termed "peptide mimetics" or "peptidomimetics". Fauchere, *J. Adv. Drug Res.* 15:29 (1986); Veber and Freidinger *TINS* p. 392 (1985); and Evans et al. *J. Med. Chem.* 30:1229 (1987), which are incorporated herein by reference. Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: $-CH_2NH-$, $-CH_2S-$, $-CH_2-CH_2-$, $-CH=CH-$ (cis and trans), $-COCH_2-$, $-CH(OH)CH_2-$, and $-CH_2SO-$, by methods well known in the art. Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch *Ann. Rev. Biochem.* 61:387 (1992), incorporated herein by reference); for example, by adding internal cysteine residues capable of forming intramolecular disulfide bridges which cyclize the peptide.

"Antibody" or "antibody peptide(s)" refer to an intact antibody, or a binding fragment thereof that competes with the intact antibody for specific binding. Binding fragments are produced by recombinant DNA techniques, or by enzymatic or chemical cleavage of intact antibodies. Binding fragments include Fab, Fab', F(ab')$_2$, Fv, and single-chain antibodies. An antibody other than a "bispecific" or "bifunctional" antibody is understood to have each of its binding sites identical. An antibody substantially inhibits adhesion of a receptor to a counterreceptor when an excess of antibody reduces the quantity of receptor bound to counterreceptor by at least about 20%, 40%, 60% or 80%, and more usually greater than about 85% (as measured in an in vitro competitive binding assay).

The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. An antibody is said to specifically bind an antigen when the dissociation constant is $\leq 1$ μM, preferably $\leq 100$ nM and most preferably $\leq 10$ nM.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^3$H, $^{14}$C, $^{15}$N, $^{35}$S, $^{90}$Y, $^{99}$Tc, $^{111}$In, $^{125}$I, $^{131}$I), fluorescent labels (e.g., FITC, rhodamine, lanthanide phosphors), enzymatic labels (e.g., horseradish peroxidase, β-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

The term "pharmaceutical agent or drug" as used herein refers to a chemical compound or composition capable of inducing a desired therapeutic effect when properly administered to a patient. Other chemistry terms herein are used according to conventional usage in the art, as exemplified by *The McGraw-Hill Dictionary of Chemical Terms* (Parker, S., Ed., McGraw-Hill, San Francisco (1985)), incorporated herein by reference).

The term "antineoplastic agent" is used herein to refer to agents that have the functional property of inhibiting a development or progression of a neoplasm in a human, particularly a malignant (cancerous) lesion, such as a carcinoma, sarcoma, lymphoma, or leukemia. Inhibition of metastasis is frequently a property of antineoplastic agents.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The term patient includes human and veterinary subjects.

Antibody Structure

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgA, and IgE, respectively. Within light and heavy chains, the variable and constant regions are joined by a "J" region of about 12 or more amino acids, with the heavy chain also including a "D" region of about 10 more amino acids. See generally, *Fundamental Immunology* Ch. 7 (Paul, W., ed., 2nd ed. Raven Press, N.Y. (1989)) (incorporated by reference in its entirety for all purposes). The variable regions of each light/heavy chain pair form the antibody binding site.

Thus, an intact antibody has two binding sites. Except in bifunctional or bispecific antibodies, the two binding sites are the same.

The chains all exhibit the same general structure of relatively conserved framework regions (FR) joined by three hyper variable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat *Sequences of proteins of Immunological Interest* (National Institutes of Health, Bethesda, Md. (1987 and 1991)), or Chothia & Lesk *J. Mol. Biol.* 196:901-917 (1987); Chothia et al. *Nature* 342:878-883 (1989).

A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann *Clin. Exp. Immunol.* 79: 315-321 (1990), Kostelny et al. *J. Immunol.* 148:1547-1553 (1992). Production of bispecific antibodies can be a relatively labor intensive process compared With production of conventional antibodies and yields and degree of purity are generally lower for bispecific antibodies. Bispecific antibodies do not exist in the form of fragments having a single binding site (e.g., Fab, Fab', and Fv).

Humanization and Display Technologies

As was discussed above in connection with human antibody generation, there are advantages to producing antibodies with reduced immunogenicity. To a degree, this can be accomplished in connection with techniques of humanization and display techniques using appropriate libraries. It will be appreciated that murine antibodies or antibodies from other species can be humanized or primatized using techniques well known in the art. See e.g., Winter and Harris *Immunol Today* 14:43-46 (1993) and Wright et al. *Crit, Reviews in Immunol.* 12125-168 (1992). The antibody of interest may be engineered by recombinant DNA techniques to substitute the CH1, CH2, CH3, hinge domains, and/or the framework domain with the corresponding human sequence (see WO 92/02190 and U.S. Pat. Nos. 5,530,101, 5,585,089, 5,693,761, 5,693,792, 5,714,350, and 5,777,085). Also, the use of Ig cDNA for construction of chimeric immunoglobulin genes is known in the art (Liu et al. *P.N.A.S.* 84:3439 (1987) and *J. Immunol.* 139:3521 (1987)). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) Sequences of Proteins of Immunological Interest, N.I.H. publication no. 91-3242. Human C region genes are readily available from known clones. The choice of isotype will be guided by the desired effector functions, such as complement fixation, or activity in antibody-dependent cellular cytotoxicity. Preferred isotypes are IgG1, IgG3 and IgG4. Either of the human light chain constant regions, kappa or lambda, may be used. The chimeric, humanized antibody is then expressed by conventional methods.

Antibody fragments, such as Fv, F(ab').sub.2 and Fab may be prepared by cleavage of the intact protein, e.g. by protease or chemical cleavage. Alternatively, a truncated gene is designed. For example, a chimeric gene encoding a portion of the F(ab')$_2$ fragment would include DNA sequences encoding the CH1 domain and hinge region of the H chain, followed by a translational stop codon to yield the truncated molecule.

Consensus sequences of H and L J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, YACs, EBV derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, e.g. SV-40 early promoter, (Okayama et al. *Mol. Cell. Bio.* 3:280 (1983)), Rous sarcoma virus LTR (Gorman et al. *P.N.A.S.* 79:6777 (1982)), and moloney murine leukemia virus LTR (Grosschedl et al. *Cell* 41:885 (1985)); native Ig promoters, etc.

Further, human antibodies or antibodies from other species can be generated through display-type technologies, including, without limitation, phage display, retroviral display, ribosomal display, and other techniques, using techniques well known in the art and the resulting molecules can be subjected to additional maturation, such as affinity maturation, as such techniques are well known in the art. Wright and Harris, supra., Hanes and Plucthau *PNAS USA* 94:4937-4942 (1997) (ribosomal display), Parmley and Smith *Gene* 73:305-318 (1988) (phage display), Scott *TIBS* 17:241-245 (1992), Cwirla et al. *PNAS USA* 87:6378-6382 (1990), Russel et al. *Nucl. Acids Research* 21:1081-1085 (1993), Hoganboom et al. *Immunol. Reviews* 130:43-68 (1992), Chiswell and McCafferty *TIBTECH* 10:80-84 (1992), and U.S. Pat. No. 5,733,743. If display technologies are utilized to produce antibodies that are not human, such antibodies can be humanized as described above.

Using these techniques, antibodies can be generated to EGF-R expressing cells, EGF-R itself, forms of EGF-R, epitopes or peptides thereof, and expression libraries thereto (see e.g. U.S. Pat. No. 5,703,057) which can thereafter be screened as described above for the activities described above.

Additional Criteria for Antibody Therapeutics

As discussed herein, the function of the EGF-R antibody appears important to at least a portion of its mode of operation. By function, we mean, by way of example, the activity of the EGF-R antibody in operation and activity in the costimulatory pathway of EGF-R. Accordingly, in certain respects, it may be desirable in connection with the generation of antibodies as therapeutic candidates against EGF-R that the antibodies be capable of fixing complement and participating in CDC. There are a number of isotypes of antibodies that are capable of the same, including, without limitation, the following: murine IgM, murine IgG2a, murine IgG2b, murine IgG3, human IgM, human IgG1, and human IgG3. It will be appreciated that antibodies that are generated need not initially possess such an isotype but, rather, the antibody as generated can possess any isotype and the antibody can be isotype switched thereafter using conventional techniques that are well known in the art. Such techniques include the use of direct recombinant techniques (see e.g., U.S. Pat. No. 4,816,397), cell-cell fusion techniques (see e.g., U.S. patent application Ser. No. 08/730,639, filed Oct. 11, 1996), among others.

In the cell-cell fusion technique, a myeloma or other cell line is prepared that possesses a heavy chain with any desired isotype and another myeloma or other cell line is prepared that possesses the light chain. Such cells can, thereafter, be fused and a cell line expressing an intact antibody can be isolated.

By way of example, the E763 antibody discussed herein is a human anti-EGF-R IgG2 antibody. If such antibody possessed desired binding to the EGF-R molecule, it could be readily isotype switched to generate a human IgM, human IgG1, or human IgG3 isotype, while still possessing the same variable region (which defines the antibody's specificity and some of its affinity). Such molecule would then be capable of fixing complement and participating in CDC.

Accordingly, as antibody candidates are generated that meet desired "structural" attributes as discussed above, they can generally be provided with at least certain of the desired "functional" attributes through isotype switching.

Design and Generation of Other Therapeutics

In accordance with the present invention and based on the activity of the antibodies that are produced and characterized herein with respect to EGF-R, the design of other therapeutic modalities beyond antibody moieties is facilitated. Such modalities include, without limitation, advanced antibody therapeutics, such as bispecific antibodies, immunotoxins, and radiolabeled therapeutics, generation of peptide therapeutics, gene therapies, particularly intrabodies, antisense therapeutics, and small molecules.

In connection with the generation of advanced antibody therapeutics, where complement fixation is a desirable attribute, it may be possible to sidestep the dependence on complement for cell killing through the use of bispecifics, immunotoxins, or radiolabels, for example.

For example, in connection with bispecific antibodies, bispecific antibodies can be generated that comprise (i) two antibodies one with a specificity to EGF-R and another to a second molecule that are conjugated together, (ii) a single antibody that has one chain specific to EGF-R and a second chain specific to a second molecule, or (iii) a single chain antibody that has specificity to EGF-R and the other molecule. Such bispecific antibodies can be generated using techniques that are well known for example, in connection with (i) and (ii) see e.g., Fanger et al. *Immunol Methods* 4:72-81 (1994) and Wright and Harris, supra. and in connection with (iii) see e.g., Traunecker et al. *Int. J. Cancer (Suppl.)* 7:51-52 (1992). In each case, the second specificity can be made to the heavy chain activation receptors, including, without limitation, CD16 or CD64 (see e.g., Deo et al. 18:127 (1997)) or CD89 (see e.g., Valerius et al. *Blood* 90:4485-4492 (1997)). Bispecific antibodies prepared in accordance with the foregoing would be likely to kill cells expressing EGF-R, and particularly those cells in which the EGF-R antibodies of the invention are effective.

In connection with immunotoxins, antibodies can be modified to act as immunotoxins utilizing techniques that are well known in the art. See e.g., Vitetta *Immunol Today* 14:252 (1993). See also U.S. Pat. No. 5,194,594. In connection with the preparation of radiolabeled antibodies, such modified antibodies can also be readily prepared utilizing techniques that are well known in the art. See e.g., Junghans et al. in *Cancer Chemotherapy and Biotherapy* 655-686 (2d edition, Chafner and Longo, eds., Lippincott Raven (1996)). See also U.S. Pat. Nos. 4,681,581, 4,735,210, 5,101,827, 5,102,990 (RE 35,500), 5,648,471, and 5,697,902. Each of immunotoxins and radiolabeled molecules would be likely to kill cells expressing EGF-R, and particularly those cells in which the antibodies of the invention are effective.

In connection with the generation of therapeutic peptides, through the utilization of structural information related to EGF-R and antibodies thereto, such as the antibodies of the invention (as discussed below in connection with small molecules) or screening of peptide libraries, therapeutic peptides can be generated that are directed against EGF-R. Design and screening of peptide therapeutics is discussed in connection with Houghten et al. *Biotechniques* 13:412-421 (1992), Houghten *PNAS USA* 82:5131-5135 (1985), Pinalla et al. *Biotechniques* 13:901-905 (1992), Blake and Litzi-Davis *BioConjugate Chem.* 3:510-513 (1992). Immunotoxins and radiolabeled molecules can also be prepared, and in a similar manner, in connection with peptidic moieties as discussed above in connection with antibodies.

Assuming that the EGF-R molecule (or a form, such as a splice variant or alternate form) is functionally active in a disease process, it will also be possible to design gene and antisense therapeutics thereto through conventional techniques. Such modalities can be utilized for modulating the function of EGF-R. In connection therewith the antibodies of the present invention facilitate design and use of functional assays related thereto. A design and strategy for antisense therapeutics is discussed in detail in International Patent Application No. WO 94/29444. Design and strategies for gene therapy are well known. However, in particular, the use of gene therapeutic techniques involving intrabodies could prove to be particularly advantageous. See e.g., Chen et al. *Human Gene Therapy* 5:595-601 (1994) and Marasco *Gene Therapy* 4:11-15 (1997). General design of and considerations related to gene therapeutics is also discussed in International Patent Application No. WO 97/38137.

Small molecule therapeutics can also be envisioned in accordance with the present invention. Drugs can be designed to modulate the activity of EGF-R based upon the present invention. Knowledge gleaned from the structure of the EGF-R molecule and its interactions with other molecules in accordance with the present invention, such as the antibodies of the invention, and others can be utilized to rationally design additional therapeutic modalities. In this regard, rational drug design techniques such as X-ray crystallography, computer-aided (or assisted) molecular modeling (CAMM), quantitative or qualitative structure-activity relationship (QSAR), and similar technologies can be utilized to focus drug discovery efforts. Rational design allows prediction of protein or synthetic structures which can interact with the molecule or specific forms thereof which can be used to modify or modulate the activity of EGF-R. Such structures can be synthesized chemically or expressed in biological systems. This approach has been reviewed in Capsey et al. *Genetically Engineered Human Therapeutic Drugs* (Stockton Press, NY (1988)). Further, combinatorial libraries can be designed and sythesized and used in screening programs, such as high throughput screening efforts.

Therapeutic Administration and Formulations

It will be appreciated that administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences ($15^{th}$ ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration.

Preparation of Antibodies

Antibodies in accordance with the invention are preferably prepared through the utilization of a transgenic mouse that has a substantial portion of the human antibody producing genome inserted but that is rendered deficient in the production of endogenous, murine, antibodies. Such mice, then, are capable of producing human immunoglobulin molecules and antibodies and are deficient in the production of murine immunoglobulin molecules and antibodies. Technologies utilized for achieving the same are disclosed in the patents, applications, and references disclosed in the Background, herein. In particular, however, a preferred embodiment of transgenic production of mice and antibodies therefrom is disclosed in U.S. patent application Ser. No. 08/759,620, filed Dec. 3, 1996, the disclosure of which is hereby incorporated by reference. See also Mendez et al. *Nature Genetics* 15:146-156 (1997), the disclosure of which is hereby incorporated by reference.

Through use of such technology, we have produced fully human monoclonal antibodies to a variety of antigens. Essentially, we immunize XenoMouse™ lines of mice with an antigen of interest, recover lymphatic cells (such as B-cells) from the mice that express antibodies, fuse such recovered cells with a myeloid-type cell line to prepare immortal hybridoma cell lines, and such hybridoma cell lines are screened and selected to identify hybridoma cell lines that produce antibodies specific to the antigen of interest. We utilized these techniques in accordance with the present invention for the preparation of antibodies specific to EGF-r. Herein, we describe the production of eight hybridoma cell lines that produce antibodies specific to EGF-r. Further, we provide a characterization of the antibodies produced by such cell lines, including nucleotide and amino acid sequence analyses of the heavy and light chains of such antibodies.

The hybridoma cell lines discussed herein are designated E1.1, E2.4, E2.5, E6.2, E6.4, E2.11, E6.3, and E7.6.3. Each of the antibodies produced by the aforementioned cell lines are fully human IgG2 heavy chains with human kappa light chains. In general, antibodies in accordance with the invention possess very high affinities, typically possessing Kd's of from about $10^{-9}$ through about $10^{-1}$ M, when measured by either solid phase and solution phase.

As will be appreciated, antibodies in accordance with the present invention can be expressed in cell lines other than hybridoma cell lines. Sequences encoding particular antibodies can be used for transformation of a suitable mammalian host cell. Transformation can be by any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216, 4,912,040, 4,740,461, and 4,959,455 (which patents are hereby incorporated herein by reference). The transformation procedure used depends upon the host to be transformed. Methods for introduction of heterologous polynucleotides into mammalian cells are well known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. Cell lines of particular preference are selected through determining which cell lines have high expression levels and produce antibodies with constitutive EGF-r binding properties.

Figure 38:
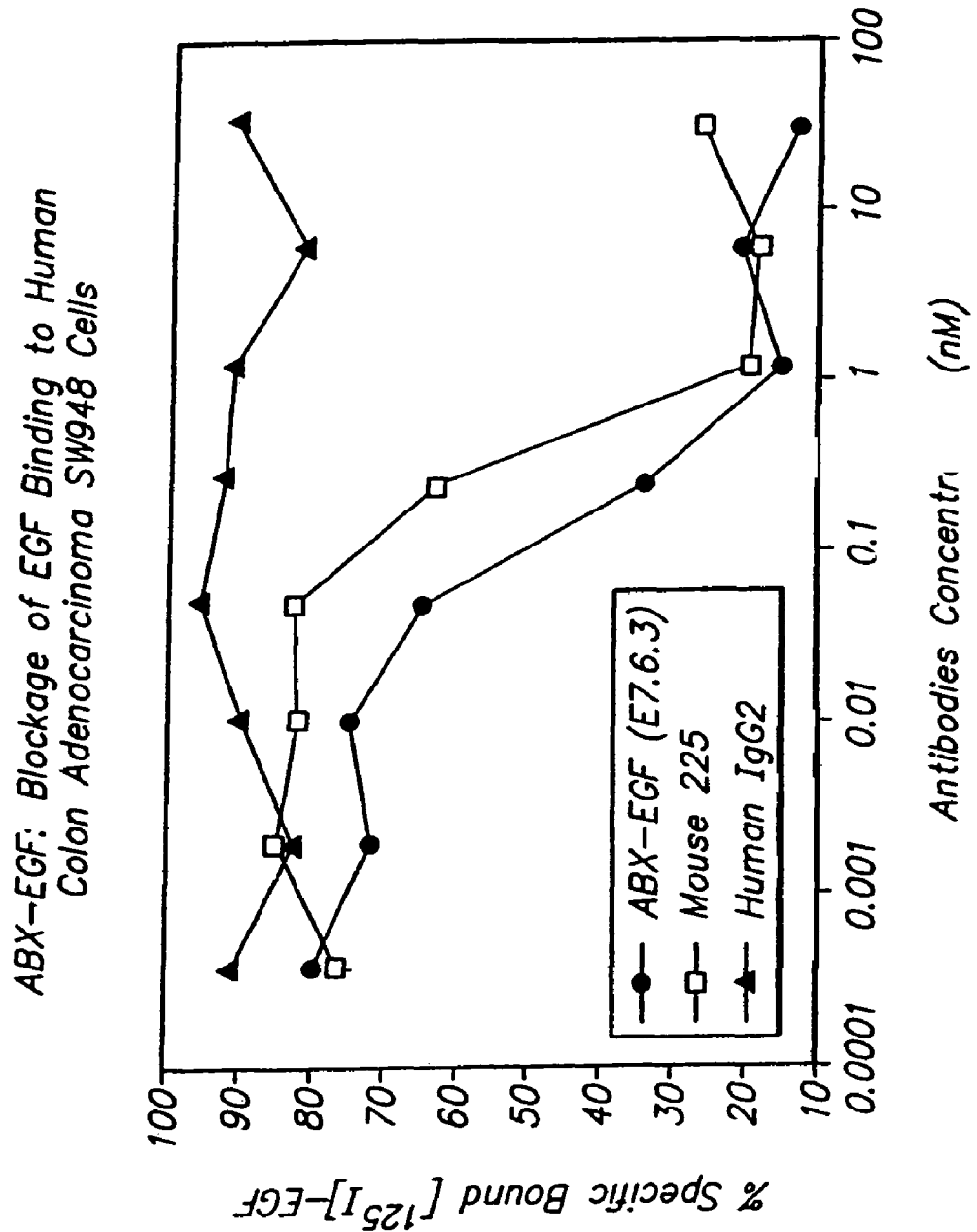
FIG. 38 shows inhibition of EGF binding to human colon carcinoma SW948 cells by human anti-EGF-r antibodies in vitro, where (○) depicts the results achieved by an anti-EGF-r antibody in accordance with the invention, (□) depicts the results achieved by the murine monoclonal antibody 225, and (▲) depicts the results achieved by a control, nonspecific, human IgG2 antibody.
Figure 39:
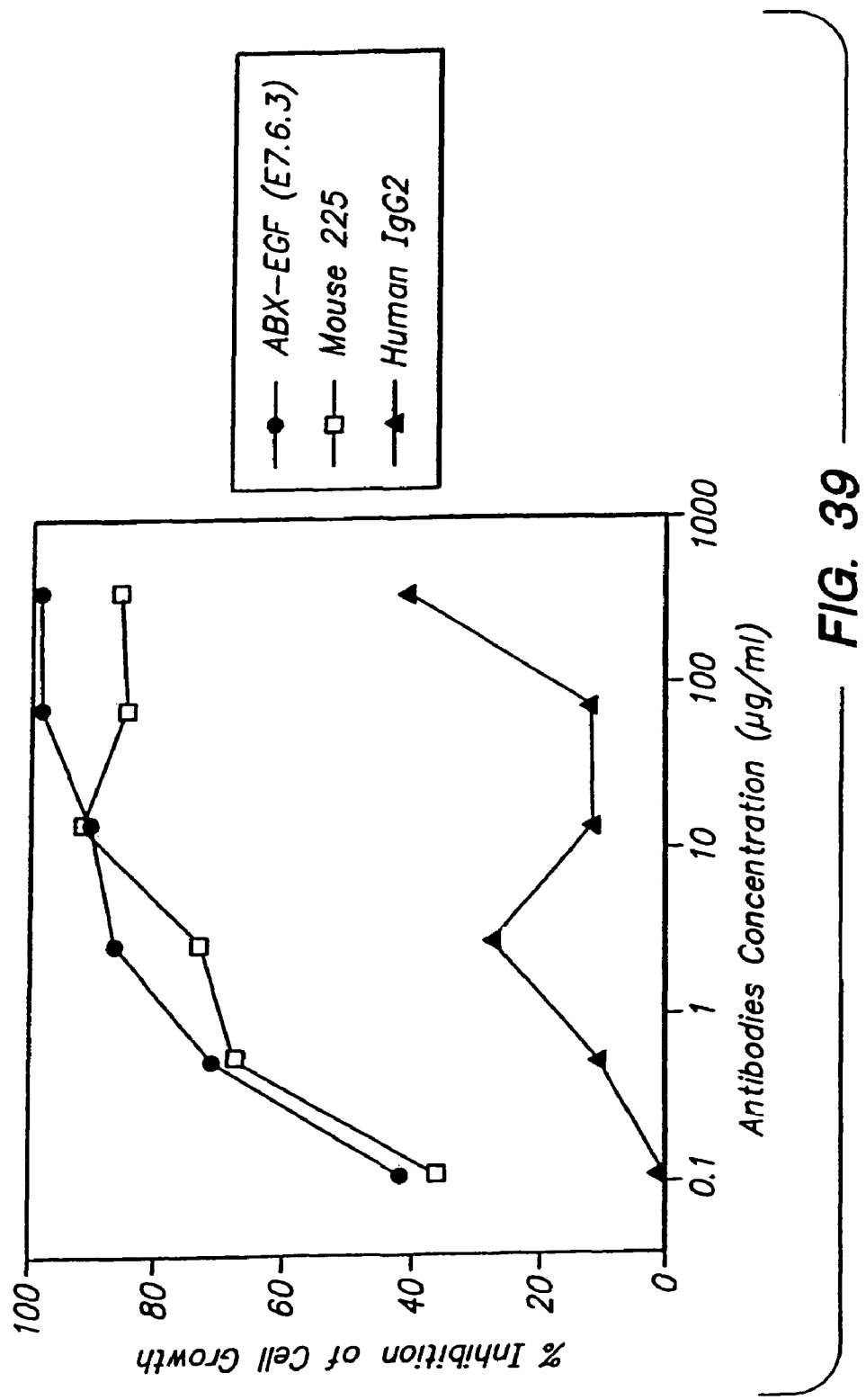
FIG. 39 shows that human anti-EGF-r antibodies derived from XenoMouse II strains inhibit growth of SW948 cells in vitro, where (●) depicts the results achieved by an anti-EGF-r antibody in accordance with the invention, (□) depicts the results achieved by the murine monoclonal antibody 225, and (▲) depicts the results achieved by a control, nonspecific, human IgG2 antibody.

Antibodies in accordance with the present invention are potent inhibitors of EGF and TGF-α binding to its receptor, EGF-r. Such results are discussed in Examples 5 and 6 and shown in FIGS. 35 through 38. Consistent with such results, and as shown in FIG. 39 and discussed in connection with Example 7, antibodies in accordance with the present invention also inhibit the growth of certain human carcinoma cell lines in vitro. Antibodies in accordance with the present invention also prevent the growth of certain human carcinomas in vivo. Such results are shown in FIGS. 40 through 42 and discussed in connection with Example 8. In Example 9, we demonstrate that antibodies in accordance with the present invention, at least in combination with an antineoplastic agent, will eradicate an existing tumor in an animal. Moreover, antibody therapy, as a monotherapy (i.e., not in combination with an antineoplastic agent) appears possible in accordance with the antibodies in accordance with the present invention, where it did not appear possible in the prior art, for example through the use of the antibody 225. Such results are discussed in connection with Example 9 and shown in FIGS. 43-44.

The results demonstrated in accordance with the present invention indicate that antibodies in accordance with the present invention possess certain qualities that may make the present antibodies more efficacious than current therapeutic antibodies against EGF-r, e.g., 225. The 225 antibody in clinical development by Imclone is a chimeric IgG1 antibody with an affinity of $2\times10^{-10}$ M, which, while appearing efficacious in combination therapy with an antineoplastic agent, does not appear very efficacious in monotherapy. In contrast, antibodies in accordance with the invention (and particularly the E2.5 and E7.6.3 antibodies of the invention) have significantly higher affinities (E2.5:$1.6\times10^{11}$ M; E7.6.3:$5.7\times10^{-11}$ M) and appear efficacious in monotherapy in addition to combination therapy with an antineoplastic agent and at lower doses than with the C225 antibody.

EXAMPLES

The following examples, including the experiments conducted and results achieved are provided for illustrative purposes only and are not to be construed as limiting upon the present invention.

Example 1

Generation of Anti-EGF-r-Antibody Producing Hybridomas

Antibodies of the invention were prepared, selected, and assayed in accordance with the present Example.

Immunization and hybridoma generation: XenoMice (8 to 10 weeks old) were immunized intraperitoneally with $2\times10^7$ A431 (ATCC CRL-7907) cells resuspended in phosphate buffered saline (PBS). This dose was repeated three times. Four days before fusion, the mice received a final injection of cells in PBS. Spleen and lymph node lymphocytes from immunized mice were fused with the non-secretory myeloma NSO-bcl2 line (Ray and Diamond, 1994) and were subjected to HAT selection as previously described (Galfre and Milstein, 1981). A large panel of hybridomas all secreting EGF-r specific human IgG$_2$κ (as detected below) antibodies were recovered. As described in Example 2, certain of the antibodies selected from the panel were selected for their ability to compete with the 225 antibody. EGFr-specific hybridomas were identified by ELISA using purified A431 cell membrane-derived EGFr protein (Sigma, St. Louis, Mo., E3641). Large quantities of antibodies were purified from ascites, derived from SCID mice inoculated with antibody-producing hybridomas, using protein-A affinity chromatography.

ELISA assay: ELISA for determination of antigen-specific antibodies in mouse serum and in hybridoma supernatants was carried out as described (Coligan et al., 1994) using affinity-purified EGF-r from A431 cells (Sigma, E-3641) to capture the antibodies. The concentrations of human and mouse immunoglobulins were determined using the following capture antibodies: rabbit anti-human IgG (Southern Biotechnology, 6145-01), goat anti-human Igκ (Vector Laboratories, AI-3060), mouse anti-human IgM (CGI/ATCC, HB-57), for human gamma, kappa, and mu Ig, respectively, and goat anti-mouse IgG (Caltag, M 30100), goat anti-mouse IgK (Southern Biotechnology, 1050-01), goat anti-mouse IgM (Southern Biotechnology, 1020-01), and goat anti-mouse λ (Southern Biotechnology, 1060-01) to capture mouse gamma, kappa, mu, and lambda Ig, respectively. The detection antibodies used in ELISA experiments were goat anti-mouse IgG-HRP (Caltag, M-30107), goat anti-mouse Igκ-HRP (Caltag, M 33007), mouse anti-human IgG2-HRP (Southern Biotechnology, 9070-05), mouse anti-human IgM-HRP (Southern Biotechnology, 9020-05), and goat anti-human kappa-biotin (Vector, BA-3060). Standards used for quantitation of human and mouse Ig were: human IgG$_2$κ (Calbiochem, 400122), human IgMκ (Cappel, 13000), mouse IgGκ (Cappel 55939), mouse IgMκ (Sigma, M-3795), and mouse IgG$_3$λ (Sigma, M-9019).

Determination of affinity constants of fully human Mabs by BIAcore: Affinity measurement of purified human monoclonal antibodies, Fab fragments, or hybridoma supernatants by plasmon resonance was carried out using the BIAcore 2000 instrument, using general procedures outlined by the manufacturers.

Based upon the general procedures outlined by the manufacture, kinetic analyses of the antibodies were performed using antigens immobilized onto the sensor surface at a low density. Soluble EGF-r purified from A431 cell membranes (Sigma, E-3641) or the recombinant extracellular domain of EGFr (20) immobilized onto the sensor surface was generally used at a surface density of between about 228 and 303 RU. The dissociation (kd or $k_{off}$) and association (ka or $k_{on}$) rates were determined using the software provided by the manufacturer (BIA evaluation 2.1). Affinity measurements of antibody in solution were carried out as described (18).

Determination of affinity constants in solution by ELISA: In order to determine antibody binding affinity in solution by ELISA, various concentrations of the monoclonal antibodies to EGF-r were incubated with EGF-r at a constant concentration until equilibrium was reached. Thereafter, the concentration of the free EGF-r in the reaction solution was determined by an indirect ELISA. Accordingly, the monoclonal antibodies at concentrations of between $3.0 \times 10^{-11}$ M through $2.7 \times 10^{-7}$ M were incubated with EGF-r at a concentration of $4 \times 10^{-10}$ M in 200 μl of PBS with 0.5% BSA for 15 hrs at room temperature. After incubation, 70 μl of each mixture was transferred into the wells of 96-well microtiter plates previously coated with the same monoclonal antibody (100 μl/well, at 2 μg/ml in coating buffer) and incubated for 15 min at room temperature. After washing with washing buffer, the EGF-r retained on the plate was detected by mouse anti-EGF-r-HRP, which binds to the carbohydrate of the EGF-r protein. The concentration of EGF-r was calculated against its standard and used for the calculation of bound and free antibodies in the original antigen-antibody reaction solution. The binding affinity of each monoclonal antibody to EGF-r was calculated using Scatchard analysis.

Receptor binding assays: The EGF receptor binding assay was carried out with A431 cells or SW948 cells ($0.4 \times 10^6$ cells per well) which were incubated with varying concentrations of antibodies in PBS binding buffer for 30 minutes at 4° C. 0.1 nM [$^{125}$I]EGF (Amersham, IM-196) or [$^{125}$I]TGF-α (Amersham) was added to each well, and the plates were incubated for 90 min at 4° C. The plates were washed five times, air-dried and counted in a scintillation counter. Anti-EGF-r mouse antibodies 225 and 528 (Calbiochem) were used as controls.

EGFr binding assays were also conducted using human recombinant [$^{125}$I]EGF or [$^{125}$I]TGFα (Amersham Life Science, Arlington Heights, Ill.) as previously described (Mendez). Briefly, human carcinoma cells growing in Dulbecco's modified Eagle's medium (DMEM) containing 10% fetal calf serum (FCS) were detached with trypsin, washed with phosphate-buffered saline (PBS) and resuspended in binding buffer (PBS containing 0.1% bovine serum albumin (Sigma) and 0.02% NaN$_3$), and distributed in 96-well Multiscreen filter plates (Millipore) at $4.0 \times 10^5$ cells/well in 50 μl. Fully human anti-EGFr or control anti-KLH MAbs, control human myeloma IgG$_2$κ Mab (Calbiochem, Cambridge, Mass., 400122), or mouse anti-EGFr 225 or 528 MAbs (Calbiochem, GR13 or GR14), diluted in binding buffer, were added in 50 μl aliquots per well. Plates were incubated for 30 min at 4° C. [$^{125}$I]-EGF or [$^{125}$I]TGFα (0.1 μCi/well in 50 μl) was added and the plates were further incubated for 90 min at 4° C. After incubation, the plates were washed five times with binding buffer, air-dried and counted in a scintillation counter. The percentage of specifically bound [$^{125}$I]EGF or [$^{125}$I]TGFα was calculated as the mean cpm detected in the presence of antibody divided by cpm detected in the presence of buffer only. The binding data obtained was fitted using GraphPad Prism (GraphPad Software, Inc. San Diego, Calif.).

Example 2

Co-Selection of Anti-EGF-r-Antibodies with the m225 Antibody

As discussed above, the antibody 225 has been demonstrated to possess a high affinity for, and effective inhibition of the binding of EGF and TGF-α to EGF-r. Thus, we expected that if we selected human antibodies against EGF-r that are prepared in accordance with the present invention with the antibody 225 in a competition assay, antibodies to the same or similar epitope to which the 225 antibody binds would be selected.

Accordingly, we conducted BIAcore assays in which soluble EGF-r purified from A431 cell membranes (Sigma, E-3641) was pretreated with the antibody 225 and thereafter treated with antibodies of the invention. Where antibodies of the invention did not bind, such antibodies of the invention were screened for binding affinity as described above.

In the following Table, affinity measurements for certain of the antibodies selected in this manner are provided:

TABLE I

| | Solid Phase (by BIAcore) | | | | In Solution |
|---|---|---|---|---|---|
| Hybridoma | $k_{on}$ (M$^{-1}$S$^{-1}$) | $K_{off}$ (S$^{-1}$) | $K_D$ (M) | Surface Density [RU] | By ELISA KD (M) |
| E1.1 | $2.3 \times 10^6$ | $1.7 \times 10^{-4}$ | $76 \times 10^{-11}$ | 228 | $1.1 \times 10^{-10}$ |
| E2.4 | $2.8 \times 10^6$ | $9.78 \times 10^{-5}$ | $3.5 \times 10^{-11}$ | 818 | $1.1 \times 10^{-10}$ |
| E2.5 | $1.2 \times 10^6$ | $1.9 \times 10^{-5}$ | $1.6 \times 10^{-11}$ | 228 | $3.6 \times 10^{-10}$ |
| E2.11 | $1.9 \times 10^6$ | $3.0 \times 10^{-4}$ | $1.6 \times 10^{-10}$ | 228 | $1.1 \times 10^{-10}$ |
| E7.6.3 | $2.0 \times 10^6$ | $1.1 \times 10^{-4}$ | $5.7 \times 10^{-11}$ | 228 | ND |

As will be observed, antibodies selected in this manner possess exceptionally high affinities and binding constants.

Example 3

Structures of Anti-EGF-r-Antibodies Prepared in Accordance with the Invention

In the following discussion, structural information related to antibodies prepared in accordance with the invention is provided.

In order to analyze structures of antibodies produced in accordance with the invention, we cloned genes encoding the heavy and light chain fragments out of the particular hybridoma. Gene cloning and sequencing was accomplished as follows:

Poly(A)+ mRNA was isolated from approximately 2×10^5 hybridoma cells derived from immunized XenoMice using a Fast-Track kit (Invitrogen). The generation of random primed cDNA was followed by PCR. Human $V_H$ or human $V_\kappa$ family specific variable region primers (Marks et. al., 1991) or a universal human $V_H$ primer, MG-30 (CAGGTGCAGCTG-GAGCAGTCIGG) (SEQ ID NO: 1) was used in conjunction with primers specific for the human Cγ2 constant region (MG-40d; 5'-GCTGAGGGAGTAGAGTCCTGAGGA-3') (SEQ ID NO:2) or Cκ constant region (hκP2; as previously described in Green et al., 1994). Sequences of human Mabs-derived heavy and kappa chain transcripts from hybridomas were obtained by direct sequencing of PCR products generated from poly(A+) RNA using the primers described above. PCR products were also cloned into pCRII using a TA cloning kit (Invitrogen) and both strands were sequenced using Prism dye-terminator sequencing kits and an ABI 377 sequencing machine. All sequences were analyzed by alignments to the "V BASE sequence directory" (Tomlinson et al., MRC Centre for Protein Engineering, Cambridge, UK) using MacVector and Geneworks software programs.

Hybridoma E1.1

The antibody secreted by the hybridoma E1.1 comprises a human IgG2 antibody having a human kappa light chain. The antibodies were analyzed for structural information related to their heavy chain and light chain gene utilization, as well as their amino acid sequences. Thus, heavy chain $V_H$, D, and $J_H$ and light chain Vκ and Jκ gene utilization was analyzed and differences between the coded product and the particular gene utilization was also analyzed. Accordingly, the antibody secreted by the hybridoma E1.1 evidenced the following gene utilization:

$V_H$-4-31
D-2
$J_H$-5
Vκ-018
Jκ-4

As reported in the V BASE sequence directory, the amino acid sequence encoded by the $V_H$ 4-31 gene was determined to be:

(SEQ ID NO: 35)
VSGGSISSGGYYWSWIRQHPGKGLEWIGYIYYSGSTYYNPSLKSRVTISV
DTSKNQFSLKLSSVTAADTAVYYCAR

As reported in the V BASE sequence directory, the amino acid sequence encoded by the Vκ (018) gene was determined to be:

(SEQ ID NO: 36)
TITCQASQDISNYLNWYQQKPGKAPKLLIYDASNLETGVPSRFSGSGSGT
DFTFTISSLQPEDIATYYCQQYDNLP

Amino acid and nucleotide sequence information respecting the heavy and light chains are provided below in connection with FIGS. 1-4. FIG. 1 is an amino acid sequence of a heavy chain immunoglobulin molecule that is secreted by the hybridoma E1.1. Differences between the sequence encoded by heavy chain variable gene 4-31 and the sequence of the E1.1 secreted heavy chain are indicated in bold and enlarged font. The contiguous sequence from CDR1 through CDR3 is indicated by underlining and CDR1, CDR2, and CDR3 sequences are each indicated by double underlining.

FIG. 2 is a nucleotide sequence of the cDNA encoding the heavy chain immunoglobulin molecule of FIG. 1 that was cloned out of the hybridoma E1.1.

FIG. 3 is an amino acid sequence of a kappa light chain immunoglobulin molecule that is secreted by the hybridoma E1.1. Differences between the sequence encoded by light chain variable gene 018 and the sequence of the E1.1 secreted light chain are indicated in bold and enlarged font. The contiguous sequence from CDR1 through CDR3 is indicated by underlining and CDR1, CDR2, and CDR3 sequences are each indicated by double underlining.

FIG. 4 is a nucleotide sequence of the cDNA encoding the kappa light chain immunoglobulin molecule of FIG. 3 that was cloned out of the hybridoma E1.1.

Hybridoma E2.4

The antibody secreted by the hybridoma E2.4 comprises a human IgG2 antibody having a human kappa light chain. The antibodies were analyzed for structural information related to their heavy chain and light chain gene utilization, as well as their amino acid sequences. Thus, heavy chain $V_H$, D, and $J_H$ and light chain Vκ and Jκ gene utilization was analyzed and differences between the coded product and the particular gene utilization was also analyzed. Accordingly, the antibody secreted by the hybridoma E2.4 evidenced the following gene utilization:

$V_H$-4-31
D-A1/A4
$J_H$-3
Vκ-018
Jκ-4

Amino acid and nucleotide sequence information respecting the heavy and light chains are provided below in connection with FIGS. 5-8. FIG. 5 is an amino acid sequence of a heavy chain immunoglobulin molecule that is secreted by the hybridoma E2.4. Differences between the sequence encoded by heavy chain variable gene 4-31 and the sequence of the E2.4 secreted heavy chain are indicated in bold and enlarged font. The contiguous sequence from CDR1 through CDR3 is indicated by underlining and CDR1, CDR2, and CDR3 sequences are each indicated by double underlining.

FIG. 6 is a nucleotide sequence of the cDNA encoding the heavy chain immunoglobulin molecule of FIG. 5 that was cloned out of the hybridoma E2.4.

FIG. 7 is an amino acid sequence of a kappa light chain immunoglobulin molecule that is secreted by the hybridoma E2.4. Differences between the sequence encoded by light chain variable gene 018 and the sequence of the E2.4 secreted light chain are indicated in bold and enlarged font. The contiguous sequence from CDR1 through CDR3 is indicated by underlining and CDR1, CDR2, and CDR3 sequences are each indicated by double underlining.

FIG. 8 is a nucleotide sequence of the cDNA encoding the kappa light chain immunoglobulin molecule of FIG. 7 that was cloned out of the hybridoma E2.4.

Hybridoma E2.5

The antibody secreted by the hybridoma E2.5 comprises a human IgG2 antibody having a human kappa light chain. The antibodies were analyzed for structural information related to their heavy chain and light chain gene utilization, as well as their amino acid sequences. Thus, heavy chain $V_H$, D, and $J_H$ and light chain Vκ and Jκ gene utilization was analyzed and differences between the coded product and the particular gene utilization was also analyzed. Accordingly, the antibody secreted by the hybridoma E2.5 evidenced the following gene utilization:

$V_H$-4-31
D-XP1/21-10
$J_H$-4
Vκ-018
Jκ-2

Amino acid and nucleotide sequence information respecting the heavy and light chain's are provided below in connection with FIGS. 9-12. FIG. 9 is an amino acid sequence of a heavy chain immunoglobulin molecule that is secreted by the hybridoma E2.5. Differences between the sequence encoded by heavy chain variable gene 4-31 and the sequence of the E2.5 secreted heavy chain are indicated in bold and enlarged font. The contiguous sequence from CDR1 through CDR3 is indicated by underlining and CDR1, CDR2, and CDR3 sequences are each indicated by double underlining.

FIG. 10 is a nucleotide sequence of the cDNA encoding the heavy chain immunoglobulin molecule of FIG. 9 that was cloned out of the hybridoma E2.5.

FIG. 11 is an amino acid sequence of a kappa light chain immunoglobulin molecule that is secreted by the hybridoma E2.5. Differences between the sequence encoded by light chain variable gene 018 and the sequence of the E2.5 secreted light chain are indicated in bold and enlarged font. The contiguous sequence from CDR1 through CDR3 is indicated by underlining and CDR1, CDR2, and CDR3 sequences are each indicated by double underlining.

FIG. 12 is a nucleotide sequence of the cDNA encoding the kappa light chain immunoglobulin molecule of FIG. 11 that was cloned out of the hybridoma E2.5.

Hybridoma E6.2

The antibody secreted by the hybridoma E6.2 comprises a human IgG2 antibody having a human kappa light chain. The antibodies were analyzed for structural information related to their heavy chain and light chain gene utilization, as well as their amino acid sequences. Thus, heavy chain $V_H$, D, and $J_H$ and light chain Vκ and Jκ gene utilization was analyzed and differences between the coded product and the particular gene utilization was also analyzed. Accordingly, the antibody secreted by the hybridoma E6.2 evidenced the following gene utilization:

$V_H$-4-31
D-? (CNTCCCTT)
$J_H$-6
Vκ-018
Jκ-1

Amino acid and nucleotide sequence information respecting the heavy and light chains are provided below in connection with FIGS. 13-16. FIG. 13 is an amino acid sequence of a heavy chain immunoglobulin molecule that is secreted by the hybridoma E6.2. Differences between the sequence encoded by heavy chain variable gene 4-31 and the sequence of the E6.2 secreted heavy chain are indicated in bold and enlarged font. The contiguous sequence from CDR1 through CDR3 is indicated by underlining and CDR1, CDR2, and CDR3 sequences are each indicated by double underlining.

FIG. 14 is a nucleotide sequence of the cDNA encoding the heavy chain immunoglobulin molecule of FIG. 13 that was cloned out of the hybridoma E6.2.

FIG. 15 is an amino acid sequence of a kappa light chain immunoglobulin molecule that is secreted by the hybridoma E6.2. Differences between the sequence encoded by light chain variable gene 018 and the sequence of the E6.2 secreted light chain are indicated in bold and enlarged font. The contiguous sequence from CDR1 through CDR3 is indicated by underlining and CDR1, CDR2, and CDR3 sequences are each indicated by double underlining.

FIG. 16 is a nucleotide sequence of the cDNA encoding the kappa light chain immunoglobulin molecule of FIG. 15 that was cloned out of the hybridoma E6.2.

Hybridoma E6.4

The antibody secreted by the hybridoma E6.4 comprises a human IgG2 antibody having a human kappa light chain. The antibodies were analyzed for structural information related to their heavy chain and light chain gene utilization, as well as their amino acid sequences. Thus, heavy chain $V_H$, D, and $J_H$ and light chain Vκ and Jκ gene utilization was analyzed and differences between the coded product and the particular gene utilization was also analyzed. Accordingly, the antibody secreted by the hybridoma E6.4 evidenced the following gene utilization:

$V_H$-4-31
D-A1/A4
$J_H$-4
Vκ-012
Jκ-2

As reported in the V BASE sequence directory, the amino acid sequence encoded by the Vκ012 gene was determined to be:

```
                                              (SEQ ID NO: 37)
TITCRASQSISSYLNWYQQKPGKAPKLLIYAASSLQSGVPSRFSGSGSGT
DFTLTISSLQPEDFATYYCQQSYSTP
```

Amino acid and nucleotide sequence information respecting the heavy and light chains are provided below in connection with FIGS. 17-20. FIG. 17 is an amino acid sequence of a heavy chain immunoglobulin molecule that is secreted by the hybridoma E6.4. Differences between the sequence encoded by heavy chain variable gene 4-31 and the sequence of the E6.4 secreted heavy chain are indicated in bold and enlarged font. The contiguous sequence from CDR1 through CDR3 is indicated by underlining and CDR1, CDR2, and CDR3 sequences are each indicated by double underlining.

FIG. 18 is a nucleotide sequence of the cDNA encoding the heavy chain immunoglobulin molecule of FIG. 17 that was cloned out of the hybridoma E6.4.

FIG. 19 is an amino acid sequence of a kappa light chain immunoglobulin molecule that is secreted by the hybridoma E6.4. Differences between the sequence encoded by light chain variable gene 012 and the sequence of the E6.4 secreted light chain are indicated in bold and enlarged font. The contiguous sequence from CDR1 through CDR3 is indicated by underlining and CDR1, CDR2, and CDR3 sequences are each indicated by double underlining.

FIG. 20 is a nucleotide sequence of the cDNA encoding the kappa light chain immunoglobulin molecule of FIG. 19 that was cloned out of the hybridoma E6.4.

Hybridoma E2.11

The antibody secreted by the hybridoma E2.11 comprises a human IgG2 antibody having a human kappa light chain. The antibodies were analyzed for structural information related to their heavy chain and light chain gene utilization, as well as their amino acid sequences. Thus, heavy chain $V_H$, D, and $J_H$ and light chain Vκ and Jκ gene utilization was analyzed and differences between the coded product and the particular gene utilization was also analyzed. Accordingly, the antibody secreted by the hybridoma E2.11 evidenced the following gene utilization:

$V_H$-4-61
D-XP1/21-10
$J_H$-4
Vκ-018
Jκ-4

As reported in the V BASE sequence directory, the amino acid sequence encoded by the $V_H$ 4-61 gene was determined to be:

(SEQ ID NO: 38)
VSGGSVSSGSYYWSWIRQPPGKGLEWIGYIYYSGSTNYNPSLKSRVTISV
DTSKNQFSLKLSSVTAADTAVYYCAR

Amino acid and nucleotide sequence information respecting the heavy and light chains are provided below in connection with FIGS. 21-24. FIG. 21 is an amino acid sequence of a heavy chain immunoglobulin molecule that is secreted by the hybridoma E2.11. Differences between the sequence encoded by heavy chain variable gene 4-61 and the sequence of the E2.11 secreted heavy chain are indicated in bold and enlarged font. The contiguous sequence from CDR1 through CDR3 is indicated by underlining and CDR1, CDR2, and CDR3 sequences are each indicated by double underlining.

FIG. 22 is a nucleotide sequence of the cDNA encoding the heavy chain immunoglobulin molecule of FIG. 21 that was cloned out of the hybridoma E2.11.

FIG. 23 is an amino acid sequence of a kappa light chain immunoglobulin molecule that is secreted by the hybridoma E2.11. Differences between the sequence encoded by light chain variable gene 018 and the sequence of the E2.11 secreted light chain are indicated in bold and enlarged font. The contiguous sequence from CDR1 through CDR3 is indicated by underlining and CDR1, CDR2, and CDR3 sequences are each indicated by double underlining.

FIG. 24 is a nucleotide sequence of the cDNA encoding the kappa light chain immunoglobulin molecule of FIG. 23 that was cloned out of the hybridoma E2.11.

Hybridoma E6.3

The antibody secreted by the hybridoma E6.3 comprises a human IgG2 antibody having a human kappa light chain. The antibodies were analyzed for structural information related to their heavy chain and light chain gene utilization, as well as their amino acid sequences. Thus, heavy chain $V_H$, D, and $J_H$ and light chain Vκ and Jκ gene utilization was analyzed and differences between the coded product and the particular gene utilization was also analyzed. Accordingly, the antibody secreted by the hybridoma E6.3 evidenced the following gene utilization:

$V_H$-4-61
D-1-2rc
$J_H$-4
Vκ-018
Jκ-4

Amino acid and nucleotide sequence information respecting the heavy and light chains are provided below in connection with FIGS. 25-28. FIG. 25 is an amino acid sequence of a heavy chain immunoglobulin molecule that is secreted by the hybridoma E6.3. Differences between the sequence encoded by heavy chain variable gene 4-61 and the sequence of the E6.3 secreted heavy chain are indicated in bold and enlarged font. The contiguous sequence from CDR1 through CDR3 is indicated by underlining and CDR1, CDR2, and CDR3 sequences are each indicated by double underlining.

FIG. 26 is a nucleotide sequence of the cDNA encoding the heavy chain immunoglobulin molecule of FIG. 25 that was cloned out of the hybridoma E6.3.

FIG. 27 is an amino acid sequence of a kappa light chain immunoglobulin molecule that is secreted by the hybridoma E6.3. Differences between the sequence encoded by light chain variable gene 018 and the sequence of the E6.3 secreted light chain are indicated in bold and enlarged font. The contiguous sequence from CDR1 through CDR3 is indicated by underlining and CDR1 CDR2, and CDR3 sequences are each indicated by double underlining.

FIG. 28 is a nucleotide sequence of the cDNA encoding the kappa light chain immunoglobulin molecule of FIG. 27 that was cloned out of the hybridoma E6.3.

Hybridoma E7.6.3

The antibody secreted by the hybridoma E7.6.3 comprises a human IgG2 antibody having a human kappa light chain. The antibodies were analyzed for structural information related to their heavy chain and light chain gene utilization, as well as their amino acid sequences. Thus, heavy chain $V_H$, D, and $J_H$ and light chain Vκ and Jκ gene utilization was analyzed and differences between the coded product and the particular gene utilization was also analyzed. Accordingly, the antibody secreted by the hybridoma E7.6.3 evidenced the following gene utilization:

$V_H$-4-61
D-XP4rc-XP1
$J_H$-3
Vκ-018
Jκ-4

Amino acid and nucleotide sequence information respecting the heavy and light chains are provided below in connection with FIGS. 29-32. FIG. 29 is an amino acid sequence of a heavy chain immunoglobulin molecule that is secreted by the hybridoma E7.6.3. Differences between the sequence encoded by heavy chain variable gene 4-61 and the sequence of the E7.6.3 secreted heavy chain are indicated in bold and enlarged font. The contiguous sequence from CDR1 through CDR3 is indicated by underlining and CDR1, CDR2, and CDR3 sequences are each indicated by double underlining.

FIG. 30 is a nucleotide sequence of the cDNA encoding the heavy chain immunoglobulin molecule of FIG. 29 that was cloned out of the hybridoma E7.6.3.

FIG. 31 is an amino acid sequence of a kappa light chain immunoglobulin molecule that is secreted by the hybridoma E7.6.3. Differences between the sequence encoded by light chain variable gene 018 and the sequence of the E7.6.3 secreted light chain are indicated in bold and enlarged font. The contiguous sequence from CDR1 through CDR3 is indicated by underlining and CDR1, CDR2, and CDR3 sequences are each indicated by double underlining.

FIG. 32 is a nucleotide sequence of the cDNA encoding the kappa light chain immunoglobulin molecule of FIG. 31 that was cloned out of the hybridoma E7.6.3.

The following antibodies that are secreted by hybridomas E20.1, E20.3, E20.8.1, E20.11.2, E20.18, E20.19.2, E20.21, E20.22, E7.5.2, and E7.8.2 bind to EGFr, but do not compete with E7.6.3 for binding to EGFr.

Hybridoma E20.1

The antibody secreted by the hybridoma E20.1 comprises a human IgG2 antibody having a human kappa light chain. The antibodies were analyzed for structural information related to their heavy chain and light chain gene utilization, as well as their amino acid sequences. Thus, heavy chain $V_H$, D, and $J_H$ and light chain Vκ and Jκ gene utilization was analyzed and differences between the coded product and the particular gene utilization was also analyzed. Accordingly, the antibody secreted by the hybridoma E20.1 evidenced the following gene utilization:

$V_H$-DP-50 (3-33)
D-DXP4
$J_H$-JH4b
Vκ-LFVK431
Jκ-JK3

The amino acid sequences encoded by the $V_H$ DP-50 (3-33) gene and Vκ LFVK431 gene are available in the V BASE sequence directory.

Amino acid and nucleotide sequence information respecting the heavy and light chains are provided below in connection with FIGS. 57-58. FIG. 57 shows a nucleotide sequence of the cDNA encoding the heavy chain immunoglobulin molecule that was cloned out of the hybridoma E20.1 and the corresponding amino acid sequence of a heavy chain immunoglobulin molecule that is secreted by the hybridoma E20.1.

FIG. 58 shows a nucleotide sequence of the cDNA encoding the light chain immunoglobulin molecule that was cloned out of the hybridoma E20.1 and the corresponding amino acid sequence of a light chain immunoglobulin molecule that is secreted by the hybridoma E20.1.

Hybridoma E20.3

The antibody secreted by the hybridoma E20.3 comprises a human IgG2 antibody having a human kappa light chain. The antibodies were analyzed for structural information related to their heavy chain and light chain gene utilization, as well as their amino acid sequences. Thus, heavy chain $V_H$, D, and $J_H$ and light chain Vκ and Jκ gene utilization was analyzed and differences between the coded product and the particular gene utilization was also analyzed. Accordingly, the antibody secreted by the hybridoma E20.3 evidenced the following gene utilization:

$V_H$-DP15 (1-8)
D-DN1
$J_H$-JH4b
Vκ-B3/DPK24
Jκ-JK4

The amino acid sequences encoded by the $V_H$ DP-15 (1-8) gene and Vκ Vκ B3/DPK24 gene are available in the V BASE sequence directory.

Amino acid and nucleotide sequence information respecting the heavy and light chains are provided below in connection with FIGS. 59-60. FIG. 59 shows a nucleotide sequence of the cDNA encoding the heavy chain immunoglobulin molecule that was cloned out of the hybridoma E20.3 and the corresponding amino acid sequence of a heavy chain immunoglobulin molecule that is secreted by the hybridoma E20.3.

FIG. 60 shows a nucleotide sequence of the cDNA encoding the light chain immunoglobulin molecule that was cloned out of the hybridoma E20.3 and the corresponding amino acid sequence of a light chain immunoglobulin molecule that is secreted by the hybridoma E20.3.

Hybridoma E20.8.1

The antibody secreted by the hybridoma E20.8.1 comprises a human IgG2 antibody having a human kappa light chain. The antibodies were analyzed for structural information related to their heavy chain and light chain gene utilization, as well as their amino acid sequences. Thus, heavy chain $V_H$, D, and $J_H$ and light chain Vκ and Jκ gene utilization was analyzed and differences between the coded product and the particular gene utilization was also analyzed. Accordingly, the antibody secreted by the hybridoma E20.8.1 evidenced the following gene utilization:

$V_H$-DP-50 (3-33)
D-D1/D21-9/D23-7
$J_H$-JH4b
Vκ-B3/IDPK24
Jκ-JK2

Amino acid and nucleotide sequence information respecting the heavy and light chains are provided below in connection with FIGS. 61-62. FIG. 61 shows a nucleotide sequence of the cDNA encoding the heavy chain immunoglobulin molecule that was cloned out of the hybridoma E20.8.1 and the corresponding amino acid sequence of a heavy chain immunoglobulin molecule that is secreted by the hybridoma E20.8.1.

FIG. 62 shows a nucleotide sequence of the cDNA encoding the light chain immunoglobulin molecule that was cloned out of the hybridoma E20.8.1 and the corresponding amino acid sequence of a light chain immunoglobulin molecule that is secreted by the hybridoma E20.8.1.

Hybridoma E20.11.2

The antibody secreted by the hybridoma 20.11.2 comprises a human IgG2 antibody having a human kappa light chain. The antibodies were analyzed for structural information related to their heavy chain and light chain gene utilization, as well as their amino acid sequences. Thus, heavy chain $V_H$, D, and $J_H$ and light chain Vκ and Jκ gene utilization was analyzed and differences between the coded product and the particular gene utilization was also analyzed. Accordingly, the antibody secreted by the hybridoma E20.11.2 evidenced the following gene utilization:

$V_H$-DP-50 (3-33)
D-DIR5
$J_H$-JH4b
Vκ-B3/DPK24
Jκ-JK1

Amino acid and nucleotide sequence information respecting the heavy and light chains are provided below in connection with FIGS. 63-64. FIG. 63 shows a nucleotide sequence of the cDNA encoding the heavy chain immunoglobulin molecule that was cloned out of the hybridoma E20.11.2 and the corresponding amino acid sequence of a heavy chain immunoglobulin molecule that is secreted by the hybridoma E20.11.2.

FIG. 64 shows a nucleotide sequence of the cDNA encoding the light chain immunoglobulin molecule that was cloned out of the hybridoma E20.11.2 and the corresponding amino acid sequence of a light chain immunoglobulin molecule that is secreted by the hybridoma E20.11.2.

Hybridoma E20.18

The antibody secreted by the hybridoma E20.18 comprises a human IgG2 antibody having a human kappa light chain. The antibodies were analyzed for structural information related to their heavy chain and light chain gene utilization, as well as their amino acid sequences. Thus, heavy chain $V_H$, D, and $J_H$ and light chain Vκ and Jκ gene utilization was analyzed and differences between the coded product and the particular gene utilization was also analyzed. Accordingly, the antibody secreted by the hybridoma E20.18 evidenced the following gene utilization:

$V_H$-DP-50 (3-33)
D-**
$J_H$-**
Vκ-B3/DPK24
Jκ-JK2

Amino acid and nucleotide sequence information respecting the heavy and light chains are provided below in connection with FIGS. 65-66. FIG. 65 shows a nucleotide sequence of the cDNA encoding the heavy chain immunoglobulin molecule that was cloned out of the hybridoma E20.18 and the corresponding amino acid sequence of a heavy chain immunoglobulin molecule that is secreted by the hybridoma E20.18.

FIG. 66 shows a nucleotide sequence of the cDNA encoding the light chain immunoglobulin molecule that was cloned out of the hybridoma E20.18 and the corresponding amino acid sequence of a light chain immunoglobulin molecule that is secreted by the hybridoma E20.18.

Hybridoma E20.19.2

The antibody secreted by the hybridoma E20.19.2 comprises a human IgG2 antibody having a human kappa light chain. The antibodies were analyzed for structural information related to their heavy chain and light chain gene utilization, as well as their amino acid sequences. Thus, heavy chain $V_H$, D, and $J_H$ and light chain Vκ and Jκ gene utilization was analyzed and differences between the coded product and the particular gene utilization was also analyzed. Accordingly, the antibody secreted by the hybridoma E20.19.2 evidenced the following gene utilization:

$V_H$-DP-71 (4-59)
D-**
$J_H$-JH4b
Vκ-B3/DPK24
Jκ-JK1

The amino acid sequence encoded by the $V_H$ DP-71 (4-59) gene is available in the V BASE sequence directory.

Amino acid and nucleotide sequence information respecting the heavy and light chains are provided below in connection with FIGS. 67-68. FIG. 67 shows a nucleotide sequence of the cDNA encoding the heavy chain immunoglobulin molecule that was cloned out of the hybridoma E20.19.2 and the corresponding amino acid sequence of a heavy chain immunoglobulin molecule that is secreted by the hybridoma E20.19.2.

FIG. 68 shows a nucleotide sequence of the cDNA encoding the light chain immunoglobulin molecule that was cloned out of the hybridoma E20.19.2 and the corresponding amino acid sequence of a light chain immunoglobulin molecule that is secreted by the hybridoma E20.19.2.

Hybridoma E20.21

The antibody secreted by the hybridoma E20.21 comprises a human IgG2 antibody having a human kappa light chain. The antibodies were analyzed for structural information related to their heavy chain and light chain gene utilization, as well as their amino acid sequences. Thus, heavy chain $V_H$, D, and $J_H$ and light chain Vκ and Jκ gene utilization was analyzed and differences between the coded product and the particular gene utilization was also analyzed. Accordingly, the antibody secreted by the hybridoma E20.21 evidenced the following gene utilization:

$V_H$-DP-65 (4-31)
D-DIR3
$J_H$-JH6b
Vκ-LFVK431
Jκ-JK3

Amino acid and nucleotide sequence information respecting the heavy chain is provided below in connection with FIG. 69. FIG. 69 shows a nucleotide sequence of the cDNA encoding the heavy chain immunoglobulin molecule that was cloned out of the hybridoma E20.21 and the corresponding amino acid sequence of a heavy chain immunoglobulin molecule that is secreted by the hybridoma E20.21.

Hybridoma E20.22

The antibody secreted by the hybridoma E20.22 comprises a human IgG2 antibody having a human kappa light chain. The antibodies were analyzed for structural information related to their heavy chain and light chain gene utilization, as well as their amino acid sequences. Thus, heavy chain $V_H$, D, and $J_H$ and light chain Vκ and Jκ gene utilization was analyzed and differences between the coded product and the particular gene utilization was also analyzed. Accordingly, the antibody secreted by the hybridoma E20.22 evidenced the following gene utilization:

$V_H$-DP-71 (4-59)
D-DIR4
$J_H$-JH6b
Vκ-??
Jκ-??

Amino acid and nucleotide sequence information respecting the heavy chain is provided below in connection with FIG. 70. FIG. 70 shows a nucleotide sequence of the cDNA encoding the heavy chain immunoglobulin molecule that was cloned out of the hybridoma E20.22 and the corresponding amino acid sequence of a heavy chain immunoglobulin molecule that is secreted by the hybridoma E20.22.

Hybridoma E7.5.2

The antibody secreted by the hybridoma E7.5.2 comprises a human IgG2 antibody having a human kappa light chain. The antibodies were analyzed for structural information related to their heavy chain and light chain gene utilization, as well as their amino acid sequences. Thus, heavy chain $V_H$, D, and $J_H$ and light chain Vκ and Jκ gene utilization was analyzed and differences between the coded product and the particular gene utilization was also analyzed. Accordingly, the antibody secreted by the hybridoma E7.5.2 evidenced the following gene utilization:

$V_H$-DP-75 (1-2)
D-A1/A1rc
$J_H$-JH4
Vκ-02
Jκ-JK2

The sequence of the VH1-2 (DP-75) VK 02 gene products are available in the V BASE sequence directory. The nucleotide and amino acid sequences of the heavy and light chains of the E7.5.2 antibody are provided in FIGS. 72 and 73.

Hybridoma E7.8.2

The antibody secreted by the hybridoma E7.8.2 comprises a human IgG2 antibody having a human kappa light chain. The antibodies were analyzed for structural information related to their heavy chain and light chain gene utilization, as well as their amino acid sequences. Thus, heavy chain $V_H$, D, and $J_H$ and light chain Vκ and Jκ gene utilization was analyzed and differences between the coded product and the particular gene utilization was also analyzed. Accordingly, the antibody secreted by the hybridoma E7.8.2 evidenced the following gene utilization:

$V_H$-DP-75 (1-2)
D-1/IR-K1
$J_H$-JH4
Vκ-012
Jκ-JK2

Example 4

Analysis of Heavy and Light Chain Amino Acid Substitutions

Figure 34:
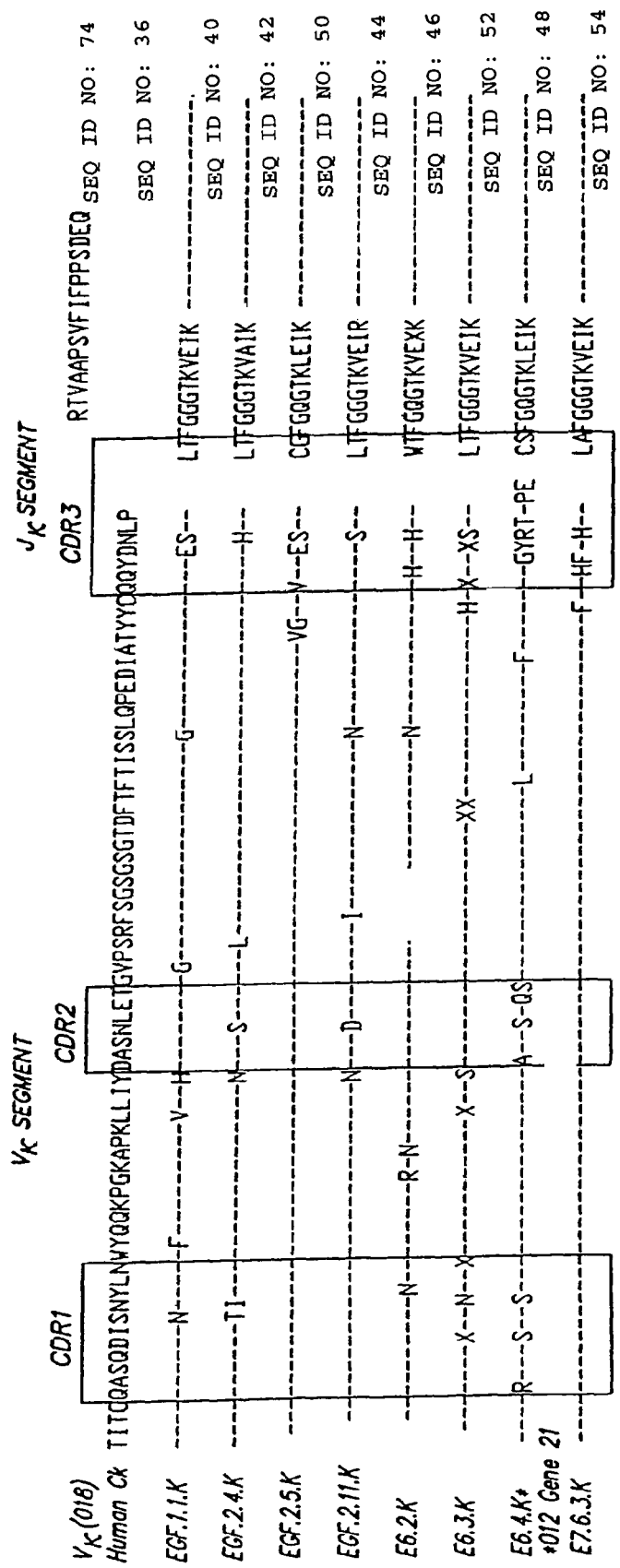

FIG. 33 provides a comparison of specific anti-EGF-r antibody heavy chain amino acid sequence comparisons with the amino acid sequence of the particular $V_H$ gene which encodes the heavy chain of the particular antibody. FIG. 34 provides a similar comparison of specific anti-EGF-r antibody light chain amino acid sequence comparisons with the amino acid sequence of the particular Vκ gene which encodes the light chain of the particular antibody. As will be observed, there are several remarkably conserved amino acid substitutions amongst the heavy and light chain sequences. In particular, in the heavy chains of the antibodies, all of the heavy chain molecules are encoded by $V_H$ 4 family genes and have a Glycine in position 10 in $V_H$ 4-31 encoded antibodies and Serine in position 10 in $V_H$ 4-61 encoded antibodies are each substituted with an Aspartic Acid. Also in the $V_H$ 4-31 heavy chains, all but one of the antibodies includes a Serine in position 7 substitution to Asparagine. A similar, though not quite as predominant substitution is observed in position 35, where a Serine in two of the $V_H$ 4-31 encoded antibodies and two of the $V_H$ 4-61 encoded antibodies is substituted with an Asparagine. Also, in two of the $V_H$ 4-31 encoded antibodies and two of the $V_H$ 4-61 encoded antibodies there are substitutions at position 28, where in each case, a Tyrosine is substituted with a Serine (E2.4) or a Histidine (E6.4, E2.11, and E7.6.3). Five of the antibodies, three of the $V_H$ 4-31 encoded antibodies and two of the $V_H$ 4-61 encoded antibodies, possess Valine to Leucine (E2.4 and E2.11) or Isoleucine (E2.5, E6.2, and E7.6.3) at position 50.

In connection with the kappa light chains amino acid sequences, all of the sequences are encoded by Vκ I family genes, with seven of the molecules being encoded by 018 genes and one (E6.4) being encoded by an 012 gene. There is a high degree of homology between the 012 and 018 gene products, as evidenced when the E6.4 molecule is compared with the 018 gene product, along with the other molecules, in FIG. 34. The E6.4 molecule possesses only two substitutions relative to the 012 gene product, as shown in FIG. 19, and only 13 substitutions relative to the 018 gene product. All of the antibodies possess a substitution at position 14 in CDR3 where an Asparagine is substituted with a Serine (E1.1, E2.5, E2.11, and E6.3), Histidine (E2.4, E6.2, and E7.6.3), or Arginine (E6.4). The remainder of the substitutions are less highly conserved. However, a number of the antibodies appear to possess substitutions within the CDR's. However, it is interesting to note that E7.6.3, which is an antibody with very high affinities, possesses no amino acid substitutions in the light chain amino acid sequence until just proximal to CDR3 and within CDR3.

It will be appreciated that each of the above-identified amino acid substitutions exist in close proximity to or within a CDR. Such substitutions would appear to bear some effect upon the binding of the antibody to the EGF receptor molecule. Further, such substitutions could have significant effect upon the affinity of the antibodies.

As was discussed above, anti-EGF-r antibodies have been demonstrated to possess certain anti-tumor activities. The following experiments were carried out in order to determine if antibodies in accordance with the present invention possessed such anti-tumor activities.

Example 5

Blockage of EGF and TGF-α Binding to Human Epidermoid Carcinoma A431 Cells by Human Anti-EGF-r Antibodies In Vitro An in vitro assay was conducted to determine if antibodies in accordance with the present invention were capable of blocking EGF binding to a human carcinoma cell line. The experiment was conducted to compare the binding of antibodies in accordance with the invention with the murine monoclonal antibody 225 which, as discussed above, has previously demonstrated anti-cancer activity.

Figure 35:
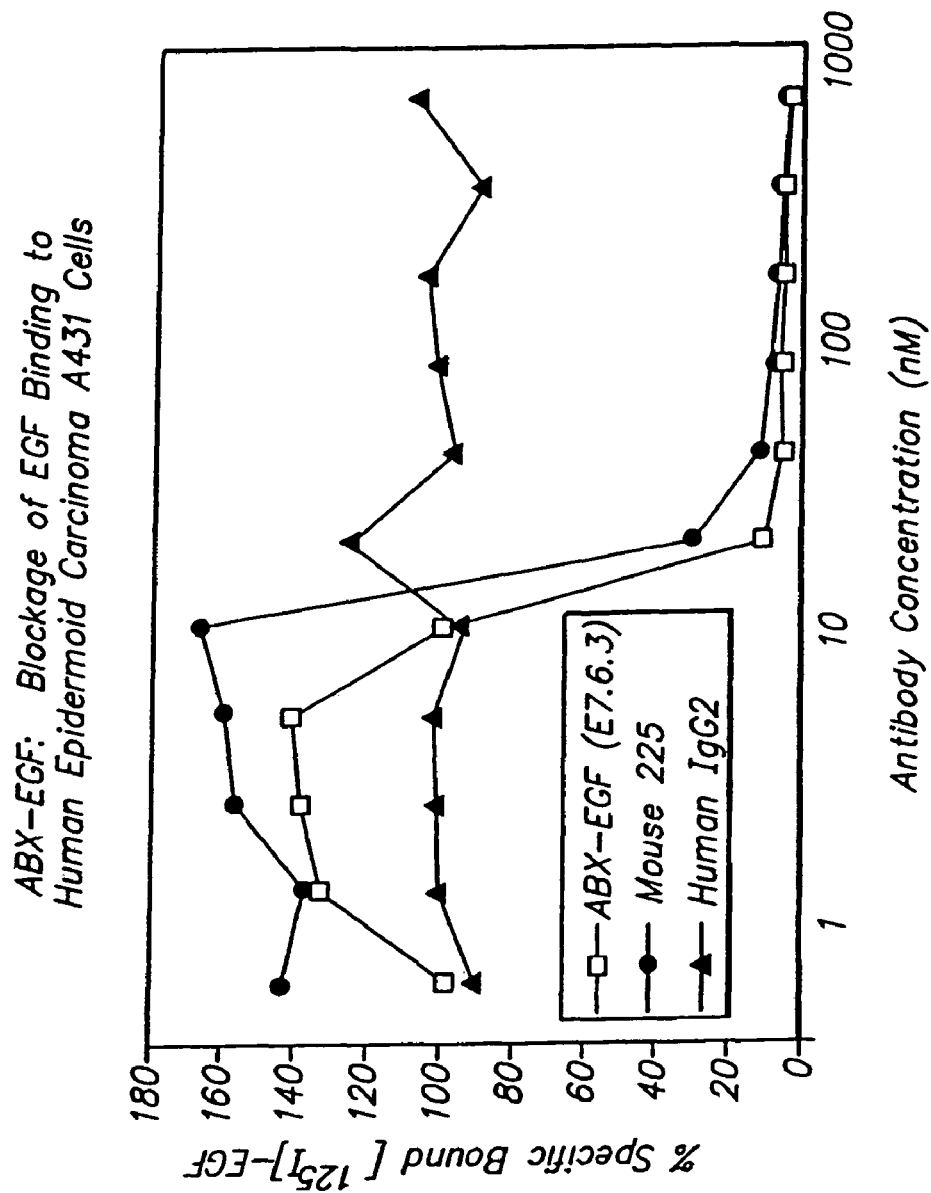

In this example, the human epidermoid carcinoma A431 cell line was utilized. The A431 cell line is known for its high expression level of EGF-r (about $2 \times 10^6$ EGF-r molecules per cell). Therefore, higher concentrations of anti-EGF-r antibodies are required to saturate all of the binding sites. The results from this example are shown in FIG. 35. In the Figure, blockage of $^{125}$I labeled EGF binding to human epidermoid carcinoma A431 cells by a human anti-EGF-r antibody in vitro is demonstrated. In the Figure, (□) depicts the results achieved by the anti-EGF-r antibody in accordance with the invention (E7.6.3), (○) depicts the results achieved by the murine monoclonal antibody 225, and (▲) depicts the results achieved by a control, nonspecific, human IgG2 antibody.

Figure 36:
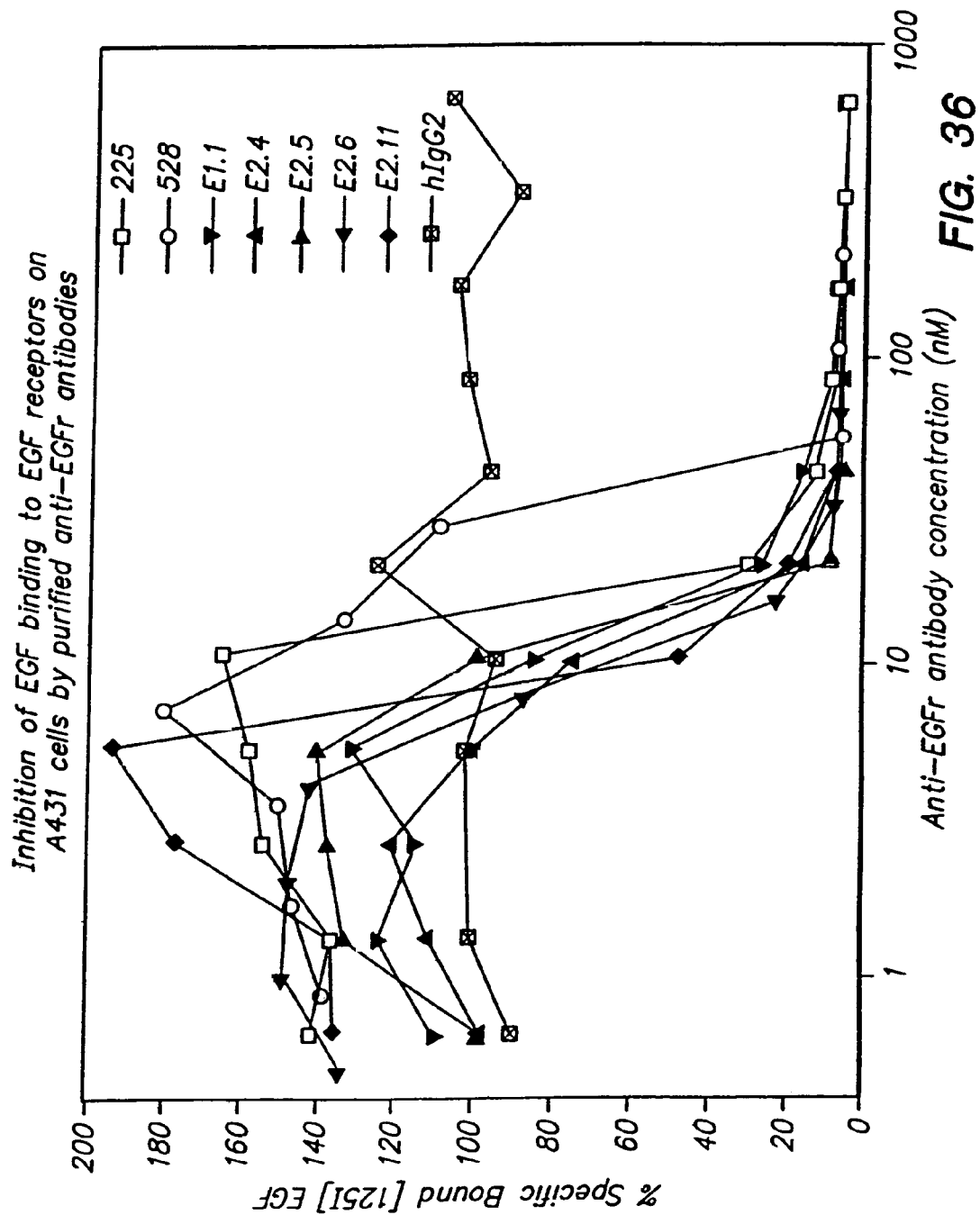

FIG. 36 shows inhibition of EGF binding to human epidermoid carcinoma A431 cells by a panel of human anti-EGF-r antibodies in accordance with the invention in vitro when compared to the 225, 528, and nonspecific human IgG2 controls. In the Figure, (□) depicts the results achieved by the murine monoclonal antibody 225, (○) depicts the results achieved by the murine monoclonal antibody 528, (▼) depicts the results achieved using the E1.1 antibody in accordance with the invention, (▲) depicts the results achieved using the E2.4 antibody in accordance with the invention, (▶) depicts the results achieved using the E2.5 antibody in accordance with the invention, (◀) depicts the results achieved using the E2.6 antibody in accordance with the invention, (♦) depicts the results achieved using the E2.11 antibody in accordance with the invention, and (▨) depicts the results achieved using a control, nonspecific human IgG2 antibody.

The results indicate that antibodies in accordance with the invention may block EGF binding to surface expressed EGF-r on A431 cells better than the 225 and 528 antibodies. Antibodies in accordance with the invention appear to begin inhibiting binding at an 8 nM concentration as compared to a 10 nM concentration for the 225 antibody.

Figure 37:
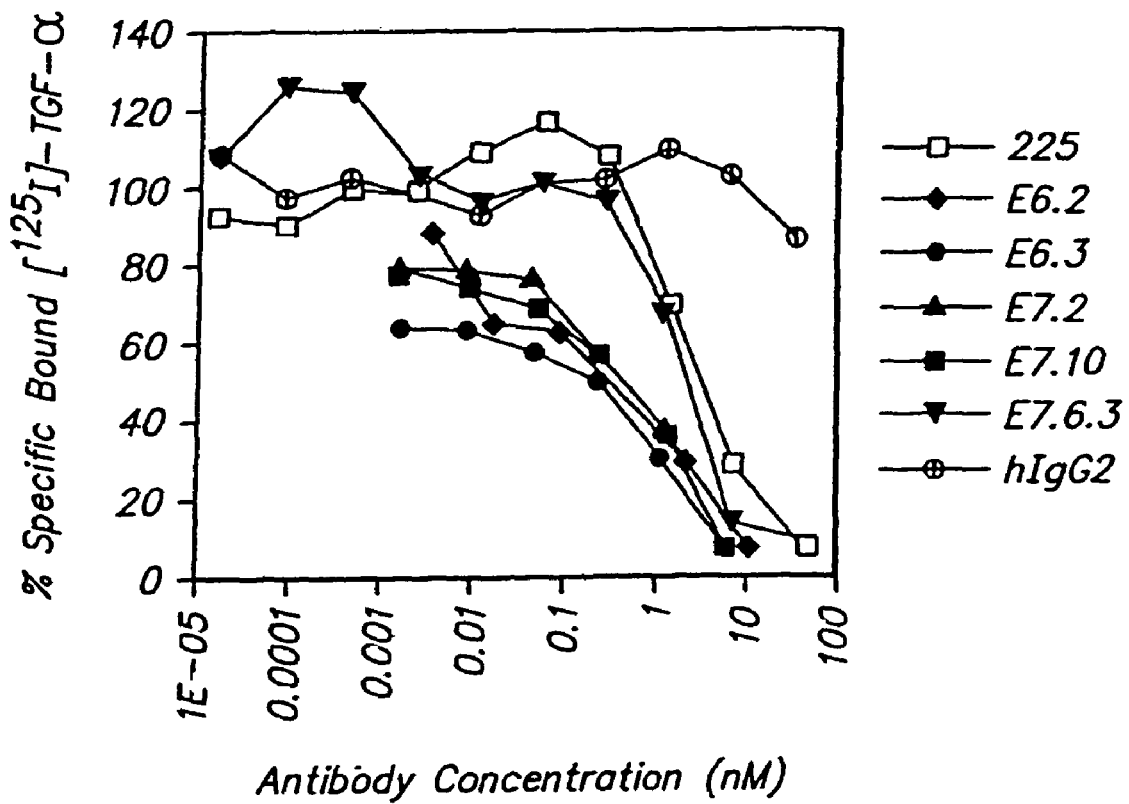

In connection with inhibition of TGF-α binding, similar efficacy is observed through use of antibodies in accordance with the invention when compared to the 225 antibody. FIG. 37 shows inhibition of TGF-α binding to human epidermoid carcinoma A431 cells by human anti-EGF-r antibodies in vitro, where (○) depicts the results achieved by the murine monoclonal antibody 225, (♦) depicts the results achieved using the E6.2 antibody in accordance with the invention, (●) depicts the results achieved using the E6.3 antibody in accordance with the invention, (▲) depicts the results achieved using the E7.2 antibody in accordance with the invention, (■) depicts the results achieved using the E7.10 antibody in accordance with the invention, (▼) depicts the results achieved using the E7.6.3, and (⊗) depicts the results achieved using a control, nonspecific human IgG2 antibody.

The results indicate that antibodies in accordance with the invention may block TGF-α binding to surface expressed EGF-r on A431 cells better than the 225 antibody. Antibodies in accordance with the invention appear to begin inhibiting binding at an 0.1 nM concentration as compared to a 1 nM concentration for the 225 antibody.

Example 6

Blockage of EGF Binding to Human Colon Adenocarcinoma SW948 Cells by Human Anti-EGF-r Antibodies In Vitro Another in vitro assay was conducted to determine if antibodies in accordance with the present invention were capable of blocking EGF binding to yet another human carcinoma cell line. The experiment was conducted to compare the binding of antibodies in accordance with the invention with the murine monoclonal antibody 225 which, as discussed above, has previously demonstrated anti-cancer activity.

In this example, the human colon adenocarcinoma SW948 cell line was utilized. In contrast to the A431 cell line, the SW948 cell line has relatively low expression of EGF-r on its surface (about 40,000 molecules per cell). Therefore, less of the anti-EGF-r antibodies are required to saturate all of the binding sites of the receptors on the cells. The results from this example are shown in FIG. 38. In the Figure, blockage of 1125 labeled EGF binding to human colon adenocarcinoma SW948 cells by a human anti-EGF-r antibody in vitro is demonstrated. In the Figure, (○) depicts the results achieved by an anti-EGF-r antibody in accordance with the invention (E7.6.3), (□) depicts the results achieved by the murine monoclonal antibody 225, and (▲) depicts the results achieved by a control, nonspecific, human IgG2 antibody.

The results indicate that the antibody in accordance with the invention blocks EGF binding to SW948 cells at least as well as the 225 antibody. In fact, the curve is slightly improved with respect to the antibody in accordance with the invention, showing inhibition at lower concentrations than the 225 antibody.

Example 7

Inhibition of Human Colon Adenocarcinoma SW948 Cell Growth by Human Anti-EGF-r Antibodies In Vitro We also conducted an in vitro assay to determine whether and to what degree, as compared to the 225 antibody, antibodies in accordance with the invention were capable of inhibiting cancer cell growth. The experiment was conducted to compare the inhibition by antibodies in accordance with the invention with the inhibition by the murine monoclonal antibody 225 which, as discussed above, has previously demonstrated anti-cancer activity.

In this example, the human colon adenocarcinoma SW948 cell line was utilized. In our hands, only the SW948 cell line showed EGF-dependent cell growth. In contrast, the A431 cell line showed growth inhibition in the presence of EGF in vitro. The results are shown in FIG. 39 where it is demonstrated that human anti-EGF-r antibodies in accordance with the present invention inhibit the growth of SW948 cells in vitro. In the Figure, (○) depicts the results achieved by an anti-EGF-r antibody in accordance with the invention (E7.6.3), (□) depicts the results achieved by the murine monoclonal antibody 225, and (▲) depicts the results achieved by a control, nonspecific, human IgG2 antibody.

The results indicate that the antibody in accordance with the invention inhibits growth of SW948 cells at least as well as the 225 antibody. In fact, the curve is slightly improved with respect to the antibody in accordance with the invention, showing an apparent 100% inhibition in cell growth at approximately 100 µg/ml whereas the 225 antibody appears to plateau at an inhibition level between 80 to 90% in the same dosage range.

Example 8

Inhibition of Human Epidermoid Carcinoma Growth in Nude Mice by Human Anti-EGF-r Antibodies In Vivo In the present experiment, we sought to determine if antibodies in accordance with the present invention were capable of inhibiting tumor cell growth in vivo. In the experiment, nude mice at the age of 8 weeks were inoculated subcutaneously with the human epidermoid carcinoma A431 cell line. Mice were injected with $5 \times 10^6$ A431 cells. One of two dosages of an antibody in accordance with the invention or one of two controls was injected intraperitoneally on the same day when the A431 cells were inoculated. Three adminstrations of either antibody or control followed and mice were followed for subcutaneous tumor formation and size. The dosages of antibody utilized were either 1.0 mg or 0.2 mg. The controls were either phosphate buffered saline or a nonspecific human IgG2 antibody.

The results from this experiment are shown in FIG. 40. In the Figure, the inhibition of human epidermoid carcinoma cell growth in nude mice through use of human anti-EGF-r antibodies in accordance with the invention in vivo is evident. In the Figure, (▲) depicts the results achieved with a dosage of 1.0 mg of a human anti-EGF-r antibody in accordance with the present invention (E7.6.3) (n=5), (▼) depicts the results achieved with a dosage of 0.2 mg of the E.7.6.3 antibody (n=4), (□) depicts the results achieved by a control, nonspecific, human IgG2 antibody (n=6), and (○) depicts the results achieved utilizing phosphate buffered saline as a control (n=6).

No tumor growth was observed in animals treated with the E7.6.3 antibody whereas control animals grew significant tumors within 25 days of tumor cell inoculation.

In the same experiment, three antibodies in accordance with the invention were compared. The results are shown in FIG. 41. Each of the antibodies in accordance with the present invention, E7.6.3 at 1 mg in 5 mice and 0.2 mg in 4 mice, E2.5 at 1 mg in 3 mice and 0.2 mg in 3 mice, and E1.1 at 1 mg in 3 mice, demonstrated inhibition of the human epidermoid carcinoma formation in the mice in comparison to controls. All of the control animals (including 6 PBS-treated animals and 6 human IgG2-treated animals) developed significant tumors within 19 days of inoculation whereas none of the the animals treated with the human anti-EGF-r antibodies in accordance with the invention developed tumors within 19 days of inoculation.

FIG. 42 shows the results of following the animals from this above-mentioned same experiment for 130 days post inoculation with the human epidermoid carcinoma. The results from this experiment are shown in FIG. 42. In the Figure, it will be observed that all of the control mice had developed tumors within 20 days of tumor cell inoculation. In contrast, the first mouse treated with an antibody in accordance with the present invention to develop a tumor was on day 70. By day 130, only 4 out of 15 of the experimental animals had developed tumors. Interestingly, none of the experimental animals treated with the 0.2 mg dosage of the E2.5 antibody developed tumors within the test period.

The above experiment in connection with this Example 8 demonstrate that antibodies in accordance with the present invention if administered contemporaneously with the inoculation of a tumor cell line appear to almost entirely prevent the initiation of tumor cell growth and initiation of the tumor. Moreover, it will be observed that the inhibitory effect on tumor cell growth appears long-lasting.

Example 9

Eradication of Human Epidermoid Carcinoma Growth in Nude Mice by Human Anti-EGF-r Antibodies in vivo While preventing tumor cell growth and/or establishment of a tumor, as discussed above in connection with the preceding example, is a positive finding, from a therapeutic point of view, eradication of an established tumor is also highly desirable. Accordingly, in the following experiments we examined whether antibodies in accordance with the invention were capable of eradicating an established tumor in a mammal. Previous data generated in connection with the 225 antibody indicated that in order to effectively eradicate an established tumor through use of the 225 antibody it was necessary to complement treatment with an antineoplastic agent. Thus, in connection with our experiments, we looked at antibody treatment both alone and in Combination with antineoplastic agent treatment.

In the experiment, nude mice were inoculated subcutaneously with $5 \times 10^6$ A431 human epidermoid carcinoma cells on day 0. Mice were treated with either antibodies, chemotherapeutic agents, and/or controls after the tumor had an opportunity to become established (size$\geq$0.4 cm$^3$). Treatments were begun and continued on days 5, 8, 10, 14, 16, and 21, with chemotherapies being administered only on days 5 and 6. Therapies consisted of an antibody in accordance with the invention (E7.6.3), the antineoplastic agent doxorubicin, and a combination of antibody and doxorubicin. Controls were phosphate buffered saline or a nonspecific human IgG2 antibody. Each treatment group consisted of 5 animals. The data generated from the experiments are shown in FIG. 43, where (▲) depicts the results achieved with a dosage of 1 mg of a human anti-EGF-r antibody in accordance with the present invention (E7.6.3) (n=5), (X) depicts the results achieved with a dosage of 125 fig of doxorubicin, (*) depicts the results achieved with a dosage of 1 mg of a human anti-EGF-r antibody in accordance with the present invention (E7.6.3) in combination with a dosage of 125 μg of doxorubicin, (■) depicts the results achieved by a control, nonspecific, human IgG2 antibody, and (♦) depicts the results achieved utilizing phosphate buffered saline as a control.

As will be observed, administration of the E7.6.3 antibody in combination with doxorubicin resulted in complete eradication tumor growth. Further, tumor growth was completely arrested through administration of the E7.6.3 antibody alone.

In a similar experiment, the results of which are shown in FIG. 44, following inoculation with the tumor, five mice were treated with 0.5 mg of the E2.5 antibody on days 5, 8, 10, 14, 16, and 21 and five mice were treated with a combination of the E2.5 antibody administered on days 5, 8, 10, 14, 16, and 21 and doxorubicin administered on days 5 and 6. In the Figure, (♦) depicts the results achieved with a dosage of 0.5 mg of a human anti-EGF-r antibody in accordance with the present invention (E2.5), (■) depicts the results achieved with a dosage of 125 μg of doxorubicin, (▲) depicts the results achieved with a dosage of 0.5 mg of a human anti-EGF-r antibody in accordance with the present invention (E2.5) in combination with a dosage of 125 μg of doxorubicin, (X) depicts the results achieved utilizing phosphate buffered saline as a control, and (*) depicts the results achieved utilizing a control, nonspecific, human IgG2 antibody.

As will be observed, administration of the E2.5 antibody by itself, or in combination with doxorubicin, resulted in near complete eradication of tumors in the mice.

Example 10

Additional Characterization of Antibodies in Accordance with the Invention

In order to further characterize antibodies in accordance with the invention, we conducted a number of additional in vitro and in vivo assays. In addition to the assays discussed above, certain of such assays were conducted in accordance with the following Materials and Methods:

A. Materials and Methods

In Vitro Tumor Cell Proliferation Assay: The effect of antibodies on the growth of human tumor cells was determined using the method described by Ishiyama et al. (21). Briefly, $2 \times 10^3$ cells in 100 μl of DMEM:F12 growth medium without serum were seeded into each well of a 96-well plate. Aliquots of each diluted antibody (100 μl/well) were added in triplicate to the wells and the cultures were incubated at 37° C. for 5 days. The controls consisted of either medium alone or medium containing dilutions of an human myeloma IgG$_2$κ control antibodies. After incubation, the medium was removed from each well by aspiration. All cells were fixed with 0.25% glutaraldehyde, then washed in 0.9% NaCl, air-dried and stained with Crystal Violet (Fisher Scientific, Pittsburgh, Pa.) for 15 min at room temperature. After washing with tap water and air-drying, 100 μl of methanol was added to each well and the $A_{595}$ of each supernatant was determined in a Spectra Max spectrophotometer (Molecular Devices, Sunnyvale, Calif.). The percentage of growth inhibition is calculated as the mean $A_{595}$ measured in medium only minus $A_{595}$ in the presence of antibody divided by mean $A_{595}$ in the presence of medium only.

Measurement of cell activation by Cytosensor microphysiometry: To assess the effect of antibody on EGF-mediated signaling, Cytosensor microphysiometry (Molecular Devices, Sunnyvale Calif.) was used. The Cytosensor detects early biochemical events in cell activation based upon increases in the rate of acid release by the cells (22). Acid release was measured as described in the user's manual provided by Molecular Devices, Inc. Briefly, A431 cells ($5 \times 10^4$) were seeded in 1 ml medium in a Cytosensor cell capsule and cultured at 37° C. for 24 h. After incubation, the cell capsules were assembled and loaded in the Cytosensor sensing chamber maintained at 37° C. The chamber was perfused (50 μl/min) with low buffer RPMI 1640 medium containing 1 mM sodium phosphate and 1 mg/ml endotoxin-free bovine serum albumin. Acid release rates were determined with 30-s potentiometric pH measurements after a 85-s pump cycle and 5-s delay (120-s total cycle time). Basal acid release rates ranged from 60 to 120 mV per second. % inhibition is calculated as the acid release in the presence of EGF only minus the acid release in the presence of EGF and antibody divided by the acid release in the presence of EGF only.

Tumor xenograft mouse models: Male BALB/c-nu/nu mice (6-8 weeks of age) were injected s.c. with $5 \times 10^6$ A431 or MDA-MB-468 (ATCC, HTB-132) cells in 100 μl PBS. Tumors sizes were measured twice a week with a vernier caliper and tumor volume was calculated as the product of length×width×height×π/6. Mice with established tumors were randomly divided into treatment groups. Animals were treated with antibodies using different regimens. Typically, mice received antibody treatment twice a week over three consecutive weeks either concomitant with the tumor cell injection (prophylactic treatment) or after tumor establishment (therapeutic treatment). The mice were followed for tumor xenograft growth and survival for at least 60 days.

Tumor histopathological evaluation: Biopsies obtained from athymic mice carrying human xenografts were fixed in 10% neutral buffered formalin, embedded in paraffin, and sectioned. The sections were then stained with hematoxylin and eosin, as described (23).

EGFr phosphorylation: 70% confluent A431 cells were pre-incubated at a low concentration of fetal bovine serum (0.5%) overnight in 37° C. The cells were then treated with 16 nM EGF in the presence or absence of different concentrations of E7.6.3 MAb for 30 minutes at 37° C. After the 30-min incubation, the cells were washed three times with cold PBS and scraped into 0.5 ml of lysis buffer (10 mM Tris, 150 mM NaCl, 5 mM EDTA, 1% Triton-100, 0.1 mg/ml PMSF, 1 μg/ml aprotinin, 1 μg/ml leupeptin and 1 mM sodium orthovanadate). After 30 minutes of incubation on ice, the lysate was centrifuged at 10,000 rpm for 5 minutes in an Eppendorf microcentrifuge at 4° C. The protein concentration in the supernatant was measured using BCA protein assay reagents (Pierce, 23223 and 23224). A small portion of the supernatant was mixed with sample buffer (Novex, LC2676) and boiled for 3 minutes. The proteins in the supernatant were then separated by electrophoresis on a 12% SDS-polyacrylamide gel. Equal amounts of total protein were loaded from each cell lysate. Mouse anti-phosphotyrosine (Zymed Laboratories, South San Francisco, AC, 03-7720) was used for detection of EGFr tyrosine phosphorylation on Western blots. ECL western blotting detection reagents (Amersham, Arlington Heights, Ill., $RPN_{21}O_6$) and the Hyperfilm ECL (Amersham, Arlington Heights, Ill., RPN1674H) were used for visualizing the signal. The integrated densities of the bands of interest were analyzed using an AGFA Scanner and the Scanalytics OneDscan software (Hewlett Packard, Mountain View, Calif.).

B. Analysis

1. Generation and Characterization of High Affinity Neutralizing Fully Human anti-EGFr MAbs from XenoMouse Strains:

As described in Example 1, we derived fully human $IgG_2\kappa$ antibodies from transgenic, XenoMouse™, mouse strains through immunization with human vulvar epidermoid carcinoma A431 cells. Such cells express approximately $1 \times 10^6$ EGFr/cell (2, 3 and data not shown). Fusion of B cells from immunized XenoMice with mouse myeloma cells yielded a panel of hybridomas that secrete human $IgG_2\kappa$ MAbs specific to the extracellular domain of human EGFr, as determined by ELISA, BIAcore, Western blots, and flow cytometry analysis (data not shown). The human $\gamma 2$ was chosen as the preferred isotype with minimal immune-associated cytotoxicity against normal EGFr-expressing tissues.

To identify human MAbs with neutralization activity, purified antibodies were evaluated for their ability to inhibit the binding of EGF and TGF$\alpha$ to human tumor cell lines that express low (colon carcinoma SW948-$5 \times 10^4$/cell) or high (A431, or breast adenocarcinoma MDA-MB-468-$1 \times 10^6$/cell) levels of EGFr. As positive controls, the commercially available murine MAbs, 225 and 528, were tested in parallel. A XenoMouse-derived $IgG_2\kappa$ antibody PK16.3.1, specific for keyhole lympet hemocyanin (KLH), or a non-specific human myeloma $IgG_2\kappa$ antibody were used as a negative control. FIG. 45A represents the results obtained with a subset of the fully human anti-EGFr MAbs tested in these assays. Three of the five human anti-EGFr antibodies shown, E7.6.3, E2.5.1 and E2.3.1, and the mouse anti-EGFr 225 and 528 MAbs blocked the binding of [$^{125}$I]EGF (0.1 nM) to A431 in a concentration-dependent manner. In contrast, E7.5.2 and E7.8.2 did not have any effect on EGF binding. The calculated $IC_{50}$ values (3.0 nM for E7.6.3, 5.6 nM for E2.5.1, 9.1 nM for E2.3.1, 8.8 nM for 225 and 15.2 nM for 528) suggested E7.6.3 as a potent neutralizing antibody. Furthermore, EGF binding to SW948 cells was also blocked by the human E7.6.3 and E2.3.1 and by the mouse 225 MAbs (FIG. 45B). The $IC_{50}$ values detected in studies with SW948 cells were 0.9 nM for E7.6.3, 0.24 nM for E2.3.1, and 0.17 nM for 225. The efficacy of E7.6.3 in neutralizing ligand binding was also demonstrated in blocking TGF$\alpha$ binding to A431 cells (data not shown). These results indicated that XenoMouse strains are capable of producing fully human anti-EGFr antibodies which recognize different epitopes on the receptor, including those involved in ligand binding.

The affinity of the purified E7.6.3 MAb to EGFr was determined to be $5 \times 10^{-11}$ M by both solid phase and solution measurements ($K_{on}$-$1.97 \times 10^6$; $K_{off}$-$1.13 \times 10^{-4}$). E7.6.3 exhibits cross-reactivity with African Green monkey EGFr but not with the mouse EGFr (data not shown). The E7.6.3 hybridoma exhibited significant levels of antibody production that reached a specific productivity rate of 12 pg/cell/day in serum-free medium growth conditions. Based on its high affinity to EGFr and its potency in blocking EGF/TGF$\alpha$ binding, E7.6.3 MAb was selected for further evaluation of its efficacy in affecting tumor cell growth in vitro and in vivo.

2. Antibodies in Accordance with the Present Invention, Such as the E7.6.3 Mab, Inhibit EGF-Mediated Tumor Cell Activation:

The ability of E7.6.3 to inhibit tumor cell activation was evaluated by examining its effects on EGF-triggered cellular responses such as the tyrosine kinase activity of EGFr, the extracellular acidification rate, and cell proliferation.

One of the first events following EGF binding to its receptor is the induction of EGFr tyrosine kinase activity, resulting in autophosphorylation of the receptor (1). As shown in FIG. 46, incubation of human EGF (16 nM) with A431 cells induced the tyrosine phosphorylation of the 170 kDa EGFr. While E7.6.3 did not activate the receptor tyrosine kinase activity, the antibody blocked EGFr tyrosine phosphorylation in a dose-dependent manner, with a nearly complete inhibition at concentration of 133 nM (antibody: EGFr molar ratio of 8:1) (FIG. 46). The E7.6.3 antibody also completely prevented the internalization of EGF (data not shown). Presumably, the interaction of E7.6.3 with the receptor led to internalization of the antibody-receptor complex but did not activate the receptor tyrosine kinase (FIG. 46).

Engagement of EGF with its receptor results in cell activation, which is reflected by changes in the extracellular acidification rate. These changes can be detected by the Cytosensor Microphysiometer, a pH-sensitive silicon sensor that measures real-time changes in the acidification of the microenvironment surrounding a population of stimulated cells (22). Using this assay, we examined the effect of E7.6.3 on EGF-mediated A431 cell activation. As shown in FIG. 47A, the addition of 1.67 nM EGF to A431 cells induced an immediate increase in the extracellular acidification rate. No effect was observed when the cells were incubated only with E.7.6.3 antibody at concentrations up to 100 nM (not shown). The concurrent addition of E7.6.3 resulted in a dose-dependent inhibition of EGF-mediated extracellular acidification (FIGS. 47A,B), whereas no effect was detected with the isotype matched control antibody PK16.3.1 (FIG. 47B).

Lastly, we examined the effect of E7.6.3 on the in vitro proliferation of the EGFr-expressing tumor cell lines A431 and MDA-MB-468, again in comparison to the mouse anti-EGFr antibodies. Both cell lines, expressing high levels of EGFr, have been shown to secrete TGF$\alpha$ and to be growth inhibited by the addition of exogenous EGF at nM concentrations (24,25). Therefore, the experiments using these two cell lines were carried out in the absence of exogenous EGF. E7.6.3 inhibited the growth of A431 cells in a dose-dependent manner, with a maximal inhibition of 60%, a level similar to that obtained with the mouse antibody 225 and higher than that observed for the 528 antibody (FIG. 48A). The control antibody did not have any effect on cell proliferation (FIG. 48A). The calculated $IC_{50}$ values for E7.6.3 (0.125 nM), 225 (0.48 nM) or 528 (0.66 nM) antibodies, indicated E7.6.3 efficacy in inhibiting A431 cell proliferation (FIG. 48A). A similar level of growth inhibition by E7.6.3 was observed with MDA-MB-468 cells (FIG. 48B). Since no exogenous EGF was added to the culture, these results indicate the ability of the human antibody to block autocrine growth stimulation and thus to inhibit EGF/TGF$\alpha$-induced tumor cell activation.

In experiments carried out with SW948 cells, 10 nM of E7.6.3 MAb blocked completely the proliferation of the cells (data not shown).

3. Antibodies in Accordance with the Invention, Such as the E7.6.3 Mab, Prevents Human Tumor Formation in Mice:

To examine the effect of E7.6.3 on tumor cell growth in vivo, the antibody was first evaluated for its ability to prevent the formation of A431 tumor xenografts in athymic mice. A431 cells ($5 \times 10^6$/mouse) were injected subcutaneously (s.c.) into mice in conjunction with intraperitoneal (i.p.) administration of either PBS (group 1), 1 mg of the control antibody PK16.3.1 (group 2), or 0.2 mg or 1 mg of E7.6.3 (groups 3 and 4). The antibody administration was repeated twice a week over three weeks, for a total dose of 1.2 mg (group 3) or 6 mg (groups 2 and 4). As shown in FIG. 52, all mice treated with either PBS or the control antibody developed tumors by day 10 after inoculation and were euthanized at day 30 due to the large size of the tumorss. In contrast, none of the mice treated with E7.6.3 antibody developed tumors for more than 8 months following the last antibody injection. The data indicated that E7.6.3 prevented the formation of A431 xenografts, probably by exerting its neutralization activity at the initial phase of the tumor cell proliferation.

4. Antibodies in Accordance with the Invention, Such as the E7.6.3 Mab, Eradicate Large Human Tumor Xenografts in Mice:

The effect of E7.6.3 on the growth of established tumors was examined on A431 tumor xenografts that reached a size of 0.13 to 1.2 cm$^3$ (calculated as length×width×height×$\pi/6$). Initially, mice bearing 0.13-0.25 cm$^3$-sized tumors were treated i.p. with 1 mg of either E7.6.3 Mab or the human myeloma IgG2κ control antibody, twice a week over three weeks. As shown in FIG. 49 and in FIG. 53, the tumors in untreated mice or mice treated with the control antibody continued their aggressive growth to reach the size of 3 cm$^3$ by day 30, at which point the mice were euthanized. In contrast, treatment with E7.6.3, not only arrested further growth of the tumors but also caused continuous tumor regression that resulted in a complete tumor eradication in all mice treated (FIGS. 49 and 53). No recurring tumors were detected for more than 250 days in any of the mice that were monitored, demonstrating a long-lasting effect of the antibody and its ability to completely eliminate all tumor cells.

We next evaluated the potency of E7.6.3 antibody to treat large established tumor xenografts. Mice bearing 0.13, 0.56, 0.73 or 1.2 cm$^3$-sized A431 tumors were treated i.p. with 1 mg E7.6.3 twice a week, over three weeks, initiated on day 7, 11, 15 or 18, respectively. As demonstrated in FIG. 49, E7.6.3 caused a profound tumor regression in all the treated mice regardless of their initial tumor size, even with tumors as large as 1.2 cm$^3$. Furthermore, this treatment led to a complete disappearance of the tumors (FIG. 49) and no tumor recurrence in any of the mouse groups for 210 days after the last antibody injection (data not shown).

As summarized in FIG. 53, the antibody effect appears to be dose-dependent with a total dose of 3 mg leading to a nearly complete tumor eradication and a total dose of 0.6 mg eliminating 65% of the established A431 xenografts.

To compare the anti-tumor activity of E7.6.3 to that of the mouse 225 antibody, which was reported to affect the growth of established A431 tumors but not cause their elimination (12,13), we used suboptimal E7.6.3 doses (0.05 mg and 0.2 mg, given twice a week for three weeks) that also caused primarily tumor regression in A431 xenografts. At these antibody doses, there was a significant difference between in the ability of E7.6.3 and 225 to arrest the growth of A431 xenografts (FIG. 49C).

E7.6.3 was also shown to be efficacious in inhibiting the growth of the breast carcinoma MDA-MB-468 xenografts (FIG. 50A). Treatment of 0.2 cm$^3$ tumor-bearing mice with 2 mg antibody once a week over 2 weeks led to a complete arrest of the tumor growth. The fact that there was no apparent change in the residual nodules for 120 days after the last antibody administration, strongly suggests that the antibody effectively eradicated these tumors.

A similar anti-tumor activity of E7.6.3 was observed when the antibody was given via different administration routes (FIG. 50B). Administration of 0.5 mg E7.6.3 into mice carrying 0.15 cm$^3$-sized A431 xenografts twice a week over three weeks by either i.p., s.c., i.v., or i.m route all caused complete tumor eradication.

The elimination of all tumor cells by E7.6.3 was further supported by the histopathological analysis of the small residual nodules observed in some of the A431 xenograft-bearing mice that were treated with the lower antibody doses. Biopsies taken from these nodules at day 79 were shown to contain a thin fibrovascular capsule lined by necrotic cells with its center filled with keratinic and calcified debris (FIG. 51A). There was no evidence of neoplastic cells, which were readily detected in tumors taken from mice treated with PBS or control antibody (FIG. 51B). A mild inflammatory infiltration of neutrophils, lymphocytes, plasma cells, macrophages and multinucleated giant cells surrounded the capsule. Taken together with the long lasting inhibitory effect, the data strongly suggest complete tumor cell eradication by E7.6.3 antibody.

C. Discussion

Utilization of XenoMouse animals for the production of human antibodies specific to the human EGFr yielded the fully human IgG$_2$κ Mab, E7.6.3, characterized by high affinity and strong neutralization activity. Its demonstrated efficacy in eradicating large established human tumor xenografts without concomitant chemotherapy strongly suggests it as a suitable candidate for antibody monotherapy in patients with EGFr-expressing tumors.

E7.6.3 exhibited strong efficacy in blocking the binding of EGF and TGFα to EGFr on the surface of different human carcinoma cell lines, including those that express high levels of receptors (FIG. 45). The complete inhibition of ligand binding to the receptors on A431 and SW948 cells resulted in an abolishment of the signaling events triggered by EGF or TGFα, including EGFr autophosphorylation and internalization, increased extracellular acidification rate, and cell proliferation. Our results indicate that E7.6.3 can block ligand-induced cell activation and that E7.6.3 does not act as an agonist to trigger cellular responses in EGFr-expressing tumors (FIGS. 2,3).

The anti-tumor activity of E7.6.3 was examined in multiple xenograft mouse experiments, in which the effects of various antibody doses on different sizes of tumors were established (FIGS. 5,6). The results obtained from these studies demonstrated the unique anti-tumor properties of E7.6.3 MAb as compared to the other reported anti-EGFr antibodies. E7.6.3 not only arrested the growth of human tumor xenografts but also completely eradicated established tumors by itself, without the need for concomitant chemotherapy. Tumor eradication of A431 xenografts was achieved in nearly all mice treated with total doses as low as 3 mg, administered over the course of 3 weeks, and a total dose of 0.6 mg led to tumor elimination in 65% of the mice (FIGS. 5, 6B, Table 2). In comparison, 8 mg of 225 and 10 mg of 528 antibodies, given over 4 and 10 weeks, respectively, had only a limited effect on A431 tumors and required the co-administration of chemotherapeutic drugs to achieve the elimination of the tumors (12,13). A direct comparison between E7.6.3 and 225 MAbs at low doses demonstrated E7.6.3 as a more potent antibody in regressing established A431 tumors and arresting their growth (FIG. 49C). The chimeric C225 MAb, which was reported to acquire higher affinity to EGFr and enhanced in vivo anti-tumor activities, achieved complete A431 tumor eradication at a total dose of 10 mg, given over 5 weeks, whereas total doses of 2.5 and 5 mg led to only 14% and 57% of tumor-free mice (14). The potent anti-tumor activity of E7.6.3 was further validated by its ability, at a 6 mg total dose, to completely eliminate established tumors as large as 1.2 cm$^3$ in all mice treated.

This anti-tumor potency of E7.6.3 is likely to originate primarily from the antibody's intrinsic activity as its human γ2 isotype was shown to minimally engage the immune system-derived effector functions, such as cell-mediated cytotoxicity or complement-dependent cytolysis. In comparison, the anti-tumor activities of the rat ICR62, mouse 528 or chimeric C225 antibodies were suggested to reflect the participation of the host immune effector functions recruited by the respective rodent γ2b or human γ1 isotypes (2,4,6,26).

The molecular mechanism(s) underlying the potent anti-tumor activity of E7.6.3 appear to be contributed to by several factors, including, (i) the antibody's ability to block ligand-triggered growth and survival signals and (ii) the effects that the antibody may exert on the cell upon its interaction with the receptor. The potency of E7.6.3 can be attributed, at least in part, to the high affinity ($5 \times 10^{-11}$ M) that the antibody exhibits to human EGFr, higher than the affinity reported for other anti-EGFr MAbs (12,14). With its high affinity, E7.6.3 can inhibit or dissociate the ligand binding to the receptors very effectively, thus depriving the cells completely from receiving essential growth and survival stimuli. Like other anti-EGFr antibodies (2,4,6), E7.6.3 MAb does not act as an agonist and does not activate cells upon binding to the receptor. The difference in efficacy between E7.6.3 and the other antibodies tested in xenograft mouse models can also be attributed to a unique E7.6.3 binding epitope on EGFr that can mediate a stronger neutralization effect or induce cell cytotoxicity. The latter factor is supported by the ability of E7.6.3 to eradicate well established human xenografts, as large as 1.2 cm$^3$. The mechanism behind the in vivo cytocidal effects of E7.6.3 may involve the induction of either programmed cell death, differentiation of the tumor cells, or modulation of expression of angiogenesis factors, mechanisms that were shown to be triggered by antibodies in cultured cells (27-31). Different mechanisms may account for the antibody effect on different tumors and in some cases probably more than one mechanism contributes to the anti-tumor activity.

The potency of E7.6.3 in eradicating well established tumors suggests that this antibody can provide effective therapy to tumors that require EGFr activation for their continuous progression and survival. As E7.6.3 does not require the presence of chemotherapy to exert it anti-tumor activity, the antibody could be applied to various EGFr-expressing human solid tumors. Furthermore, being a fully human antibody, E7.6.3 is expected to have a long serum half life and minimal immunogenicity with repeated administration, including in all immunocompetent patients. In addition, bearing a human γ2 constant region that interacts poorly with the effector arm of the immune system, E7.6.3 MAb may not induce cytotoxic effects on normal EGFr-expressing tissues such as liver and skin.

Utilization of Mabs directed to growth factor receptors as cancer therapeutics has been validated recently by the tumor responses obtained from clinical trials with Herceptin™, the humanized anti-HER2 antibody, in patients with HER2 over-expressing metastatic breast cancer (32, 33). The potent in vivo anti-tumor activity of E7.6.3, as demonstrated in this report, suggests it as a good candidate for assessing the therapeutic potential of anti-EGFr therapy in EGFr-expressing human tumors.

Example 12

Valency of Human Anti-EGF-r Antibodies

Valency has been indicated to play a role in certain in connection with certain antibodies that bind to EGFr. For example, Masui et al. *Cancer Research* 46:5592-5598 (1986) conducted certain investigations related to the 528 and 225 antibodies and postulated that valency of the antibodies could play a role in the mechanism of action of the antibodies. It was unclear for the paper, however, whether the effects observed were based upon valency or upon a form of complement fixation/cytotoxicity. More recently, investigations have highlighted that valency may play an important role in connection with either the facilitation or prevention of certain dimerization events in connection with certain cell-surface receptors in oncogenesis. See, for example, Chanty A. *J. Biol. Chem.* 270:3068-3073 (1995); Wallasch et al. *EMBO J.* 14:4267-4275 (1995); Earp et al. *Breast Cancer Research Treatment* 35:115-132 (1995); and Zhang et al. *J. Biol. Chem.* 271:3884-3890 (1996).

Based upon the results observed in FIG. 45A, we observed a significantly different slope between the inhibition curve for E7.6.3 antibody and that for the 225 antibody. Such difference may be based upon valency. Accordingly, in order to further investigate the valency of the E7.6.3 antibody, we plan to conduct saturation studies on the E7.6.3 antibody (or other antibodies in accordance with the invention) as compared to the 225 and/or 528 antibody. In the studies, the test antibodies will be iodinated with radioactive iodine using conventional techniques and varying quantities of the test antibodies (until saturation) will be introduced to wells containing known numbers of EGF receptors. Bound antibodies will be determined using counting.

A difference in valency could be indicative of a role of antibodies in accordance with the invention in effecting dimerization of EGF receptor.

Example 13

Human Clinical Trials for the Treatment and Diagnosis of Human Carcinomas through use of Human Anti-EGF-r Antibodies In Vivo Introduction Antibodies in accordance with the present invention are indicated in the treatment of certain solid tumors. Based upon a number of factors, including EGF-r expression levels, among others, the following tumor types appear to present preferred indications: breast, ovarian, colon, prostate, bladder and non-small cell lung cancer. In connection with each of these indications, three clinical pathways appear to offer distinct potentials for clinical success:

Adjunctive therapy: In adjunctive therapy, patients would be treated with antibodies in accordance with the present invention in combination with a chemotherapeutic or antineoplastic agent and/or radiation therapy. The primary targets listed above will be treated under protocol by the addition of antibodies of the invention to standard first and second line therapy. Protocol designs will address effectiveness as assessed by reduction in tumor mass as well as the ability to reduce usual doses of standard chemotherapy. These dosage reductions will allow additional and/or prolonged therapy by reducing dose-related toxicity of the chemotherapeutic agent. Prior art anti-EGF-r antibodies have been, or are being, utilized in several adjunctive clinical trials in combination with the chemotherapeutic or antineoplastic agents adriamycin (C225: advanced prostrate carcinoma), cisplatin (C225: advanced head and neck and lung carcinomas), taxol (C225: breast cancer), and doxorubicin (C225: preclinical).

Monotherapy: In connection with the use of the antibodies in accordance with the present invention in monotherapy of tumors, the antibodies will be adminstered to patients without a chemotherapeutic or antineoplastic agent. Preclinical results generated through use of antibodies in accordance with the present invention and discussed herein have demonstrated similar results with both adjunctive therapy and/or as a stand-alone therapy. Moreover, monotherapy has apparently been conducted clinically in end stage cancer patients with extensive metastatic disease. Patients appeared to show some disease stabilization. Id. Trials will be designed to demonstrate an effect in refractory patients with (cancer) tumor.

Imaging Agent: Through binding a radionuclide (e.g., yttrium ($^{90}$Y)) to antibodies in accordance with the present invention, it is expected that radiolabeled antibodies in accordance with the present invention can be utilized as a diagnostic, imaging agent. In such a role, antibodies of the invention will localize to both solid tumors, as well as, metastatic lesions of cells expressing the EGF receptor. In connection with the use of the antibodies of the invention as imaging agents, the antibodies can be used in assisting surgical treatment of solid tumors, as both a pre-surgical screen as well as a post operative follow to determine what tumor remain and/or returns. An ($^{111}$In)-C225 antibody has been used as an imaging agent in a Phase I human clinical trial in patients having unresectable squamous cell lung carcinomas. Divgi et al. *J. Natl. Cancer Inst.* 83:97-104 (1991). Patients were followed with standard anterior and posterior gamma camera. Preliminary data indicated that all primary lesions and large metastatic lestions were identified, while only one-half of small metastatic lesions (under 1 cm) were detected.

Dose and Route of Administration

While specific dosing for antibodies in accordance with the invention has not yet been determined, certain dosing considerations can be determined through comparison with the similar product (ImClone C225) that is in the clinic. The C225 antibody is typically being administered with doses in the range of 5 to 400 mg/m$^2$, with the lower doses used only in connection with the safety studies. Antibodies in accordance with the invention have a one-log higher affinity than the C225 antibody. Further, antibodies in accordance with the present invention are fully human antibodies, as compared to the chimeric nature of the C225 antibody and, thus, antibody clearance would be expected to be slower. Accordingly, we would expect that dosing in patients with antibodies in accordance with the invention can be lower, perhaps in the range of 50 to 300 mg/m$^2$, and still remain efficacious. Dosing in mg/m$^2$, as opposed to the conventional measurement of dose in mg/kg, is a measurement based on surface area and is a convenient dosing measurement that is designed to include patients of all sizes from infants to adults.

Three distinct delivery approaches are expected to be useful for delivery of the antibodies in accordance with the invention. Conventional intravenous delivery will presumably be the standard delivery technique for the majority of tumors. However, in connection with tumors in the peritoneal cavity, such as tumors of the ovaries, biliary duct, other ducts, and the like, intraperitoneal administration may prove favorable for obtaining high dose of antibody at the tumor and to minimize antibody clearance. In a similar manner certain solid tumors possess vasculature that is appropriate for regional perfusion. Regional perfusion will allow the obtention of a high dose of the antibody at the site of a tumor and will minimize short term clearance of the antibody.

Clinical Development Plan (CDP)

Overview: The CDP will follow and develop treatments of anti-EGF-r antibodies in accordance with the invention in connection with adjunctive therapy, monotherapy, and as an imaging agent. Trials will be initially utilized to demonstrate safety and will thereafter be utilized to address efficacy in repeat doses. Trails will be open label comparing standard chemotherapy with standard therapy plus antibodies in accordance with the invention. As will be appreciated, one criteria that can be utilized in connection with enrollment of patients can be EGF-r expression levels of patient tumors as determined in biopsy.

As with any protein or antibody infusion based therapeutic, safety concerns are related primarily to (i) cytokine release syndrome, i.e., hypotension, fever, shaking, chills, (ii) the development of an immunogenic response to the material (i.e., development of human antibodies by the patient to the human antibody therapeutic, or HAHA response), and (iii) toxicity to normal cells that express the EGF receptor, e.g., hepatocytes which express EGF-r. Standard tests and follow up will be utilized to monitor each of these safety concerns. In particular, liver function will be monitored frequently during clinical trails in order to assess damage to the liver, if any.

Human Clinical Trial: Adjunctive Therapy with Human Anti-EGF-r Antibody and Chemotherapeutic Agent A phase I human clinical trial will be initiated to assess the safety of six intravenous doses of a human anti-EGF-r antibody in accordance with the invention in connection with the treatment of a solid tumor, e.g., breast cancer. In the study, the safety of single doses of antibodies in accordance with the invention when utilized as an adjunctive therapy to an antineoplastic or chemotherapeutic agent, such as cisplatin, topotecan, doxorubicin, adriamycin, taxol, or the like, will be assessed. The trial design will include delivery of six, single doses of an antibody in accordance with the invention with dosage of antibody escalating from approximately about 25 mg/m$^2$ to about 275 mg/m$^2$ over the course of the treatment in accordance with the following schedule:

|  | Day 0 | Day 7 | Day 14 | Day 21 | Day 28 | Day 35 |
| --- | --- | --- | --- | --- | --- | --- |
| Mab Dose | 25 mg/m$^2$ | 75 mg/m$^2$ | 125 mg/m$^2$ | 175 mg/m$^2$ | 225 mg/m$^2$ | 275 mg/m$^2$ |
| Chemotherapy (standard dose) | + | + | + | + | + | + |

Patients will be closely followed for one-week following each administration of antibody and chemotherapy. In particular, patients will be assessed for the safety concerns mentioned above: (i) cytokine release syndrome, i.e., hypotension, fever, shaking, chills, (ii) the development of an immunogenic response to the material (i.e., development of human antibodies by the patient to the human antibody therapeutic, or HAHA response), and (iii) toxicity to normal cells that express the EGF receptor, e.g., hepatocytes which express EGF-r. Standard tests and follow up will be utilized to monitor each of these safety concerns. In particular, liver function will be monitored frequently during clinical trails in order to assess damage to the liver, if any.

Patients will also be assessed for clinical outcome, and particularly reduction in tumor mass as evidenced by MRI or other imaging.

Assuming demonstration of safety and an indication of efficacy, Phase II trials would likely be initiated to further explore the efficacy and determine optimum dosing.

Human Clinical Trial: Monotherapy with Human Anti-EGF-r Antibody

Assuming that the antibodies in accordance with the present invention appear safe in connection with the above-discussed adjunctive trial, a human clinical trial to assess the efficacy and optimum dosing for monotherapy. Such trial could be accomplished, and would entail the same safety and outcome analyses, to the above-described adjunctive trial with the exception being that patients will not receive chemotherapy concurrently with the receipt of doses of antibodies in accordance with the invention.

Human Clinical Trial: Diagnostic Imaging with Anti-EGF-r Antibody

Once again, assuming that the adjunctive therapy discussed above appears safe within the safety criteria discussed above, a human clinical trial can be conducted concerning the use of antibodies in accordance with the present invention as a diagnostic imaging agent. It is expected that the protocol would be designed in a substantially similar manner to that described in Divgi et al. *J. Natl. Cancer Inst.* 83:97-104 (1991).

Example 14

Additional Characterization of Antibodies in Accordance with the Invention

In order to further characterize antibodies in accordance with the invention, we conducted a number of additional in vivo assays. In addition to the assays discussed above (i.e., in connection with Example 10), certain of such assays were conducted in accordance with the following Materials and Methods:

A. Materials and Methods

Tumor xenograft mouse models: In this experiment, we evaluated the following tumor cell lines: three human pancreatic carcinoma cell lines (HPAC, BxPC-3, HS766T (each obtained from the ATCC: HPAC (ATCC, CRL-2219), BxPC-3 (ATCC, CRL-1687), HS766T (ATCC, HTB-134))), the human kidney carcinoma cell line, SK-RC-29 (obtained from the Memorial Sloan-Kettering Cancer Center, NY, N.Y.), and the human colon carcinoma cell line, SW707 (obtained from the Deutsches Krebsforschungzentrum (German Cancer Research Institute), Heidelberg, Del.). Male BALB/c-nu/nu mice (6-8 weeks of age) were injected s.c. with $5\times10^6$ A431 or HPAC, BxPC-3, HS766T, SK-RC-29, or SW707 cells in 100 µl PBS. Tumors sizes were measured twice a week with a vernier caliper and tumor volume was calculated as the product of length×width×height×$\pi$/6. Mice with established tumors were randomly divided into treatment groups. Mice received antibody treatment twice a week over three consecutive after tumor establishment. Tumors were measured twice a week.

B. Analysis

1. Antibodies in Accordance with the Invention, Such as the E7.6.3 Mab, Eradicate Human Tumor Xenografts in Mice.

To understand the underlying mechanism of the in vivo anti-tumor activity of E7.6.3, mice bearing A431 tumors were treated i.p with two different human anti-EGF-r Mabs, E7.6.3 or E7.5.2 (1 mg/mouse). Although both Mabs bind human EGF-r, only E7.6.3 blocks the binding of EGF or TGFα to EGF-r while E7.5.2 does not. As shown in Figure A, the tumors were completely eradicated on day 60 by the neutralizing antibody E7.6.3 while E7.5.2 had almost no effect on tumor growth as compared to the control. The data suggest that the in vivo anti-tumor activity of anti-EGF-r antibody requires the blockade of EGF-r binding sites.

2. Antibodies in Accordance with the Invention, Such as the E7.6.3 Mab, Does Not Affect EGF-r Negative Human Tumor Xenografts in Mice.

To understand the underlying mechanism of the in vivo anti-tumor activity of E7.6.3, human colon tumor cells SW707 which do not express EGF-r were injected s.c. into nude mice. Mice bearing established SW707 tumors were treated i.p with 1 mg of human anti-EGF-r Mab, E7.6.3. Control mice received no treatment. As shown in Figure F, treatment with E7.6.3 at 1 mg twice a week for three weeks failed to affect the growth of SW707 tumor indicating that the in vivo anti-tumor activity of anti-EGF-r antibody is antigen-specific.

3. Antibodies in Accordance with the Invention, Such as the E7.6.3 Mab, Inhibits the Growth of Multiple Human Tumor Xenografts in Mice:

The effect of E7.6.3 on the growth of multiple different human tumors was examined in xenograft mice. Three human pancreatic tumor cell lines, HPAC, BxPC-3 or HS766T, or a human renal tumor SK-RC-29 were injected into nude mice. The mice bearing the established tumors were treated i.p. with 1 mg of E.7.6.3 twice a week for three weeks. E7.6.3 treatment resulted in growth inhibition of HPAC during and 12 days after antibody treatment. Nevertheless, the inhibitory effect disappeared 12 days after termination of the treatment suggesting that for some tumors a sustained inhibition of tumor growth may require a prolonged antibody treatment. In contrast, administration of E7.6.3 twice a week for three weeks led to a significant and extended tumor growth arrest of BxPC-3, HS766T and SK-RC-29. Since the expression level of EGF-r on HPAC is much lower than BxPC-3, HS766T and SK-RC-29 (data not shown), it appears possible that tumors that have high levels of EGF-r expressed on their cell surfaces respond preferentially to the anti-EGFr antibody treatment.

Example 15

Additional Characterization of Antibodies in Accordance with the Invention

Example 10 presented information related to the inhibition of EGF-r phosphorylation and preliminary data related to the internalization of the EGF-r by cells. Further to the detailed discussion in Example 10 related to additional characterization of the antibodies in accordance with the present invention, we have demonstrated additional activities that appear to be important to the activity of the E7.6.3 antibody of the invention the Materials and Methods Internalization of EGFr In order to study the effect anti-EGF-r antibodies on internalization of EGF-r, confluent A431 cells in 24 well plates were washed and incubated with 10 ng/ml of $^{125}$I-EGF or 200 ng/ml of $^{125}$I-E7.6.3 at 4° C. for 90 min, and then incubated at 37° C. for different times to allow internalization. The plates were then placed on ice and washed. Surface-bound ligand was collected by two washes with 0.5 M acetic acid, 150 mM NaCl, and the cells were lysed with 1 ml of 1N NaOH for 30 min at 37° C. The radioactivity in the acetic acid and NaOH was counted in β-counter. See FIG. 80.

EGF and EGFr Degradation

In order to study the effect of anti-EGF-r antibodies on degradation of EGF-r, 70% confluent A431 cells were labeled with $^{35}$S-Methionine in methionine free medium containing 10% FBS for 16 hrs. After labeling, the cells were washed with PBS and incubated with serum free DMEM/F12 medium for 1 hr. The cells were then treated with 16 nM of EGF and 133 nM of either the E7.6.3 antibody, 225 antibody for 30 min, or a negative control. As controls, either K221 (a human IgG2 anti-IL18 antibody) or a murine anti-IgG1 antibody were used. After the 30-min incubation with the antibody, the cells were washed three times with cold PBS and scraped into 0.5 ml of lysis buffer (10 mM Tris, 150 mM NaCl, 5 mM EDTA, 1% triton-100, 0.1 mg/ml PMSF, 1 µg/ml aprotinin, 1 µg/ml leupeptin, 50 mM NaF, 40 mM β-glycerol phosphate, 10 mM pyrophosphate, 10 mM Hepes pH 7.3, and 1 mM sodium orthovanadate). After 30 minutes of incubation on ice, the lysate was centrifuged at 10,000 rpm for 5 minutes in an Eppendorf centrifuge at 4° C. 100 µl of lysate was immunoprecipitated using the E7.5.2 (discussed above, a non-neutralizing human anti-EGFr antibody) using protein A Sepharose beads. The protein A Sepharose-E7.5.2-protein (in lysate) complex were washed three times, mixed with 2×SDS sample buffer and boiled for 4 min. The proteins in samples were separated by electrophoresis on a 10% SDS-polyacrylamide gel. The gels were then fixed and dried before exposing to a film. See FIGS. 81 and 82.

EGF-r Threonine Phosphorylation

In order to study the effects of anti-EGF-r antibodies on threonine phosphorylation of EGF-r, 70% confluent A431 cells were labeled with $^{35}$S-Methionine in methionine free medium containing 10% FBS for 16 hrs. After labeling, the cells were washed with PBS and incubated with serum free DMEM/F12 medium for 1 hr. The cells were then treated with or without EGF (5 or 10 nM) in the absence or presence of the E7.6.3 antibody or the 225 antibody (200 nM) for 30 minutes. The K2.2.1 antibody was used as a negative control. After the 30-min incubation, the cells were washed three times with cold PBS and scraped into 0.5 ml of lysis buffer (10 mM Tris, 150 mM NaCl, 5 mM EDTA, 1% triton-100, 0.1 mg/ml PMSF, 1 µg/ml aprotinin, 1 µg/ml leupeptin, 50 mM NaF, 40 mM β-glycerol phosphate, 10 mM pyrophasphate, 10 mM Hepes pH 7.3, and 1 mM sodium orthovanadate). After 30 minutes of incubation on ice, the lysate was centrifuged at 10,000 rpm for 5 minutes in an Eppendorf centrifuge at 4° C. Two sets of 100 µl of lysate were prepared and immunoprecipitated with the E7.5.2 antibody or rabbit anti-phosphothreonine antibody (available from Zymed, South San Francisco, Calif.) using protein A Sepharose beads. The protein A Sepharose-antibody-protein (in lysate) complex were washed three times, mixed with 2×SDS sample buffer and boiled for 4 min. The proteins in samples were separated by electrophoresis on a 10% SDS-polyacrylamide gel. The gels were then fixed and dried before exposing to a film (film exposure and visualization was accomplished as described in Example 10). See FIG. 83.

In another experiment, in an effort to reduce the autocrine production of EGF by cells, we used 70% confluent A431 cells were pre-incubated at a low concentration of fetal bovine serum (0.5%) overnight in 37° C. The cells were then treated with 16 nM EGF in the presence or absence of different concentrations of E7.6.3 MAb for 30 minutes at 37° C. After the 30-min incubation, the cells were washed three times with cold PBS and scraped into 0.5 ml of lysis buffer (10 mM Tris, 150 mM NaCl, 5M EDTA, 1-% Triton-100, 0.1 mg/ml PMSF, 1 µg/ml aprotinin, 1 µg/ml leupeptin and 1 mM sodium orthovanadate). After 30 minutes of incubation on ice, the lysate was centrifuged at 10,000 rpm for 5 minutes in an Eppendorf centrifuge at 4° C. Two sets of 100 µl of lysate were prepared and immunoprecipitated with the E7.5.2 antibody or rabbit anti-phosphothreonine antibody (available from Zymed, South San Francisco, Calif.) using protein A Sepharose beads. The protein A. Sepharose-antibody-protein (in lysate) complex were washed three times, mixed with 2×SDS sample buffer and boiled for 4 min. The proteins in samples were separated by electrophoresis on a 10% SDS-polyacrylamide gel. The gels were then fixed and dried before exposing to a film (film exposure and visualization was accomplished as described in Example 10). See FIG. 84.

Vascular Endothelial Cell Growth Factor (VEGF) Production in Tumor Cells

In order to study the effects of anti-EGF-r antibodies on the upregulation of VEGF production in tumor cells, 70% confluent A431 cells in 24 well plates were washed with PBS and re-feed with fresh medium. The cells were treated with or without various antibodies as indicated and incubated for 48 or 96 hrs. At the end of culture, medium was collected and VEGF concentration in the medium was determined using ELISA kit (VEGF ELISA kit purchased from R&D, Minneopolis, Minn.). E752 and K221 were used as negative controls. Four individual experiments are presented. See FIG. 85.

VEGF Production in Endothelial Cells

In order to study the effects of anti-EGF-r antibodies on the upregulation of VEGF production in endotelial cells, 70% confluent ECV304 cells (ATCC: CRL-1998) in 24 well plates were washed with PBS and re-fed with fresh medium. The cells were treated with or without EGF in the presence or absence of various antibodies as indicated and incubated for 24 hrs. At the end of culture, medium was collected and VEGF concentration in the medium was determined using ELISA kit (VEGF ELISA kit purchased from R&D, Minneopolis, Minn.). K221 was used as negative controls. See FIG. 86.

Discussion

The above experiments provide important additional information about antibodies in accordance with the invention. For example, in FIG. 80 demonstrates that EGF-r is internalized after binding to either EGF (panel A) or the E7.6.3 antibody (panel B). Thereafter, a question arises is whether EGF-r is then degraded once internalized. FIG. 81 demonstrates that E7.6.3 is not degraded (panel B) and that the degradation of EGF provides a positive control (panel A). With respect to the degradation of EGF-r, FIG. 82 provides a series of immunoprecipitation blots that compare the effects of various antibodies on EGF-r degradation. As will be observed, when EGF binds to EGF-R, EGF-r degradation is induced. Panel A. Also, the 225 antibody induced EGF-r degradation. Treatment with either E7.6.3 or the non-specific K221 antibodies did not induce degradation of the receptor. In panel B, similar results are observed with the additional demonstration that the murine IgG1 did not induce degradation. Since the 225 antibody is a murine IgG1, the murine IgG1 acts as a negative control for 225 and indicates that the induction of degradation by 225 is specific. In panel C, EGF induced degradation of the receptor is shown. The results demonstrate that the E7.6.3 antibody completely inhibit the effect of EGF induced tGF-r degradation. In contrast, the 225 antibody did not inhibit the EGF induced EGF-r degradation.

From the data related EGF-r tyrosine phosphorylation, discussed in Example 10, where both the E7.6.3 and 225 antibodies inhibited EGF-r tyrosine phosphorylation and the difference between E7.6.3 and 225 with respect to the effect on EGF-r degradation, we sought to determine if there were additional phosphorylation differences related to the receptor. Accordingly, an experiment was conducted to view threonine phosphorylation of EGF-r. In FIG. 83, panel A shows immunoprecipitation of EGF-r by the E7.5.2 antibody, indicating that the quantity of EGF-r was the same. In panel B, shows immunoprecipitation by the rabbit anti-phosphothreonine antibody. As will be observed, significant threonine phosphorylation of the receptor is preserved by treatment with the E7.6.3 antibody. In contrast, a majority of the threonine phosphorylation is vitiated in treatement with the 225 antibody. An interesting additional band of threonine phosphorylation was seen at about 63 KD in the E7.6.3 treated cells.

Such additional band was further explored in connection with the results presented in FIG. 84. In this experiment, in an effort to reduce the autocrine production of EGF by cells, we raised the cells with almost no FBS. In the control group, spontaneous threonine phosphorylation is seen in a band at about 63 KD. EGF dramatically reduced such phosphorylation. EGF in combination with several neutralizing anti-EGF-r antibodies, including E7.6.3, partially restored such phosphorylation.

We also studied the production of vascular endothelial cell growth factor (VEGF) in tumor (A431) cells. VEGF is an important modulator of growth of endothelial cells and a potent angiogenic factor. It is believed to be important to new blood vessel formation in tumors. E.g., Liu and Ellis *Pathobiology* 66:247-252 (1998). In FIG. 85, the levels of VEGF production were examined and E7.6.3 significantly (>70%) inhibited VEGF production. In contrast, the 225 antibody inhibited VEGF production by much less than 50%, more accurately around 25%. The antibodies E752 and K221 were used as negative controls and they do not inhibit VEGF production.

In addition to the tumor cell work, we have completed preliminary experiments with respect to vascular endothelial cells. In addition to being recruited to sites of angiogenesis, such cells express EGF-r on their surfaces. Wilson and Lloyd *Invest. Opthamol. & Visual Science* 32:2747-2756 (1991). In FIG. 86, based on the data from 24 hour incubation, it will be observed that when such endothelial cells are stimulated with EGF, the VEGF production is increased. However, treatment with the E763 antibody inhibits the VEGF production by at least 40%. The 225 antibody on the other hand inhibits VEGF production by significantly less (20%).

A table summarizing certain of the above demonstrated similarities and differences between the E763 antibody and the 225 antibody is provided below:

TABLE II

| Characteristic | E7.6.3 | 225 |
|---|---|---|
| Inhibition of Tyrosine Phosphorylation | + | + |
| Internalization of EGF-r | + | + |
| Inhibition of EGF-r Degradation | | |
| EGF-r | + | − |
| EGF-induced | + | − |
| Thr-Phosphorylation | | |
| EGF-r | + | +/− |
| 63 KD Protein | + | − |
| Inhibition of VEGF Production | | |
| Tumor Cells | >50% | <50% |
| Endothelial Cells | >40% | <40% |

The data presented herein demonstrates the significant functional differences between the E763 and the 225 antibodies. In particular, the results with respect to VEGF production and the potential inhibition of endothelial cell proliferation within a tumor during the growth of a tumor lead naturally to a study of the downstream conditions of tumor growth. For example, it is expected that the E763 antibody may act to inhibit tumor cells and cells that depend on VEGF for their growth such as endothelial cells. In addition, other downstream molecules such as the VEGF receptor in endothelial cells and the activity of tPA in tumor cells and endothelial cells are expected to be affected by antibodies in accordance with the invention. Accordingly, these results enable the selection of other antibodies based on the foregoing functional properties of E763 in addition to the structural properties that are also discussed herein. The data also enables the potential study of other therapeutic moieties in the treatment and eradication of tumors.

INCORPORATION BY REFERENCE

All references cited herein, including patents, patent applications, papers, text books, and the like, and the references cited therein, to the extent that they are not already, are hereby incorporated herein by reference in their entirety. In addition, the following references are also incorporated by reference herein in their entirety, including the references cited in such references:

Abertsen et al., "Construction and characterization of a yeast artificial chromosome library containing seven haploid human genome equivalents." *Proc. Natl. Acad. Sci.* 87:4256 (1990).

Anand et al., "Construction of yeast artificial chromosome libraries with large inserts using fractionation by pulsed-field gel electrophoresis." *Nucl. Acids Res.* 17:3425-3433 (1989).

Berman et al. "Content and organization of the human Ig VH locus: definition of three new $V_H$ families and linkage to the Ig $C_H$ locus." *EMBO J.* 7.727-738 (1988).

Brezinschek et al., "Analysis of the heavy chain repertoire of human peripheral B-cells using single-cell polymerase chain reaction." *J. Immunol.* 155:190-202 (1995).

Brownstein et al., "Isolation of single-copy human genes from a library of yeast artificial chromosome clones." *Science* 244:1348-135I (1989).

Bruggeman et al. *PNAS USA* 86:6709-6713 (1989).

Bruggemann et al., "Human antibody production in transgenic mice: expression from 100 kb of the human IgH locus." *Eur. J. Immunol.* 21:1323-1326 (1991).

Bruggeman, M. and Neuberger, M. S. in *Methods: A companion to Methods in Enzymology* 2:159-165 (Lerner et al. eds. Academic Press (1991)).

Bruggemann, M. and Neuberger, M. S. "Strategies for expressing human antibody repertoires in transgenic mice." *Immunology Today* 17:391-397 (1996).

Chen et al. "Immunoglobulin gene rearrangement in B-cell deficient mice generated by targeted deletion of the $J_H$ locus" *International Immunology* 5:647-656 (1993)

Choi et al. "Transgenic mice containing a human heavy chain immunoglobulin gene fragment cloned in a yeast artificial chromosome" *Nature Genetics* 4:117-123 (1993)

Coligan et al., Unit 2.1, "Enzyme-linked immunosorbent assays," in *Current protocols in immunology* (1994).

Cook, G. P. and Tomlinson, I. M., "The human immunoglobulin $V_H$ repertoire." *Immunology Today* 16:237-242 (1995).

Cox et al., "A directory of human germ-line Vκ segments reveals a strong bias in their usage." *Eur. J. Immunol.* 24:827-836 (1994).

Dariavach et al., "The mouse IgH 3'-enhancer." *Eur. J. Immunol.* 21:1499-1504 (1991).

Den Dunnen et al., "Reconstruction of the 2.4 Mb human DMD-gene by homologous YAC recombination." *Human Molecular Genetics* 1:19-28 (1992).

Feeney, A. J. "Lack of N regions in fetal and neonatal mouse immunoglobulin V-D-J junctional sequences." *J. Exp. Med.* 172:137-1390 (1990).

Fishwild et al., "High-avidity human IgGκmonoclonal antibodies from a novel strain of minilocus transgenic mice." *Nature Biotech.* 14:845-851 (1996).

Flanagan, J. G. and Rabbitts, T. H., "Arrangement of human immunoglobulin heavy chain constant region genes implies evolutionary duplication of a segment containing g, e, and a genes." *Nature* 300:709-713 (1982).

Galfre, G. and Milstein, C., "Preparation of monoclonal antibodies: strategies and procedures." *Methods Enzymol.* 73:3-46 (1981).

Gemmill et al., "Protocols for pulsed field gel electrophoresis: Separation and detection of large DNA molecules." *Advances in Genome Biology* 1:217-251 (1991).

Gill et al., "Monoclonal anti-epidermal growth factor receptor antibodies which are inhibitors of epidermal growth factor binding and antagonists of epidermal growth factor-stimulated tyrosine protein kinase activity." *J. Biol. Chem.* 259:7755 (1984).

Green et al., "Antigen-specific human monoclonal antibodies from mice engineered with human Ig heavy and light chain YACs." *Nature Genetics* 7:13-21 (1994).

Hermanson et al., "Rescue of end fragments of yeast artificial chromosomes by homologous recombination in yeast." *Nucleic Acids Res.* 19:4943-4948 (1991).

Huber et al., "The human immunoglobulin κ locus. Characterization of the partially duplicated L regions." *Eur. J. Immunol.* 23:2860-2967 (1993).

Jakobovits, A., "Humanizing the mouse genome." *Current Biology* 4:761-763 (1994).

Jakobovits, A., "Production of fully human antibodies by transgenic mice." *Current Opinion in Biotechnology* 6:561-566 (1995).

Jakobovits et al., "Germ-line transmission and expression of a human-derived yeast artificial-chromosome." *Nature* 362:255-258 (1993).

Jakobovits, A. et al.; "Analysis of homozygous mutant chimeric mice: Deletion of the immunoglobulin heavy-chain joining region blocks B-cell development and antibody production." *Proc. Natl. Acad. Sci. USA* 90:2551-2555 (1993).

Kawamoto et al., "Growth stimulation of A431 cells by epidermal growth factor: Identification of high affinity receptors for EGF by an anti-receptor monoclonal antibody." *Proc. Nat. Acad. Sci., USA* 80:1337-1341 (1983).

Lonberg et al., "Antigen-specific human antibodies from mice comprising four distinct genetic modifications." *Nature* 368:856-859 (1994).

Lusti-Marasimhan et al., "Mutation of Leu25 and Val27 introduces CC chemokine activity into interleukin-8." *J. Biol. Chem.* 270:2716-2721 (1995).

Marks et al., "Oligonucleotide primers for polymerase chain reaction amplification of human immunoglobulin variable genes and design of family-specific oligonucleotide probes." *Eur. J. Immunol.* 21:985-991 (1991).

Matsuda et al., "Structure and physical map of 64 variable segments in the 3' 0.8-megabase region of the human immunoglobulin heavy-chain locus." *Nature Genetics* 3:88-94 (1993).

Max, E. *Molecular genetics of immunoglobulins. Fundamental Immunology.* 315-382 (Paul, W E, ed., New York: Raven Press (1993)).

Mendez et al., "A set of YAC targeting vectors for the interconversion of centric and acentric arms." *Cold Spring Harbor Laboratory Press, Genome Mapping and Sequencing meeting,* 163 (1993).

Mendez et al., "Analysis of the structural integrity of YACs comprising human immunoglobulin genes in yeast and in embryonic stem cells." *Genomics* 26:294-307 (1995).

Ray, S. and Diamond, B., "Generation of a fusion partner to sample the repertoire of Splenic B-cells destined for apoptosis." *Proc. Natl. Acad. Sci. USA* 91:5548-5551 (1994).

Sato et al., "Biological effects in vitro of monoclonal antibodies to human epidermal growth factor receptors" *Mol. Biol. Med.* 1:51.1-529 (1983).

Schiestl, R. H. and Gietz, R. D., "High efficiency transformation of intact yeast cells using stranded nucleic acids as a carrier." *Curr. Genet.* 16:339-346 (1989).

Sherman et al., "Laboratory Course Manual for Methods in Yeast Genetics." (Cold Spring Harbor Laboratory Press, Cold Spring Harbor, N.Y. (1986)).

Silverman et al., "Meiotic recombination between yeast artificial chromosomes yields a single clone containing the entire BCL2 protooncogene." *Proc. Natl. Acad. Sci. USA* 87:9913-9917 (19_).

Srivastava, A. and Schlessinger, D., "Vectors for inserting selectable markers in vector arms and human DNA inserts of yeast artificial chromosomes (YACs)." *Gene* 103:53-59 (1991).

Taylor et al., "A transgenic mouse that expresses a diversity of human sequence heavy and light chain immunoglobulins." *Nucleic Acids Research* 20:6287-6295 (1992).

Taylor et al., "Human immunoglobulin transgenes undergo rearrangement, somatic mutation and class switching in mice that lack endogenous IgM." *International Immunology* 6:579-591 (1994).

Tuaillon et al., "Human immunoglobulin heavy-chain minilocus recombination in transgenic mice: gene-segment use in m and g transcripts." *Proc. Natl. Acad. Sci. USA* 90:3720-3724 (1993).

Tuaillon et al. "Analysis of direct and inverted $DJ_H$ rearrangements in a human Ig heavy chain transgenic minilocus" *J. Immunol.* 154:6453-6465 (1995)

Vaughan et al., "Human antibodies with subnanomolar affinities isolated from a large non-immunized phage display library." *Nature Biotech.* 14:309-314 (1996).

Wagner et al., "The diversity of antigen-specific monoclonal antibodies from transgenic mice bearing human immunoglobulin gene miniloci." *Eur. J. Immunol.* 24:2672-2681 (1994).

Weichhold et al., "The human immunoglobulin κ locus consists of two copies that are organized in opposite polarity." *Genomics* 16:503-511 (1993).

Yamada, M. et al., "Preferential utilization of specific immunoglobulin heavy chain diversity and joining segments in adult human peripheral blood B lymphocytes." *J. Exp. Med.* 173:395-407 (1991).

1. Ullrich, A. and Schlessinger, J. Signal transduction by receptors with tyrosine kinase activity. (Review). Cell, 61: 203-212, 1990.
2. Baselga, J. and Mendelsohn, J. Receptor blockade with monoclonal antibodies as anti-cancer therapy. (Review). Pharmacol Ther, 64: 127-154, 1994.
3. Mendelsohn, J. and Baselga, J. Antibodies to growth factors and receptors. (Review). In: V. T. DeVita, S. Hellman and S. A. Rosenberg (eds.), Biologic Therapy of Cancer, pp. 607-623, Philadelphia: J. B. Lippincott Company. 1995.
4. Fan, Z. and Mendelsohn, J. Therapeutic application of anti-growth factor receptor antibodies. (Review). Curr Opin Oncol, 10: 67-73, 1998.
5. Riedel, H., Massoglia, S., Schlessinger, J., and Ullrich, A. Ligand activation of overexpressed epidermal growth factor receptors transforms NIH 3T3 mouse fibroblasts. Proc Natl Acad Sci USA, 85: 1477-1481, 1988.
6. Modjtahedi, H. and Dean, C. The receptor for EGF and its ligands: expression, prognostic value and target for therapy in cancer (Review). Intl J of Oncology, 4: 277-296, 1994.
7. Gullick, W. J. Prevalence of aberrant expression of the epidermal growth factor receptor in human cancers. Br Medical Bulletin, 47: 87-98, 1991.
8. Salomon, D. S., Brandt, R., Ciardiello, F., and Normanno, N. Epidermal growth factor-related peptides and their receptors in human malignancies. Crit Rev Oncol Hematol, 19: 183-232, 1995.
9. Aboud-Pirak, E., Hurwitz, E., Pirak, M. E., Bellot, F., Schlessinger, J., and Sela, M. Efficacy of antibodies to epidermal growth factor receptor against KB carcinoma in vitro and in nude mice. J of the National Cancer Inst, 80: 1605-1611, 1988.
10. Modjtahedi, H., Styles, J. M., and Dean, C. J. The human EGF receptor as a target for cancer therapy: six new rat mAbs against the receptor on the breast carcinoma MDA-MB 468. Br J Cancer, 67: 247-253, 1993.
11. Modjtahedi, H., Eccles, S., Box, G., Styles, J., and Dean, C. Immunotherapy of human tumour xenografts overexpressing the EGF receptor with rat antibodies that block growth factor-receptor interaction. Br J Cancer, 67: 2611993.
12. Fan, Z., Baselga, J., Masui, H., and Mendelsohn, J. Antitumor effect of anti-epidermal growth factor receptor monoclonal antibodies plus cis-diamminedichloroplatinum on well established A431 cell xenografts. Cancer Research, 53: 4637-4642, 1993.
13. Baselga, J., Norton, L., Masui, H., Pandiella, A., Coplan, K., Miller, W. H., and Mendelsohn, J. Antitumor effects of doxorubicin in combination with anti-epidermal growth factor receptor monoclonal antibodies. J of the National Cancer Inst, 85: 1327-1333, 1993.
14. Goldstein, N. I., Prewett, M., Zuklys, K., Rockwell, P., and Mendelsohn, J. Biological efficacy of a chimeric antibody ot the epidermal growth factor receptor in a human tumor xenograft model. Clinical Cancer Research, 1: 1311-1318, 1995.
15. Prewett, M., Rockwell, R., Rockell, R. F., Giorgio, N. A., Mendelsohn, J., Scher, H. I., and Goldstein, N. I. The biologic effects of C225, a chimeric monoclonal antibody to the EGFR, on human prostate carcinoma. J Immunother Emphasis Tumor Immunol, 19: 419-427, 1996.
16. Slovin, S. F., Kelley, W. K., Cohen, R., Cooper, M., Malone, T., Weingard, K., Waksal, H., Falcey, J., Mendelsohn, J., and Scher, H. I. Epidermal gowth factor receptor (EGF-r) monoclonal antibody (MoAb) C225 and doxorubicin (DOC) in androgen-independent (AI) prostate cancer (PC): results of a phase Ib/IIa study. Proc Am Soc Clin Oncol, 16: 311a1997.(Abstract)
17. Falcey, J., Pfister, D., Cohen, R., Cooper, M., Bowden, C., Burtness, B., Mendelsohn, J., and Waksal, H. A study of anti-epidermal growth factor receptor (EGFr) monoclonal antibody C225 and cisplatin in patients (pts) with head and neck or lung carcinomas. Proc Am Soc Clin Oncol, 16: 383a1997.(Abstract)
18. Mendez, M. J., Green, L. L., Corvalan, J. R. F., Jia, X.-C., Maynard-Currie, C. E., Yang, X.-D., Gallo, M. L., Louie, D. M., Lee, D. V., Erickson, K. L., Luna, J., Roy, C. M.-N., Abderrahim, H., Kirschenbaum, F., Noguchi, M., Smith, D. H., Fukushima, A., Hales, J. F., Finer, M. H., Davis, C. G., Zsebo, K. M., and Jakobovits, A. Functional transplant of megabase human immunoglobulin loci recapitulates human antibody response in mice. Nat Gen, 15: 146-156, 1997.
19. Jakobovits, A. The long-awaited magic bullets: therapeutic human monoclonal antibodies from transgenic mice. Exp Opin Invest Drugs, 7: 607-614, 1998.
20. Debanne, M. T., Pacheco-Oliver, M. C., and O'Connor-McCourt, M. D. Purification of the extracellular domain of the epidermal growth factor receptor produced by recombinant baculovirus-infected insect cells in a 10-L reactor. In: C. D. Richardson (ed.), Baculovirus Expression Protocols, pp. 349-361, Totowa, N.J.: Humana Press Inc. 1995.
21. Ishiyama, M., Tominaga, H., Shiga, M., Sasamoto, K., Ohkura, Y., and Ueno, K. A combined assay of cell viability and in vitro cytotoxicity with a highly water-soluable tetrazolium salt, neutral red and crystal violet. Biol Pharm Bull, 19: 1518-1520, 1996.
22. McConnell, H. M., Owicki, J. C., Parce, J. W., Miller, D. L., Baxter, G. T., Wada, H. G., and Pitchford, S. The cytosensor microphysiometer: biological applications of silicon technology. Science, 257: 1906-1912, 1992.
23. Bogovski, P. Tumours of the skin. In: V. S. Turusov and U. Mohr (eds.), Tumours of Mouse, pp. 1-26, Lyon: IARC Scientific Publications. 1994.
24. Ennis, B. W., Valverius, E. M., Bates, S. E., Lippman, M. E., Bellot, F., Kris, R., Schlessinger, J., Masui, H., Goldenberg, A., Mendelsohn, J., and Dickson, R. B. Anti-epidermal growth factor receptor antibodies inhibit the autocrine-stimulated growth of MDA-468 human breast cancer cells. Molecular Endocrinology, 3: 1830-1838, 1989.
25. Kawamoto, T., Mendelsohn, J., Gordon, A. L., Sato, G. H., Lazar, C. S., and Gill, G. N. Relation of epidermal growth factor receptor concentration to growth of human epidermoid carcinoma A431 cells. J of Biological Chemistry, 259: 7761-7766, 1984.
26. Masui, H., Moroyama, T., and Mendelsohn, J. Mechanism of antitumor activity in mice for anti-epidermal growth factor receptor monoclonal antibodies with different isotypes. Cancer Research, 46: 5592-5598, 1986.
27. Wu, X., Fan, Z., Masui, H., Rosen, N., and Mendelsohn, J. Apoptosis induced by an anti-epidermal growth factor receptor monoclonal antibody in human colorectal carcinoma cell line and its delay by insulin. J Clin Invest, 95: 1897-1905, 1995.
28. Sturgis, E. M., Sacks, P. G., Masui, H., Mendelsohn, J., and Schantz, S. P. Effects of antiepidermal growth factor receptor antibody 528 on the proliferation and differentiation of head and neck cancer. Otolaryngol Head Neck Surg, 111: 633-643, 1994.
29. Modjtahedi, H., Eccles, S., Sandle, J., Box, G., Titley, J., and Dean, C. Differentiation or immune destruction: two pathways for therapy of squamous cell carcinomas with antibodies to the epidermal growth factor receptor. Cancer Res, 54: 1695-1701, 1994.
30. Viloria Petit, A. M., Rak, J., Hung, M.-C., Rockwell, P., Goldstein, N., Fendly, B., and Kerbel, R. S. Neutralizing antibodies against epidermal growth factor and ErbB-2/neu receptor tyrosine kinases down-regulate vascular endothelial growth factor production by tumor cells in vitro and in vivo: angiogenic implications for signal transduction therapy of solid tumors. Am J Pathol, 151: 1523-1530, 1997.
31. Kita, Y., Tseng, J., Horan, T., Wen, J., Philo, J., Chang, D., Ratzkin, B., Pacifici, R., Brankow, D., Hu, S., Luo, Y., Wen, D., Arakawa, T., and Nicolson, M. ErbB receptor activation, cell morphology changes, and apoptosis induced by anti-Her2 monoclonal antibodies. Biochem Biophys Res Commun, 226: 59-69, 1996.
32. Slamon, D., Leyland-Jones, B., Shak, S., Paton, V., Bajamonde, A., Fleming, T., Eiermann, W., Wolter, J., Baselga, J., and Norton, L. Addition of Herceptin™ (human anti-Her2 antibody) to first line chemotherapy for HER2 overexpressing metastatic breast cancer (Her2+/mbc) markedly increases anticancer activity: a randomized, multinational controlled phase III trial. Proc of ASCO, 17: 98a, 1998.(Abstract)
33. Cobleigh, M. A., Bogel, C. L., Tripathy, D., Robert, N. J., Scholl, S., Fegrenbacher, L., Paton, V., Shak, S., Lieberman, G., and Slamon, D. Efficacy and safety of Herceptin™ (humanized anti-Her2 antibody) as a single agent in 222 women with Her2 overexpression who relapsed following chemotherapy for metastatic breast cancer. Proc of ASCO, 17: 97a, 1998.(Abstract)

EQUIVALENTS

The foregoing description and Examples detail certain preferred embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

What we claim is:

1. An isolated human antibody that binds to human epidermal growth factor receptor (EGF-r), comprising:
   a) a heavy chain immunoglobulin molecule comprising an amino acid sequence having at least 95% sequence identity to the amino acid sequence encoded by the nucleotide sequence set forth in SEQ ID NO: 17; and
   b) a light chain immunoglobulin molecule comprising an amino acid sequence having at least 95% sequence identity to the amino acid sequence encoded by the nucleotide sequence set forth in SEQ ID NO: 18;
wherein the antibody specifically binds to EGF-r.

2. The antibody of claim 1, wherein the heavy chain immunoglobulin molecule comprises an amino acid sequence having at least 99% sequence identity to the amino acid sequence encoded by the nucleotide sequence set forth in SEQ ID NO: 17.

3. The antibody of claim 1 or claim 2, wherein the light chain immunoglobulin molecule comprises an amino acid sequence having at least 99% sequence identity to the amino acid sequence encoded by the nucleotide sequence set forth in SEQ ID NO: 18.

4. The antibody of claim 1, wherein the heavy chain immunoglobulin molecule comprises the amino acid sequence set forth in SEQ ID NO: 76.

5. The antibody of claim 1 or claim 4, wherein the light chain immunoglobulin molecule comprises an amino acid sequence set forth in SEQ ID NO: 54.

6. An isolated human antibody comprising a heavy chain immunoglobulin molecule comprising amino acids 8 to 85 of SEQ ID NO: 76, and comprising a light chain immunoglobulin molecule comprising amino acids 5 to 78 of SEQ ID NO: 54, wherein the antibody specifically binds to EGF-r.

7. An isolated human antibody comprising a heavy chain immunoglobulin molecule comprising:
   a) a CDR1 comprising amino acids 8 to 15 of SEQ ID NO: 76;
   b) a CDR2 comprising amino acids 29 to 45 of SEQ ID NO: 76; and
   c) a CDR3 comprising amino acids 77 to 85 of SEQ ID NO: 76;
and comprising a light chain immunoglobulin molecule comprising:
   d) a CDR1 comprising amino acids 5 to 15 of SEQ ID NO: 54;
   e) a CDR2 comprising amino acids 31 to 37 of SEQ ID NO: 54; and
   f) a CDR3 comprising amino acids 70 to 78 of SEQ ID NO: 54;
wherein the antibody specifically binds to EGF-r.

8. An isolated human antibody comprising a heavy chain immunoglobulin molecule comprising the amino acid sequence of SEQ ID NO: 76, and a light chain immunoglobulin molecule comprising the amino acid sequence of SEQ ID NO: 54.

9. The antibody of any one of claims 1, 6, 7 and 8, wherein the antibody is a binding fragment.

10. The antibody of any one of claims 1, 6, 7 and 8, wherein the antibody is an IgG2 antibody.

11. The antibody of any one of claims 1, 6, 7 and 8, wherein the antibody specifically binds EGF-r with a dissociation constant of less than or equal to 10 nM.

* * * * *